US011938153B2

(12) United States Patent
Lynn et al.

(10) Patent No.: US 11,938,153 B2
(45) Date of Patent: Mar. 26, 2024

(54) METHODS OF TREATING T CELL EXHAUSTION BY INHIBITING OR MODULATING T CELL RECEPTOR SIGNALING

(71) Applicant: THE BOARD OF TRUSTEES OF THE LELAND STANFORD JUNIOR UNIVERSITY, Stanford, CA (US)

(72) Inventors: Rachel Lynn, Stanford, CA (US); Crystal Mackall, Stanford, CA (US); Tom J. Wandless, Stanford, CA (US); Evan Weber, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 930 days.

(21) Appl. No.: 16/499,760

(22) PCT Filed: Mar. 30, 2018

(86) PCT No.: PCT/US2018/025459
§ 371 (c)(1),
(2) Date: Sep. 30, 2019

(87) PCT Pub. No.: WO2018/083888
PCT Pub. Date: Oct. 4, 2018

(65) Prior Publication Data
US 2021/0032363 A1 Feb. 4, 2021

Related U.S. Application Data

(60) Provisional application No. 62/479,930, filed on Mar. 31, 2017.

(51) Int. Cl.
| | | |
|---|---|---|
| *A61K 35/17* | (2015.01) | |
| *A61K 31/5025* | (2006.01) | |
| *A61K 31/506* | (2006.01) | |
| *A61P 35/00* | (2006.01) | |
| *C07K 14/705* | (2006.01) | |
| *C07K 14/725* | (2006.01) | |
| *C07K 16/30* | (2006.01) | |
| *C12N 5/0783* | (2010.01) | |
| *C12N 9/90* | (2006.01) | |

(52) U.S. Cl.
CPC .......... *A61K 35/17* (2013.01); *A61K 31/5025* (2013.01); *A61K 31/506* (2013.01); *A61P 35/00* (2018.01); *C07K 14/7051* (2013.01); *C07K 14/70521* (2013.01); *C07K 14/70578* (2013.01); *C07K 16/3084* (2013.01); *C12N 5/0636* (2013.01); *C12N 9/90* (2013.01); *C07K 2317/622* (2013.01); *C07K 2319/02* (2013.01); *C07K 2319/03* (2013.01); *C07K 2319/33* (2013.01); *C12N 2501/727* (2013.01); *C12N 2510/00* (2013.01)

(58) Field of Classification Search
CPC ..... A61K 35/17; A61P 35/00; C07K 14/7051; C07K 14/70521; C07K 14/70578; C07K 16/3084; C07K 2317/622; C07K 2319/02; C07K 2319/03; C07K 2319/33; C12N 5/0636; C12N 9/90; C12N 2510/00
USPC ....................................................... 424/93.21
See application file for complete search history.

(56) References Cited

U.S. PATENT DOCUMENTS

| | | | |
|---|---|---|---|
| 9,334,330 B2 | 5/2016 | Birkle et al. | |
| 9,394,368 B2 | 7/2016 | Brogdon et al. | |
| 9,446,105 B2 | 9/2016 | Powell, Jr. | |
| 9,499,629 B2 | 11/2016 | June et al. | |
| 9,598,489 B2 | 3/2017 | Powell, Jr. | |
| 9,624,306 B2 | 4/2017 | Morgan et al. | |
| 9,629,877 B2 | 4/2017 | Cooper et al. | |
| 9,765,342 B2 | 9/2017 | Kochenderfer | |
| 9,777,061 B2 | 10/2017 | Ebersbach et al. | |
| 9,790,282 B2 | 10/2017 | Orentas et al. | |
| 9,815,901 B2 | 11/2017 | Brogdon et al. | |
| 9,845,362 B2 | 12/2017 | Mukherjee | |
| 11,413,309 B2 | 8/2022 | Rosen et al. | |
| 2005/0113564 A1 | 5/2005 | Campana et al. | |

(Continued)

FOREIGN PATENT DOCUMENTS

| | | |
|---|---|---|
| WO | 2005044996 | 5/2005 |
| WO | 2008122051 | 10/2008 |

(Continued)

OTHER PUBLICATIONS

EP Search Report, EP Patent Application No. 18777667.9, dated Dec. 4, 2020, 7 pages.
A. Juillerat et al. "Design of chimeric antigen receptors with integrated controllable transient functions" Scientific Reports, vol. 6, Jan. 11, 2016, pp. 1-7.
A. Long et al. "4-1BB costimulation ameliorates T cell exhuastion induced by tonic signaling of chimeric antigen receptors" Nature Medicine, vol. 21, No. 6, May 4, 2015, pp. 581-590.

(Continued)

*Primary Examiner* — Yan Xiao
(74) *Attorney, Agent, or Firm* — Brian E. Davy; Bozicevic, Field & Francis LLP

(57) ABSTRACT

The present invention relates to T cell compositions and methods of using the same in the context of therapy and treatment. In particular, the invention provides chimeric antigen receptor (CAR) T cells that are modified to maintain functionality under conditions in which unmodified CAR T cells display exhaustion. Compositions and methods disclosed herein find use in inhibiting or reversing CAR T cell exhaustion (e.g., by modulating CAR surface expression) thereby enhancing CAR T cell function. Compositions and methods of the invention fmd use in both clinical and research settings, for example, within the fields of biology, immunology, medicine, and oncology.

14 Claims, 43 Drawing Sheets
Specification includes a Sequence Listing.

(56) References Cited

U.S. PATENT DOCUMENTS

| | | | |
|---|---|---|---|
| 2009/0123944 | A1 | 5/2009 | Finney et al. |
| 2012/0178168 | A1 | 7/2012 | Wandless et al. |
| 2014/0004132 | A1 | 1/2014 | Brenner et al. |
| 2014/0178438 | A1 | 6/2014 | Sahin et al. |
| 2014/0274909 | A1 | 9/2014 | Orentas et al. |
| 2015/0140071 | A1 | 5/2015 | Rajasekaran |
| 2017/0239294 | A1 | 8/2017 | Thomas-Tikhonenko et al. |
| 2019/0112380 | A1 | 4/2019 | Chaudhary |
| 2020/0181573 | A1 | 6/2020 | Rosen et al. |
| 2021/0169880 | A1 | 6/2021 | Hudecek et al. |
| 2021/0393628 | A1 | 12/2021 | Mackall |
| 2022/0401487 | A1 | 12/2022 | Rosen et al. |

FOREIGN PATENT DOCUMENTS

| | | | |
|---|---|---|---|
| WO | 2014/127261 | 8/2014 | |
| WO | 2015132604 | 9/2015 | |
| WO | WO 2015179801 | 11/2015 | |
| WO | 2016014789 | 1/2016 | |
| WO | WO 2016011264 | 1/2016 | |
| WO | WO 2016111645 | 7/2016 | |
| WO | WO-2016134284 A1 * | 8/2016 | ......... A61K 39/0011 |
| WO | WO 2017025638 | 2/2017 | |
| WO | 2017181119 | 10/2017 | |

OTHER PUBLICATIONS

International Search Report & Written Opinion, Int'l Patent Application No. PCT/US2018/025459, dated Sep. 24, 2018, 14 pages.
Iwamoto et al. A General Chemical Method to Regulate Protein Stability in the Mammalian Central Nervous System. Chemistry and Biology, Sep. 24, 2010, vol. 17, No. 9, pp. 981-988.
Jonnalagadda, M. et al. Engineering Human T Cells for Resistance to Methotrexate and Mycophenolate Mofetil as an In Vivo Cell Selection Strategy, PLOS One, Jun. 2013, vol. 8, issue 6, e65519.
Abbas Mirshafiey et al. (2014) "Receptor Tyrosine Kinase and Tyrosine Kinase Inhibitors: New Hope for Success in Multiple Sclerosis Therapy" Innovations in clinical neuroscience, pp. 23-36.
Araujo et al. (2010) "Dasatinib: A potent SRC inhibitor in clinical development for the treatment of solid tumors" Cancer Treatment Review, 36(2010):492-500.
Brian Rini: (2014) "Future Approaches in Immunotherapy" Seminars in Oncology, vol. 41, pp. S30-S40.
Chames et al. (2009) "Therapeutic antibodies: successes, limitations and hopes for the future" British J. of Pharmacology, 157, 220-233.
Cherkassky et al. (2016) "Human CAR T cells with cell-intrinsic PD-1 checkpoint blockade resist tumor-mediated inhibition" J Clin Invest, vol. 126, No. 8, pp. 3130-3144.
D'Aloia et al. (2018) "CAR-T cells: the long and winding road to solid tumors" Cell Death & Disease 9(3), 282, pp. 1-12.
Gargett & Brown (2014) "The inducible caspase-9 suicide gene system as a "safety switch" to limit on-target, off-tumor toxicities of chimeric antigen receptor T cells" Frontiers in Pharmacology 5, 235, 7 pages.
Gomes-Silva et al. (2017) "Tonic 4-1BB Costimulation in Chimeric Antigen Receptors Impedes T Cell Survival and Is Vector-Dependent" Cell Reports 21, 17-26.
Gura (1997) "Systems for Identifying New Drugs Are Often Faulty" Science, 278:1041-1042.
Gust et al. (2017) "Endothelial Activation and Blood-Brain Barrier Disruption in Neurotoxicity after Adoptive Immunotherapy with CD19 CAR-T Cells" Cancer discovery, pp. 1405-1419 doi: 10.1158/2159-8290.cd-17-0698.
International Search Report & Written Opinion, International Patent Application No. PCT/US2018/025394, dated Aug. 8, 2018, 19 pages.
Kaiser (2006) "First pass at cancer genoome reveals complex landscape" Science, 313:1370.
Kreutzman et al. (2010) "Mono/oligoclonal T and NK cells are common in chronic myeloid leukemia patients at diagnosis and expand during dasatinib therapy" Blood, 116(5):772-782.
Lee et al. (2016) "Long-term outcomes following CD19 CAR T cell therapy for B-All are superior in patients receiving a fludarabine/cyclophosphamide preparative regimen and post-CAR hematopoietic stem cell transplantation" Blood, vol. 128, Issue 22.
Leonard et al. (2016) "Targeting BCL-2 and ABL/LYN in Philadelphia chromosome-positive acute lymphoblastic leukemia" 8(354):354ra114.
Lim & June (2017) "The Principles of Engineering Immune Cells to Treat Cancer" Cell 168, 724-740.
Long et al. (2015) "4-1BB costimulation ameliorates T cell exhaustion induced by tonic signaling of chimeric antigen receptors" Nature Medicine 21, 581-590.
Maude et al. (2014) "Chimeric Antigen Receptor T Cells for Sustained Remissions in Leukemia" The New England Journal of Medicine 371, 1507-1517.
Sakuishi et al. (2010) "Targeting Tim-3 and PD-1 pathways to reverse T cell exhaustion and restore anti-tumor immunity" J. Exp. Med, vol. 207, No. 10, pp. 2187-2194.
Schade et al. (2008) "Dasatinib, a small-molecule protein tyrosine kinase inhibitor, inhibits T-cell activation and proliferation" Blood, vol. 111, No. 3, pp. 1366-1377.
Shinsuke Noguchi et al. (2015) "Disclosures" Blood, vol. 126, No. 23, pp. 2219-2219.
Third Party Observation, Application No. EP20180775932, dated Jan. 6, 2022, 4 pages.
Turtle et al. (2016) "CD19 Car-T cells of defined CD4+:CD8+ composition in adult B cell ALL patients" Journal of Clinical Investigation 126, 2123-2138.
Wang et al. (2014) "Current advances in T-cell-based cancer immunotherapy" Immunotherapy, vol. 6, No. 12, pp. 1265-1278.
Wherry & Kurachi (2015) "Molecular and cellular insights into T cell exhaustion" Nature Reviews Immunology, 15(8):486-99.
Wu et al. (2014) "Dasatinib promotes the potential of proliferation and antitumor responses of human γ8T cells in a long-term induction ex vivo environment" Leukemia, 28:206-210.
Xu & Tang (2013) "Cytokine release syndrome in cancer immunotherapy with chimeric antigen receptor engineered T cells" Cancer Letters 343, 172-178.
Ye et al. (2015) "T-cell exhaustion in chronic hepatitis B infection: current knowledge and clinical significance" Cell Death and Disease, vol. 6, p. e1694, pp. 1-10.
Banaszynski et al. (2006) "A Rapid, Reversible, and Tunable Method to Regulate Protein Function in Living Cells Using Synthetic Small Molecules" Cell, 126(5):995-1004.
Chan et al. (2011) "Conformational Control Inhibition of the BCR-ABL1 Tyrosine Kinase, Including the Gatekeeper T315I Mutant, by the Switch-Control Inhibitor DCC-2036" Cancer Cell, 19, 556-568.
Mestermann et al. (2019) "The tyrosine kinase inhibitor dasatinib acts as a pharmacologic on/off switch for CAR T cells" Sci. Transl. Med. 11:eaau5907.
Seggewiss et al. (2005) "Imatinib inhibits T-cell receptor-mediated T-cell proliferation and activation in a dose-dependent manner" Blood, 105(6) 2473-2479.
Weichsel et al. (2008) "Profound Inhibition of Antigen-Specific T-Cell Effector Functions by Dasatinib" Clin. Cancer Res. 14(8):2484-2491.

\* cited by examiner

*Data collected on day 14, gated on CD8+

*Gated on CAR+

FIG. 25

| SEQ ID NO: | | |
|---|---|---|
| 1 | FKBP12 destabilization domain (E31G, F36V, R71G, K105E) nucleic acid sequence | ATGGTGCAGGTGGAAACCATCTCCCCAGGAGACGGGCGCACCTTCCCCAAGCGCGGCCAGACCTGCGTGGTGCACTACACCGGGATGCTTGGAGATGGAAAGAAAGTTGACTCCTCCCGGGACAGAAACAAGCCCTTTAAGTTTATGCTAGGCAAGCAGGAGGTGATCCGAGGCTGGGAAGAAGGGGTTGCCCAGATGAGTGTGGGTCAGGGAGCCAAACTGACTATATCTCCAGATTATGCCTATGGTGCCACTGGGCACCCAGGCATCATCCCACCACATGCCACTCTCGTCTTCGATGTGGAGCTTCTAGAACTGGAA |
| 2 | FKBP12 destabilization domain (E31G, F36V, R71G, K105E) Amino acid sequence | MVQVETISPGDGRTFPKRGQTCVVHYTGMLGDGKKVDSSRDRNKPFKFMLGKQEVIRGWEEGVAQMSVGQGAKLTISPDYAYGATGHPGIIPPHATLVFDVELLELE |
| 3 | ecDHFR destabilization domain (R12H, N18T, V19A, G67S) nucleic acid sequence | ATGATCAGTCTGATTGCGGCGTTAGCGGTAGATCACGTTATCGGCATGGAAACCGTCATGCCGTGGAACCTGCCTGCCGATCTCGCCTGGTTTAAACGCAACACCTTAAATAAACCCGTGATTATGGGCCGCCATACCTGGGAATCAATCGGTCGTCCGTTGCCAGGACGCAAAAATATTATCCTCAGCAGTCAACCGAGTACGGACGATCGCGTAACGTGGGTGAAGTCGGTGGATGAAGCCATCGCGGCGTGTGGTGACGTACCAGAAATCATGGTTATTGGCGGCGGTCGCGTTTATGAACAGTTCTTGCCAAAAGCGCAAAAACTGTATCTGACGCATATCGACGCAGAAGTGGAAGGCGACACCCATTTCCCGGATTACGAGCCGGATGACTGGGAATCGGTATTCAGCGAATTCCACGATGCTGATGCGCAGAACTCTCACAGCTATTGCTTTGAGATTCTGGAGCGGCGA |
| 4 | ecDHFR destabilization domain (R12H, N18T, V19A, G67S) Amino acid sequence | MISLIAALAVDHVIGMETVMPWNLPADLAWFKRNTLNKPVIMGRHTWESIGRPLPGRKNIILSSQPSTDDRVTWVKSVDEAIAACGDVPEIMVIGGGRVYEQFLPKAQKLYLTHIDAEVEGDTHFPDYEPDDWESVFSEFHDADAQNSHSYCFEILERR |
| 5 | ecDHFR destabilization domain (R12Y, G67S, Y100I) nucleic acid sequence | ATGATCAGTCTGATTGCGGCGTTAGCGGTAGATTACGTTATCGGCATGGAAAACGCCATGCCGTGGAACCTGCCTGCCGATCTCGCCTGGTTTAAACGCAACACCTTAAATAAACCCGTGATTATGGGCCGCCATACCTGGGAATCAATCGGTCGTCCGTTGCCAGGACGCAAAAATATTATCCTCAGCAGTCAACCGAGTACGGACGATCGCGTAACGTGGGTGAAGTCGGTGGATGAAGCCATCGCGGCGTGTGGTGACGTACCAGAAATCATGGTGATTGGCGGCGGTCGCGTTATTGAACAGTTCTTGCCAAAAGCGCAAAAACTGTATCTGACGCATATCGACGCAGAAGTGGAAGGCGACACCCATTTCCCGGATTACGAGCCGGATGACTGGGAATCGGTATTCAGCGAATTCCACGATGCTGATGCGCAGAACTCTCACAGCTATTGCTTTGAGATTCTGGAGCGGCGA |
| 6 | ecDHFR destabilization domain (R12Y, G67S, Y100I) Amino acid sequence | MISLIAALAVDYVIGMENAMPWNLPADLAWFKRNTLNKPVIMGRHTWESIGRPLPGRKNIILSSQPSTDDRVTWVKSVDEAIAACGDVPEIMVIGGGRVIEQFLPKAQKLYLTHIDAEVEGDTHFPDYEPDDWESVFSEFHDADAQNSHSYCFEILERR |
| 7 | CD19.28z.FKBP nucleic acid sequence | ATGCTGCTGCTCGTGACATCTCTGCTGCTGTGCGAGCTGCCCCACCCCGCCTTTCTGCTGATCCCCGATATCGACATCCAGATGACACAGACTACATCCTCCCTGTCTGCCTCTCTGGGAGACAGAGTCACCATCAGTTGCAGGGCAAGTCAGGACATTAGTAAATATTTAAATTGGTATCAGCAGAAACCAGATGGAACTGTTAAACTCCTGATCTACCATACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTACACGTTCGGAGGGGGGACTAAGTTGGAAATAACAGGCTCCACCTCTGGATCCGGCAAGCCCGGATCTGGCGAGGGATCCACCAAGGGCGAGGTGAAACTGCAGGAGTCAGGACCTGGCCTGGTGGCGCCCTCACAGAGCCTGTCCGTCACATGTACTGTCTCAGGGGTCTCATTACCCGACTATGGTGTAAGCTGGATTCGCCAGCCTCCACGAAAGGGTCTGGAGTGGCTG |

FIG. 25 (cont'd)

| | | |
|---|---|---|
| | | GGAGTAATATGGGGTAGTGAAACCACATACTATAATTCAGCT<br>CTCAAATCCAGACTGACCATCATCAAGGACAACTCCAAGAGC<br>CAAGTTTTCTTAAAAATGAACAGTCTGCAAACTGATGACACA<br>GCCATTTACTACTGTGCCAAACATTATTACTACGGTGGTAGCT<br>ATGCTATGGACTACTGGGGTCAAGGAACCTCAGTCACCGTCT<br>CCTCAGCTAGCTTCGAAATTGAAGTTATGTATCCTCCTCCTTA<br>CCTAGACAATGAGAAGAGCAATGGAACCATTATCCATGTGAA<br>AGGGAAACACCTTTGTCCAAGTCCCCTATTTCCCGGACCTTCT<br>AAGCCCTTTTGGGTGCTGGTGGTGGTTGGGGGAGTCCTGGCT<br>TGCTATAGCTTGCTAGTAACAGTGGCCTTTATTATTTTCTGGG<br>TGAGGAGTAAGAGGAGCAGGCTCCTGCACAGTGACTACATG<br>AACATGACTCCCCGCCGCCCCGGGCCCACCCGCAAGCATTAC<br>CAGCCCTATGCCCCACCACGCGACTTCGCAGCCTATCGCTCCC<br>ATATGAGAGTGAAGTTCAGCAGGAGCGCAGACGCCCCCGCGT<br>ACAAGCAGGGCCAGAACCAGCTCTATAACGAGCTCAATCTAG<br>GACGAAGAGAGGAGTACGATGTTTTGGACAAGAGACGTGGC<br>CGGGACCCTGAGATGGGGGGAAAGCCGAGAAGGAAGAACCC<br>TCAGGAAGGCCTGTACAATGAACTGCAGAAAGATAAGATGG<br>CGGAGGCCTACAGTGAGATTGGGATGAAAGGCGAGCGCCGG<br>AGGGGCAAGGGGCACGATGGCCTTTACCAGGGTCTCAGTACA<br>GCCACCAAGGACACCTACGACGCCCTTCACATGCAGGCCCTG<br>CCCCCTCGCGGAGTGCAGGTGGAAACCATCTCCCCAGGAGAC<br>GGGCGCACCTTCCCCAAGCGCGGCCAGACCTGCGTGGTGCAC<br>TACACCGGGATGCTTGGAGATGGAAAGAAAGTTGACTCCTCC<br>CGGGACAGAAACAAGCCCTTTAAGTTTATGCTAGGCAAGCAG<br>GAGGTGATCCGAGGCTGGGAAGAAGGGGTTGCCCAGATGAG<br>TGTGGGTCAGGGAGCCAAACTGACTATATCTCCAGATTATGC<br>CTATGGTGCCACTGGGCACCCAGGCATCATCCCACCACATGC<br>CACTCTCGTCTTCGATGTGGAGCTTCTAGAACTGGAATGA |
| 8 | CD19.28z.FKBP<br>Amino acid sequence | MLLLVTSLLLCELPHPAFLLIPDIDIQMTQTTSSLSASLGDRVTISC<br>RASQDISKYLNWYQQKPDGTVKLLIYHTSRLHSGVPSRFSGSGS<br>GTDYSLTISNLEQEDIATYFCQQGNTLPYTFGGGTKLEITGSTSGS<br>GKPGSGEGSTKGEVKLQESGPGLVAPSQSLSVTCTVSGVSLPDY<br>GVSWIRQPPRKGLEWLGVIWGSETTYYNSALKSRLTIIKDNSKS<br>QVFLKMNSLQTDDTAIYYCAKHYYYGGSYAMDYWGQGTSVT<br>VSSASFEIEVMYPPPYLDNEKSNGTIIHVKGKHLCPSPLFPGPSKP<br>FWVLVVVGGVLACYSLLVTVAFIIFWVRSKRSRLLHSDYMNMT<br>PRRPGPTRKHYQPYAPPRDFAAYRSHMRVKFSRSADAPAYKQG<br>QNQLYNELNLGRREEYDVLDKRRGRDPEMGGKPRRKNPQEGL<br>YNELQKDKMAEAYSEIGMKGERRRGKGHDGLYQGLSTATKDT<br>YDALHMQALPPRGVQVETISPGDGRTFPKRGQTCVVHYTGMLG<br>DGKKVDSSRDRNKPFKFMLGKQEVIRGWEEGVAQMSVGQGAK<br>LTISPDYAYGATGHPGIIPPHATLVFDVELLELE |
| 9 | CD19.28z.FKBP<br>Leader sequence<br>nucleic acid sequence | ATGCTGCTGCTCGTGACATCTCTGCTGCTGTGCGAGCTGCCCC<br>ACCCCGCCTTTCTGCTGATCCCC |
| 10 | CD19.28z.FKBP<br>Leader sequence<br>Amino acid sequence | MLLLVTSLLLCELPHPAFLLIP |
| 11 | FMC63 scFv (CD19<br>binding domain)<br>nucleic acid sequence | GACATCCAGATGACACAGACTACATCCTCCCTGTCTGCCTCTC<br>TGGGAGACAGAGTCACCATCAGTTGCAGGGCAAGTCAGGAC<br>ATTAGTAAATATTTAAATTGGTATCAGCAGAAACCAGATGGA<br>ACTGTTAAACTCCTGATCTACCATACATCAAGATTACACTCAG<br>GAGTCCCATCAAGGTTCAGTGGCAGTGGGTCTGGAACAGATT<br>ATTCTCTCACCATTAGCAACCTGGAGCAAGAAGATATTGCCA<br>CTTACTTTTGCCAACAGGGTAATACGCTTCCGTACACGTTCGG<br>AGGGGGGACTAAGTTGGAAATAACAGGCTCCACCTCTGGATC<br>CGGCAAGCCCGGATCTGGCGAGGGATCCACCAAGGGCGAGG<br>TGAAACTGCAGGAGTCAGGACCTGGCCTGGTGGCGCCCTCAC<br>AGAGCCTGTCCGTCACATGTACTGTCTCAGGGGTCTCATTACC |

FIG. 25 (cont'd)

| | | |
|---|---|---|
| | | CGACTATGGTGTAAGCTGGATTCGCCAGCCTCCACGAAAGGG TCTGGAGTGGCTGGGAGTAATATGGGGTAGTGAAACCACATA CTATAATTCAGCTCTCAAATCCAGACTGACCATCATCAAGGA CAACTCCAAGAGCCAAGTTTTCTTAAAAATGAACAGTCTGCA AACTGATGACACAGCCATTTACTACTGTGCCAAACATTATTA CTACGGTGGTAGCTATGCTATGGACTACTGGGGTCAAGGAAC CTCAGTCACCGTCTCCTCA |
| 12 | FMC63 scFv (CD19 binding domain) Amino acid sequence | DIQMTQTTSSLSASLGDRVTISCRASQDISKYLNWYQQKPDGTV KLLIYHTSRLHSGVPSRFSGSGSGTDYSLTISNLEQEDIATYFCQQ GNTLPYTFGGGTKLEITGSTSGSGKPGSGEGSTKGEVKLQESGPG LVAPSQSLSVTCTVSGVSLPDYGVSWIRQPPRKGLEWLGVIWGS ETTYYNSALKSRLTIIKDNSKSQVFLKMNSLQTDDTAIYYCAKH YYYGGSYAMDYWGQGTSVTVSS |
| 13 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 14 | CD28 hinge region Amino acid sequence | IEVMYPPPYLDNEKSNGTIIHVKGKHLCPSPLFPGPSKP |
| 15 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 16 | Amino acid sequence | FWVLVVVGGVLACYSLLVTVAFIIFWV |
| 17 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 18 | CD28 transmembrane region Amino acid sequence | RSKRSRLLHSDYMNMTPRRPGPTRKHYQPYAPPRDFAAYRS |
| 19 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 20 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 21 | FKBP12 destabilization domain (E31G, F36V, R71G, K105E) nucleic acid sequence | GGAGTGCAGGTGGAAACCATCTCCCCAGGAGACGGGCGCAC CTTCCCCAAGCGCGGCCAGACCTGCGTGGTGCACTACACCGG GATGCTTGGAGATGGAAAGAAAGTTGACTCCTCCCGGGACAG AAACAAGCCCTTTAAGTTTATGCTAGGCAAGCAGGAGGTGAT CCGAGGCTGGGAAGAAGGGGTTGCCCAGATGAGTGTGGGTC AGGGAGCCAAACTGACTATATCTCCAGATTATGCCTATGGTG CCACTGGGCACCCAGGCATCATCCCACCACATGCCACTCTCG TCTTCGATGTGGAGCTTCTAGAACTGGAA |
| 22 | FKBP12 destabilization domain (E31G, F36V, R71G, K105E) Amino acid sequence | GVQVETISPGDGRTFPKRGQTCVVHYTGMLGDGKKVDSSRDRN KPFKFMLGKQEVIRGWEEGVAQMSVGQGAKLTISPDYAYGATG HPGIIPPHATLVFDVELLELE |
| 23 | CD19.28z.ecDHFR nucleic acid sequence | ATGCTGCTGCTCGTGACATCTCTGCTGCTGTGCGAGCTGCCCC ACCCCGCCTTTCTGCTGATCCCCGATATCGACATCCAGATGAC ACAGACTACATCCTCCCTGTCTGCCTCTCTGGGAGACAGAGT CACCATCAGTTGCAGGGCAAGTCAGGACATTAGTAAATATTT AAATTGGTATCAGCAGAAACCAGATGGAACTGTTAAACTCCT GATCTACCATACATCAAGATTACACTCAGGAGTCCCATCAAG |

FIG. 25 (cont'd)

| | | |
|---|---|---|
| | | GTTCAGTGGCAGTGGGTCTGGAACAGATTATTCTCTCACCATT<br>AGCAACCTGGAGCAAGAAGATATTGCCACTTACTTTTGCCAA<br>CAGGGTAATACGCTTCCGTACACGTTCGGAGGGGGGACTAAG<br>TTGGAAATAACAGGCTCCACCTCTGGATCCGGCAAGCCCGGA<br>TCTGGCGAGGGATCCACCAAGGGCGAGGTGAAACTGCAGGA<br>GTCAGGACCTGGCCTGGTGGCGCCCTCACAGAGCCTGTCCGT<br>CACATGTACTGTCTCAGGGGTCTCATTACCCGACTATGGTGTA<br>AGCTGGATTCGCCAGCCTCCACGAAAGGGTCTGGAGTGGCTG<br>GGAGTAATATGGGGTAGTGAAACCACATACTATAATTCAGCT<br>CTCAAATCCAGACTGACCATCATCAAGGACAACTCCAAGAGC<br>CAAGTTTTCTTAAAAATGAACAGTCTGCAAACTGATGACACA<br>GCCATTTACTACTGTGCCAAACATTATTACTACGGTGGTAGCT<br>ATGCTATGGACTACTGGGGTCAAGGAACCTCAGTCACCGTCT<br>CCTCAGCTAGCTTCGAAATTGAAGTTATGTATCCTCCTCCTTA<br>CCTAGACAATGAGAAGAGCAATGGAACCATTATCCATGTGAA<br>AGGGAAACACCTTTGTCCAAGTCCCCTATTTCCCGGACCTTCT<br>AAGCCCTTTTGGGTGCTGGTGGTGGTTGGGGGAGTCCTGGCT<br>TGCTATAGCTTGCTAGTAACAGTGGCCTTTATTATTTTCTGGG<br>TGAGGAGTAAGAGGAGCAGGCTCCTGCACAGTGACTACATG<br>AACATGACTCCCCGCCGCCCCGGGCCCACCCGCAAGCATTAC<br>CAGCCCTATGCCCCACCACGCGACTTCGCAGCCTATCGCTCCC<br>ATATGAGAGTGAAGTTCAGCAGGAGCGCAGACGCCCCCGCGT<br>ACAAGCAGGGCCAGAACCAGCTCTATAACGAGCTCAATCTAG<br>GACGAAGAGAGGAGTACGATGTTTTGGACAAGAGACGTGGC<br>CGGGACCCTGAGATGGGGGGAAAGCCGAGAAGGAAGAACCC<br>TCAGGAAGGCCTGTACAATGAACTGCAGAAAGATAAGATGG<br>CGGAGGCCTACAGTGAGATTGGGATGAAAGGCGAGCGCCGG<br>AGGGGCAAGGGGCACGATGGCCTTTACCAGGGTCTCAGTACA<br>GCCACCAAGGACACCTACGACGCCCTTCACATGCAGGCCCTG<br>CCCCCTCGCATCAGTCTGATTGCGGCGTTAGCGGTAGATTAC<br>GTTATCGGCATGGAAAACGCCATGCCGTGGAACCTGCCTGCC<br>GATCTCGCCTGGTTTAAACGCAACACCTTAAATAAACCCGTG<br>ATTATGGGCCGCCATACCTGGGAATCAATCGGTCGTCCGTTG<br>CCAGGACGCAAAAATATTATCCTCAGCAGTCAACCGAGTACG<br>GACGATCGCGTAACGTGGGTGAAGTCGGTGGATGAAGCCATC<br>GCGGCGTGTGGTGACGTACCAGAAATCATGGTGATTGGCGGC<br>GGTCGCGTTATTGAACAGTTCTTGCCAAAAGCGCAAAAACTG<br>TATCTGACGCATATCGACGCAGAAGTGGAAGGCGACACCCAT<br>TTCCCGGATTACGAGCCGGATGACTGGGAATCGGTATTCAGC<br>GAATTCCACGATGCTGATGCGCAGAACTCTCACAGCTATTGC<br>TTTGAGATTCTGGAGCGGCGATGA |
| 24 | CD19.28z.ecDHFR<br>Amino acid sequence | MLLLVTSLLLCELPHPAFLLIPDIDIQMTQTTSSLSASLGDRVTISC<br>RASQDISKYLNWYQQKPDGTVKLLIYHTSRLHSGVPSRFSGSGS<br>GTDYSLTISNLEQEDIATYFCQQGNTLPYTFGGGTKLEITGSTSGS<br>GKPGSGEGSTKGEVKLQESGPGLVAPSQSLSVTCTVSGVSLPDY<br>GVSWIRQPPRKGLEWLGVIWGSETTYYNSALKSRLTIIKDNSKS<br>QVFLKMNSLQTDDTAIYYCAKHYYYGGSYAMDYWGQGTSVT<br>VSSASFEIEVMYPPPYLDNEKSNGTIIHVKGKHLCPSPLFPGPSKP<br>FWVLVVVGGVLACYSLLVTVAFIIFWVRSKRSRLLHSDYMNMT<br>PRRPGPTRKHYQPYAPPRDFAAYRSHMRVKFSRSADAPAYKQG<br>QNQLYNELNLGRREEYDVLDKRRGRDPEMGGKPRRKNPQEGL<br>YNELQKDKMAEAYSEIGMKGERRRGKGHDGLYQGLSTATKDT<br>YDALHMQALPPRISLIAALAVDYVIGMENAMPWNLPADLAWFK<br>RNTLNKPVIMGRHTWESIGRPLPGRKNIILSSQPSTDDRVTWVKS<br>VDEAIAACGDVPEIMVIGGGRVIEQFLPKAQKLYLTHIDAEVEG<br>DTHFPDYEPDDWESVFSEFHDADAQNSHSYCFEILERR |
| 25 | CD19.28z.ecDHFR<br>nucleic acid sequence | ATGCTGCTGCTCGTGACATCTCTGCTGCTGTGCGAGCTGCCCC<br>ACCCCGCCTTTCTGCTGATCCCC |
| 26 | CD19.28z.ecDHFR<br>Amino acid sequence | MLLLVTSLLLCELPHPAFLLIP |

FIG. 25 (cont'd)

| | | |
|---|---|---|
| 27 | FMC63 scFv (CD19 binding domain) nucleic acid sequence | GACATCCAGATGACACAGACTACATCCTCCCTGTCTGCCTCTCTGGGAGACAGAGTCACCATCAGTTGCAGGGCAAGTCAGGACATTAGTAAATATTTAAATTGGTATCAGCAGAAACCAGATGGAACTGTTAAACTCCTGATCTACCATACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTACACGTTCGGAGGGGGGACTAAGTTGGAAATAACAGGCTCCACCTCTGGATCCGGCAAGCCCGGATCTGGCGAGGGATCCACCAAGGGCGAGGTGAAACTGCAGGAGTCAGGACCTGGCCTGGTGGCGCCCTCACAGAGCCTGTCCGTCACATGTACTGTCTCAGGGGTCTCATTACCCGACTATGGTGTAAGCTGGATTCGCCAGCCTCCACGAAAGGGTCTGGAGTGGCTGGGAGTAATATGGGGTAGTGAAACCACATACTATAATTCAGCTCTCAAATCCAGACTGACCATCATCAAGGACAACTCCAAGAGCCAAGTTTTCTTAAAAATGAACAGTCTGCAAACTGATGACACAGCCATTTACTACTGTGCCAAACATTATTACTACGGTGGTAGCTATGCTATGGACTACTGGGGTCAAGGAACCTCAGTCACCGTCTCCTCA |
| 28 | FMC63 scFv (CD19 binding domain) Amino acid sequence | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 29 | CD28 hinge region nucleic acid sequence | ATTGAAGTTATGTATCCTCCTCCTTACCTAGACAATGAGAAGAGCAATGGAACCATTATCCATGTGAAAGGGAAACACCTTTGTCCAAGTCCCCTATTTCCCGGACCTTCTAAGCCC |
| 30 | CD28 hinge region Amino acid sequence | IEVMYPPPYLDNEKSNGTIIHVKGKHLCPSPLFPGPSKP |
| 31 | CD28 transmembrane region nucleic acid sequence | TTTTGGGTGCTGGTGGTGGTTGGGGGAGTCCTGGCTTGCTATAGCTTGCTAGTAACAGTGGCCTTTATTATTTTCTGGGTG |
| 32 | CD28 transmembrane region Amino acid sequence | FWVLVVVGGVLACYSLLVTVAFIIFWV |
| 33 | CD28 intracellular domain nucleic acid sequence | AGGAGTAAGAGGAGCAGGCTCCTGCACAGTGACTACATGAACATGACTCCCCGCCGCCCCGGGCCCACCCGCAAGCATTACCAGCCCTATGCCCCACCACGCGACTTCGCAGCCTATCGCTCC |
| 34 | CD28 intracellular domain Amino acid sequence | RSKRSRLLHSDYMNMTPRRPGPTRKHYQPYAPPRDFAAYRS |
| 35 | CD3 zeta intracellular domain nucleic acid sequence | AGAGTGAAGTTCAGCAGGAGCGCAGACGCCCCCGCGTACAAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAGGCCCTGCCCCCTCGC |
| 36 | CD3 zeta intracellular domain Amino acid sequence | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 37 | ecDHFR destabilization domain (R12Y, G67S, Y100I) nucleic acid sequence | ATCAGTCTGATTGCGGCGTTAGCGGTAGATTACGTTATCGGCATGGAAAACGCCATGCCGTGGAACCTGCCTGCCGATCTCGCCTGGTTTAAACGCAACACCTTAAATAAACCCGTGATTATGGGCCGCCATACCTGGGAATCAATCGGTCGTCCGTTGCCAGGACGCAAAAATATTATCCTCAGCAGTCAACCGAGTACGGACGATCGCGTAACGTGGGTGAAGTCGGTGGATGAAGCCATCGCGGCGTGT |

FIG. 25 (cont'd)

| | | |
|---|---|---|
| | | GGTGACGTACCAGAAATCATGGTGATTGGCGGCGGTCGCGTT ATTGAACAGTTCTTGCCAAAAGCGCAAAAACTGTATCTGACG CATATCGACGCAGAAGTGGAAGGCGACACCCATTTCCCGGAT TACGAGCCGGATGACTGGGAATCGGTATTCAGCGAATTCCAC GATGCTGATGCGCAGAACTCTCACAGCTATTGCTTTGAGATTC TGGAGCGGCGA |
| 38 | ecDHFR destabilization domain (R12Y, G67S, Y100I) Amino acid sequence | ISLIAALAVDYVIGMENAMPWNLPADLAWFKRNTLNKPVIMGR HTWESIGRPLPGRKNIILSSQPSTDDRVTWVKSVDEAIAACGDVP EIMVIGGGRVIEQFLPKAQKLYLTHIDAEVEGDTHFPDYEPDDW ESVFSEFHDADAQNSHSYCFEILERR |
| 39 | GD2.28z.FKBP nucleic acid sequence | ATGCTGCTGCTCGTGACATCTCTGCTGCTGTGCGAGCTGCCCC ACCCCGCCTTTCTGCTGATCCCCGATATCCTGCTGACCCAGAC CCCTCTGAGCCTGCCTGTGTCTCTGGGCGATCAGGCCAGCATC AGCTGCAGATCCAGCCAGAGCCTGGTGCACCGGAACGGCAA CACCTACCTGCACTGGTATCTGCAGAAGCCCGGCCAGAGCCC CAAGCTGCTGATTCACAAGGTGTCCAACCGGTTCAGCGGCGT GCCCGACAGATTTTCTGGCAGCGGCTCCGGCACCGACTTCAC CCTGAAGATCAGCCGGGTGGAAGCCGAGGACCTGGGCGTGT ACTTCTGCAGCCAGTCCACCCACGTGCCCCCCCTGACATTTGG CGCCGGAACAAAGCTGGAACTGAAGGGCAGCACAAGCGGCA GCGGCAAGCCTGGATCTGGCGAGGGAAGCACCAAGGGCGAA GTGAAGCTGCAGCAGAGCGGCCCCTCTCTGGTGGAACCTGGC GCCTCTGTGATGATCTCCTGCAAGGCCAGCGGCAGCTCCTTC ACCGGCTACAACATGAACTGGGTGCGCCAGAACATCGGCAA GAGCCTGGAATGGATCGGCGCCATCGACCCCTACTACGGCGG CACCAGCTACAACCAGAAGTTCAAGGGCAGAGCCACCCTGAC CGTGGACAAGAGCAGCTCCACCGCCTACATGCACCTGAAGTC CCTGACCAGCGAGGACAGCGCCGTGTACTACTGCGTGTCCGG CATGGAATACTGGGGCCAGGGCACAAGCGTGACCGTGTCCTC TGCTAGCTTCGAAATTGAAGTTATGTATCCTCCTCCTTACCTA GACAATGAGAAGAGCAATGGAACCATTATCCATGTGAAAGG GAAACACCTTTGTCCAAGTCCCCTATTTCCCGGACCTTCTAAG CCCTTTTGGGTGCTGGTGGTGGTTGGGGGAGTCCTGGCTTGCT ATAGCTTGCTAGTAACAGTGGCCTTTATTATTTTCTGGGTGAG GAGTAAGAGGAGCAGGCTCCTGCACAGTGACTACATGAACAT GACTCCCCGCCGCCCCGGGCCCACCCGCAAGCATTACCAGCC CTATGCCCCACCACGCGACTTCGCAGCCTATCGCTCCAGAGT GAAGTTCAGCAGGAGCGCAGACGCCCCCGCGTACAAGCAGG GCCAGAACCAGCTCTATAACGAGCTCAATCTAGGACGAAGAG AGGAGTACGATGTTTTGGACAAGAGACGTGGCCGGGACCCTG AGATGGGGGGAAAGCCGAGAAGGAAGAACCCTCAGGAAGGC CTGTACAATGAACTGCAGAAAGATAAGATGGCGGAGGCCTA CAGTGAGATTGGGATGAAAGGCGAGCGCCGGAGGGGCAAGG GGCACGATGGCCTTTACCAGGGTCTCAGTACAGCCACCAAGG ACACCTACGACGCCCTTCACATGCAGGCCCTGCCCCCTCGCG GAGTGCAGGTGGAAACCATCTCCCCAGGAGACGGGCGCACCT TCCCCAAGCGCGGCCAGACCTGCGTGGTGCACTACACCGGGA TGCTTGGAGATGGAAAGAAAGTTGACTCCTCCCGGGACAGAA ACAAGCCCTTTAAGTTTATGCTAGGCAAGCAGGAGGTGATCC GAGGCTGGGAAGAAGGGGTTGCCCAGATGAGTGTGGGTCAG GGAGCCAAACTGACTATATCTCCAGATTATGCCTATGGTGCC ACTGGGCACCCAGGCATCATCCCACCACATGCCACTCTCGTC TTCGATGTGGAGCTTCTAGAACTGGAATGA |
| 40 | GD2.28z.FKBP Amino acid sequence | MLLLVTSLLLCELPHPAFLLIPDILLTQTPLSLPVSLGDQASISCRS SQSLVHRNGNTYLHWYLQKPGQSPKLLIHKVSNRFSGVPDRFSG SGSGTDFTLKISRVEAEDLGVYFCSQSTHVPPLTFGAGTKLELKG STSGSGKPGSGEGSTKGEVKLQQSGPSLVEPGASVMISCKASGSS FTGYNMNWVRQNIGKSLEWIGAIDPYYGGTSYNQKFKGRATLT VDKSSSTAYMHLKSLTSEDSAVYYCVSGMEYWGQGTSVTVSSA SFEIEVMYPPPYLDNEKSNGTIIHVKGKHLCPSPLFPGPSKPFWVL |

FIG. 25 (cont'd)

| | | |
|---|---|---|
| | | VVVGGVLACYSLLVTVAFIIFWVRSKRSRLLHSDYMNMTPRRP GPTRKHYQPYAPPRDFAAYRSRVKFSRSADAPAYKQGQNQLYN ELNLGRREEYDVLDKRRGRDPEMGGKPRRKNPQEGLYNELQK DKMAEAYSEIGMKGERRRGKGHDGLYQGLSTATKDTYDALHM QALPPRGVQVETISPGDGRTFPKRGQTCVVHYTGMLGDGKKVD SSRDRNKPFKFMLGKQEVIRGWEEGVAQMSVGQGAKLTISPDY AYGATGHPGIIPPHATLVFDVELLELE |
| 41 | GD2.28z.FKBP Leader sequence nucleic acid sequence | ATGCTGCTGCTCGTGACATCTCTGCTGCTGTGCGAGCTGCCCC ACCCCGCCTTTCTGCTGATCCCC |
| 42 | GD2.28z.FKBP Leader sequence Amino acid sequence | MLLLVTSLLLCELPHPAFLLIP |
| 43 | 14G2a scFv (GD2 binding domain) nucleic acid sequence | GATATCCTGCTGACCCAGACCCCTCTGAGCCTGCCTGTGTCTC TGGGCGATCAGGCCAGCATCAGCTGCAGATCCAGCCAGAGCC TGGTGCACCGGAACGGCAACACCTACCTGCACTGGTATCTGC AGAAGCCCGGCCAGAGCCCCAAGCTGCTGATTCACAAGGTGT CCAACCGGTTCAGCGGCGTGCCCGACAGATTTTCTGGCAGCG GCTCCGGCACCGACTTCACCCTGAAGATCAGCCGGGTGGAAG CCGAGGACCTGGGCGTGTACTTCTGCAGCCAGTCCACCCACG TGCCCCCCCTGACATTTGGCGCCGGAACAAAGCTGGAACTGA AGGGCAGCACAAGCGGCAGCGGCAAGCCTGGATCTGGCGAG GGAAGCACCAAGGGCGAAGTGAAGCTGCAGCAGAGCGGCCC CTCTCTGGTGGAACCTGGCGCCTCTGTGATGATCTCCTGCAAG GCCAGCGGCAGCTCCTTCACCGGCTACAACATGAACTGGGTG CGCCAGAACATCGGCAAGAGCCTGGAATGGATCGGCGCCATC GACCCCTACTACGGCGGCACCAGCTACAACCAGAAGTTCAAG GGCAGAGCCACCCTGACCGTGGACAAGAGCAGCTCCACCGCC TACATGCACCTGAAGTCCCTGACCAGCGAGGACAGCGCCGTG TACTACTGCGTGTCCGGCATGGAATACTGGGGCCAGGGCACA AGCGTGACCGTGTCCTCT |
| 44 | 14G2a scFv (GD2 binding domain) Amino acid sequence | DILLTQTPLSLPVSLGDQASISCRSSQSLVHRNGNTYLHWYLQKP GQSPKLLIHKVSNRFSGVPDRFSGSGSGTDFTLKISRVEAEDLGV YFCSQSTHVPPLTFGAGTKLELKGSTSGSGKPGSGEGSTKGEVK LQQSGPSLVEPGASVMISCKASGSSFTGYNMNWVRQNIGKSLE WIGAIDPYYGGTSYNQKFKGRATLTVDKSSSTAYMHLKSLTSED SAVYYCVSGMEYWGQGTSVTVSS |
| 45 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 46 | CD28 hinge region Amino acid sequence | IEVMYPPPYLDNEKSNGTIIHVKGKHLCPSPLFPGPSKP |
| 47 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 48 | CD28 transmembrane region Amino acid sequence | FWVLVVVGGVLACYSLLVTVAFIIFWV |
| 49 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 50 | CD28 intracellular domain Amino acid sequence | RSKRSRLLHSDYMNMTPRRPGPTRKHYQPYAPPRDFAAYRS |
| 51 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG |

FIG. 25 (cont'd)

| | | |
|---|---|---|
| | | GCAAGGGGCACGATGGCCTTTACCAGGGTCTCAGTACAGCCA CCAAGGACACCTACGACGCCCTTCACATGCAGGCCCTGCCCC CTCGC |
| 52 | CD3 zeta intracellular domain<br>Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 53 | FKBP12 destabilization domain (E31G, F36V, R71G, K105E)<br>nucleic acid sequence | GGAGTGCAGGTGGAAACCATCTCCCCAGGAGACGGGCGCAC CTTCCCCAAGCGCGGCCAGACCTGCGTGGTGCACTACACCGG GATGCTTGGAGATGGAAAGAAAGTTGACTCCTCCCGGGACAG AAACAAGCCCTTTAAGTTTATGCTAGGCAAGCAGGAGGTGAT CCGAGGCTGGGAAGAAGGGGTTGCCCAGATGAGTGTGGGTC AGGGAGCCAAACTGACTATATCTCCAGATTATGCCTATGGTG CCACTGGGCACCCAGGCATCATCCCACCACATGCCACTCTCG TCTTCGATGTGGAGCTTCTAGAACTGGAA |
| 54 | FKBP12 destabilization domain (E31G, F36V, R71G, K105E)<br>Amino acid sequence | GVQVETISPGDGRTFPKRGQTCVVHYTGMLGDGKKVDSSRDRN KPFKFMLGKQEVIRGWEEGVAQMSVGQGAKLTISPDYAYGATG HPGIIPPHATLVFDVELLELE |
| 55 | GD2.28z.ecDHFR (R12Y, G67S, Y100I)<br>nucleic acid sequence | ATGCTGCTGCTCGTGACATCTCTGCTGCTGTGCGAGCTGCCCC ACCCCGCCTTTCTGCTGATCCCCGATATCCTGCTGACCCAGAC CCCTCTGAGCCTGCCTGTGTCTCTGGGCGATCAGGCCAGCATC AGCTGCAGATCCAGCCAGAGCCTGGTGCACCGGAACGGCAA CACCTACCTGCACTGGTATCTGCAGAAGCCCGGCCAGAGCCC CAAGCTGCTGATTCACAAGGTGTCCAACCGGTTCAGCGGCGT GCCCGACAGATTTTCTGGCAGCGGCTCCGGCACCGACTTCAC CCTGAAGATCAGCCGGGTGGAAGCCGAGGACCTGGGCGTGT ACTTCTGCAGCCAGTCCACCCACGTGCCCCCCCTGACATTTGG CGCCGGAACAAAGCTGGAACTGAAGGGCAGCACAAGCGGCA GCGGCAAGCCTGGATCTGGCGAGGGAAGCACCAAGGGCGAA GTGAAGCTGCAGCAGAGCGGCCCCTCTCTGGTGGAACCTGGC GCCTCTGTGATGATCTCCTGCAAGGCCAGCGGCAGCTCCTTC ACCGGCTACAACATGAACTGGGTGCGCCAGAACATCGGCAA GAGCCTGGAATGGATCGGCGCCATCGACCCCTACTACGGCGG CACCAGCTACAACCAGAAGTTCAAGGGCAGAGCCACCCTGAC CGTGGACAAGAGCAGCTCCACCGCCTACATGCACCTGAAGTC CCTGACCAGCGAGGACAGCGCCGTGTACTACTGCGTGTCCGG CATGGAATACTGGGGCCAGGGCACAAGCGTGACCGTGTCCTC TGCTAGCTTCGAAATTGAAGTTATGTATCCTCCTCCTTACCTA GACAATGAGAAGAGCAATGGAACCATTATCCATGTGAAAGG GAAACACCTTTGTCCAAGTCCCCTATTTCCCGGACCTTCTAAG CCCTTTTGGGTGCTGGTGGTGGTTGGGGGAGTCCTGGCTTGCT ATAGCTTGCTAGTAACAGTGGCCTTTATTATTTTCTGGGTGAG GAGTAAGAGGAGCAGGCTCCTGCACAGTGACTACATGAACAT GACTCCCCGCCGCCCGGGCCCACCCGCAAGCATTACCAGCC CTATGCCCCACCACGCGACTTCGCAGCCTATCGCTCCAGAGT GAAGTTCAGCAGGAGCGCAGACGCCCCCGCGTACAAGCAGG GCCAGAACCAGCTCTATAACGAGCTCAATCTAGGACGAAGAG AGGAGTACGATGTTTTGGACAAGAGACGTGGCCGGGACCCTG AGATGGGGGGAAAGCCGAGAAGGAAGAACCCTCAGGAAGGC CTGTACAATGAACTGCAGAAAGATAAGATGGCGGAGGCCTA CAGTGAGATTGGGATGAAAGGCGAGCGCCGGAGGGGCAAGG GGCACGATGGCCTTTACCAGGGTCTCAGTACAGCCACCAAGG ACACCTACGACGCCCTTCACATGCAGGCCCTGCCCCCTCGCA TCAGTCTGATTGCGGCGTTAGCGGTAGATTACGTTATCGGCAT GGAAAACGCCATGCCGTGGAACCTGCCTGCCGATCTCGCCTG GTTTAAACGCAACACCTTAAATAAACCCGTGATTATGGGCCG CCATACCTGGGAATCAATCGGTCGTCCGTTGCCAGGACGCAA AAATATTATCCTCAGCAGTCAACCGAGTACGGACGATCGCGT AACGTGGGTGAAGTCGGTGGATGAAGCCATCGCGGCGTGTGG TGACGTACCAGAAATCATGGTGATTGGCGGCGGTCGCGTTAT |

FIG. 25 (cont'd)

| | | |
|---|---|---|
| | | TGAACAGTTCTTGCCAAAAGCGCAAAAACTGTATCTGACGCATATCGACGCAGAAGTGGAAGGCGACACCCATTTCCCGGATTACGAGCCGGATGACTGGGAATCGGTATTCAGCGAATTCCACGATGCTGATGCGCAGAACTCTCACAGCTATTGCTTTGAGATTCTGGAGCGGCGATGA |
| 56 | GD2.28z.ecDHFR (R12Y, G67S, Y100I) Amino acid sequence | MLLLVTSLLLCELPHPAFLLIPDILLTQTPLSLPVSLGDQASISCRSSQSLVHRNGNTYLHWYLQKPGQSPKLLIHKVSNRFSGVPDRFSGSGSGTDFTLKISRVEAEDLGVYFCSQSTHVPPLTFGAGTKLELKGSTSGSGKPGSGEGSTKGEVKLQQSGPSLVEPGASVMISCKASGSSFTGYNMNWVRQNIGKSLEWIGAIDPYYGGTSYNQKFKGRATLTVDKSSSTAYMHLKSLTSEDSAVYYCVSGMEYWGQGTSVTVSSASFEIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRISLIAALAVDYVIGMENAMPWNLPADLAWFKRNTLNKPVIMGRHTWESIGRPLPGRKNIILSSQPSTDDRVTWVKSVDEAIAACGDVPEIMVIGGGRVIEQFLPKAQKLYLTHIDAEVEGDTHFPDYEPDDWESVFSEFHDADAQNSHSYCFEILERR |
| 57 | GD2.28z.ecDHFR (R12Y, G67S, Y100I) Leader sequence nucleic acid sequence | ATGCTGCTGCTCGTGACATCTCTGCTGCTGTGCGAGCTGCCCCACCCCGCCTTTCTGCTGATCCCC |
| 58 | GD2.28z.ecDHFR (R12Y, G67S, Y100I) Leader sequence Amino acid sequence | MLLLVTSLLLCELPHPAFLLIP |
| 59 | 14G2a scFv (GD2 binding domain) nucleic acid sequence | GATATCCTGCTGACCCAGACCCCTCTGAGCCTGCCTGTGTCTCTGGGCGATCAGGCCAGCATCAGCTGCAGATCCAGCCAGAGCCTGGTGCACCGGAACGGCAACACCTACCTGCACTGGTATCTGCAGAAGCCCGGCCAGAGCCCCAAGCTGCTGATTCACAAGGTGTCCAACCGGTTCAGCGGCGTGCCCGACAGATTTTCTGGCAGCGGCTCCGGCACCGACTTCACCCTGAAGATCAGCCGGGTGGAAGCCGAGGACCTGGGCGTGTACTTCTGCAGCCAGTCCACCCACGTGCCCCCCCTGACATTTGGCGCCGGAACAAAGCTGGAACTGAAGGGCAGCACAAGCGGCAGCGGCAAGCCTGGATCTGGCGAGGGAAGCACCAAGGGCGAAGTGAAGCTGCAGCAGAGCGGCCCCTCTCTGGTGGAACCTGGCGCCTCTGTGATGATCTCCTGCAAGGCCAGCGGCAGCTCCTTCACCGGCTACAACATGAACTGGGTGCGCCAGAACATCGGCAAGAGCCTGGAATGGATCGGCGCCATCGACCCCTACTACGGCGGCACCAGCTACAACCAGAAGTTCAAGGGCAGAGCCACCCTGACCGTGGACAAGAGCAGCTCCACCGCCTACATGCACCTGAAGTCCCTGACCAGCGAGGACAGCGCCGTGTACTACTGCGTGTCCGGCATGGAATACTGGGGCCAGGGCACAAGCGTGACCGTGTCCTCT |
| 60 | 14G2a scFv (GD2 binding domain) Amino acid sequence | DILLTQTPLSLPVSLGDQASISCRSSQSLVHRNGNTYLHWYLQKPGQSPKLLIHKVSNRFSGVPDRFSGSGSGTDFTLKISRVEAEDLGVYFCSQSTHVPPLTFGAGTKLELKGSTSGSGKPGSGEGSTKGEVKLQQSGPSLVEPGASVMISCKASGSSFTGYNMNWVRQNIGKSLEWIGAIDPYYGGTSYNQKFKGRATLTVDKSSSTAYMHLKSLTSEDSAVYYCVSGMEYWGQGTSVTVSS |
| 61 | CD28 hinge region nucleic acid sequence | ATTGAAGTTATGTATCCTCCTCCTTACCTAGACAATGAGAAGAGCAATGGAACCATTATCCATGTGAAAGGGAAACACCTTTGTCCAAGTCCCCTATTTCCCGGACCTTCTAAGCCC |
| 62 | CD28 hinge region Amino acid sequence | IEVMYPPPYLDNEKSNGTIIHVKGKHLCPSPLFPGPSKP |
| 63 | CD28 transmembrane region nucleic acid sequence | TTTTGGGTGCTGGTGGTGGTTGGGGGAGTCCTGGCTTGCTATAGCTTGCTAGTAACAGTGGCCTTTATTATTTTCTGGGTG |

FIG. 25 (cont'd)

| 64 | CD28 transmembrane region Amino acid sequence | FWVLVVVGGVLACYSLLVTVAFIIFWV |
|---|---|---|
| 65 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 66 | CD28 intracellular domain Amino acid sequence | RSKRSRLLHSDYMNMTPRRPGPTRKHYQPYAPPRDFAAYRS |
| 67 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 68 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 69 | ecDHFR destabilization domain (R12Y, G67S, Y100I) nucleic acid sequence | ATCAGTCTGATTGCGGCGTTAGCGGTAGATTACGTTATCGGC ATGGAAAACGCCATGCCGTGGAACCTGCCTGCCGATCTCGCC TGGTTTAAACGCAACACCTTAAATAAACCCGTGATTATGGGC CGCCATACCTGGGAATCAATCGGTCGTCCGTTGCCAGGACGC AAAAATATTATCCTCAGCAGTCAACCGAGTACGGACGATCGC GTAACGTGGGTGAAGTCGGTGGATGAAGCCATCGCGGCGTGT GGTGACGTACCAGAAATCATGGTGATTGGCGGCGGTCGCGTT ATTGAACAGTTCTTGCCAAAAGCGCAAAAACTGTATCTGACG CATATCGACGCAGAAGTGGAAGGCGACACCCATTTCCCGGAT TACGAGCCGGATGACTGGGAATCGGTATTCAGCGAATTCCAC GATGCTGATGCGCAGAACTCTCACAGCTATTGCTTTGAGATTC TGGAGCGGCGA |
| 70 | ecDHFR destabilization domain (R12Y, G67S, Y100I) Amino acid sequence | ISLIAALAVDYVIGMENAMPWNLPADLAWFKRNTLNKPVIMGR HTWESIGRPLPGRKNIILSSQPSTDDRVTWVKSVDEAIAACGDVP EIMVIGGGRVIEQFLPKAQKLYLTHIDAEVEGDTHFPDYEPDDW ESVFSEFHDADAQNSHSYCFEILERR |
| 71 | GD2.28z.ecDHFR (R12H, N18T, V19A, G67S) nucleic acid sequence | ATGCTGCTGCTCGTGACATCTCTGCTGCTGTGCGAGCTGCCCC ACCCCGCCTTTCTGCTGATCCCCGATATCCTGCTGACCCAGAC CCCTCTGAGCCTGCCTGTGTCTCTGGGCGATCAGGCCAGCATC AGCTGCAGATCCAGCCAGAGCCTGGTGCACCGGAACGGCAA CACCTACCTGCACTGGTATCTGCAGAAGCCCGGCCAGAGCCC CAAGCTGCTGATTCACAAGGTGTCCAACCGGTTCAGCGGCGT GCCCGACAGATTTTCTGGCAGCGGCTCCGGCACCGACTTCAC CCTGAAGATCAGCCGGGTGGAAGCCGAGGACCTGGGCGTGT ACTTCTGCAGCCAGTCCACCCACGTGCCCCCCCTGACATTTGG CGCCGGAACAAAGCTGGAACTGAAGGGCAGCACAAGCGGCA GCGGCAAGCCTGGATCTGGCGAGGGAAGCACCAAGGGCGAA GTGAAGCTGCAGCAGAGCGGCCCCTCTCTGGTGGAACCTGGC GCCTCTGTGATGATCTCCTGCAAGGCCAGCGGCAGCTCCTTC ACCGGCTACAACATGAACTGGGTGCGCCAGAACATCGGCAA GAGCCTGGAATGGATCGGCGCCATCGACCCCTACTACGGCGG CACCAGCTACAACCAGAAGTTCAAGGGCAGAGCCACCCTGAC CGTGGACAAGAGCAGCTCCACCGCCTACATGCACCTGAAGTC CCTGACCAGCGAGGACAGCGCCGTGTACTACTGCGTGTCCGG CATGGAATACTGGGGCCAGGGCACAAGCGTGACCGTGTCCTC TGCTAGCTTCGAAATTGAAGTTATGTATCCTCCTCCTTACCTA GACAATGAGAAGAGCAATGGAACCATTATCCATGTGAAAGG GAAACACCTTTGTCCAAGTCCCCTATTTCCCGGACCTTCTAAG |

FIG. 25 (cont'd)

| | | |
|---|---|---|
| | | CCCTTTTGGGTGCTGGTGGTGGTTGGGGGAGTCCTGGCTTGCT<br>ATAGCTTGCTAGTAACAGTGGCCTTTATTATTTTCTGGGTGAG<br>GAGTAAGAGGAGCAGGCTCCTGCACAGTGACTACATGAACAT<br>GACTCCCCGCCGCCCCGGGCCCACCCGCAAGCATTACCAGCC<br>CTATGCCCCACCACGCGACTTCGCAGCCTATCGCTCCCATATG<br>AGAGTGAAGTTCAGCAGGAGCGCAGACGCCCCCGCGTACAA<br>GCAGGGCCAGAACCAGCTCTATAACGAGCTCAATCTAGGACG<br>AAGAGAGGAGTACGATGTTTTGGACAAGAGACGTGGCCGGG<br>ACCCTGAGATGGGGGGAAAGCCGAGAAGGAAGAACCCTCAG<br>GAAGGCCTGTACAATGAACTGCAGAAAGATAAGATGGCGGA<br>GGCCTACAGTGAGATTGGGATGAAAGGCGAGCGCCGGAGGG<br>GCAAGGGGCACGATGGCCTTTACCAGGGTCTCAGTACAGCCA<br>CCAAGGACACCTACGACGCCCTTCACATGCAGGCCCTGCCCC<br>CTCGCATCAGTCTGATTGCGGCGTTAGCGGTAGATTACGTTAT<br>CGGCATGGAAAACGCCATGCCGTGGAACCTGCCTGCCGATCT<br>CGCCTGGTTTAAACGCAACACCTTAAATAAACCCGTGATTAT<br>GGGCCGCCATACCTGGGAATCAATCGGTCGTCCGTTGCCAGG<br>ACGCAAAAATATTATCCTCAGCAGTCAACCGAGTACGGACGA<br>TCGCGTAACGTGGGTGAAGTCGGTGGATGAAGCCATCGCGGC<br>GTGTGGTGACGTACCAGAAATCATGGTGATTGGCGGCGGTCG<br>CGTTATTGAACAGTTCTTGCCAAAAGCGCAAAAACTGTATCT<br>GACGCATATCGACGCAGAAGTGGAAGGCGACACCCATTTCCC<br>GGATTACGAGCCGGATGACTGGGAATCGGTATTCAGCGAATT<br>CCACGATGCTGATGCGCAGAACTCTCACAGCTATTGCTTTGA<br>GATTCTGGAGCGGCGATGA |
| 72 | ecDHFR destabilization<br>domain (R12Y, G67S,<br>Y100I)<br>Amino acid sequence | MLLLVTSLLLCELPHPAFLLIPDILLTQTPLSLPVSLGDQASISCRS<br>SQSLVHRNGNTYLHWYLQKPGQSPKLLIHKVSNRFSGVPDRFSG<br>SGSGTDFTLKISRVEAEDLGVYFCSQSTHVPPLTFGAGTKLELKG<br>STSGSGKPGSGEGSTKGEVKLQQSGPSLVEPGASVMISCKASGSS<br>FTGYNMNWVRQNIGKSLEWIGAIDPYYGGTSYNQKFKGRATLT<br>VDKSSSTAYMHLKSLTSEDSAVYYCVSGMEYWGQGTSVTVSSA<br>SFEIEVMYPPPYLDNEKSNGTIIHVKGKHLCPSPLFPGPSKPFWVL<br>VVVGGVLACYSLLVTVAFIIFWVRSKRSRLLHSDYMNMTPRRP<br>GPTRKHYQPYAPPRDFAAYRSHMRVKFSRSADAPAYKQGQNQL<br>YNELNLGRREEYDVLDKRRGRDPEMGGKPRRKNPQEGLYNEL<br>QKDKMAEAYSEIGMKGERRRGKGHDGLYQGLSTATKDTYDAL<br>HMQALPPRISLIAALAVDYVIGMENAMPWNLPADLAWFKRNTL<br>NKPVIMGRHTWESIGRPLPGRKNIILSSQPSTDDRVTWVKSVDEA<br>IAACGDVPEIMVIGGGRVIEQFLPKAQKLYLTHIDAEVEGDTHFP<br>DYEPDDWESVFSEFHDADAQNSHSYCFEILERR |
| 73 | GD2.28z.ecDHFR (R12H,<br>N18T, V19A, G67S)<br>Leader sequence<br>nucleic acid sequence | ATGCTGCTGCTCGTGACATCTCTGCTGCTGTGCGAGCTGCCCC<br>ACCCCGCCTTTCTGCTGATCCCC |
| 74 | GD2.28z.ecDHFR (R12H,<br>N18T, V19A, G67S)<br>Leader sequence<br>Amino acid sequence | MLLLVTSLLLCELPHPAFLLIP |
| 75 | 14G2a scFv (GD2<br>binding domain)<br>nucleic acid sequence | GATATCCTGCTGACCCAGACCCCTCTGAGCCTGCCTGTGTCTC<br>TGGGCGATCAGGCCAGCATCAGCTGCAGATCCAGCCAGAGCC<br>TGGTGCACCGGAACGGCAACACCTACCTGCACTGGTATCTGC<br>AGAAGCCCGGCCAGAGCCCCAAGCTGCTGATTCACAAGGTGT<br>CCAACCGGTTCAGCGGCGTGCCCGACAGATTTTCTGGCAGCG<br>GCTCCGGCACCGACTTCACCCTGAAGATCAGCCGGGTGGAAG<br>CCGAGGACCTGGGCGTGTACTTCTGCAGCCAGTCCACCCACG<br>TGCCCCCCCTGACATTTGGCGCCGGAACAAAGCTGGAACTGA<br>AGGGCAGCACAAGCGGCAGCGGCAAGCCTGGATCTGGCGAG<br>GGAAGCACCAAGGGCGAAGTGAAGCTGCAGCAGAGCGGCCC<br>CTCTCTGGTGGAACCTGGCGCCTCTGTGATGATCTCCTGCAAG<br>GCCAGCGGCAGCTCCTTCACCGGCTACAACATGAACTGGGTG |

FIG. 25 (cont'd)

| | | |
|---|---|---|
| | | CGCCAGAACATCGGCAAGAGCCTGGAATGGATCGGCGCCATC GACCCCTACTACGGCGGCACCAGCTACAACCAGAAGTTCAAG GGCAGAGCCACCCTGACCGTGGACAAGAGCAGCTCCACCGCC TACATGCACCTGAAGTCCCTGACCAGCGAGGACAGCGCCGTG TACTACTGCGTGTCCGGCATGGAATACTGGGGCCAGGGCACA AGCGTGACCGTGTCCTCT |
| 76 | 14G2a scFv (GD2 binding domain) Amino acid sequence | DILLTQTPLSLPVSLGDQASISCRSSQSLVHRNGNTYLHWYLQKP GQSPKLLIHKVSNRFSGVPDRFSGSGSGTDFTLKISRVEAEDLGV YFCSQSTHVPPLTFGAGTKLELKGSTSGSGKPGSGEGSTKGEVK LQQSGPSLVEPGASVMISCKASGSSFTGYNMNWVRQNIGKSLE WIGAIDPYYGGTSYNQKFKGRATLTVDKSSSTAYMHLKSLTSED SAVYYCVSGMEYWGQGTSVTVSS |
| 77 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 78 | CD28 hinge region Amino acid sequence | IEVMYPPPYLDNEKSNGTIIHVKGKHLCPSPLFPGPSKP |
| 79 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 80 | CD28 transmembrane region Amino acid sequence | FWVLVVVGGVLACYSLLVTVAFIIFWV |
| 81 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 82 | CD28 intracellular domain Amino acid sequence | RSKRSRLLHSDYMNMTPRRPGPTRKHYQPYAPPRDFAAYRS |
| 83 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 84 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 85 | ecDHFR destabilization domain (R12H, N18T, V19A, G67S) nucleic acid sequence | ATGATCAGTCTGATTGCGGCGTTAGCGGTAGATCACGTTATC GGCATGGAAACCGTCATGCCGTGGAACCTGCCTGCCGATCTC GCCTGGTTTAAACGCAACACCTTAAATAAACCCGTGATTATG GGCCGCCATACCTGGGAATCAATCGGTCGTCCGTTGCCAGGA CGCAAAAATATTATCCTCAGCAGTCAACCGAGTACGGACGAT CGCGTAACGTGGGTGAAGTCGGTGGATGAAGCCATCGCGGCG TGTGGTGACGTACCAGAAATCATGGTTATTGGCGGCGGTCGC GTTTATGAACAGTTCTTGCCAAAAGCGCAAAAACTGTATCTG ACGCATATCGACGCAGAAGTGGAAGGCGACACCCATTTCCCG GATTACGAGCCGGATGACTGGGAATCGGTATTCAGCGAATTC CACGATGCTGATGCGCAGAACTCTCACAGCTATTGCTTTGAG ATTCTGGAGCGGCGA |
| 86 | ecDHFR destabilization domain (R12H, N18T, V19A, G67S) Amino acid sequence | ISLIAALAVDYVIGMENAMPWNLPADLAWFKRNTLNKPVIMGR HTWESIGRPLPGRKNIILSSQPSTDDRVTWVKSVDEAIAACGDVP EIMVIGGGRVIEQFLPKAQKLYLTHIDAEVEGDTHFPDYEPDDW ESVFSEFHDADAQNSHSYCFEILERR |
| 87 | HA-GD2.28z.FKBP nucleic acid sequence | ATGGAATTCGGCCTGAGCTGGCTGTTTCTGGTGGCCATTCTGA AGGGCGTGCAGTGCTCCAGAGACATCCTGCTGACACAGACAC CTCTGAGCCTGCCTGTGTCTCTGGGAGATCAGGCCAGCATCA |

FIG. 25 (cont'd)

| | | |
|---|---|---|
| | | GCTGTAGAAGCAGCCAGAGCCTGGTGCACAGAAACGGCAAT<br>ACCTACCTGCACTGGTATCTGCAGAAGCCCGGCCAGTCTCCT<br>AAGCTGCTGATCCACAAGGTGTCCAACAGATTCAGCGGCGTG<br>CCCGATAGATTTTCTGGCTCTGGCAGCGGCACCGACTTCACCC<br>TGAAGATCTCTAGAGTGGAAGCCGAGGACCTGGGCGTGTACT<br>TCTGTAGCCAGAGCACACATGTGCCTCCACTGACCTTTGGCG<br>CTGGCACCAAACTGGAACTTAAAGGCGGCGGAGGATCTGGTG<br>GTGGTGGATCTGCGGAGGCGGTTCTGAAGTGAAACTGCAGC<br>AGTCTGGCCCCTCTCTGGTTGAACCTGGCGCCTCTGTGATGAT<br>CTCTTGCAAGGCCAGCGGCAGCAGCTTCACCGGCTACAACAT<br>GAACTGGGTCCGACAGAACATCGGCAAGAGCCTGGAATGGA<br>TCGGCGCCATCGATCCTTACTACGGCGGCACCAGCTACAACC<br>AGAAGTTCAAGGGCAGAGCCACACTGACCGTGGACAAGAGC<br>AGCAGCACAGCCTACATGCACCTGAAGTCCCTGACAAGCGAG<br>GACAGCGCCGTGTACTACTGTGTGTCCGGCATGAAGTATTGG<br>GGCCAGGGCACAAGCGTGACCGTGTCTAGCGCTAAGACCACA<br>CCTCCTAGCGTGTACGGCAGAGTGACAGTGTCCAGCGCCGAG<br>CCTAAGAGCTGCGACAAGACACACACCTGTCCTCCATGTCCA<br>GCTCCAGAACTGCTCGGCGGACCCTCCGTTTTCCTGTTTCCAC<br>CTAAGCCAAAGGACACCCTCATGATCAGCAGAACCCCTGAAG<br>TGACCTGCGTGGTGGTCGATGTGTCCCACGAGGATCCCGAAG<br>TGAAGTTCAATTGGTACGTGGACGGCGTGGAAGTGCACAACG<br>CCAAGACCAAGCCTAGAGAGGAACAGTACAACAGCACCTAC<br>AGAGTGGTGTCCGTGCTGACCGTGCTGCATCAGGACTGGCTG<br>AACGGCAAAGAGTACAAGTGCAAAGTCTCCAACAAGGCCCT<br>GCCTGCTCCTATCGAGAAAACCATCAGCAAGGCCAAGGGCCA<br>GCCAAGAGAACCCCAGGTTTACACACTGCCTCCAAGCAGGGA<br>CGAGCTGACCAAGAATCAGGTGTCCCTGACCTGCCTGGTCAA<br>GGGCTTCTACCCTTCCGATATCGCCGTGGAATGGGAGAGCAA<br>TGGCCAGCCTGAGAACAACTACAAGACAACCCCTCCTGTGCT<br>GGACAGCGACGGCTCATTCTTCCTGTACAGCAAGCTGACAGT<br>GGATAAGTCCCGGTGGCAGCAGGGCAATGTGTTCAGCTGTTC<br>TGTGATGCACGAGGCCCTGCACAACCACTACACCCAGAAAAG<br>CCTGTCTCTGAGCCCCGGCAAGAAGGACCCTAAAGCTAGCTT<br>CGAAATTGAAGTTATGTATCCTCCTCCTTACCTAGACAATGAG<br>AAGAGCAATGGAACCATTATCCATGTGAAAGGGAAACACCTT<br>TGTCCAAGTCCCCTATTTCCCGGACCTTCTAAGCCCTTTTGGG<br>TGCTGGTGGTGGTTGGGGGAGTCCTGGCTTGCTATAGCTTGCT<br>AGTAACAGTGGCCTTTATTATTTTCTGGGTGAGGAGTAAGAG<br>GAGCAGGCTCCTGCACAGTGACTACATGAACATGACTCCCCG<br>CCGCCCCGGGCCCACCCGCAAGCATTACCAGCCCTATGCCCC<br>ACCACGCGACTTCGCAGCCTATCGCTCCAGAGTGAAGTTCAG<br>CAGGAGCGCAGACGCCCCCGCGTACAAGCAGGGCCAGAACC<br>AGCTCTATAACGAGCTCAATCTAGGACGAAGAGAGGAGTAC<br>GATGTTTTGGACAAGAGACGTGGCCGGGACCCTGAGATGGGG<br>GGAAAGCCGAGAAGGAAGAACCCTCAGGAAGGCCTGTACAA<br>TGAACTGCAGAAAGATAAGATGGCGGAGGCCTACAGTGAGA<br>TTGGGATGAAAGGCGAGCGCCGGAGGGGCAAGGGGCACGAT<br>GGCCTTTACCAGGGTCTCAGTACAGCCACCAAGGACACCTAC<br>GACGCCCTTCACATGCAGGCCCTGCCCCTCGCGGAGTGCAG<br>GTGGAAACCATCTCCCCAGGAGACGGGCGCACCTTCCCCAAG<br>CGCGGCCAGACCTGCGTGGTGCACTACACCGGGATGCTTGGA<br>GATGGAAAGAAAGTTGACTCCTCCCGGGACAGAAACAAGCC<br>CTTTAAGTTTATGCTAGGCAAGCAGGAGGTGATCCGAGGCTG<br>GGAAGAAGGGGTTGCCCAGATGAGTGTGGGTCAGGGAGCCA<br>AACTGACTATATCTCCAGATTATGCCTATGGTGCCACTGGGC<br>ACCCAGGCATCATCCCACCACATGCCACTCTCGTCTTCGATGT<br>GGAGCTTCTAGAACTGGAATGA |
| 88 | HA-GD2.28z.FKBP<br>Amino acid sequence | MEFGLSWLFLVAILKGVQCSRDILLTQTPLSLPVSLGDQASISCRS<br>SQSLVHRNGNTYLHWYLQKPGQSPKLLIHKVSNRFSGVPDRFSG |

FIG. 25 (cont'd)

| | | |
|---|---|---|
| | | SGSGTDFTLKISRVEAEDLGVYFCSQSTHVPPLTFGAGTKLELKG GGGSGGGGSGGGGSEVKLQQSGPSLVEPGASVMISCKASGSSFT GYNMNWVRQNIGKSLEWIGAIDPYYGGTSYNQKFKGRATLTVD KSSSTAYMHLKSLTSEDSAVYYCVSGMKYWGQGTSVTVSSAKT TPPSVYGRVTVSSAEPKSCDKTHTCPPCPAPELLGGPSVFLFPPKP KDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSRDELTKNQVSLTCLVKGFYPSDI AVEWESNGQPENNYKTTPPVLDSDGSFFLYSKLTVDKSRWQQG NVFSCSVMHEALHNHYTQKSLSLSPGKKDPKASFEIEVMYPPPY LDNEKSNGTIIHVKGKHLCPSPLFPGPSKPFWVLVVVGGVLACY SLLVTVAFIIFWVRSKRSRLLHSDYMNMTPRRPGPTRKHYQPYA PPRDFAAYRSRVKFSRSADAPAYKQGQNQLYNELNLGRREEYD VLDKRRGRDPEMGGKPRRKNPQEGLYNELQKDKMAEAYSEIG MKGERRRGKGHDGLYQGLSTATKDTYDALHMQALPPRGVQVE TISPGDGRTFPKRGQTCVVHYTGMLGDGKKVDSSRDRNKPFKF MLGKQEVIRGWEEGVAQMSVGQGAKLTISPDYAYGATGHPGII PPHATLVFDVELLELE |
| 89 | HA-GD2.28z.FKBP nucleic acid sequence | ATGGAATTCGGCCTGAGCTGGCTGTTTCTGGTGGCCATTCTGA AGGGCGTGCAGTGCTCCAGA |
| 90 | HA-GD2.28z.FKBP Amino acid sequence | MEFGLSWLFLVAILKGVQCSR |
| 91 | High affinity 14G2a scFv (GD2 binding domain) nucleic acid sequence | GACATCCTGCTGACACAGACACCTCTGAGCCTGCCTGTGTCTC TGGGAGATCAGGCCAGCATCAGCTGTAGAAGCAGCCAGAGC CTGGTGCACAGAAACGGCAATACCTACCTGCACTGGTATCTG CAGAAGCCCGGCCAGTCTCCTAAGCTGCTGATCCACAAGGTG TCCAACAGATTCAGCGGCGTGCCCGATAGATTTTCTGGCTCTG GCAGCGGCACCGACTTCACCCTGAAGATCTCTAGAGTGGAAG CCGAGGACCTGGGCGTGTACTTCTGTAGCCAGAGCACACATG TGCCTCCACTGACCTTTGGCGCTGGCACCAAACTGGAACTTA AAGGCGGCGGAGGATCTGGTGGTGGTGGATCTGGCGGAGGC GGTTCTGAAGTGAAACTGCAGCAGTCTGGCCCCTCTCTGGTT GAACCTGGCGCCTCTGTGATGATCTCTTGCAAGGCCAGCGGC AGCAGCTTCACCGGCTACAACATGAACTGGGTCCGACAGAAC ATCGGCAAGAGCCTGGAATGGATCGGCGCCATCGATCCTTAC TACGGCGGCACCAGCTACAACCAGAAGTTCAAGGGCAGAGC CACACTGACCGTGGACAAGAGCAGCAGCACAGCCTACATGC ACCTGAAGTCCCTGACAAGCGAGGACAGCGCCGTGTACTACT GTGTGTCCGGCATGAAGTATTGGGGCCAGGGCACAAGCGTGA CCGTGTCTAGCGCTAAGACCACACCTCCTAGCGTGTACGGCA GAGTGACAGTGTCCAGCGCCGAGCCTAAGAGCTGCGACAAG ACACACACCTGTCCTCCATGTCCAGCTCCAGAACTGCTCGGC GGACCCTCCGTTTTCCTGTTTCCACCTAAGCCAAAGGACACCC TCATGATCAGCAGAACCCCTGAAGTGACCTGCGTGGTGGTCG ATGTGTCCCACGAGGATCCCGAAGTGAAGTTCAATTGGTACG TGGACGGCGTGGAAGTGCACAACGCCAAGACCAAGCCTAGA GAGGAACAGTACAACAGCACCTACAGAGTGGTGTCCGTGCTG ACCGTGCTGCATCAGGACTGGCTGAACGGCAAAGAGTACAA GTGCAAAGTCTCCAACAAGGCCCTGCCTGCTCCTATCGAGAA AACCATCAGCAAGGCCAAGGGCCAGCCAAGAGAACCCCAGG TTTACACACTGCCTCCAAGCAGGGACGAGCTGACCAAGAATC AGGTGTCCCTGACCTGCCTGGTCAAGGGCTTCTACCCTTCCGA TATCGCCGTGGAATGGGAGAGCAATGGCCAGCCTGAGAACA ACTACAAGACAACCCCTCCTGTGCTGGACAGCGACGGCTCAT TCTTCCTGTACAGCAAGCTGACAGTGGATAAGTCCCGGTGGC AGCAGGGCAATGTGTTCAGCTGTTCTGTGATGCACGAGGCCC TGCACAACCACTACACCCAGAAAAGCCTGTCTCTGAGCCCCG GCAAGAAGGACCCTAAA |
| 92 | High affinity 14G2a scFv (GD2 binding domain) | DILLTQTPLSLPVSLGDQASISCRSSQSLVHRNGNTYLHWYLQKP GQSPKLLIHKVSNRFSGVPDRFSGSGSGTDFTLKISRVEAEDLGV |

FIG. 25 (cont'd)

| | | |
|---|---|---|
| | Amino acid sequence | YFCSQSTHVPPLTFGAGTKLELKGGGGSGGGGSGGGGSEVKLQ QSGPSLVEPGASVMISCKASGSSFTGYNMNWVRQNIGKSLEWIG AIDPYYGGTSYNQKFKGRATLTVDKSSSTAYMHLKSLTSEDSAV YYCVSGMKYWGQGTSVTVSSAKTTPPSVYGRVTVSSAEPKSCD KTHTCPPCPAPELLGGPSVFLFPPKPKDTLMISRTPEVTCVVVDV SHEDPEVKFNWYVDGVEVHNAKTKPREEQYNSTYRVVSVLTVL HQDWLNGKEYKCKVSNKALPAPIEKTISKAKGQPREPQVYTLPP SRDELTKNQVSLTCLVKGFYPSDIAVEWESNGQPENNYKTTPPV LDSDGSFFLYSKLTVDKSRWQQGNVFSCSVMHEALHNHYTQKS LSLSPGKKDPK |
| 93 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 94 | CD28 hinge region Amino acid sequence | IEVMYPPPYLDNEKSNGTIIHVKGKHLCPSPLFPGPSKP |
| 95 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 96 | CD28 transmembrane region Amino acid sequence | FWVLVVVGGVLACYSLLVTVAFIIFWV |
| 97 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 98 | CD28 intracellular domain Amino acid sequence | RSKRSRLLHSDYMNMTPRRPGPTRKHYQPYAPPRDFAAYRS |
| 99 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 100 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 101 | FKBP12 destabilization domain (E31G, F36V, R71G, K105E) nucleic acid sequence | GGAGTGCAGGTGGAAACCATCTCCCCAGGAGACGGGCGCAC CTTCCCCAAGCGCGGCCAGACCTGCGTGGTGCACTACACCGG GATGCTTGGAGATGGAAAGAAAGTTGACTCCTCCCGGGACAG AAACAAGCCCTTTAAGTTTATGCTAGGCAAGCAGGAGGTGAT CCGAGGCTGGGAAGAAGGGGTTGCCCAGATGAGTGTGGGTC AGGGAGCCAAACTGACTATATCTCCAGATTATGCCTATGGTG CCACTGGGCACCCAGGCATCATCCCACCACATGCCACTCTCG TCTTCGATGTGGAGCTTCTAGAACTGGAA |
| 102 | FKBP12 destabilization domain (E31G, F36V, R71G, K105E) Amino acid sequence | GVQVETISPGDGRTFPKRGQTCVVHYTGMLGDGKKVDSSRDRN KPFKFMLGKQEVIRGWEEGVAQMSVGQGAKLTISPDYAYGATG HPGIIPPHATLVFDVELLELE |
| 103 | HA-GD2.28z.ecDHFR nucleic acid sequence | ATGGAATTCGGCCTGAGCTGGCTGTTTCTGGTGGCCATTCTGA AGGGCGTGCAGTGCTCCAGAGACATCCTGCTGACACAGACAC CTCTGAGCCTGCCTGTGTCTCTGGGAGATCAGGCCAGCATCA GCTGTAGAAGCAGCCAGAGCCTGGTGCACAGAAACGGCAAT ACCTACCTGCACTGGTATCTGCAGAAGCCCGGCCAGTCTCCT AAGCTGCTGATCCACAAGGTGTCCAACAGATTCAGCGGCGTG CCCGATAGATTTTCTGGCTCTGGCAGCGGCACCGACTTCACCC TGAAGATCTCTAGAGTGGAAGCCGAGGACCTGGGCGTGTACT TCTGTAGCCAGAGCACACATGTGCCTCCACTGACCTTTGGCG |

FIG. 25 (cont'd)

| | | |
|---|---|---|
| | | CTGGCACCAAACTGGAACTTAAAGGCGGCGGAGGATCTGGTG<br>GTGGTGGATCTGGCGGAGGCGGTTCTGAAGTGAAACTGCAGC<br>AGTCTGGCCCCTCTCTGGTTGAACCTGGCGCCTCTGTGATGAT<br>CTCTTGCAAGGCCAGCGGCAGCAGCTTCACCGGCTACAACAT<br>GAACTGGGTCCGACAGAACATCGGCAAGAGCCTGGAATGGA<br>TCGGCGCCATCGATCCTTACTACGGCGGCACCAGCTACAACC<br>AGAAGTTCAAGGGCAGAGCCACACTGACCGTGGACAAGAGC<br>AGCAGCACAGCCTACATGCACCTGAAGTCCCTGACAAGCGAG<br>GACAGCGCCGTGTACTACTGTGTGTCCGGCATGAAGTATTGG<br>GGCCAGGGCACAAGCGTGACCGTGTCTAGCGCTAAGACCACA<br>CCTCCTAGCGTGTACGGCAGAGTGACAGTGTCCAGCGCCGAG<br>CCTAAGAGCTGCGACAAGACACACACCTGTCCTCCATGTCCA<br>GCTCCAGAACTGCTCGGCGGACCCTCCGTTTTCCTGTTTCCAC<br>CTAAGCCAAAGGACACCCTCATGATCAGCAGAACCCCTGAAG<br>TGACCTGCGTGGTGGTCGATGTGTCCCACGAGGATCCCGAAG<br>TGAAGTTCAATTGGTACGTGGACGGCGTGGAAGTGCACAACG<br>CCAAGACCAAGCCTAGAGAGGAACAGTACAACAGCACCTAC<br>AGAGTGGTGTCCGTGCTGACCGTGCTGCATCAGGACTGGCTG<br>AACGGCAAGAGTACAAGTGCAAAGTCTCCAACAAGGCCCT<br>GCCTGCTCCTATCGAGAAAACCATCAGCAAGGCCAAGGGCCA<br>GCCAAGAGAACCCCAGGTTTACACACTGCCTCCAAGCAGGGA<br>CGAGCTGACCAAGAATCAGGTGTCCCTGACCTGCCTGGTCAA<br>GGGCTTCTACCCTTCCGATATCGCCGTGGAATGGGAGAGCAA<br>TGGCCAGCCTGAGAACAACTACAAGACAACCCCTCCTGTGCT<br>GGACAGCGACGGCTCATTCTTCCTGTACAGCAAGCTGACAGT<br>GGATAAGTCCCGGTGGCAGCAGGGCAATGTGTTCAGCTGTTC<br>TGTGATGCACGAGGCCCTGCACAACCACTACACCCAGAAAAG<br>CCTGTCTCTGAGCCCCGGCAAGAAGGACCCTAAAGCTAGCTT<br>CGAAATTGAAGTTATGTATCCTCCTCCTTACCTAGACAATGAG<br>AAGAGCAATGGAACCATTATCCATGTGAAAGGGAAACACCTT<br>TGTCCAAGTCCCCTATTTCCCGGACCTTCTAAGCCCTTTTGGG<br>TGCTGGTGGTGGTTGGGGGAGTCCTGGCTTGCTATAGCTTGCT<br>AGTAACAGTGGCCTTTATTATTTTCTGGGTGAGGAGTAAGAG<br>GAGCAGGCTCCTGCACAGTGACTACATGAACATGACTCCCCG<br>CCGCCCCGGGCCCACCCGCAAGCATTACCAGCCCTATGCCCC<br>ACCACGCGACTTCGCAGCCTATCGCTCCAGAGTGAAGTTCAG<br>CAGGAGCGCAGACGCCCCCGCGTACAAGCAGGGCCAGAACC<br>AGCTCTATAACGAGCTCAATCTAGGACGAAGAGAGGAGTAC<br>GATGTTTTGGACAAGAGACGTGGCCGGGACCCTGAGATGGGG<br>GGAAAGCCGAGAAGGAAGAACCCTCAGGAAGGCCTGTACAA<br>TGAACTGCAGAAAGATAAGATGGCGGAGGCCTACAGTGAGA<br>TTGGGATGAAAGGCGAGCGCCGGAGGGGCAAGGGGCACGAT<br>GGCCTTTACCAGGGTCTCAGTACAGCCACCAAGGACACCTAC<br>GACGCCCTTCACATGCAGGCCCTGCCCCTCGCATCAGTCTG<br>ATTGCGGCGTTAGCGGTAGATTACGTTATCGGCATGGAAAAC<br>GCCATGCCGTGGAACCTGCCTGCCGATCTCGCCTGGTTTAAA<br>CGCAACACCTTAAATAAACCCGTGATTATGGGCCGCCATACC<br>TGGGAATCAATCGGTCGTCCGTTGCCAGGACGCAAAAATATT<br>ATCCTCAGCAGTCAACCGAGTACGGACGATCGCGTAACGTGG<br>GTGAAGTCGGTGGATGAAGCCATCGCGGCGTGTGGTGACGTA<br>CCAGAAATCATGGTGATTGGCGGCGGTCGCGTTATTGAACAG<br>TTCTTGCCAAAAGCGCAAAAACTGTATCTGACGCATATCGAC<br>GCAGAAGTGGAAGGCGACACCCATTTCCCGGATTACGAGCCG<br>GATGACTGGGAATCGGTATTCAGCGAATTCCACGATGCTGAT<br>GCGCAGAACTCTCACAGCTATTGCTTTGAGATTCTGGAGCGG<br>CGATGA |
| 104 | HA-GD2.28z.ecDHFR<br>Amino acid sequence | MEFGLSWLFLVAILKGVQCSRDILLTQTPLSLPVSLGDQASISCRS<br>SQSLVHRNGNTYLHWYLQKPGQSPKLLIHKVSNRFSGVPDRFSG<br>SGSGTDFTLKISRVEAEDLGVYFCSQSTHVPPLTFGAGTKLELKG<br>GGGSGGGGSGGGGSEVKLQQSGPSLVEPGASVMISCKASGSSFT |

FIG. 25 (cont'd)

| | | |
|---|---|---|
| | | GYNMNWVRQNIGKSLEWIGAIDPYYGGTSYNQKFKGRATLTVD KSSSTAYMHLKSLTSEDSAVYYCVSGMKYWGQGTSVTVSSAKT TPPSVYGRVTVSSAEPKSCDKTHTCPPCPAPELLGGPSVFLFPPKP KDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSRDELTKNQVSLTCLVKGFYPSDI AVEWESNGQPENNYKTTPPVLDSDGSFFLYSKLTVDKSRWQQG NVFSCSVMHEALHNHYTQKSLSLSPGKKDPKASFEIEVMYPPPY LDNEKSNGTIIHVKGKHLCPSPLFPGPSKPFWVLVVVGGVLACY SLLVTVAFIIFWVRSKRSRLLHSDYMNMTPRRPGPTRKHYQPYA PPRDFAAYRSRVKFSRSADAPAYKQGQNQLYNELNLGRREEYD VLDKRRGRDPEMGGKPRRKNPQEGLYNELQKDKMAEAYSEIG MKGERRRGKGHDGLYQGLSTATKDTYDALHMQALPPRISLIAA LAVDYVIGMENAMPWNLPADLAWFKRNTLNKPVIMGRHTWES IGRPLPGRKNIILSSQPSTDDRVTWVKSVDEAIAACGDVPEIMVIG GGRVIEQFLPKAQKLYLTHIDAEVEGDTHFPDYEPDDWESVFSE FHDADAQNSHSYCFEILERR |
| 105 | HA-GD2.28z.ecDHFR Leader sequence nucleic acid sequence | ATGGAATTCGGCCTGAGCTGGCTGTTTCTGGTGGCCATTCTGA AGGGCGTGCAGTGCTCCAGA |
| 106 | HA-GD2.28z.ecDHFR Leader sequence Amino acid sequence | MEFGLSWLFLVAILKGVQCSR |
| 107 | High affinity 14G2a scFv (GD2 binding domain) nucleic acid sequence | GACATCCTGCTGACACAGACACCTCTGAGCCTGCCTGTGTCTC TGGGAGATCAGGCCAGCATCAGCTGTAGAAGCAGCCAGAGC CTGGTGCACAGAAACGGCAATACCTACCTGCACTGGTATCTG CAGAAGCCCGGCCAGTCTCCTAAGCTGCTGATCCACAAGGTG TCCAACAGATTCAGCGGCGTGCCCGATAGATTTTCTGGCTCTG GCAGCGGCACCGACTTCACCCTGAAGATCTCTAGAGTGGAAG CCGAGGACCTGGGCGTGTACTTCTGTAGCCAGAGCACACATG TGCCTCCACTGACCTTTGGCGCTGGCACCAAACTGGAACTTA AAGGCGGCGGAGGATCTGGTGGTGGTGGATCTGGCGGAGGC GGTTCTGAAGTGAAACTGCAGCAGTCTGGCCCCTCTCTGGTT GAACCTGGCGCCTCTGTGATGATCTCTTGCAAGGCCAGCGGC AGCAGCTTCACCGGCTACAACATGAACTGGGTCCGACAGAAC ATCGGCAAGAGCCTGGAATGGATCGGCGCCATCGATCCTTAC TACGGCGGCACCAGCTACAACCAGAAGTTCAAGGGCAGAGC CACACTGACCGTGGACAAGAGCAGCAGCACAGCCTACATGC ACCTGAAGTCCCTGACAAGCGAGGACAGCGCCGTGTACTACT GTGTGTCCGGCATGAAGTATTGGGGCCAGGGCACAAGCGTGA CCGTGTCTAGCGCTAAGACCACACCTCCTAGCGTGTACGGCA GAGTGACAGTGTCCAGCGCCGAGCCTAAGAGCTGCGACAAG ACACACACCTGTCCTCCATGTCCAGCTCCAGAACTGCTCGGC GGACCCTCCGTTTTCCTGTTTCCACCTAAGCCAAAGGACACCC TCATGATCAGCAGAACCCCTGAAGTGACCTGCGTGGTGGTCG ATGTGTCCCACGAGGATCCCGAAGTGAAGTTCAATTGGTACG TGGACGGCGTGGAAGTGCACAACGCCAAGACCAAGCCTAGA GAGGAACAGTACAACAGCACCTACAGAGTGGTGTCCGTGCTG ACCGTGCTGCATCAGGACTGGCTGAACGGCAAGAGTACAA GTGCAAAGTCTCCAACAAGGCCCTGCCTGCTCCTATCGAGAA AACCATCAGCAAGGCCAAGGGCCAGCCAAGAGAACCCCAGG TTTACACACTGCCTCCAAGCAGGGACGAGCTGACCAAGAATC AGGTGTCCCTGACCTGCCTGGTCAAGGGCTTCTACCCTTCCGA TATCGCCGTGGAATGGGAGAGCAATGGCCAGCCTGAGAACA ACTACAAGACAACCCCTCCTGTGCTGGACAGCGACGGCTCAT TCTTCCTGTACAGCAAGCTGACAGTGGATAAGTCCCGGTGGC AGCAGGGCAATGTGTTCAGCTGTTCTGTGATGCACGAGGCCC TGCACAACCACTACACCCAGAAAAGCCTGTCTCTGAGCCCCG GCAAGAAGGACCCTAAA |
| 108 | High affinity 14G2a scFv | DILLTQTPLSLPVSLGDQASISCRSSQSLVHRNGNTYLHWYLQKP |

FIG. 25 (cont'd)

| | | |
|---|---|---|
| | (GD2 binding domain Amino acid sequence | GQSPKLLIHKVSNRFSGVPDRFSGSGSGTDFTLKISRVEAEDLGV YFCSQSTHVPPLTFGAGTKLELKGGGGSGGGGSGGGGSEVKLQ QSGPSLVEPGASVMISCKASGSSFTGYNMNWVRQNIGKSLEWIG AIDPYYGGTSYNQKFKGRATLTVDKSSSTAYMHLKSLTSEDSAV YYCVSGMKYWGQGTSVTVSSAKTTPPSVYGRVTVSSAEPKSCD KTHTCPPCPAPELLGGPSVFLFPPKPKDTLMISRTPEVTCVVVDV SHEDPEVKFNWYVDGVEVHNAKTKPREEQYNSTYRVVSVLTVL HQDWLNGKEYKCKVSNKALPAPIEKTISKAKGQPREPQVYTLPP SRDELTKNQVSLTCLVKGFYPSDIAVEWESNGQPENNYKTTPPV LDSDGSFFLYSKLTVDKSRWQQGNVFSCSVMHEALHNHYTQKS LSLSPGKKDPK |
| 109 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 110 | CD28 hinge region Amino acid sequence | IEVMYPPPYLDNEKSNGTIIHVKGKHLCPSPLFPGPSKP |
| 111 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 112 | CD28 transmembrane region Amino acid sequence | FWVLVVVGGVLACYSLLVTVAFIIFWV |
| 113 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 114 | CD28 intracellular domain Amino acid sequence | RSKRSRLLHSDYMNMTPRRPGPTRKHYQPYAPPRDFAAYRS |
| 115 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 116 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 117 | ecDHFR destabilization domain (R12Y, G67S, Y100I) nucleic acid sequence | ATCAGTCTGATTGCGGCGTTAGCGGTAGATTACGTTATCGGC ATGGAAAACGCCATGCCGTGGAACCTGCCTGCCGATCTCGCC TGGTTTAAACGCAACACCTTAAATAAACCCGTGATTATGGGC CGCCATACCTGGGAATCAATCGGTCGTCCGTTGCCAGGACGC AAAAATATTATCCTCAGCAGTCAACCGAGTACGGACGATCGC GTAACGTGGGTGAAGTCGGTGGATGAAGCCATCGCGGCGTGT GGTGACGTACCAGAAATCATGGTGATTGGCGGCGGTCGCGTT ATTGAACAGTTCTTGCCAAAAGCGCAAAAACTGTATCTGACG CATATCGACGCAGAAGTGGAAGGCGACACCCATTTCCCGGAT TACGAGCCGGATGACTGGGAATCGGTATTCAGCGAATTCCAC GATGCTGATGCGCAGAACTCTCACAGCTATTGCTTTGAGATTC TGGAGCGGCGA |
| 118 | ecDHFR destabilization domain (R12Y, G67S, Y100I) Amino acid sequence | ISLIAALAVDYVIGMENAMPWNLPADLAWFKRNTLNKPVIMGR HTWESIGRPLPGRKNIILSSQPSTDDRVTWVKSVDEAIAACGDVP EIMVIGGGRVIEQFLPKAQKLYLTHIDAEVEGDTHFPDYEPDDW ESVFSEFHDADAQNSHSYCFEILERR |
| 119 | Her2.28z.FKBP nucleic acid sequence | ATGCTGCTGCTCGTGACATCTCTGCTGCTGTGCGAGCTGCCCC ACCCCGCCTTTCTGCTGATCCCCGATATCCAGATGACCCAGTC CCCGAGCTCCCTGTCCGCCTCTGTGGGCGATAGGGTCACCAT CACCTGCCGTGCCAGTCAGGATGTGAATACTGCTGTAGCCTG |

FIG. 25 (cont'd)

| | | |
|---|---|---|
| | | GTATCAACAGAAACCAGGAAAAGCTCCGAAACTACTGATTTA CTCGGCATCCTTCCTTTATTCTGGAGTCCCTTCTCGCTTCTCTG GATCTAGATCTGGGACGGATTTCACTCTGACCATCAGCAGTC TGCAGCCGGAAGACTTCGCAACTTATTACTGTCAGCAACATT ATACTACTCCTCCCACGTTCGGACAGGGTACCAAGGTGGAGA TCAAAGGGTCTACATCTGGATCTGGGAAGCCGGGTTCTGGTG AGGGTTCTGGTGAGGTTCAGCTGGTGGAGTCTGGCGGTGGCC TGGTGCAGCCAGGGGGCTCACTCCGTTTGTCCTGTGCAGCTTC TGGCTTCAACATTAAAGACACCTATATACACTGGGTGCGTCA GGCCCCGGGTAAGGGCCTGGAATGGGTTGCAAGGATTTATCC TACGAATGGTTATACTAGATATGCCGATAGCGTCAAGGGCCG TTTCACTATAAGCGCAGACACATCCAAAAACACAGCCTACCT GCAGATGAACAGCCTGCGTGCTGAGGACACTGCCGTCTATTA TTGTTCTAGATGGGGAGGGGACGGCTTCTATGCTATGGACGT GTGGGGTCAAGGAACCCTGGTCACCGTCTCCTCGGCTAGCGA ACAAAAACTCATCTCAGAAGAGGATCTGTTCGAAATTGAAGT TATGTATCCTCCTCCTTACCTAGACAATGAGAAGAGCAATGG AACCATTATCCATGTGAAAGGGAAACACCTTTGTCCAAGTCC CCTATTTCCCGGACCTTCTAAGCCCTTTTGGGTGCTGGTGGTG GTTGGGGGAGTCCTGGCTTGCTATAGCTTGCTAGTAACAGTG GCCTTTATTATTTTCTGGGTGAGGAGTAAGAGGAGCAGGCTC CTGCACAGTGACTACATGAACATGACTCCCCGCCGCCCCGGG CCCACCCGCAAGCATTACCAGCCCTATGCCCCACCACGCGAC TTCGCAGCCTATCGCTCCAGAGTGAAGTTCAGCAGGAGCGCA GACGCCCCCGCGTACAAGCAGGGCCAGAACCAGCTCTATAAC GAGCTCAATCTAGGACGAAGAGAGGAGTACGATGTTTTGGAC AAGAGACGTGGCCGGGACCCTGAGATGGGGGGAAAGCCGAG AAGGAAGAACCCTCAGGAAGGCCTGTACAATGAACTGCAGA AAGATAAGATGGCGGAGGCCTACAGTGAGATTGGGATGAAA GGCGAGCGCCGGAGGGGCAAGGGGCACGATGGCCTTTACCA GGGTCTCAGTACAGCCACCAAGGACACCTACGACGCCCTTCA CATGCAGGCCCTGCCCCCTCGCGGAGTGCAGGTGGAAACCAT CTCCCCAGGAGACGGGCGCACCTTCCCCAAGCGCGGCCAGAC CTGCGTGGTGCACTACACCGGGATGCTTGGAGATGGAAAGAA AGTTGACTCCTCCCGGGACAGAAACAAGCCCTTTAAGTTTAT GCTAGGCAAGCAGGAGGTGATCCGAGGCTGGGAAGAAGGGG TTGCCCAGATGAGTGTGGGTCAGGGAGCCAAACTGACTATAT CTCCAGATTATGCCTATGGTGCCACTGGGCACCCAGGCATCA TCCCACCACATGCCACTCTCGTCTTCGATGTGGAGCTTCTAGA ACTGGAATGA |
| 120 | Her2.28z.FKBP Amino acid sequence | MLLLVTSLLLCELPHPAFLLIPDIQMTQSPSSLSASVGDRVTITCR ASQDVNTAVAWYQQKPGKAPKLLIYSASFLYSGVPSRFSGSRSG TDFTLTISSLQPEDFATYYCQQHYTTPPTFGQGTKVEIKGSTSGS GKPGSGEGSGEVQLVESGGGLVQPGGSLRLSCAASGFNIKDTYI HWVRQAPGKGLEWVARIYPTNGYTRYADSVKGRFTISADTSKN TAYLQMNSLRAEDTAVYYCSRWGGDGFYAMDVWGQGTLVTV SSASEQKLISEEDLFEIEVMYPPPYLDNEKSNGTIIHVKGKHLCPS PLFPGPSKPFWVLVVVGGVLACYSLLVTVAFIIFWVRSKRSRLLH SDYMNMTPRRPGPTRKHYQPYAPPRDFAAYRSRVKFSRSADAP AYKQGQNQLYNELNLGRREEYDVLDKRRGRDPEMGGKPRRKN PQEGLYNELQKDKMAEAYSEIGMKGERRRGKGHDGLYQGLST ATKDTYDALHMQALPPRGVQVETISPGDGRTFPKRGQTCVVHY TGMLGDGKKVDSSRDRNKPFKFMLGKQEVIRGWEEGVAQMSV GQGAKLTISPDYAYGATGHPGIIPPHATLVFDVELLELE |
| 121 | Her2.28z.FKBP Leader sequence nucleic acid sequence | ATGCTGCTGCTCGTGACATCTCTGCTGCTGTGCGAGCTGCCCC ACCCCGCCTTTCTGCTGATCCCC |
| 122 | Her2.28z.FKBP Leader sequence Amino acid sequence | MLLLVTSLLLCELPHPAFLLIP |

FIG. 25 (cont'd)

| 123 | 4D5 scFv (Her2 binding domain) nucleic acid sequence | CAGATGACCCAGTCCCCGAGCTCCCTGTCCGCCTCTGTGGGC GATAGGGTCACCATCACCTGCCGTGCCAGTCAGGATGTGAAT ACTGCTGTAGCCTGGTATCAACAGAAACCAGGAAAAGCTCCG AAACTACTGATTTACTCGGCATCCTTCCTTTATTCTGGAGTCC CTTCTCGCTTCTCTGGATCTAGATCTGGGACGGATTTCACTCT GACCATCAGCAGTCTGCAGCCGGAAGACTTCGCAACTTATTA CTGTCAGCAACATTATACTACTCCTCCCACGTTCGGACAGGGT ACCAAGGTGGAGATCAAAGGGTCTACATCTGGATCTGGGAAG CCGGGTTCTGGTGAGGGTTCTGGTGAGGTTCAGCTGGTGGAG TCTGGCGGTGGCCTGGTGCAGCCAGGGGGCTCACTCCGTTTG TCCTGTGCAGCTTCTGGCTTCAACATTAAAGACACCTATATAC ACTGGGTGCGTCAGGCCCCGGGTAAGGGCCTGGAATGGGTTG CAAGGATTTATCCTACGAATGGTTATACTAGATATGCCGATA GCGTCAAGGGCCGTTTCACTATAAGCGCAGACACATCCAAAA ACACAGCCTACCTGCAGATGAACAGCCTGCGTGCTGAGGACA CTGCCGTCTATTATTGTTCTAGATGGGGAGGGGACGGCTTCTA TGCTATGGACGTGTGGGGTCAAGGAACCCTGGTCACCGTCTC CTCGGCTAGC |
| 124 | 4D5 scFv (Her2 binding domain) Amino acid sequence | QMTQSPSSLSASVGDRVTITCRASQDVNTAVAWYQQKPGKAPK LLIYSASFLYSGVPSRFSGSRSGTDFTLTISSLQPEDFATYYCQQH YTTPPTFGQGTKVEIKGSTSGSGKPGSGEGSGEVQLVESGGGLV QPGGSLRLSCAASGFNIKDTYIHWVRQAPGKGLEWVARIYPTNG YTRYADSVKGRFTISADTSKNTAYLQMNSLRAEDTAVYYCSRW GGDGFYAMDVWGQGTLVTVSSAS |
| 125 | MYC tag nucleic acid sequence | GAACAAAAACTCATCTCAGAAGAGGATCTG |
| 126 | MYC tag Amino acid sequence | EQKLISEEDL |
| 127 | CD28 hinge region nucleic acid sequence | ATTGAAGTTATGTATCCTCCTCCTTACCTAGACAATGAGAAG AGCAATGGAACCATTATCCATGTGAAAGGGAAACACCTTTGT CCAAGTCCCCTATTTCCCGGACCTTCTAAGCCC |
| 128 | CD28 hinge region Amino acid sequence | IEVMYPPPYLDNEKSNGTIIHVKGKHLCPSPLFPGPSKP |
| 129 | CD28 transmembrane region nucleic acid sequence | TTTTGGGTGCTGGTGGTGGTTGGGGGAGTCCTGGCTTGCTATA GCTTGCTAGTAACAGTGGCCTTTATTATTTTCTGGGTG |
| 130 | CD28 transmembrane region Amino acid sequence | FWVLVVVGGVLACYSLLVTVAFIIFWV |
| 131 | CD28 intracellular domain nucleic acid sequence | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| 132 | CD28 intracellular domain Amino acid sequence | RSKRSRLLHSDYMNMTPRRPGPTRKHYQPYAPPRDFAAYRS |
| 133 | CD3 zeta intracellular domain nucleic acid sequence | AGAGTGAAGTTCAGCAGGAGCGCAGACGCCCCCGCGTACAA GCAGGGCCAGAACCAGCTCTATAACGAGCTCAATCTAGGACG AAGAGAGGAGTACGATGTTTTGGACAAGAGACGTGGCCGGG ACCCTGAGATGGGGGGAAAGCCGAGAAGGAAGAACCCTCAG GAAGGCCTGTACAATGAACTGCAGAAAGATAAGATGGCGGA GGCCTACAGTGAGATTGGGATGAAAGGCGAGCGCCGGAGGG GCAAGGGGCACGATGGCCTTTACCAGGGTCTCAGTACAGCCA CCAAGGACACCTACGACGCCCTTCACATGCAGGCCCTGCCCC CTCGC |
| 134 | CD3 zeta intracellular domain Amino acid sequence | RVKFSRSADAPAYKQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 135 | FKBP12 destabilization domain (E31G, F36V, R71G, K105E) | GGAGTGCAGGTGGAAACCATCTCCCCAGGAGACGGGCGCAC CTTCCCCAAGCGCGGCCAGACCTGCGTGGTGCACTACACCGG GATGCTTGGAGATGGAAAGAAAGTTGACTCCTCCCGGGACAG |

FIG. 25 (cont'd)

| | nucleic acid sequence | AAACAAGCCCTTTAAGTTTATGCTAGGCAAGCAGGAGGTGAT CCGAGGCTGGGAAGAAGGGGTTGCCCAGATGAGTGTGGGTC AGGGAGCCAAACTGACTATATCTCCAGATTATGCCTATGGTG CCACTGGGCACCCAGGCATCATCCCACCACATGCCACTCTCG TCTTCGATGTGGAGCTTCTAGAACTGGAA |
|---|---|---|
| 136 | FKBP12 destabilization domain (E31G, F36V, R71G, K105E) Amino acid sequence | GVQVETISPGDGRTFPKRGQTCVVHYTGMLGDGKKVDSSRDRN KPFKFMLGKQEVIRGWEEGVAQMSVGQGAKLTISPDYAYGATG HPGIIPPHATLVFDVELLELE |

METHODS OF TREATING T CELL EXHAUSTION BY INHIBITING OR MODULATING T CELL RECEPTOR SIGNALING

CROSS REFERENCE TO RELATED APPLICATIONS

This application is a U.S. 371 national phase entry of International Patent Application No. PCT/US2018/025459, filed March 30, 2018, which claims the benefit of U.S. provisional application Serial No. 62/479,930, filed March 31, 2017, which are incorporated herein by reference in their entireties.

STATEMENT REGARDING FEDERALLY SPONSORED RESEARCH OR DEVELOPMENT

This invention was made with Government support under contract CA232568 awarded by the National Institutes of Health. The Government has certain rights in the invention.

FIELD OF THE INVENTION

The present invention relates to methods of treating T cell exhaustion. In particular, the invention relates to methods of preventing or reversing T cell exhaustion by transiently inhibiting T cell receptor (TCR) signaling to restore T cell function.

BACKGROUND

T cells are immune cells that become activated via T cell receptor (TCR) signaling and co-stimulation following engagement with antigen. Physiologic activation through the T cell receptor renders T cells capable of mediating potent antitumor and/or anti-infective effects. During resolution of an acute inflammatory response, a subset of activated effector T cells differentiate into long-lived memory cells. By contrast, in patients with chronic infections or cancer, T cells may undergo pathologic differentiation toward a state of dysfunction, which has been termed T cell exhaustion. T cell exhaustion is characterized by marked changes in metabolic function, transcriptional programming, loss of effector function (e.g, cytokine secretion, killing capacity), and co-expression of multiple surface inhibitory receptors. The root cause of T cell exhaustion is persistent antigen exposure leading to continuous TCR signaling. Prevention or reversal of T cell exhaustion has been long sought as a means to enhance T cell effectiveness (e.g., in patients with cancer or chronic infections).

SUMMARY

The invention relates to methods of treating T cell T cell exhaustion by transiently inhibiting T cell receptor (TCR) signaling. In one aspect, the present invention provides compositions and methods for use in preventing chimeric antigen receptor (CAR) T cell exhaustion. In particular, the invention provides CAR T cells modified to maintain functionality under conditions in which unmodified CAR T cells become dysfunctional (e.g., display exhaustion). CAR T cells modified according to the invention (e.g., via modulation of CAR surface expression), compositions containing same, and methods of using same enhance T cell functionality including, for example, activity against cancer or infectious disease.

In some embodiments, CAR T cell exhaustion is inhibited or reversed via modulation of CAR surface expression. In some embodiments, modulation of CAR surface expression is made possible via fusion of a regulatable destabilization domain (RDD) to a CAR T cell. In some embodiments, the RDD is a ligand-regulatable destabilization domain. For example, regulation of CAR expression is achieved, in some embodiments, by fusing the CAR with an RDD, which renders the resulting modified CAR protein unstable and prone to proteasomal degradation. By adding a ligand such as a small molecule or drug (e.g., Shield-1 or trimethoprim (TMP)), the modified CAR protein is shielded from degradation and the CAR construct comprising an RDD is stably expressed (see Banaszynski et al., (2006) Cell 126: 995-1004; Banaszynski et al., (2008) Nat Med 14: 1123-1127;. Iwamoto et al., (2010). Chem Biol 17: 981-988.)

In some embodiments, the RDD comprises a binding domain derived from dihydrofolate reductase (DHFR) RDD. In some embodiments, the DHFR-derived RDD comprises a binding domain from a bacterial DHFR. In some embodiments, the bacterial DHFR is an *Escherichia coli* DHFR. In some embodiments, the DHFR-derived RDD comprises a binding domain from human DHFR. In some embodiments, the RDD comprises a binding domain derived from an FK506 Binding Protein (FKBP). In some embodiments, the FKBP is FKBP12. In some embodiments, the nucleic acid sequence of a FKBP DD comprises the sequence set forth in SEQ ID NO: 1. In one embodiment, the FKBP DD comprise the nucleic acid sequence that encodes the amino acid sequence of SEQ ID NO: 2. In another embodiment, the FKBP DD portion of the CAR of the invention comprises the amino acid sequence set forth in SEQ ID NO. 2.

In some embodiments, an ecDHFR destabilization domain is used. In some embodiments, the nucleic acid sequence of an ecDHFR DD comprises the sequence set forth in SEQ ID NO: 3. In one embodiment, the ecDHFR DD comprise the nucleic acid sequence that encodes the amino acid sequence of SEQ ID NO: 4. In another embodiment, the ecDHFR DD portion of the CAR of the invention comprises the amino acid sequence set forth in SEQ ID NO. 4. In other embodiments, the nucleic acid sequence of an ecDHFR DD comprises the sequence set forth in SEQ ID NO: 5. In one embodiment, the ecDHFR DD comprise the nucleic acid sequence that encodes the amino acid sequence of SEQ ID NO: 6. In another embodiment, the ecDHFR DD portion of the CAR of the invention comprises the amino acid sequence set forth in SEQ ID NO. 6.

The invention is not limited by the type of ligand. In some embodiments, Shield-1 or trimethoprim (TMP) is used to stabilize and promote stable surface expression a fusion protein containing a DHFR RDD or a FKBP RDD.

In some embodiments, a T cell is provided that is genetically engineered to express a CAR comprising an RDD (e.g., fused to the CAR) that marks the CAR for degradation (e.g., ubiquitin-mediated and/or proteasomal degradation) such that the addition or presence of a stabilizing small molecule drug that directly interacts (e.g., binds) with the RDD prevents CAR degradation, and removal (e.g., by metabolic clearance) or absence of the stabilizing small molecule drug that directly interacts with the RDD allows CAR degradation to occur. While an understanding of a mechanism is not needed to practice the present invention, and while the present invention is not limited to any particular mechanism, in some embodiments, tonic CAR signaling is prevented by allowing degradation or destruction of CAR proteins such that surface expression levels of any CAR proteins are below the concentration necessary to permit tonic CAR signaling. In some embodiments, modulation (e.g., reduction) of CAR protein levels and CAR surface expression via use of a such a "drug on" RDD to the CAR reinvigorates exhausted T cells that have already developed the hallmarks of T cell exhaustion due to tonic CAR signaling. For example, CAR T cells that are exposed to the stabilizing small molecule demonstrate all of the phenotypic and functional hallmarks of T cell exhaustion. However, when the stabilizing small molecule is removed and CAR protein levels are reduced by protein degradation, the phenotypic and functional indicators of T cell exhaustion are reversed and effector T cell function is restored.

In another aspect, the invention provides a genetically modified T cell comprising an isolated nucleic acid sequence encoding a chimeric antigen receptor (CAR), wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecules, the nucleic acid sequence of a CD3 zeta signaling domain, and the nucleic acid sequence of an RDD domain.

The invention additionally includes a vector comprising an isolated nucleic acid sequence encoding a chimeric antigen receptor (CAR), wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecule, the nucleic acid sequence of a CD3 zeta signaling domain, and the nucleic acid sequence of an RDD domain.

In addition, the invention includes methods for providing anti-tumor immunity in a subject having cancer. The methods comprise administering to the subject an effective amount of a genetically modified T cell comprising an isolated nucleic acid sequence encoding a chimeric antigen receptor (CAR), wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecule, the nucleic acid sequence of a CD3 zeta signaling domain, and the nucleic acid sequence of an RDD domain, thereby providing anti-tumor immunity in the subject. In some embodiments, the subject is a human.

Further included in the invention is a method for stimulating a beneficial and/or therapeutic T cell-mediated immune response to a cell population, tumor or tissue in a subject. The method comprises administering to the subject an effective amount of a genetically modified T cell comprising an isolated nucleic acid sequence encoding a chimeric antigen receptor (CAR), wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecule, the nucleic acid sequence of a CD3 zeta signaling domain, and the nucleic acid sequence of an RDD domain domain, thereby stimulating a T cell-mediated immune response in the subject.

Also provided here are methods of treating cancer in a subject. The methods comprise administering to a subject having cancer a therapeutically effective amount of a genetically modified T cell comprising an isolated nucleic acid sequence encoding a chimeric antigen receptor (CAR), wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecule, the nucleic acid sequence of a CD3 zeta signaling domain, and the nucleic acid sequence of an RDD domain, thereby treating cancer in the subject.

The invention further includes a method of generating a persisting population of genetically engineered T cells (e.g., memory T cells) in a subject diagnosed with cancer, the method comprising: administering to the subject an effective amount of a genetically modified T cell comprising an isolated nucleic acid sequence encoding a chimeric antigen receptor (CAR), wherein the wherein the isolated nucleic acid sequence comprises nucleic acid sequence (e.g., human, mouse, or humanized mouse nucleic acid sequence) of a tumor antigen-binding domain (e.g., a single chain variable fragment, or scFv), the nucleic acid sequence of a transmembrane domain, the nucleic acid sequence of an intracellular domain of one or more costimulatory molecule, the nucleic acid sequence of a CD3 zeta signaling domain, and the nucleic acid sequence of an RDD domain, wherein the persisting population of genetically engineered T cells persists in the subject (e.g., for weeks, a month, months, etc.) after administration. In some embodiments, the persisting population of genetically engineered T cells persists in the human for at least three months after administration.

The invention is not limited by the means of expressing a CAR containing an RDD. In some embodiments, a CAR is expressed constitutively. In other embodiments, a CAR is expressed in a regulated fashion (e.g., using a system to regulate expression via a small molecule or using an endogenously regulated system). A CAR, in another embodiment, is genetically integrated into the cellular DNA using a retroviral, lentiviral or other viral vector or via CRISPR/Cas9 based system. In yet another embodiment, a CAR is expressed via RNA or an oncolytic virus or other transient expression system known in the art. CARs can be delivered ex vivo into T cells for adoptive transfer, or delivered via in vivo genetic transfer.

The invention is not limited by the type of T cell genetically modified to express and/or contain a CAR of the invention. In some embodiments, the T cells are CD3+ T cells (e.g., CD4+ and/or CD8+ T cells). In certain embodiments, the T cells are CD8+ T cells. In other embodiments, the T cells are CD4+ T cells. In some embodiments, the T cells are natural killer (NK) T cells. In some embodiments, the T cells are alpha beta T cells. In some embodiments, the T cells are gamma delta T cells. In some embodiments, the T cells are a combination of CD4+ and CD8 T+ cells (e.g., CD3+). In certain embodiments, the T cells are memory T cells. In certain embodiments, the memory T cells are central memory T cells. In other embodiments, the memory T cells are effector memory T cells. In some embodiments, the T cells are tumor-infiltrating lymphocytes (TILs). In certain embodiments, the T cells are a combination of CD8+ T cells, CD4+ T cells, NK T cells, memory T cells, and/or gamma delta T cells. In some embodiments, the T cells are cytokine-induced killer cells.

In some embodiments, CAR T cells include peripheral blood derived T cells genetically modified with a CAR that recognizes and responds to tumor antigens. Such receptors are generally composed of extracellular domains comprising a single-chain antibody (scFv) specific for tumor antigen, a transmembrane domain, and an intracellular signaling domain (See, e.g., Westwood, J. A. et al, 2005, Proc. Natl. Acad. Sci., USA, 102(52):19051-19056). In other embodiments, the T cell is engineered to express a CAR of human or murine origin that recognizes a tumor antigen. The invention is not limited by the type of tumor antigen recognized. Indeed, any CAR that recognizes a tumor antigen finds use in the compositions and methods of the invention. Examples include, but are not limited to, a CAR that recognize an antigen selected from HER2, CD19, CD20, CD22, CD30, CD33/IL3Ra, CD123, CD38, receptor tyrosine kinase-like orphan receptor 1 (ROR1), ErbB3/4, Glycolipid F77, epidermal growth factor receptor (EGFR), EGFR variant III (EGFRvIII), melanoma antigen recognized by T cells 1 (MART-1), EphA2, FAP, human carcinoembryonic antigen (CEA), EGP2, EGP40, mesothelin, TAG72, prostate-specific membrane antigen (PSMA), NKG2D ligands, B7-H6, IL-13 receptor a2, IL-11 receptor a, MUC1, MUC16, CA9, disialoganglioside 2 (GD2), GD3, tyrosine protein kinase Met (c-Met) or hepatocyte growth factor receptor (HGFR), HMW-MAA, CD171, Lewis Y, G250/CAIX, melanoma antigen gene (MAGE) Family Member A3 (MAGE-A3), HLA-AI, MAGE Al, NY-ESO-1, PSC1, folate receptor-a, CD44v7/8, 8H9, NCAM, VEGF receptors, Fetal AchR, NKG2D ligands, CD44v6, TEM1, TEM8, GP1000, p53, Epstein-Barr Virus (EBV) protein or antigen, or other viral-associated antigens expressed by a tumor.

The invention is not limited by the type CAR. Indeed, any CAR that binds with specificity to a desired antigen (e.g., tumor antigen or other type of antigen) may be modified as disclosed and described herein in order to modulate the CAR's surface expression. In certain embodiments, the CAR comprises an antigen-binding domain. In certain embodiments, the antigen-binding domain is a single-chain variable fragment (scFv) containing heavy and light chain variable regions that bind with specificity to a desired antigen. In some embodiments, the CAR comprises a transmembrane domain and a signaling domain comprising one or more immunoreceptor tyrosine-based activation motifs (ITAMs). In some embodiments, the transmembrane domain comprises a transmembrane domain of a protein selected from the group consisting of the T-cell receptor (TCR) alpha chain, the TCR beta chain, CD3 zeta, CD28, CD3 epsilon, CD45, CD4, CDS, CD8, CD9, CD16, CD22, CD33, CD37, CD64, CD80, CD86, CD134, CD137, and CD154. The intracellular signaling domain, in some embodiments, comprises a functional signaling domain of a 4-1BB polypeptide, a functional signaling domain of a CD3 zeta polypeptide, or both. In some embodiments, the CAR comprises one or more co-stimulatory domains (e.g., domains that provide a second signal to stimulate T cell activation). The invention is not limited by the type of co-stimulatory domain. Indeed, any co-stimulatory domain known in the art may be used including, but not limited to, CD28, OX40/CD134, 4-1BB/CD137/TNFRSF9, the high affinity immunoglobulin E receptor-gamma subunit (FcεRIγ), ICOS/CD278, interleukin 2 subunit beta (ILRβ) or CD122, cytokine receptor common subunit gamma (IL-2Rγ) or CD132, and CD40. In one embodiment, the co-stimulatory domain is 4-1BB.

The invention is not limited to any particular RDD or the domain within the CAR to which the RDD is fused. In some embodiments, the RDD is fused to the CAR antigen-binding domain. In other embodiments, the RDD is fused to a hinge or transmembrane CAR domain. In still further embodiments, the RDD is fused to a cytoplasmic CAR stimulatory domain such as, but not limited to, CD28, 4-1BB, OX-40. In yet other embodiments, the RDD is fused to a CAR CD3 zeta domain. Indeed, according to the present methods and compositions, cells comprising a CAR comprising an RDD may have the RDD attached to any portion of the CAR provided the CAR retains antigen-specific activity.

In another aspect, the invention provides a method of treating a disease or condition in a subject comprising administering to the subject (e.g., a patient) having a disease or condition an effective amount of CAR T cells comprising a CAR containing or fused to an RDD. The invention is not limited by the type of disease or condition treated. Indeed, any disease or condition that is treatable (e.g., for which signs or symptoms of the disease are ameliorated upon treatment) via administration of CAR T cells can be treated in an improved and more effective manner using compositions and methods of the invention. In one embodiment, the disease or condition is cancer. In another embodiment, the disease or condition is an infectious disease. The invention is not limited by the type of cancer or by the type of infectious disease. Indeed, any cancer or disease known in the art for which CAR T cell therapy is used for treatment may be treated with the compositions and methods of the invention. For example, compositions and methods of the invention can be used to modify any CAR T cell therapy known in the art via genetically introducing an RDD into the CAR of therapeutic CAR T cells. In some embodiments, administration to a subject (e.g., a patient) having a disease or condition of an effective amount of CAR T cells of the invention inhibits or reverses T cell exhaustion in the patient (e.g., compared to a subject receiving the same amount of CAR T cells lacking a DD).

In another aspect, the invention provides a method of maintaining, regaining, or enhancing functionality of CAR T cells (e.g., CAR T cells that would otherwise experience antigen induced tonic signaling and exhaustion in the context of treating a disease or condition) via selective modulation (e.g., reduction) of CAR cell surface expression. In some embodiments, incorporation of an RDD into the CAR allows modulation (e.g., reduction) of CAR expression during culture and expansion of T cells in vitro or ex vivo, which in turn enhances functionality (e.g., effector function) of the CAR T cells in the context of treating a disease or condition in a subject. The invention is not limited by the type of functionality maintained, regained or enhanced. In some embodiments, the functionality is antigen induced cytokine production. In other embodiments, the functionality is CAR T cell cytotoxicity (e.g., increased recognition of tumor targets). In still other embodiments, the functionality is increased memory cell formation and/or enhanced proliferation in response to antigen. In some embodiments, modulation (e.g., reduction) of CAR cell surface expression results in measurable reduction of markers indicative of exhaustion including, but not limited to, PD-1, TIM-3, and LAG-3 in the CAR T cells. In other embodiments, modulation (e.g., reduction) of CAR cell surface expression results in a reduction in the levels of CAR T cell programmed cell death. In still further embodiments, modulation (e.g., reduction) of CAR cell surface expression on CAR T cells significantly enhances clinical efficacy of CAR T cell therapy.

In another aspect, the invention provides methods of treating or delaying the progression of cancer in a patient comprising administering to the patient a therapeutically effective amount of a composition comprising CAR T cells modified (e.g., genetically) to express a CAR containing or fused to an RDD. In certain embodiments, the therapeutically effective amount of the composition comprising modified CAR T cells reduces the number of cancer cells in the patient following such treatment. In certain embodiments, the therapeutically effective amount of the composition comprising modified CAR T cells reduces and/or eliminates the tumor burden in the patient following such treatment. In certain embodiments, the method further comprises administering radiation therapy to the patient. In certain embodiments, the radiation therapy is administered before, at the same time as, and/or after the patient receives the therapeutically effective amount of the composition comprising modified CAR T cells. In certain embodiments, the method further comprises administering to the patient one or more anticancer agents and/or one or more chemotherapeutic agents. In certain embodiments, the one or more anticancer agents and/or one or more chemotherapeutic agents are administered before, at the same time as, and/or after the patient receives the therapeutically effective amount of the composition comprising modified CAR T cells. In certain embodiments, treatment of a patient with a therapeutically effective amount of modified CAR T cells and a course of an anticancer agent produces a greater tumor response and clinical benefit in such patient compared to those treated with the modified CAR T cells or anticancer drugs/radiation alone. Since the doses for all approved anticancer drugs and radiation treatments are known, the present invention contemplates the various combinations of them with the modified CAR T cells.

In certain embodiments, the invention provides a therapeutically effective amount of a composition comprising CAR T cells modified according to the present disclosure (e.g., for use in treating or delaying the progression of cancer in a subject). As described herein, the composition may be administered before, during, or after other types of cancer treatment (e.g., chemotherapy, surgical resection of cancer, or radiation therapy). The invention also provides the use of the composition to induce cell cycle arrest and/or apoptosis. The invention also relates to the use of the compositions for sensitizing cells to additional agent(s), such as inducers of apoptosis and/or cell cycle arrest, and chemoprotection of normal cells through the induction of cell cycle arrest. Compositions of the invention are useful for the treatment, amelioration, or prevention of disorders, such as any type of cancer or infectious disease and additionally any cells responsive to induction of apoptotic cell death (e.g., disorders characterized by dysregulation of apoptosis, including hyperproliferative diseases such as cancer). In certain embodiments, the compositions can be used to treat, ameliorate, or prevent a cancer that additionally is characterized by resistance to cancer therapies (e.g., those cancer cells which are chemoresistant, radiation resistant, hormone resistant, and the like). The invention also provides pharmaceutical compositions comprising the composition (e.g., immunotherapeutic compositions) comprising modified CAR T cells of the invention in a pharmaceutically acceptable carrier.

In another embodiment, the invention provides a method of treating or delaying the progression of cancer in a patient comprising administering to the patient a therapeutically effective amount of a composition comprising CAR T cells modified (e.g., genetically) according to the present disclosure in combination with a therapeutically effective amount of an inhibitor of TCR signaling (e.g., in order to prevent T cell exhaustion). Multiple cycles of treatment may be administered to a subject. In certain embodiments, the inhibitor of TCR signaling is administered according to a standard dosing regimen (e.g., daily or intermittently). In another embodiment, the inhibitor of TCR signaling is administered for a period of time sufficient to restore at least partial T cell function, then discontinued.

These and other embodiments of the subject invention will readily occur to those of skill in the art in view of the disclosure herein.

DESCRIPTION OF THE DRAWINGS

FIG. 15A shows that CAR expression is regulatable in vivo, and that the dynamic range of CAR surface expression achieved in vitro is similar to that observed in vivo. FIG. 15B shows that mice that received injections of the stabilizing drug trimethoprim (TMP) not only exhibited CAR expression, but that the higher-expressing CAR T cells in this group also exhibit higher CD69 surface expression, indicating that they became activated in response to the tumor in vivo. FIG. 15C shows differences in the tumor burden of mice which received daily injections of vehicle versus mice that received TMP. Mice that received TMP, and thus expressed CAR on the surface, show a greater capacity to control tumor growth than mock and vehicle controls.

FIG. 17B, shows a similar trend for cells that co-express Tbet and Blimp-1, which are transcription factors correlated with T cell exhaustion.

FIG. 25 provides a table of nucleic acid and amino acid sequences useful in embodiments of the invention described herein.

DEFINITIONS

Figure 1:
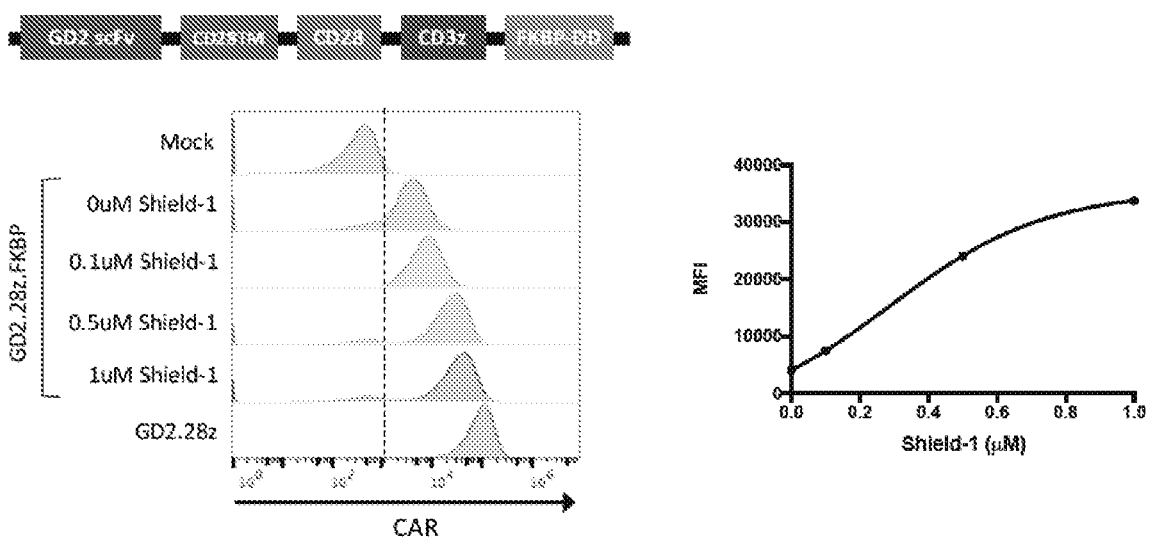
FIG. 1: Characterization of the GD2.28z.FKBP CAR. T cells were transduced with lentivirus encoding the GD2.28z.FKBP CAR on day 1 after activation and subsequently cultured with various concentrations of shield-1 in the growth medium. On day 7, CAR expression was quantified via FACS.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

"T cell exhaustion" refers to decrease of T cell function, which may occur as a result of an infection (e.g., a chronic infection) or a disease. T cell exhaustion is associated with increased expression of PD-1, TIM-3, and LAG-3, apoptosis, and reduced cytokine secretion. Accordingly, the terms "ameliorate T cell exhaustion," "inhibit T cell exhaustion," "reduce T cell exhaustion" and the like refer to a condition of restored functionality of T cells characterized by one or more of the following: decreased expression and/or level of one or more of PD-1, TIM-3, and LAG-3; increased memory cell formation and/or maintenance of memory markers (e.g., CD62L); prevention of apoptosis; increased antigen-induced cytokine (e.g., IL-2) production and/or secretion; enhanced cytotoxicity/killing capacity; increased recognition of tumor targets with low surface antigen; enhanced proliferation in response to antigen.

As used herein, the terms "antigen-binding domain," as in "GD2-binding domain" may refer to any antigen-specific biding domain (e.g., GD2 specific binding domain) known to one of skilled in the art. In one example, a GD2 binding domain comprises a single-chain variable fragment (scFv) comprising the variable regions of the heavy ($V_H$) and light chains ($V_L$) of an antibody binding specifically to GD2. Anti-GD2 antibodies, antibody fragments, and their variants are well known in the art and include, for example, 14G2a, ch14.18, hu14.18K322A, m3F8, hu3F8-IgG1, hu3F8-IgG4, HM3F8, UNITUXIN, DMAb-20 or any other antibody that binds with specificity to GD2. In one embodiment, the GD2 binding domain is a homologue, a variant, an isomer, or a functional fragment of an anti-GD2 antibody. Each possibility represents a separate embodiment of the present invention.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies may be multimers of individual immunoglobulin molecules.

The antibodies of the present invention may exist in a variety of forms including, for example, polyclonal antibodies, monoclonal antibodies, Fv, Fab and F(ab)$_2$, as well as single chain antibodies, human antibodies, and humanized antibodies (see Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and preferably refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. Kappa and lamda light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. Moreover, a skilled artisan will understand that an antigen need not be encoded by a "gene" at all. It is readily apparent that an antigen can be generated, synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, antibodies (or antigen-binding portions thereof), and CAR T cells of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual. "Allogeneic" refers to a graft derived from a different animal of the same species. "Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as used herein, includes a molecule on an antigen presenting cell (APC) (e.g., dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

An "effective amount" as used herein, means an amount which provides a therapeutic or prophylactic benefit.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of a disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system. As used herein, the term "exogenous" refers to any material introduced from or produced outside an organism, cell, tissue or system.

The term "expression" as used herein relates to the transcription and/or translation of a particular nucleotide sequence driven by its promoter. "Expression" also refers to the presence of a protein on the surface of a cell (e.g., CAR expression on the surface of a T cell).

The term "transfected" or "transformed" or "transduced" as used herein refers to a process by which exogenous nucleic acid is transferred or introduced into a host cell. A "transfected" or "transformed" or "transduced" cell is one that has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A "lentivirus" as used herein refers to a genus of the Retroviridae family. Lentiviruses are unique among the retroviruses in being able to infect non-dividing cells. Lentivirus-derived vectors can deliver a significant amount of genetic information into the DNA of a host cell, so they are one of the most efficient methods of a gene delivery vector. HIV, SIV, and FIV are all examples of lentiviruses.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the B cell receptor (BCR) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence. As used herein, the term "promoter/regulatory sequence" means a nucleic acid sequence required for expression of a gene product operably linked to the promoter/regulatory sequence. In some instances, this sequence may be the core promoter sequence and in other instances, this sequence may also include an enhancer sequence and other regulatory elements required for expression of the gene product. The promoter/regulatory sequence may, for example, be one that expresses the gene product in a tissue specific manner. A "constitutive" promoter is a nucleotide sequence which, when operably linked with a polynucleotide encoding a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide encoding a gene, causes the gene product to be produced in a cell substantially only if the cell is a cell of the tissue type corresponding to the promoter.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

By the term "modulating," as used herein, refers to mediating a detectable increase or decrease in the level of an activity in a subject (e.g., a response in a subject or the expression of a protein in a cell). Modulating the level of activity can occur in the presence of a treatment or compound, or in the absence of the treatment or compound. By way of example, to modulate the level of chimeric antigen receptor (CAR) expression on the surface of a CAR T cell genetically modified with a CAR containing a regulatable destabilization domain (RDD) means to increase CAR expression via exposure of the CAR T cell to a small molecule/drug that stabilizes the RDD compared with the level of CAR expression in the absence of the small molecule/drug. Similarly, it is possible to modulate the level of chimeric antigen receptor (CAR) expression on the surface of a CAR T cell genetically modified with a CAR containing a regulatable destabilization domain (RDD) by decreasing CAR expression via removal of the stabilizing small molecule/drug that stabilizes the RDD compared with the level of CAR expression in the presence of the small molecule/drug. The term encompasses perturbing and/or affecting a native signal or response or non-modulated expression thereby mediating a beneficial therapeutic response in a subject, preferably, a human.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein and are intended to include living organisms in which an immune response can be elicited (e.g., mammals). Examples of subjects include humans, dogs, cats, mice, rats, and transgenic species thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, enhanced expression of IL-2 and/or IFN-γ, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The terms "sensitize" and "sensitizing," as used herein, refer to making, through the administration of a first agent, an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors for developing cancer. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the type and/or stage of cancer is not known. The term further includes people who previously had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, etc.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue and the stage of the cancer.

DETAILED DESCRIPTION

The invention is based on the discovery that transient inhibition or modulation of TCR signaling, via modulation of chimeric antigen receptor (CAR) surface expression in CAR T cells, can prevent or reverse CAR T cell exhaustion and restore CAR T cell function. T cells that express CARs undergo tonic, antigen-independent signaling due to receptor clustering and replicate the fundamental biology of T cell exhaustion, as shown by high levels of PD-1, TIM-3, and LAG-3 expression, diminished antigen-induced cytokine production and excessive programmed cell death. A GD2.28z CAR fused to an FKBP12 destabilization domain (DD) (GD2.28z.FKBP) was generated and the regulatable DD (RDD) conferred instability to the CAR and induced rapid CAR protein degradation (see, Banaszynski et. al, Cell 2006). Surface expression was observed to be rapidly and dose-dependently regulated by adding or subtracting trimethoprim or the stabilizing rapalog shield-1 (S1) in culture medium. Similar regulatability of CAR expression was also accomplished using an *E. coli* DHFR mutant fused to the CAR (GD2.28z.DHFR), which was regulated in a dose-dependent manner with trimethoprim (see Examples 1 and 2, FIGS. 2, 12-13, 22-24).

Because tonic signaling is highly dependent upon CAR receptor levels in CAR T cells, control of CAR expression levels can be used to regulate the level of tonic signaling (e.g., in vitro or in vivo). Since tonic signaling is highly dependent upon CAR receptor levels, precise control of CAR expression levels also precisely regulated levels of tonic signaling. Drug regulated control of levels of CAR expression therefore allowed modulation of the duration and intensity of GD2.28z CAR tonic signaling. Using this system, phenotypic and functional changes associated with exhaustion were reversed upon cessation of CAR signaling (see Examples 1 and 2). Removal of the small molecule or drug (S1 or trimethoprim) from the culture medium and consequent removal of surface CAR on day 7 post-activation reversed canonical exhaustion marker expression to control levels by day 10 (see Example 1, FIG. 2). This was illustrated by measuring levels of PD-1/TIM-3/LAG-3 triple expressing cell which is highly specific for dysfunctional, exhausted T cells. By Day 10, increases in levels of triple expressing exhausted cells exist, but that removal of S1 on Day 7 resulted in normalization of these levels by Day 10. Similar results were obtained on day 14 (see Example 1).

Thus, in some embodiments, the invention provides the ability to control, with precision, CAR T cell signaling and/or activity via modulation of surface expression of CAR. For example, as detailed herein (see Example 2), the invention provides the ability to titrate down the dose of stabilizing drug, resulting in a rapid decrease of CAR expression, which in turn inhibits and/or eliminates CAR T cell signaling and/or activity.

Thus, in some embodiments, regulatable DD-CAR technology can be used to address several important challenges currently facing the field of CAR T cell therapy. First, the rapid on/off switching of DD-CAR surface expression in response to drug allows for precise regulation of CAR activity, and thus provides an opportunity to mitigate CAR T cell toxicity (e.g., cytokine release syndrome (CRS) or on-target off-tumor toxicity) while preserving the option to continue therapy once the toxicity has resolved (See Example 2). Second, expansion of CAR T cells in the absence of stabilizing drug prevents CAR tonic signaling and in turn enhances the functional capacity of these cells (See Example 2). Last, toggling DD-CAR expression in vivo via iterative drug dosing may be one method by which CAR T cell exhaustion is prevented or reversed and/or memory could be induced (See Example 2).

Accordingly, the invention provides CAR T cells modified to express a CAR fused to an RDD) (e.g., a FKBP RDD or a DHFR RDD) that provides control, in a dose- and time-dependent manner, over CAR expression on the surface of CAR T cells. The ability to control CAR expression on the surface of CAR T cells in turn permits the ability to maintain functionality of the CAR T cells under conditions in which unmodified CAR T cells (that is, CAR T cells lacking a CAR fused to an RDD domain) display T cell exhaustion or lack of functionality. In this way, compositions and methods of the invention find use in preventing exhaustion of CAR T cells and enhancement of CAR T cell functionality (e.g., activity against cancer or infectious disease).

The invention is not limited by the type of CAR T cells functionality maintained, regained or enhanced (e.g., prolonged). Indeed, compositions comprising CAR T cells modified to express a CAR fused to an RDD domain and methods utilizing the same may be used to maintain, regain, or enhance CAR T cell functionality including, but not limited to, cytotoxic activities against tumor cells; promotion of CAR T cell survival and function; induction of cytokine expression such as expression of interleukin-2 (IL-2) to promote T cell survival, expression of Fas Ligand (FasL) and/or tumor necrosis factor-related apoptosis inducing ligand (TRAIL) to induce tumor cell apoptosis, and/or to induce interferon (IFN)-gamma to activate innate immune responses (e.g., against cancer); and/or potentiate the induction of cell cycle arrest and/or apoptosis. In some embodiments, CAR T cells of the invention sensitize cancer cells to induction of cell cycle arrest and/or apoptosis, including cells that are normally resistant to such inducing stimuli.

Modification of CAR T cells to express a CAR fused to an RDD domain (e.g., mutant FKBP or DHFR) significantly enhanced functionality of CAR T cells exposed to conditions that induce CAR T cell exhaustion (See, e.g., Examples 1 and 2). While an understanding of a mechanism is not needed to practice the present invention, and while the present invention is not limited to any particular mechanism of action, reduction of expression of CAR on the CAR T cell surface prevents dysfunction of the CAR T cells associated with CAR T cell exhaustion. In some embodiments, use of a T cell modified to express a CAR comprising an RDD of the invention prolongs the anti-tumor response of the CAR T cell compared to CAR T cell expressing the same CAR but without the RDD.

Thus, the invention provides compositions and methods for reducing CAR T cell exhaustion comprising CAR T cells modified to express a CAR fused to an RDD domain (e.g., FKBP12 or mutant DHFR) thereby providing the ability to strictly regulate the level of CAR expression on the CAR T cell surface. The invention is not limited by the disease or condition that can be treated using modified CAR T cells of the invention. Indeed, the compositions and methods provided herein may be useful in the treatment of any disease for which increased activity of CAR T cells may provide a therapeutic benefit.

Accordingly, the invention provides a composition comprising CAR T cells modified to express a CAR fused to an RDD domain. The invention is not limited by the type of modified CAR T cell. In some embodiments, the CAR T cells are CD3+ T cells (e.g., CD4+ and/or CD8+ T cells). In certain embodiments, the CAR T cells are CD8+ T cells. In other embodiments, the CAR T cells are CD4+ T cells. In some embodiments, the CAR T cells are natural killer (NK) T cells. In some embodiments, the CAR T cells are gamma delta T cells. In some embodiments, the CAR T cells are alpha beta T cells. In some embodiments, the CAR T cells are a combination of CD4+ and CD8 T+ cells (e.g., that are CD3+). In certain embodiments, the CAR T cells are memory T cells. In certain embodiments, the CAR T cells are a combination of CD8+ T cells, CD4+ T cells, NK T cells, memory T cells, alpha beta T cells and/or gamma delta T cells. In some embodiments, the CAR T cells are cytokine-induced killer T cells. In some embodiments, the CAR T cells are tumor infiltrating lymphocytes. In some embodiments, the CAR T cells are engineered to express a tumor antigen specific CAR. In another embodiment, the CAR T cells are engineered to express a CAR specific for an infectious disease antigen. In some embodiments, the CAR T cells are anti-tumor T cells. In some embodiments, the composition further comprises a pharmaceutically acceptable carrier (e.g., buffer).

Thus, in one aspect, the present invention provides compositions and methods for treating cancer, among other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In some embodiments, the invention provides a T cell engineered to express a CAR wherein the CAR T cell exhibits an antitumor property. The CAR of the invention can be engineered to comprise an extracellular domain having an antigen-binding domain fused to an intracellular signaling domain of the CD3 zeta chain. The CAR of the invention when expressed in a T cell is able to redirect antigen recognition based on the antigen-binding specificity. An exemplary antigen is GD2 as this antigen is expressed on a variety of cancers including neuroblastoma, osteosarcomas and some sarcomas (see, e.g., Thomas et al., PLoS One, 2016. 11(3): p. e0152196; Long et al., Nature Medicine, 2015. 21(6): p. 581-590; Long et al., Cancer Immunology Research, 2016. 4(10): p. 869-880; Yu et al., N Engl J Med, 2010. 363(14): p. 1324-34; Perez Horta et al., Immunotherapy, 2016. 8(9): p. 1097-117; Heczey et al, Molecular Therapy). However, the invention is not limited to targeting GD2. Rather, the invention includes any antigen-binding moiety that when bound to its cognate antigen, affects a tumor cell so that the tumor cell fails to grow, is prompted to die, or otherwise is affected so that the tumor burden in a patient is diminished or eliminated. The antigen-binding moiety is preferably fused with an intracellular domain from one or more of a costimulatory molecule, a CD3 zeta chain, and an RDD.

The present invention provides chimeric antigen receptor (CAR) comprising an extracellular and intracellular domain. In some embodiments, the CAR of the invention is fully human. The extracellular domain comprises a target-specific binding element otherwise referred to as an antigen-binding moiety. The intracellular domain or otherwise the cytoplasmic domain comprises a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link domains (e.g., the transmembrane domain to either the extracellular domain or the cytoplasmic domain in the polypeptide chain). A spacer domain may comprise up to 300 amino acids, preferably 10 to 100 amino acids and most preferably 25 to 50 amino acids.

Chimeric Antigen Receptor Constructs

As described herein, a CAR T cell of the invention genetically modified to express a CAR fused to an RDD may contain a CAR that comprises a target-specific binding element otherwise referred to as an antigen-binding moiety. The choice of moiety depends upon the type and number of ligands that define the surface of a target cell. For example, the antigen-binding domain may be chosen to recognize a ligand that acts as a cell surface marker on target cells associated with a particular disease state. Examples of cell surface markers that may act as ligands for the antigen moiety domain of the CAR include those associated with viral, bacterial and parasitic infections, autoimmune disease and cancer cells.

As used herein, the term "antigen" refers to a molecule capable of being bound by an antibody or T-cell receptor. An antigen is additionally capable of inducing a humoral immune response and/or cellular immune response leading to the production of B and/or T lymphocytes. Embodiments of the present invention involve nucleic acids, including nucleic acids encoding an antigen-specific chimeric antigen receptor (CAR) polypeptide, including a CAR that has been humanized to reduce immunogenicity (hCAR), a transmembrane domain, one or more intracellular signaling domains (e.g., a costimulatory domain and/or CD3 zeta), and an RDD domain. It is contemplated that human CAR nucleic acids are human genes that enhance cellular immunotherapy for human patients. In certain embodiments, the CAR recognizes an epitope comprised of the shared space between one or more antigens. In some embodiments, the CAR is specific for a carbohydrate antigen.

Non-human antigen-binding regions have typically been used in constructing chimeric antigen receptors. However, a potential problem with using non-human antigen-binding regions, such as murine monoclonal antibodies, is the lack of human effector functionality. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, in some embodiments, antigen-binding regions of human antibodies are used (e.g., because they do not elicit strong a HAMA response). In some embodiments, the antigen-binding domains may be chimeric (i.e., human/mouse chimeras) or humanized to minimize such immunogenicity. However, in other embodiments, antigen-binding regions of murine antibodies are used.

In some embodiments, the CAR comprises: a) an extracellular domain comprising an antigen-binding region, b) a transmembrane domain, c) an intracellular signaling domain, and d) an RDD. For example, in some embodiments, the CAR comprises an anti-GD2 antigen-binding domain, a CD28 transmembrane domain, CD3-zeta, CD28 and/or 4-1BB stimulatory domain, and an RDD (e.g., a DHFR or FKBP DD). As described in detail herein, many different CARs containing an RDD and methods of using the same are made possible. In one embodiment, the CAR comprises a) an extracellular domain comprising an antigen-binding region comprising SEQ ID NO: 44, b) a transmembrane domain comprising SEQ ID NO: 48, c) an intracellular signaling domain comprising SEQ ID NO: 50 and/or SEQ ID NO: 52, and d) an RDD comprising SEQ ID NO: 54. In another embodiment, a CAR comprises a) an extracellular domain comprising an antigen-binding region comprising SEQ ID NO: 60, b) a transmembrane domain comprising SEQ ID NO: 64, c) an intracellular signaling domain comprising SEQ ID NO: 66 and/or SEQ ID NO: 68, and d) an RDD comprising SEQ ID NO: 70. In another embodiment, a CAR comprises a) an extracellular domain comprising an antigen-binding region comprising SEQ ID NO: 76, b) a transmembrane domain comprising SEQ ID NO: 80, c) an intracellular signaling domain comprising SEQ ID NO: 82 and/or SEQ ID NO: 84, and d) an RDD comprising SEQ ID NO: 86. In still another embodiment, a CAR comprises a) an extracellular domain comprising an antigen-binding region comprising SEQ ID NO: 92, b) a transmembrane domain comprising SEQ ID NO: 96, c) an intracellular signaling domain comprising SEQ ID NO: 98 and/or SEQ ID NO: 100, and d) an RDD comprising SEQ ID NO: 102. In another embodiment, a CAR comprises a) an extracellular domain comprising an antigen-binding region comprising SEQ ID NO: 108, b) a transmembrane domain comprising SEQ ID NO: 112, c) an intracellular signaling domain comprising SEQ ID NO: 114 and/or SEQ ID NO: 116, and d) an RDD comprising SEQ ID NO: 118. In another embodiment, a CAR comprises a) an extracellular domain comprising an antigen-binding region comprising SEQ ID NO: 124, b) a transmembrane domain comprising SEQ ID NO: 130, c) an intracellular signaling domain comprising SEQ ID NO: 132 and/or SEQ ID NO: 134, and d) an RDD comprising SEQ ID NO: 136.

Antigen-Binding Region

In certain embodiments, the binding region comprises complementary-determining regions (CDRs) of a monoclonal antibody, variable regions of a monoclonal antibody, and/or antigen-binding fragments thereof. A CDR is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor (e.g., antibody or TCR) that can come into contact with the antigen-each heavy and light chain contains three CDRs. Because most sequence variation associated with immunoglobulins and T-cell receptors are found in the CDRs, these regions are sometimes referred to as hypervariable domains.

A CAR may be engineered to target a tumor antigen of interest by way of engineering a desired antigen-binding moiety that specifically binds to an antigen on a tumor cell. As used herein, a "tumor antigen" or "hyperproliferative disorder antigen" or "antigen associated with a hyperproliferative disorder" or "cancer antigen," refers to antigens that are common to specific hyperproliferative disorders such as cancer. Exemplary antigens mentioned herein are included by way of example. The examples are not intended to be exclusive and further examples will be readily apparent to those of skill in the art.

Tumor antigens are moieties (e.g., proteins, carbohydrates, etc.) that are produced by tumor cells that elicit an immune response, particularly T-cell mediated immune responses. Thus, an antigen-binding moiety can be selected based on the particular type of cancer to be treated. Tumor antigens are well known in the art and include, for example, a glioma-associated antigen, carcinoembryonic antigen (CEA), beta-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, and other tumor antigens described herein or known in the art.

A tumor antigen may comprise one or more antigenic cancer antigens/epitopes associated with a malignant tumor. Malignant tumors express a number of proteins that can serve as target antigens for an immune attack. These molecules include but are not limited to tissue-specific antigens such as melanoma antigen recognized by T cells 1 (MART-1), tyrosinase and GP100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Still another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

The tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on some normal cells under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Examples of TSA or TAA include, but are not limited to, differentiation antigens such as MART-1/MelanA (MART-1), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/ neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO-1, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.291\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In some embodiments, intracellular tumor associated antigens are targeted, such as HA-1, survivin, WT1, and p53. This can be achieved by a CAR expressed on a T cell that recognizes the processed peptide derived from the intracellular tumor associated antigen in the context of HLA.

Depending on the desired antigen to be targeted, a CAR can be engineered to include the appropriate antigen-binding moiety specific to the desired antigen target. For example, if GD2 is the desired antigen that is to be targeted, an antibody for GD2 (e.g., 14G2a, ch14.18, hu14.18K322A, m3F8, hu3F8-IgG1, hu3F8-IgG4, HM3F8, UNITUXIN, DMAb-20 or any other antibody that binds with specificity to GD2) can be used as the antigen-binding moiety for incorporation into the CAR of the invention.

In some embodiments, the antigen is a pathogen-specific antigen. The invention is not limited by the type of pathogen-specific antigen. A pathogen-specific antigen may be from any pathogen including, but not limited to, a fungus, bacteria, or virus. Exemplary viral pathogens include those of the families of Adenoviridae, EpsteinBarr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis,* and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes,* and *Salmonella*. In one embodiment the pathogen receptor Dectin-1 is used to generate a CAR that recognizes the carbohydrate structure on the cell wall of fungi. T cells genetically modified to express a CAR based on the specificity of Dectin-1 recognize Aspergillus and target (e.g., inhibit) hyphal growth. In another embodiment, CARs are made based on an antibody recognizing viral determinants (e.g., the glycoproteins from CMV or Ebola) to interrupt viral infection and pathology.

In some embodiments, the invention includes a full length CAR cDNA or coding region. The antigen-binding regions or domain can comprise a fragment of the $V_H$ and $V_L$ chains of a single-chain variable fragment (scFv) derived from a particular human monoclonal antibody, such as those described in U.S. Pat. Nos. 7,109,304; 8,822,196; 9,868, 774; 9,790,282; 9,765,342; 9,624,306; 9,522,915; 9,359, 447; 9,845,362; 9,815,901; 9,777,061; 9,598,489; 9,394, 368; 9,446,105; and 9,334,330, each of which is incorporated herein by reference. The fragment can also be any number of different antigen-binding domains of a human antigen-specific antibody. In a more specific embodiment, the fragment is an antigen-specific scFv encoded by a sequence that is optimized for human codon usage for expression in human cells.

The antibody can be multimeric, such as a diabody or multimers. The multimers can be formed by cross pairing of the variable portion of the light and heavy chains into what has been referred to as a diabody (see Winter et al., Protein Eng. 1996 Mar;9(3):299-305). The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose (e.g., a single one of the Fc domains, e.g., either the CH2 or CH3 domain from human immunoglobulin, can be used). The hinge, CH2 and CH3 region of a human immunoglobulin that has been modified to improve dimerization can also be used.

The antigen-binding domain of a CAR can be any domain that binds to antigen including but not limited to monoclonal antibodies, polyclonal antibodies, synthetic antibodies, human antibodies, humanized antibodies, and fragments thereof. In some instances, it is beneficial for the antigen-binding domain to be derived from the same species in which the CAR will ultimately be used in. For example, for use in humans, it may be beneficial for the antigen-binding domain of the CAR to comprise a human antibody or fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, W098/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen. Anti-tumor antigen antibodies directed against the tumor antigen can be obtained from the immunized, transgenic mice using conventional hybridoma technology. The human immunoglobulin transgenes harbored by the transgenic mice rearrange during B cell differentiation, and subsequently undergo class switching and somatic mutation. For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen-binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen-binding. These framework substitutions are identified by methods well-known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties).

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen-binding.

A "humanized" antibody retains a similar antigenic specificity as the original antibody, i.e., in the present invention, the ability to bind human GD2. However, using certain methods of humanization, the affinity and/or specificity of binding of the antibody for human GD2 may be increased using methods of "directed evolution," as described by Wu et al., J. Mol. Biol., 294:151 (1999), the contents of which are incorporated herein by reference herein in their entirety.

In one embodiment, the antigen-binding moiety portion of the CAR of the invention targets GD2. In some embodiments, the antigen-binding moiety portion in the CAR of the invention is a fully human anti-GD2 scFV. In some embodiments, the nucleic acid sequence of the anti-GD2 scFV comprises the sequence set forth in SEQ ID NO: 43. In one embodiment, the anti-GD2 scFV comprises the nucleic acid sequence that encodes the amino acid sequence of SEQ ID NO: 44. In another embodiment, the anti-GD2 scFV portion of the CAR of the invention comprises the amino acid sequence set forth in SEQ ID NO: 44. In other embodiments, the nucleic acid sequence of the anti-GD2 scFV comprises the sequence set forth in SEQ ID NO: 87. In one embodiment, the anti-GD2 scFV comprises the nucleic acid sequence that encodes the amino acid sequence of SEQ ID NO: 88. In another embodiment, the anti-GD2 scFV portion of the CAR of the invention comprises the amino acid sequence set forth in SEQ ID NO: 88.

In other embodiments, the antigen-binding moiety portion of the CAR of the invention targets Her2. In some embodiments, the nucleic acid sequence of the anti-Her2 scFV comprises the sequence set forth in SEQ ID NO: 123. In one embodiment, the anti-Her2 scFV comprises the nucleic acid sequence that encodes the amino acid sequence of SEQ ID NO: 124. In another embodiment, the anti-Her2 scFV portion of the CAR of the invention comprises the amino acid sequence set forth in SEQ ID NO: 124.

In other embodiments, the antigen-binding moiety portion of the CAR of the invention targets CD19. In some embodiments, the nucleic acid sequence of the anti-CD19 scFV comprises the sequence set forth in SEQ ID NO: 11. In one embodiment, the anti-CD19 scFV comprises the nucleic acid sequence that encodes the amino acid sequence of SEQ ID NO: 12. In another embodiment, the anti-CD19 scFV portion of the CAR of the invention comprises the amino acid sequence set forth in SEQ ID NO: 12.

Transmembrane Domain

With respect to the transmembrane domain, the CAR can be designed to comprise a transmembrane domain that is fused to the extracellular domain of the CAR. In one embodiment, a transmembrane domain that naturally is associated with one of the domains in the CAR is used. In some embodiments, the transmembrane domain is selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions that find particular use in this invention include, but are not limited to, a transmembrane region derived from (i.e. comprise at least the transmembrane region(s) of) the alpha or beta chain of the T-cell receptor, CD28, CD3 zeta, CD3 epsilon, CD45, CD4, CDS, CD8, CD9, CD16, CD22, CD33, CD37, CD64, CD80, CD86, CD134, CD137, or CD154. In some embodiments, a variety of human hinges can be employed as well including the human Ig (immunoglobulin) hinge.

In some embodiments, the transmembrane domain is synthetic, in which case it comprises predominantly hydrophobic residues such as leucine and valine. In some embodiments, triplet of phenylalanine, tryptophan and valine will be found at each end of a synthetic transmembrane domain. Optionally, a short oligo- or polypeptide linker, preferably between 2 and 10 amino acids in length forms the linkage between the transmembrane domain and the cytoplasmic signaling domain of the CAR.

In one embodiment, the transmembrane domain in the CAR of the invention is the CD28 transmembrane domain. In one embodiment, the CD28 transmembrane domain comprises the nucleic acid sequence of SEQ ID NO: 15. In one embodiment, the CD28 transmembrane domain comprises the nucleic acid sequence that encodes the amino acid sequence of SEQ ID NO: 16. In another embodiment, the CD28 transmembrane domain comprises the amino acid sequence of SEQ ID NO: 16.

In some embodiments, a CD28 hinge region is attached to the CD28 transmembrane domain of the CAR. In one embodiment, the CD28 hinge domain comprises the nucleic acid sequence of SEQ ID NO: 13. In one embodiment, the CD28 hinge domain comprises the nucleic acid sequence that encodes the amino acid sequence of SEQ ID NO: 14. In another embodiment, the CD28 hinge domain comprises the amino acid sequence of SEQ ID NO: 14.

Intracellular or Cytoplasmic Domains

The intracellular signaling domain of a CAR of the invention is responsible for activation of at least one of the normal effector functions of the T cell in which the chimeric receptor has been placed. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus, the term "intracellular signaling domain" refers to the portion of a protein that transduces the effector function signal and directs the cell to perform a specialized function. While usually the entire intracellular signaling domain is employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal.

Examples of intracellular signaling domains include, but are not limited to, cytoplasmic sequences of the T cell receptor (TCR) and co-receptors that act in concert to initiate signal transduction following antigen receptor engagement, as well as any derivative or variant of these sequences and any synthetic sequence that has the same functional capability. It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from CD3 zeta, FcR gamma, FcR beta, CD3 gamma, CD3 delta, CD3 epsilon, CDS, CD22, CD79a, CD79b, and CD66d. In some embodiments, the cytoplasmic signaling molecule in the CAR of the invention comprises a cytoplasmic signaling sequence derived from CD3 zeta.

The cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3-zeta chain portion and a costimulatory signaling region or domain. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like. In some embodiments, the CARs described herein comprise an ITAM-containing CD3-zeta domain in combination with CD28 or 4-1BB as the co-stimulatory signaling element. In some embodiments, the CARs described herein comprise an ITAM-containing CD3-zeta domain in combination with at least one other costimulatory domain are within the scope of the invention.

An intracellular signaling domain may comprise CD3-zeta or any of its homologs (e.g., eta, delta, gamma, or epsilon), MB 1 chain, B29, Fc RIII, Fc RI, and combinations of signaling molecules, such as CD3-zeta and CD28, CD27, 4-1BB, DAP-10, OX40, and combinations thereof. Intracellular signaling portions of other members of the families of activating proteins can be used, such as FcγRIII and FcγRI (see, Gross et al. (1992), Stancovski et al. (1993), Moritz et al. (1994), Hwu et al. (1995), Weijtens et al. (1996), and Hekele et al. (1996) for disclosures of cTCR's using these alternative transmembrane and intracellular domains.

The cytoplasmic signaling sequences within the cytoplasmic signaling portion of the CAR of the invention may be linked to each other in any order. Optionally, a short oligo- or polypeptide linker, preferably between 2 and 10 amino acids in length may form the linkage. A glycine-serine doublet provides a particularly suitable linker. The antigen-specific extracellular domain and the intracellular signaling-domain may be linked by a transmembrane domain, such as the human IgG$_{4Fc}$ hinge and Fc regions. Alternatives include the human CD4 transmembrane domain, the human CD28 transmembrane domain, the human CD3-zeta transmembrane domain, or a cysteine mutated human CD3-zeta transmembrane, or other transmembrane domains from other human transmembrane signaling proteins, such as CD16 and CD8 and erythropoietin receptor.

In some embodiments, any part of the endogenous T cell receptor complex is utilized in the intracellular domain. One or multiple cytoplasmic domains may be employed, as so-called third generation CARs have at least two or three signaling domains fused together for additive or synergistic effect, for example.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB and/or OX-40.

In one embodiment, the cytoplasmic domain in a CAR of the invention comprises the signaling domain of CD28 and the signaling domain of CD3-zeta, wherein the signaling domain of CD28 comprises the nucleic acid sequence set forth in SEQ ID NO: 17 and the signaling domain of CD3-zeta comprises the nucleic acid sequence set forth in SEQ ID NO: 19. In one embodiment, the signaling domain of CD28 comprises the nucleic acid sequence that encodes the amino acid sequence of SEQ ID NO: 18. In another embodiment, the signaling domain of CD28 comprises the amino acid sequence of SEQ ID NO: 18. In one embodiment, the signaling domain of CD3-zeta comprises the nucleic acid sequence that encodes the amino acid sequence of SEQ ID NO: 20. In another embodiment, the signaling domain of CD3-zeta comprises the amino acid sequence of SEQ ID NO: 20.

Regulatable Destabilization Domain

The regulatable destabilization domain (RDD) of a CAR of the invention is utilized to modulate (e.g., reduce) in a time and/or dose dependent manner the expression of the CAR on the surface of a T cell. In this way, CAR T cell exhaustion can be prevented/inhibited or reversed leading to a maintained, regained or enhanced functionality (e.g., prolonged effector functions) of CAR T cells.

For example, in some embodiments, a CAR T cell genetically engineered to express a CAR containing an RDD (e.g., fused to the CAR) marks the CAR for ubiquitin mediated degradation, such that when in the presence of a stabilizing small molecule that binds the RDD, CAR degradation is prevented, and removal or absence of the stabilizing small molecule that binds the RDD allows CAR degradation to occur. In some embodiments, modulation of CAR protein levels and CAR surface expression via fusion of an RDD to the CAR reverses exhaustion of CAR T cells that have already developed the hallmarks of T cell exhaustion due to tonic CAR signaling. For example, CAR T cells that are exposed to the stabilizing small molecule demonstrate all of the phenotypic and functional hallmarks of T cell exhaustion. However, when the stabilizing small molecule is removed and CAR protein levels are reduced by protein degradation, the phenotypic and functional indicators of T cell exhaustion are reversed and T cell function is restored.

The invention is not limited to any particular RDD. Indeed, any RDD that confers CAR instability such that rapid CAR protein degradation occurs when the RDD is not stabilized by the presence of its cognate small molecule, yet whose structure or presence within the CAR does not disrupt CAR function may be used in the invention. A non-limiting example of an RDD is derived from the FK506 binding protein (FKBP), referred to herein as an FKBP DD (see Banaszynski et. al, Cell 2006). Surface expression of a CAR containing the FKBP RDD can be rapidly and dose-dependently regulated by adding or subtracting the stabilizing rapalog shield-1 (S1) to CAR T cells or to an organism treated with CAR T cells comprising an FKBP DD. Another non-limiting example of an RDD is derived from E. coli dihydrofolate reductase (DHFR), referred to herein as a DHFR DD, which can be rapidly and dose-dependently regulated with the stabilizing small molecule drug trimethoprim. As described herein, in some embodiments, CAR expression is achieved in vivo using a clinically established and well tolerated dose of trimethoprim (see Kremers et al., J Clin Pharmacol. 1974 Feb-Mar;14(2):112-7). For example, maximum expression of a CAR comprising the trimethoprim-controlled DHFR RDD occurred at about 500 nM of trimethoprim, well within the compound's EC50 of 50 nM. This is well within the mean steady-state plasma concentration of trimethoprim when taken 160 mg twice a day (1.72 µg/mL, about 6 µM). In some embodiments, CAR expression is achieved in vivo using a dose that is below a clinically established dose of trimethoprim.

In some embodiments, the DHFR DD is derived from E. coli DHFR. In some embodiments, the DHFR DD is derived from human DHFR. Similarly, the invention is not limited by the type RDD used. For example, any DHFR that contains mutations that achieve destabilization of the DHFR domain and any protein attached thereto may be used. For example, any RDD (DHFR or FKBP DD) that confers instability/destabilization such that rapid protein degradation occurs when the RDD is not stabilized, using for example trimethoprim or S1, yet whose structure or presence within a CAR does not disrupt CAR effector function can be used. In some embodiments, an E. coli DHFR DD of SEQ ID NO. 6 that contains mutations at amino acids 12 and 100 is used.

The invention is not limited by the location of the RDD within the CAR. For example, in some embodiments, an RDD is fused (e.g., genetically linked) on the N- or the C-terminus of the CAR. A CAR can be expressed with an RDD fused to an intracellular component of the CAR, fused to an extracellular component of the CAR, or fused to a hinge or transmembrane region. Exemplary intracellular components of the CAR include, but are not limited to, a co-stimulatory domain or the CD3-zeta domain. In some embodiments, the intracellular domain is the CD3-zeta domain.

The intracellular component of the CAR (e.g., CD3-zeta) may be linked to an RDD in a random or specified order. Optionally, a short oligo- or polypeptide linker, preferably between 2 and 10 amino acids in length may form the linkage.

CAR Expression Vectors and Genetically Modified T cells

The present invention encompasses a DNA construct comprising sequences of a CAR, wherein the sequence comprises the nucleic acid sequence of an antigen-binding moiety (e.g., a tumor antigen-binding domain or a pathogen antigen-binding domain) operably linked to the nucleic acid sequence of an intracellular domain which is operably linked to the nucleic acid sequence of an RDD. An exemplary intracellular domain that can be used in the CAR of the invention includes but is not limited to the intracellular domain of CD3-zeta, CD27, CD28 and the like. In some instances, the CAR can comprise any combination of CD3-zeta, CD28, 4-1BB, and the like. Exemplary DDs that can be used in the CAR of the invention include but are not limited to a DHFR DD and a FKBP DD.

In one embodiment, the CAR of the invention comprises anti-GD2 scFv, human CD28 hinge and transmembrane domain, and CD28 and CD3-zeta signaling domains. In one embodiment the anti-GD2 scFv is fully human. In one embodiment, the CAR of the invention comprises the nucleic acid sequence set forth in SEQ ID NO: 7. In another embodiment, the CAR of the invention comprises the nucleic acid sequence that encodes the amino acid sequence of SEQ ID NO: 8. In another embodiment, the CAR of the invention comprises the amino acid sequence set forth in SEQ ID NO: 8.

In some embodiments, the CAR of the invention comprises the nucleic acid sequence set forth in SEQ ID NO: 23. In another embodiment, the CAR of the invention comprises the nucleic acid sequence that encodes the amino acid sequence of SEQ ID NO: 24. In another embodiment, the CAR of the invention comprises the amino acid sequence set forth in SEQ ID NO: 24.

In other embodiments, a CAR of the invention comprises the nucleic acid sequence set forth in SEQ ID NO: 39. In another embodiment, the CAR of the invention comprises the nucleic acid sequence that encodes the amino acid sequence of SEQ ID NO: 40. In another embodiment, the CAR of the invention comprises the amino acid sequence set forth in SEQ ID NO: 40.

In still other embodiments, a CAR of the invention comprises the nucleic acid sequence set forth in SEQ ID NO: 55. In other embodiments, a CAR of the invention comprises the nucleic acid sequence that encodes the amino acid sequence of SEQ ID NO: 56. In other embodiments, the CAR of the invention comprises the amino acid sequence set forth in SEQ ID NO: 56.

In still other embodiments, a CAR of the invention comprises the nucleic acid sequence set forth in SEQ ID NO: 71. In other embodiments, a CAR of the invention comprises the nucleic acid sequence that encodes the amino acid sequence of SEQ ID NO: 72. In other embodiments, the CAR of the invention comprises the amino acid sequence set forth in SEQ ID NO: 72.

In other embodiments, a CAR of the invention comprises the nucleic acid sequence set forth in SEQ ID NO: 87. In other embodiments, a CAR of the invention comprises the nucleic acid sequence that encodes the amino acid sequence of SEQ ID NO: 88. In other embodiments, the CAR of the invention comprises the amino acid sequence set forth in SEQ ID NO: 88.

In other embodiments, a CAR of the invention comprises the nucleic acid sequence set forth in SEQ ID NO: 103. In other embodiments, a CAR of the invention comprises the nucleic acid sequence that encodes the amino acid sequence of SEQ ID NO: 104. In other embodiments, the CAR of the invention comprises the amino acid sequence set forth in SEQ ID NO: 104.

In some embodiments, a CAR of the invention comprises the nucleic acid sequence set forth in SEQ ID NO: 119. In other embodiments, a CAR of the invention comprises the nucleic acid sequence that encodes the amino acid sequence of SEQ ID NO: 120. In other embodiments, the CAR of the invention comprises the amino acid sequence set forth in SEQ ID NO: 120.

In some embodiments, the invention provides isolated nucleic acid segments and expression cassettes incorporating DNA sequences that encode a CAR fused to an RDD. Vectors of the present invention are designed, primarily, to deliver desired genes to immune cells, preferably T cells under the control of regulated eukaryotic promoters, for example, EF1α promoter MNDU3 promoter, CMV promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

CAR molecules fused to an RDD are recombinant and are distinguished by their ability to both bind antigen and transduce activation signals via immunoreceptor activation motifs (ITAM's) present in their cytoplasmic tails. CAR constructs utilizing an antigen-binding moiety (for example, generated from single chain antibodies (scFv)) afford the additional advantage of being HLA-independent in that they do not require an antigen be presented by a major histocompatibility complex (MHC) protein, but rather bind native antigen on the target cell surface in an HLA-independent fashion.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transponsons.

The expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence.

Expression constructs of the invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

Nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, lentivirus vectors are used. In other embodiments, adenovirus vectors are used. A number of adenovirus vectors are known in the art.

Additional promoter elements, e.g., enhancers, can be used to regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Individual elements can function either cooperatively or independently to activate transcription.

In some embodiments, the vector comprises a promoter. In some embodiments, the promoter is a constitutive promoter. In some embodiments, the constitutive promoter comprises the immediate early cytomegalovirus (CMV) promoter sequence. This promoter sequence is a strong constitutive promoter sequence capable of driving high levels of expression of any polynucleotide sequence operatively linked thereto. In some embodiments, the constitutive promoter comprises the eukaryotic translation elongation factor-1 alpha promoter sequence. In some embodiments, the constitutive promoter is selected from the group consisting of the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, and a Rous sarcoma virus promoter. In some embodiments, the constitutive promoter is selected from the group consisting of the actin I promoter, the myosin promoter, a hemoglobin promoter, and the creatine kinase promoter. In some embodiments, the promoter is an inducible promoter. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

In some embodiments, nucleic acids encoding the CAR constructs are delivered into cells using a lentiviral or retroviral vector. CAR-expressing lentiviral or adenoviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the desired CAR can be expressed in the cells by way of transponsons.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

Types and Sources of T Cells

In one aspect, the CAR T cells provided herein are autologous CAR T cells. In some embodiments, the autologous CAR T cells are manufactured from T cells obtained from a subject or patient to be treated. In some embodiments, the T cells obtained from a subject are isolated from samples comprising peripheral blood mononuclear cells, bone marrow, lymph node tissue, cord blood, thymus tissue, tissue from a site of infection, ascites, pleural effusion, spleen tissue, and tumors. In certain embodiments, any number of T cell lines available in the art, may be used. In certain embodiments of the present invention, T cells can be obtained from a unit of blood collected from a subject using any number of techniques known to the skilled artisan, such as FICOLL™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium, magnesium, and other divalent cations. After washing, the cells may be resuspended in a variety of biocompatible buffers, such as, for example, $Ca^{2+}$ free, $Mg^{2+}$-free PBS, PlasmaLyte A, or other saline solution with or without buffer. Alternatively, the undesirable components of the apheresis sample may be removed and the cells directly resuspended in culture medium.

In another embodiment, T cells are isolated from peripheral blood lymphocytes by lysing the red blood cells and depleting the monocytes, for example, by centrifugation through a PERCOLL™ gradient or by counterflow centrifugal elutriation.

Specific subpopulations of T cells can be further isolated by positive or negative selection techniques. Exemplary subpopulations of T cells include $CD3^+$, $CD28^+$, $CD4^+$, $CD8^+$, $CD45RA^+$, and $CD45RO^+$ T cells. For example, in one embodiment, T cells are isolated by incubation with anti-$CD3$/anti-CD28-conjugated beads, such as DYNABEADS™ M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan recognizes that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

T cells can also be frozen after a washing step. In some embodiments, the freeze and subsequent thaw step provides a more uniform product by removing granulocytes and to some extent monocytes in the cell population. After the washing step that removes plasma and platelets, the cells may be suspended in a freezing solution.

In certain embodiments, cryopreserved cells are thawed and washed as described herein and allowed to rest (e.g., for one hour or more) at room temperature prior to use according to the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of An anti-CD28 antibody such as B-T3, XR-CD28 (Diaclone, Besancon, France) can be used as can other methods commonly known in the art (see Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts.

In further embodiments of the present invention, T cells are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

For example, cell surface proteins may be ligated by allowing paramagnetic beads to which anti-CD3 and anti-CD28 are attached to contact the T cells. In one embodiment the cells (for example, $10^4$ to $10^9$ T cells) and beads (for example, DYNABEADS™ M-450 CD3/CD28 T paramagnetic beads at a ratio of 1:1) are combined in a buffer, preferably PBS (without divalent cations such as, calcium and magnesium). Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, may also be included. The target cells are maintained under conditions necessary to support growth, for example, an appropriate temperature (e.g., 37C.) and atmosphere (e.g., air plus 5% $CO_2$).

As described herein, CAR T cells tonically signal in the absence of tumor antigen when the CAR is expressed on the T cell surface. Tonic signaling is demonstrated by Western blotting in which the CAR CD3-zeta domain is phosphorylated at baseline (see Example 2, FIG. 16). Tonic signaling leads to T cell exhaustion, rendering the CAR T cells ineffective. Tonic signaling was prevented in RDD-CAR T cells by expanding them in the absence of stabilizing drug. When CAR expression was reduced or inhibited and not expressed on the T cell surface (in the absence of the appropriate small molecule—in this case, shield-1—the CAR is not expressed on the cell surface—"always OFF"), or if the CAR was expressed at one point but then removed from the surface for a period of time (e.g., 72 hours—CAR OFF D7), an attenuation in the CD3-zeta phosphorylation was observed. Furthermore, when the CAR is not expressed on the surface (no shield-1, "CAR always OFF"), or cultured in shield-1 for 7 days and then removed, only a fraction of cells that co-express exhaustion markers were observed (see Example 2, FIG. 17). Therefore, in some embodiments, the present invention provides that inhibiting CAR expression using an RDD-CAR of the invention has a profound effect on how CAR T cells are regulated on a transcriptional level by preventing or reversing CAR tonic signaling.

Accordingly, in some embodiments, because CARs tonically signal in the absence of antigen (e.g., during culture), expanding RDD-CAR T cells without stabilizing drug so that CAR expression on the surface is inhibited augments CAR T cell effector function when used therapeutically to treat a patient compared to T cells in which the CAR is continuously expressed (e.g., when expanded in vitro or ex vivo).

In some embodiments, suppression of CAR expression during expansion in vitro generates and/or leads to healthier, more functional CAR T cells (e.g., with normal effector function) compared to CAR T cells in which CAR expression during expansion in vitro is not suppressed. Thus, in some embodiments, CAR expression is modulated (e.g., reduced) in T cells containing a CAR of the invention comprising an RDD (e.g., DHFR DD regulated by trimethoprim) during culture and expansion by adding drug to increase expression or removing drug to decrease expression. In some embodiments, suppressing CAR expression during culture and/or expansion inhibits tonic signaling in vitro leading to or generating T cells with better effector function in the context in treating a condition or disease in a subject compared to T cells in which tonic signaling was not inhibited.

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Applications

The present invention provides, in some embodiments, a cell (e.g., T cell) modified to express a CAR that combines an antigen recognition domain of a specific antibody with an intracellular domain of CD3-zeta, CD28, 4-1BB, or any combinations thereof, and an RDD. Therefore, in the presence of its target antigen, the modified T cell elicits a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a subject comprising the step of administering to the subject a T cell that expresses a CAR, wherein the CAR comprises a binding moiety that specifically interacts with a predetermined target, a zeta chain portion comprising for example the intracellular domain of human CD3-zeta, a costimulatory signaling region, and an RDD.

In some embodiments, the present invention provides a cellular therapy where T cells are genetically modified to express a CAR containing an RDD and the CAR T cell is infused to a recipient in need thereof. The infused cell is able to kill tumor cells expressing the CAR T cell's target antigen in the recipient. Unlike other biologic therapies, CAR T cells are able to replicate in vivo resulting in long-term persistence that can lead to sustained tumor control. In some embodiments, a CAR T cell comprising a CAR including an RDD displays a prolonged anti-tumor response (e.g., compared to CAR T cell comprising a CAR lacking an RDD). In some embodiments, inclusion of an RDD within the CAR serves as a type of safety switch to inhibit CAR T cell activity/functionality (e.g., to mitigate CAR toxicity). For example, in some embodiments, removal of a stabilizing small molecule or drug (e.g., trimethoprim) from the CAR T cells results in rapidly reduced or inhibited expression of the CAR on the surface of the CAR T cell, thereby effectively shutting down or preventing targeting and effector functions of the CAR T cell. In particular, as shown in Example 2, the IC50 (the time it takes for 50% of surface CAR to be degraded), was observed to be less than 2 hours in the absence of stabilizing drug/molecule (see Example 2, FIG. 13). Therefore, in some embodiments, removing stabilizing drugs from patients who receive DD-CARs serves as a rapid and reversible safety switch. Thus, the invention provides, in some embodiments, the ability to mitigate or eliminate toxicity events that may occur with CAR T cell therapies, such as, but not limited to, cytokine release syndrome (CRS) or on-target off-tumor toxicity. Further, in the context of on-target off-tumor toxicity, in some embodiments, the invention makes possible the ability to titrate down the dose of stabilizing drug such that a CAR T cell therapy recognizes a desired target (e.g., tumor antigen) but not healthy tissue.

In one embodiment, the CAR T cells of the invention undergo robust in vivo T cell expansion and persist for an extended period of time. In another embodiment, the CAR T cells of the invention evolve into specific memory T cells that can be reactivated to inhibit any additional tumor formation or growth. For example, GD2-specific CAR T cells of the invention can undergo robust in vivo T cell expansion and persist at high levels for an extended amount of time in blood and bone marrow and form specific memory T cells.

The anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen-binding moiety in the CAR. For example, GD2-specific CAR T cells elicit an immune response specific against cells expressing GD2.

While the data disclosed herein specifically describe lentiviral vectors comprising anti-GD2 scFv (e.g. 14G2a scFv), CD28 hinge and transmembrane domain, CD28 and CD3-zeta signaling domains, and RDD of FKBP or DHFR, the invention should be construed to include any number of variations for each of the components of the construct as described elsewhere herein. That is, the invention includes the use of any antigen-binding moiety in the CAR to generate a CAR-mediated T-cell response specific to the antigen-binding moiety. For example, the antigen-binding moiety in the CAR of the invention can target a tumor antigen for the purposes of treating cancer. Similarly, the invention includes use of any hinge, transmembrane domain, stimulation domain and/or regulatable destabilization domain in a CAR to generate a CAR-mediated T-cell response. Indeed, methods described herein provide the ability to characterize and identify CAR T cells that possess desired effector functions and that are regulatable via the incorporation of an RDD into the CAR.

In one embodiment, the antigen bind moiety portion of the CAR of the invention is designed to treat a particular cancer. GD2 is expressed on a variety of cancers including neuroblastoma, osteosarcomas and some sarcomas (see, e.g., Thomas et al., PLoS One, 2016. 11(3): p. e0152196; Long et al., Nature Medicine, 2015. 21(6): p. 581-590; Long et al., Cancer Immunology Research, 2016. 4(10): p. 869-880; Yu et al., N Engl J Med, 2010. 363(14): p. 1324-34; Perez Horta et al., Immunotherapy, 2016. 8(9): p. 1097-117; Heczey et al, Molecular Therapy). Thus, CARs designed to target GD2 can be used to treat any disease or disorder, including neuroblastoma, osteosarcoma, and other sarcomas, characterized by cells and/or tissues displaying or overexpressing GD2. However, the invention is not limited to targeting GD2. Indeed, the invention includes any antigen-binding moiety that when bound to its cognate antigen, affects a tumor cell so that the tumor cell fails to grow, is prompted to die, or otherwise is affected so that the tumor burden in a patient is diminished or eliminated. For example, FRα is a glycosylphosphatidylinositol-anchored protein that is overexpressed on the surface of cancer cells in a variety of epithelial malignancies, but is limited in normal tissue. As such, CARs designed to target FRα can be used to treat any disease or disorders, including but not limited to epithelial cancers, characterized by cells and/or tissues displaying an overexpression of FRα. For example, the CAR designed to target FRα can be used to treat cancers and disorders including but are not limited to ovarian cancer, lung cancer, breast cancer, renal cancer, colorectal cancer, other solid cancers and the like.

The CAR-modified T cells of the invention may also serve as a type of vaccine for ex vivo immunization and/or in vivo therapy in a mammal. Preferably, the mammal is a human. With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

A procedure for ex vivo expansion of hematopoietic stem and progenitor cells is described in U.S. Pat. No. 5,199,942, incorporated herein by reference and can be applied to the cells of the present invention. The present invention is not limited to any particular method of ex vivo expansion of the cells. Briefly, ex vivo culture and expansion of T cells comprises: (1) collecting CD34+hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

In particular, the CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the CAR-modified T cells of the invention.

CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise CAR T cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). A pharmaceutical composition comprising the CAR T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by a person of ordinary skill in the art by monitoring the patient for signs of disease and adjusting the treatment accordingly.

In certain embodiments, it may be desired to administer genetically modified T cells to a subject and then subsequently redraw blood (or have an apheresis performed), activate T cells therefrom according to the present invention, and reinfuse the patient with these activated and expanded T cells. This process can be carried out multiple times every few weeks.

The administration of a composition described herein may be carried out in any convenient manner. In some embodiments, the T cell compositions of the present invention are preferably administered by i.v. injection. However, the administration is not limited only to this route. The compositions of T cells may be injected directly into a tumor, lymph node, or site of infection. The compositions described herein may be administered to a patient subcutaneously, intradermally, intratumorally, intranodally, intramedullary, intramuscularly, by intravenous (i.v.) injection, or intraperitoneally. Compositions may also be administered, for example, by injection, transfusion, implantation, or transplantation.

In certain embodiments of the present invention, cells activated and expanded using the methods described herein, or other methods known in the art where T cells are expanded to therapeutic levels, are administered to a patient in conjunction with (e.g., before, simultaneously or following) any number of treatment modalities (e.g., for cancer or infectious disease). Exemplary treatment modalities include, but are not limited to, treatment with agents such as antiviral therapy, cidofovir and interleukin-2, Cytarabine (also known as ARA-C) or natalizumab treatment for MS patients or efalizumab treatment for psoriasis patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The efficacy of any of the methods described herein may be tested in various models known in the art, such as clinical or pre-clinical models. Suitable pre-clinical models are exemplified herein. For any exemplary model, after developing tumors, mice are randomly recruited into treatment groups receiving treatment or control treatment. Tumor size (e.g., tumor volume) is measured during the course of treatment, and overall survival rate is also monitored.

In some embodiments, a sample is obtained prior to treatment with T cells (e.g., alone or in combination with another therapy described herein) as a baseline for measuring response to treatment. In some embodiments, the sample is a tissue sample (e.g., formalin-fixed and paraffin-embedded (FFPE), archival, fresh or frozen). In some embodiments, the sample is whole blood. In some embodiments, the whole blood comprises immune cells, circulating tumor cells and any combinations thereof.

Responsiveness to treatment may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see Eisenhauer et al., Eur J Cancer 2009;45: 228-47; Topalian et al., N Engl J Med 2012;366:2443-54; Wolchok et al., Clin Can Res 2009;15:7412-20; and Therasse, P., et al. J. Natl. Cancer Inst. 92:205-16 (2000). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria2 (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment >4 weeks from the date first documented.

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein. All publications, patents, and patent applications cited herein are hereby incorporated by reference in their entirety for all purposes.

EXAMPLES

The following examples illustrate but do not limit the compounds, compositions, and methods of the present invention. Other suitable modifications and adaptations of the variety of conditions and parameters normally encountered in clinical therapy and which are obvious to those skilled in the art are within the spirit and scope of the invention.

Example 1

A Method of Preventing or Reversing T Cell Exhaustion by Inhibiting or Modulating TCR Signaling Introduction We previously reported that GD2-CAR expressing T cells develop functional exhaustion within 10 days in culture and are characterized by co-expression of inhibitory receptors, failure to secrete cytokines in response to tumor antigen, and aberrant metabolic function (Long et. al, Nat Med 2015). Control cultures included untransduced T cells (mock) and those expressing CD19-CAR, which does not manifest tonic signaling or develop exhaustion in vitro. Previous work also demonstrated that the zeta chain was required for exhaustion in this system, with CD28 signaling enhancing the potency of the signaling stimulus in inducing exhaustion. Using this model system, we have now optimized a robust, manipulatable, and reproducible in vitro human model of T cell exhaustion to evaluate approaches to prevent or reverse T cell exhaustion.

Results

We engineered a GD2.28z CAR fused to an FKBP12 mutant destabilization domain (Banaszynski et. al, Cell 2006) (GD2.28z.FKBP) which confers its instability to the CAR and induces rapid protein degradation. We observed that surface expression could be rapidly and dose-dependently regulated by adding or subtracting the stabilizing rapalog shield-1 (S1) in culture medium (FIG. 1). Similar regulatability of CAR expression was also accomplished using an *E. coli* DHFR mutant (GD2.28z.DHFR, not shown), which could be regulated by trimethoprim, an antibiotic that is commonly used clinically.

Figure 2:
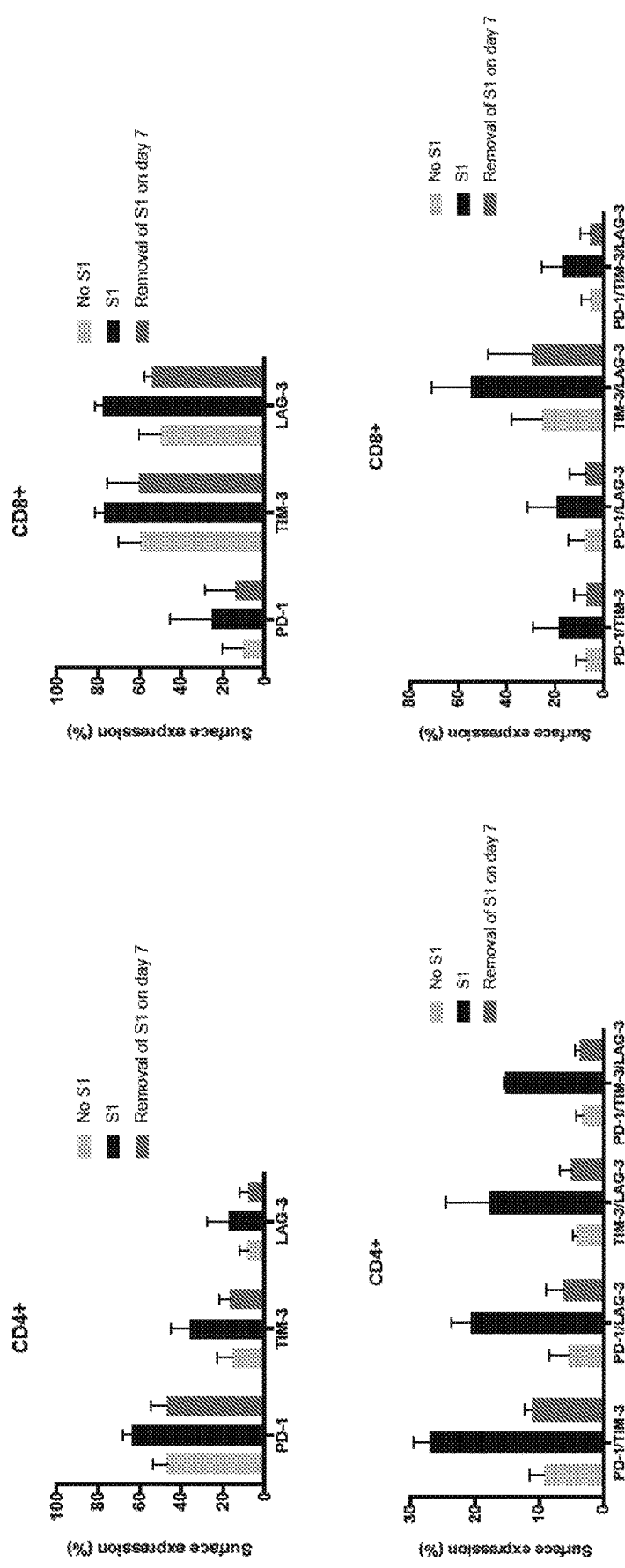
FIG. 2: Removal of S1 from culture medium results in reversal of T cell exhaustion marker surface expression.

Since tonic signaling is highly dependent upon GD2-CAR receptor levels, precise control of CAR expression levels also precisely regulates levels of tonic signaling. Drug regulated control of levels of CAR expression therefore also allowed modulation of the duration and intensity of GD2.28z tonic signaling. Using this system, we demonstrated that phenotypic and functional changes associated with exhaustion were reversed upon cessation of CAR signaling. As shown in FIG. 2, removal of S1 drug from the culture medium and consequent removal of surface CAR on day 7 post-activation reverses canonical exhaustion marker expression to control levels by day 10 (FIG. 2, n=3). This is most well illustrated by measuring levels of PD-1/TIM-3/LAG-3 triple expressing cell which is highly specific for dysfunctional, exhausted T cells. We demonstrate that Day 10 clear induces increases in levels of triple expressing exhausted cells, but that removal of S1 on Day 7 results in normalization of these levels by Day 10. Similar results were obtained on day 14 for cells in which S1 was removed from culture medium on day 7 or day 10 (not shown).

Figure 3:
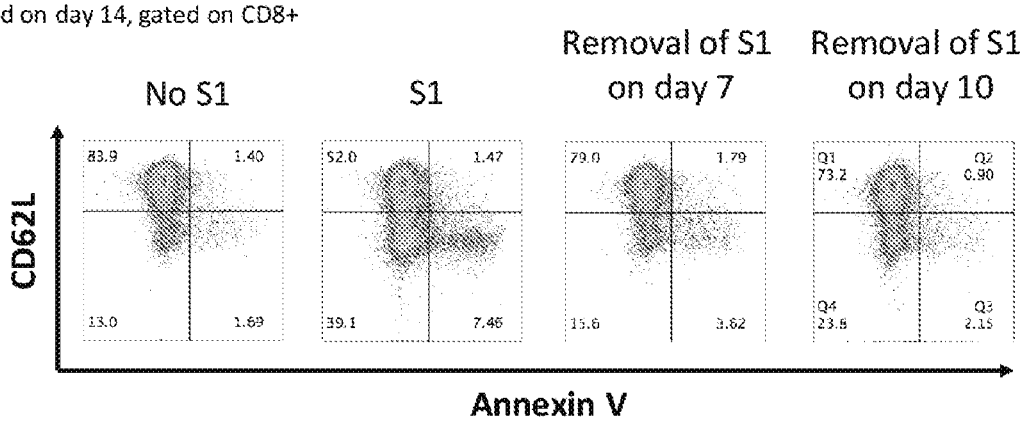
FIG. 3: Removal of S1 from culture medium results in maintenance of CD62L expression and prevention of apoptosis.

Additionally, removal of S1 on day 7 or 10, allow transient degradation of CAR proteins results in maintenance of memory markers (ex. CD62L) and prevention of apoptosis (i.e., annexin V staining) by day 14 compared to T cells that received S1 for the entire duration of the culture (S1) (FIG. 3).

Because phenotypic markers may not be entirely predictive of T cell function, we also performed functional experiments on CAR T cells provided transient drug exposure in culture. CAR T cells were washed, resuspended in media containing S1, and mixed at a 1:1 ratio with Nalm6 leukemic cells stably expressing surface GD2. Culture supernatants were harvested approximately 24 hours later and cytokine levels were evaluated via ELISA.

Figure 4:
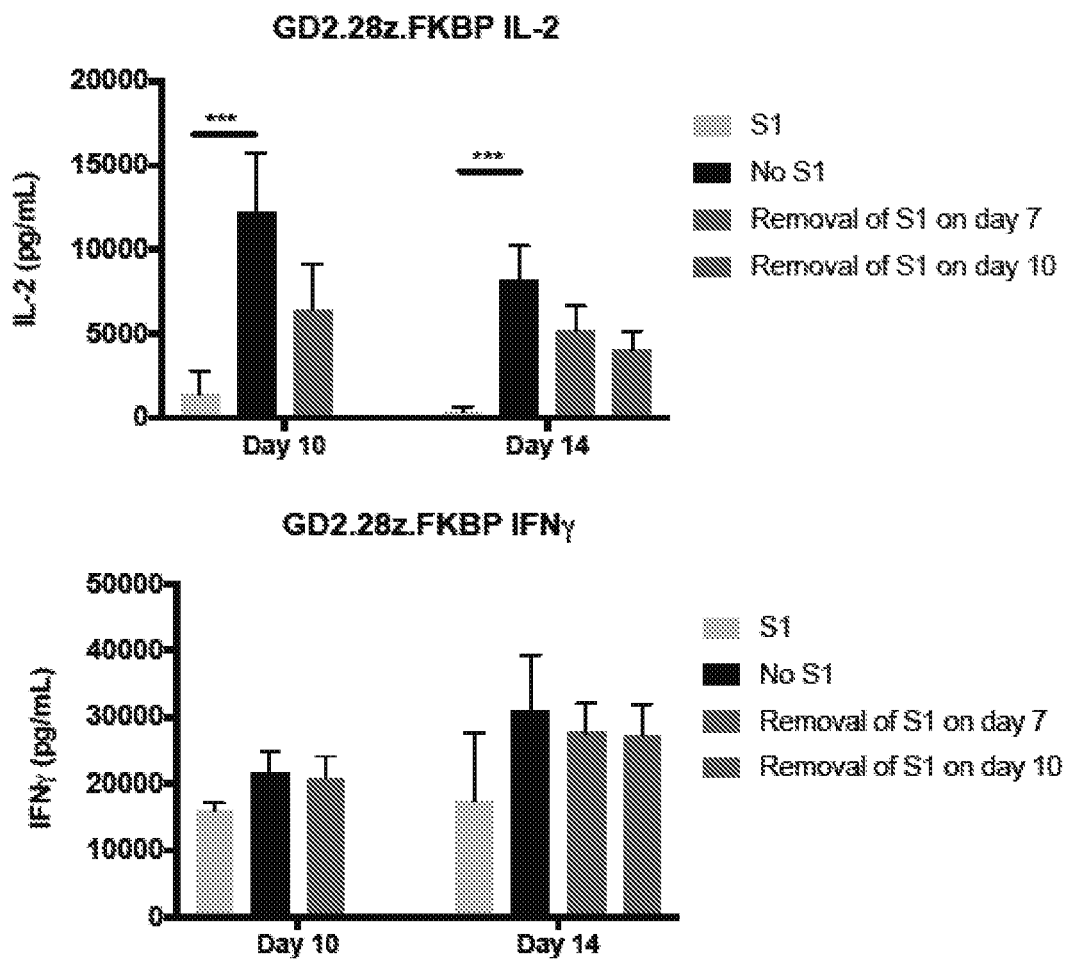
FIG. 4: Removal of S1 from culture medium results in reversal of function T cell exhaustion.

Similar to GD2.28z CAR that lacks a destabilization domain and therefore have persistent high levels of CAR signaling, cells expressing the GD2.28z.FKBP CAR that experienced continuous drug treatment (FIG. 4, grey bars) secreted minimal amounts of IL-2 on both day 10 and day 14 post-activation, consistent with T cell exhaustion. Alternatively, CAR T cells that were not exposed to drug during culture (black bars) and therefore did not experience tonic signaling demonstrated significant bioactivity as measured by IL-2 production. Finally, CAR T cells that were exposed to drug during the initial 7 or 10 days of culture and therefore acquired phenotypic and functional evidence of T cell exhaustion, but had drug removed from the culture medium on day 7 or day 10 (blue and red bars, respectively) displayed a restored capacity to secrete IL-2 in response to tumor antigen.

Remarkably, exhausted T cells on day 10 (grey bar, day 10 ELISA) could be reinvigorated by removing S1 from the culture medium and "rested" for only 4 days (red bar, day 14 ELISA). Similar, but less dramatic augmentation of IFNγ secretion in conditions in which S1 was removed from culture medium was also observed. These functional data cannot be attributed to differential CAR surface expression, as all groups exhibited similar levels of surface CAR at the conclusion of this co-culture assay (not shown).

Figure 5:
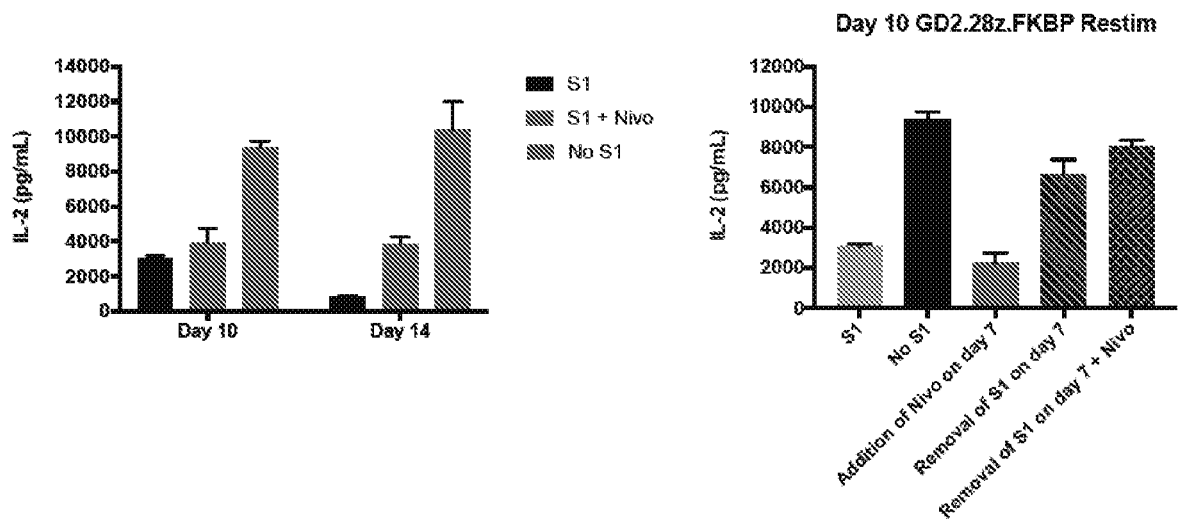
FIG. 5: Removal of surface CAR results in more effective prevention of T cell exhaustion compared PD-1/PDL-1 blockade.

We then compared whether prevention or reversal of T cell exhaustion by removal of surface CAR was more or less potent than treatment with well-characterized anti-PD-1 checkpoint inhibitor, nivolumab (Nivo). CAR T cells were either treated with continuous S1 (and thus exhibit continuous tonic signaling), continuous S1+ nivolumab, or no S1 until the time of the co-culture assay. Interestingly, nivolumab treatment resulted in only modest augmentation of IL-2 secretion at day 10, which was sustained until day 14, suggesting that nivolumab only partially prevented the onset of T cell exhaustion in this system (FIG. 5).

Conversely, culturing CAR T cells without S1, then adding it back to the medium just prior to the co-culture assay (left chart, blue bars), resulted in a far superior prevention of exhaustion, as IL-2 secretion was augmented 5-10 fold compared to CAR T cells that experienced continuous S1 (black bars). Further, removing tonic signaling on day 7 by removing S1 from the culture medium also resulted in superior IL-2 secretion compared to CAR T cells that experienced continuous S1, and those that experienced continuous S1 and were simultaneously treated with S1. Collectively, these data demonstrate that modulating tonic signaling exhibits more potent effects on prevention or reversal of exhaustion compared to PD-1 blockade.

Functional studies by several groups, including our lab have verified that co-expression of PD-1, TIM-3, and LAG-3 (triple positive, TP) denotes an exhausted cell subset that is highly dysfunctional. We thus sought to analyze whether cessation of tonic signaling in this cell subset could reverse their phenotype and restore their ability to secrete IL-2 in response to tumor antigen. A high affinity version of our GD2.28z CAR (HA-GD2.28z), which exhibits an even more dramatic exhausted phenotype, was fused to the FKBP12 mutant destabilization domain in order to control its surface expression. On day 10 post-activation, HA-GD2.28z.FKBP CAR T cells that had experienced continuous S1 treatment were sorted in order to isolate a pure PD-1/TIM-3/LAG-3 exhausted population. "Triple positive" exhausted cells were then re-cultured either with or without S1 to test whether removal of tonic signaling could restore their function. FACS and co-culture assays were conducted 4 days later.

Figure 6:
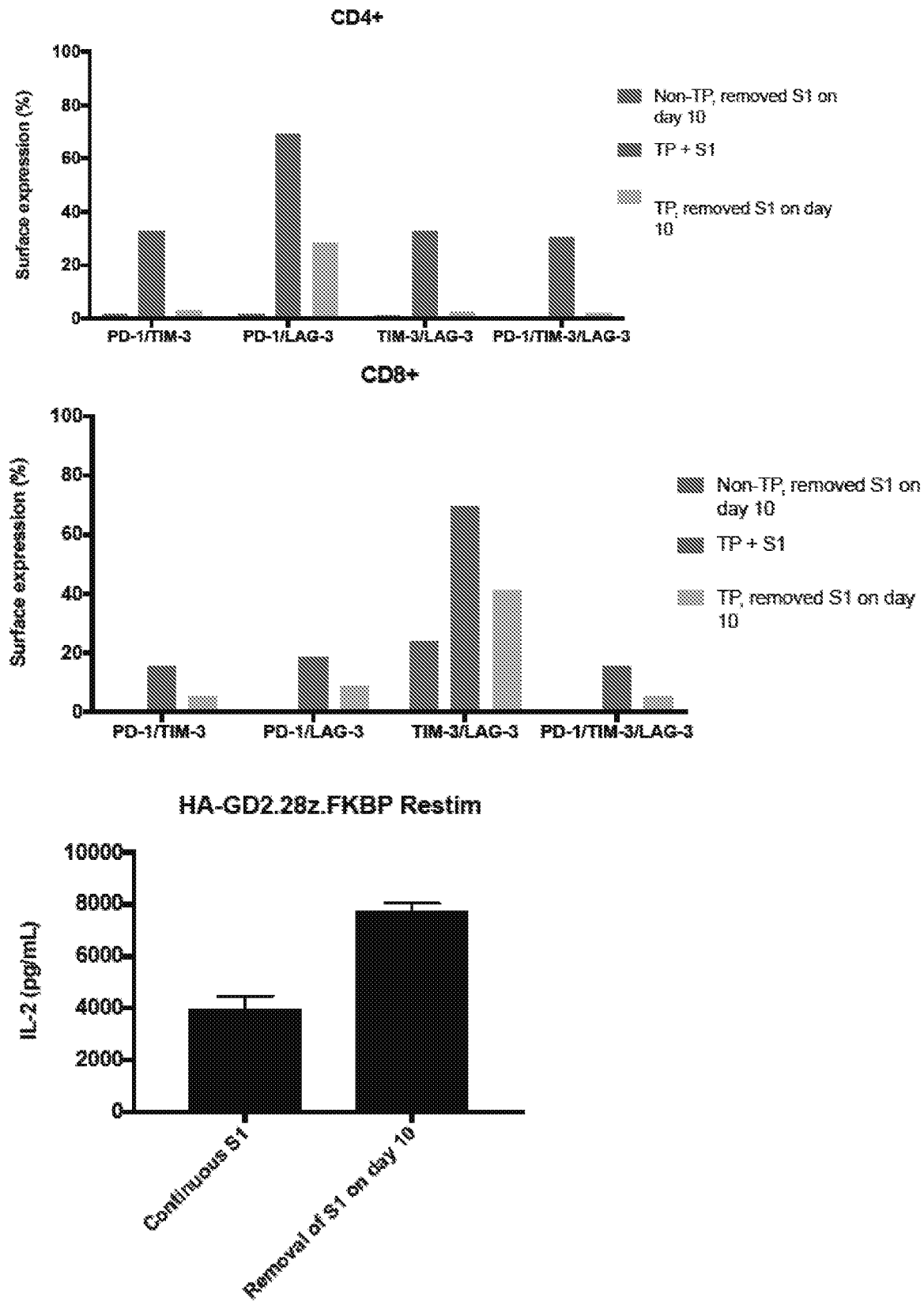
FIG. 6: Removal of surface CAR rescues exhaustion in PD-1/TIM-3/LAG-3 triple positive CAR T cells after only 4 days.

Removal of S1 resulted in a dramatic reversal of the exhausted phenotype. After only 4 days without S1 in the medium, pre-sorted triple positive cells exhibited far less expression of exhaustion markers in both CD4+ and CD8+ CAR T cells (FIG. 6). Importantly, these phenotypic changes also conferred functional augmentation in IL-2 secretion, as removal of S1 resulted in a 2-fold increase in IL-2 secretion compared to triple positive cells that received continuous S1 treatment from days 10-14 (FIG. 6).

We hypothesized that we could recapitulate the effects of removing surface CAR, and thus tonic signaling, by simply inhibiting kinases in the TCR signaling pathway that are also integral to CAR signaling. One such kinase is Lck, which acts to phosphorylate CD3-zeta in response to TCR or CAR ligation. Dasatinib, a potent receptor tyrosine kinase inhibitor and BCR/ABL antagonist, has also been shown to inhibit T cell activation, proliferation, and cytokine secretion by binding to and inhibiting Lck at low concentrations (Schade et. al, Blood, 2008 and Lee et. al, Leukemia, 2010).

Figure 7:
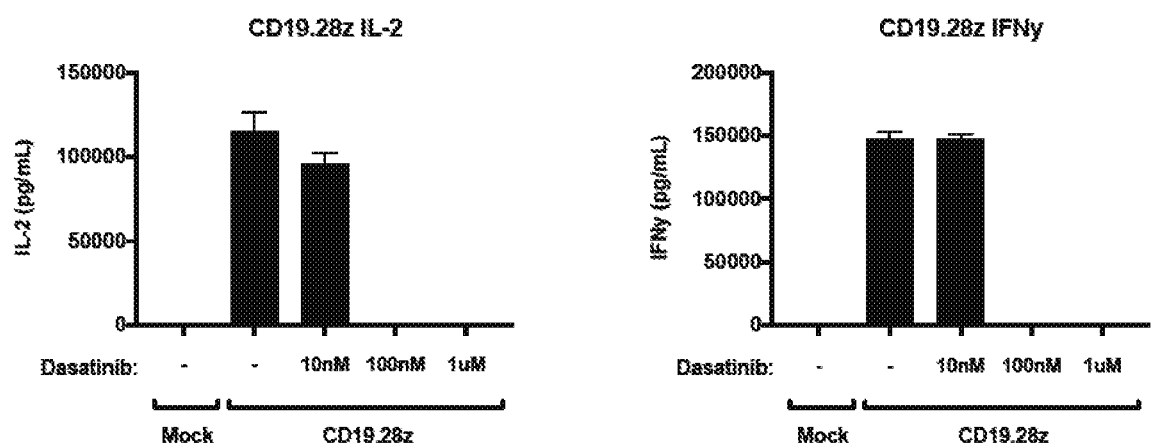
FIG. 7: Dasatinib inhibits cytokine secretion of CAR T cells in response to tumor antigen.

At 100 nM and 1 µM concentrations, dasatinib potently inhibits CD19.28z CAR T cell cytokine secretion in response to tumor antigen on day 14 post-activation (FIG. 7), proving that dasatinib disrupts CAR signaling.

Figure 8:
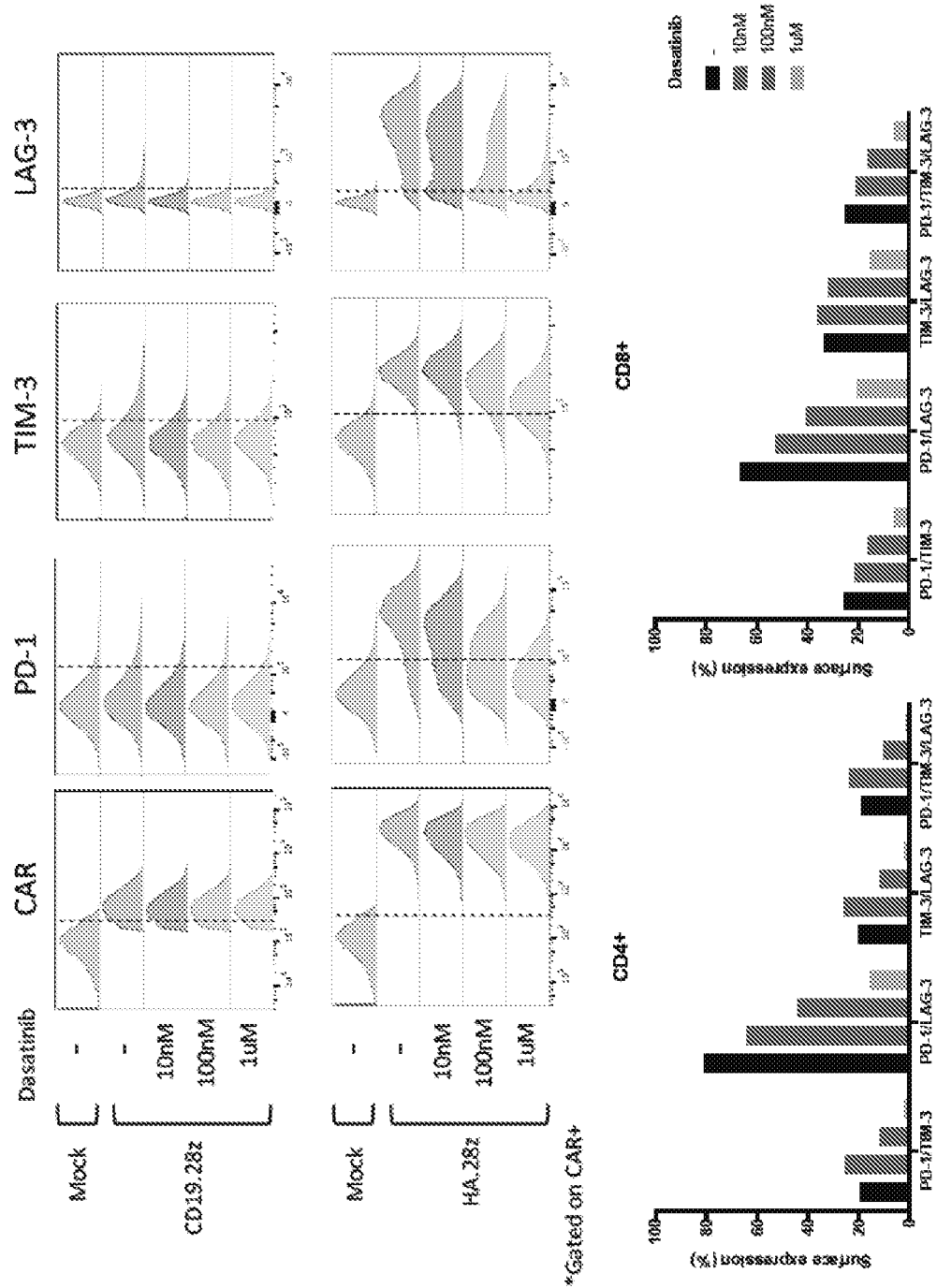
FIG. 8: Dasatinib reverses exhaustion marker expression and co-expression.

We then asked whether transient dasatinib exposure could reverse T cell exhaustion by treating HA-GD2.28z CAR T cells with dasatinib on days 10-14 post-activation. Cells were treated with dasatinib for 4 days, then drug was extensively washed from the media, and cells were re-cultured for an additional 24 hours before examining their phenotype and function via FACS and tumor co-culture assays. Interestingly, 4-day treatment with dasatinib reversed exhaustion marker expression and co-expression in a dose-dependent manner (FIG. 8).

Figure 9:
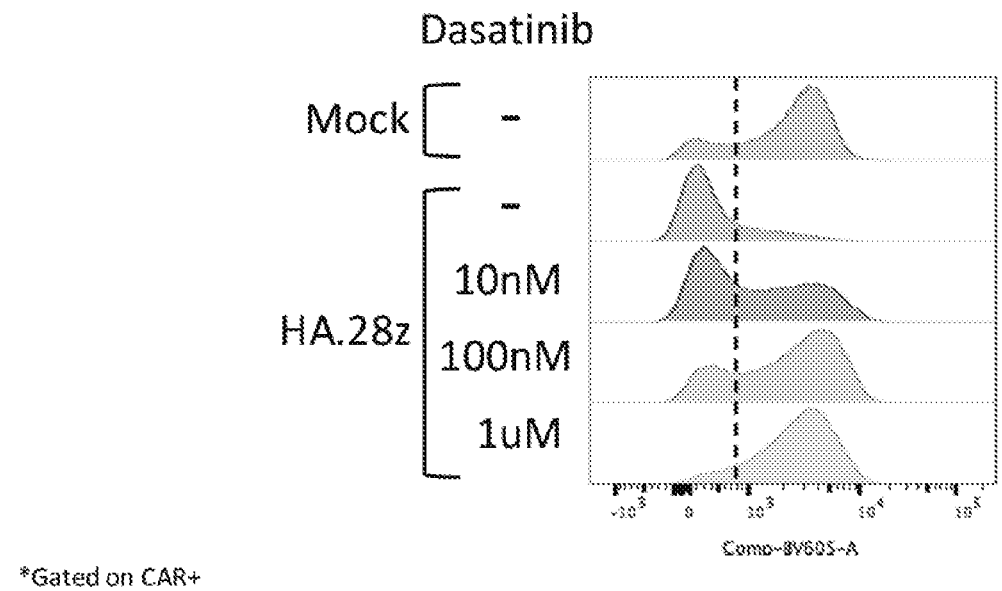
FIG. 9: Dasatinib treatment results in maintenance of CD62L expression.

Furthermore, dasatinib treatment resulted in preservation of T cell memory via maintenance of CD62L expression in a dose-dependent manner (FIG. 9.).

Figure 10:
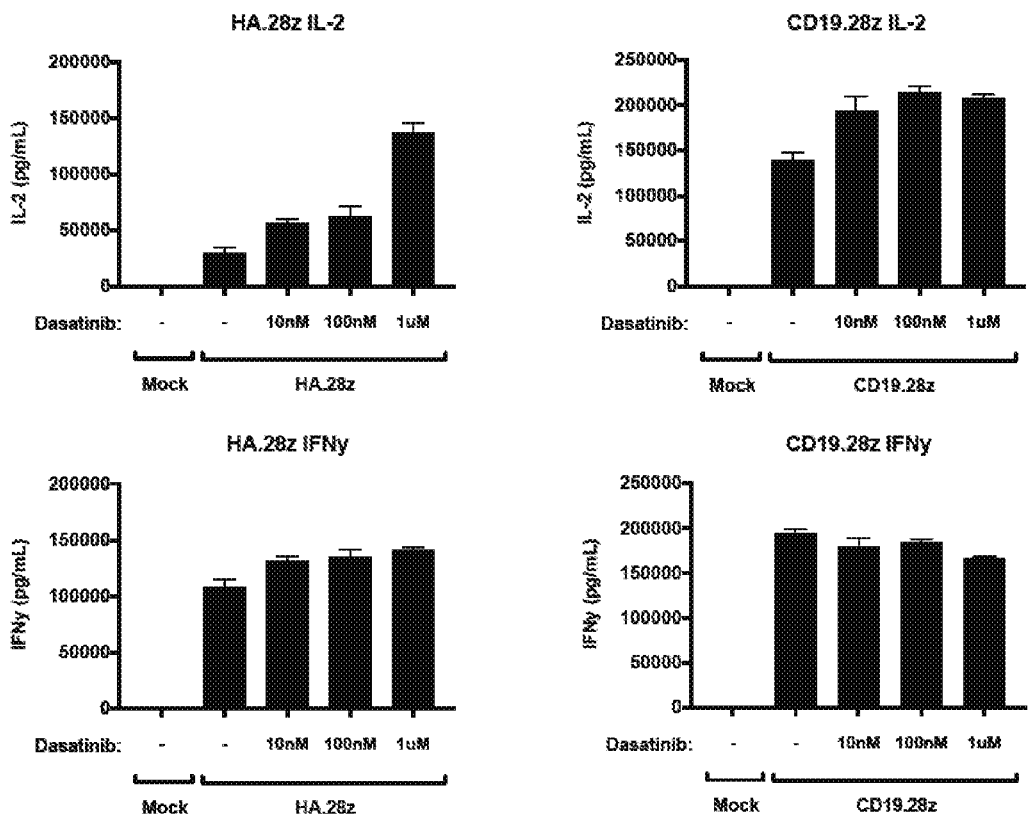
FIG. 10: Dasatinib Treatment results in augmented IL-2 and IFNγ secretion in response to tumor antigen.
Figure 11:
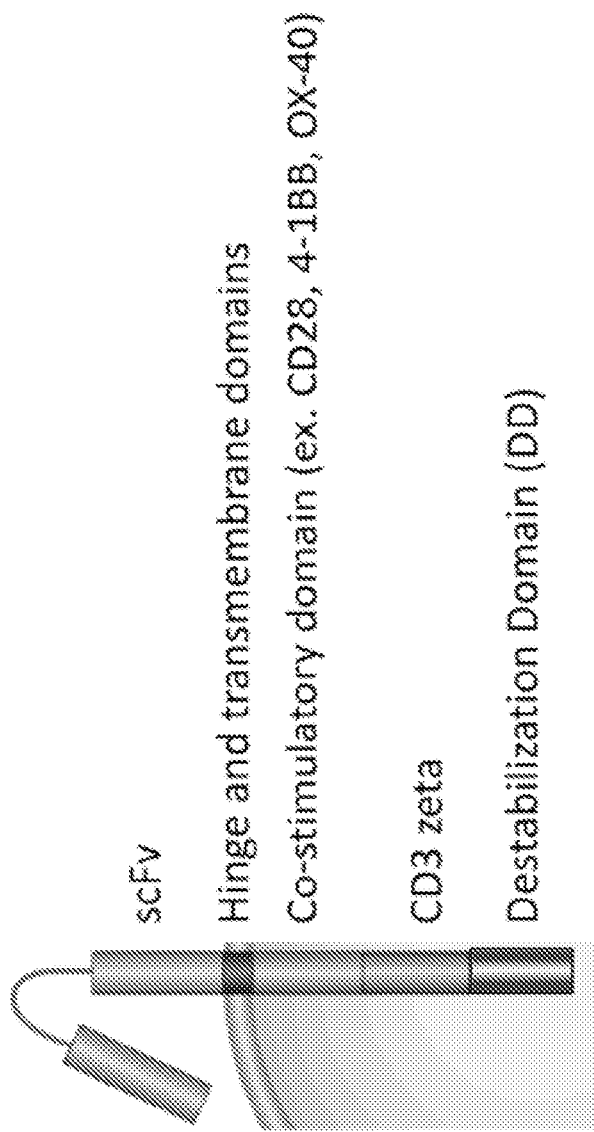
FIG. 11 depicts a schematic of a chimeric antigen receptor (CAR) in one embodiment of the invention. For example, the CAR may contain an extracellular antigen-binding domain (e.g., a single chain variable fragment (scFv)) and extracellular hinge region, a transmembrane domain, an intracellular co-stimulatory domain (e.g., containing CD28 or 4-1BB domains), an intracellular CD3 zeta domain, and a regulatable destabilization domain (RDD).
Figure 12:
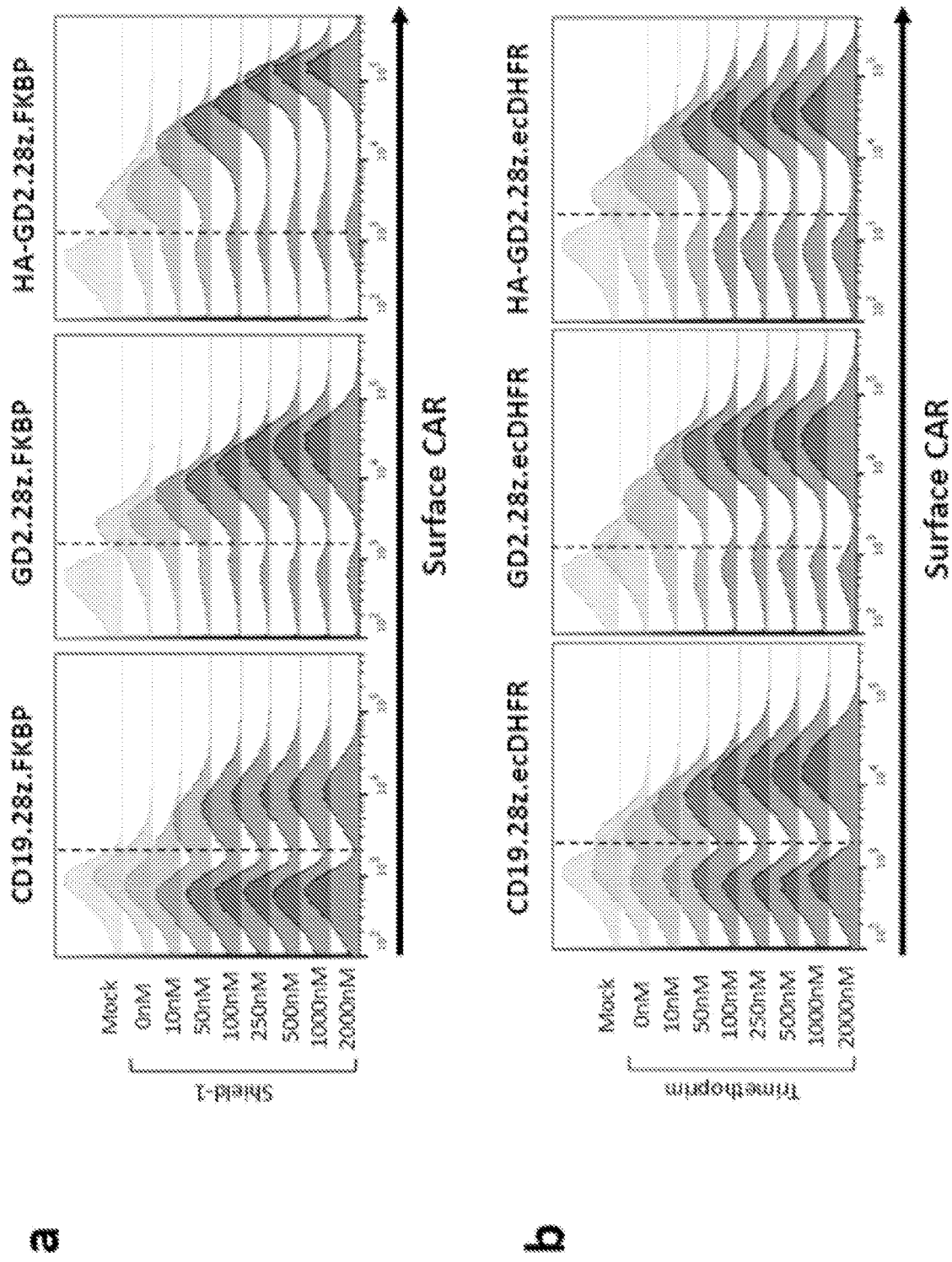
FIG. 12 shows dose-dependent regulation of several different CARs of multiple sizes containing an RDD fused at a C-terminus position. A) CARs fused to an FKBP12 DD that can be regulated by the rapalog shield-1. B) CARs fused to an *E. coli* derived DHFR DD that can be regulated by trimethoprim.
Figure 13:
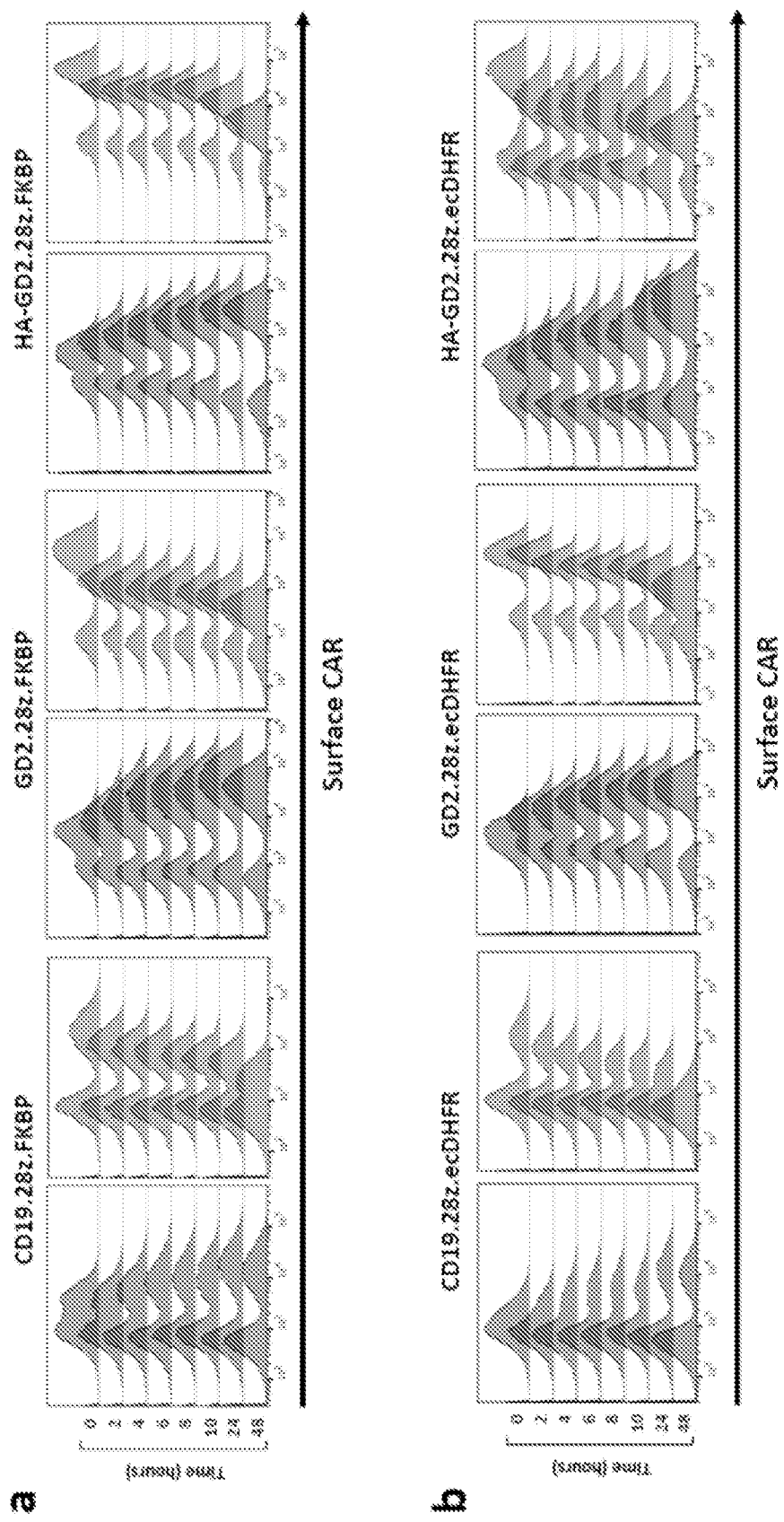
FIG. 13 shows rapid CAR protein stabilization or destabilization in the presence or absence of stabilizing drug/small molecule, respectively. In general, IC50, that is, the time it takes for 50% of surface CAR to be degraded, was less than 2 hours.

Finally, similar to removal of surface CAR, dasatinib treatment reinvigorated exhausted T cells in a functionally significant manner, as dasatinib-treated CAR T cells secreted more IL-2 (and to a lesser extent, IFNγ) in response to tumor antigen compared to those that never received dasatinib (FIG. 10).

Collectively, these data demonstrate that selective inhibition or modulation of TCR signaling can substantially enhance the function of exhausted T cells that experience continuous antigen exposure in the context of cancer or chronic infection. In future studies, we will conduct in vivo studies to assess the feasibility of exhaustion reversal in this setting and whether such reversal can enhance antitumor effects in murine models.

Example 2

Prevention of CAR T Cell Exhaustion and Enhancement of CAR T Cell Effector Function Via Introduction of a Destabilization Domain Into the CAR Experiments were conducted in order to test whether it would be possible to control CAR T cell activity by tuning CAR T cell surface expression, thus offering a method by which CAR T cells could be turned "off" in patients experiencing toxicity without completely eliminating the cells (in stark contrast to a suicide switch). Experiments were also conducted during development of embodiments of the invention in order to determine whether expansion of CAR T cells in the absence of surface CAR in vitro would allow mitigation of CAR tonic signaling, which may yield a healthier, more efficacious infusion product. Finally, experiments were conducted in order to test whether regulation of CAR surface expression using regulatable, drug-sensitive destabilization domains would allow for prevention or reversal of T cell exhaustion and/or maintenance/induction of T cell memory.

Materials and Methods

Cells and Culture Conditions

NALM6-GL (acute lymphoblastic leukemia line, stably transfected with GFP and luciferase) and NALM6-GL-GD2 (stably transfected to overexpress GD2 synthetase) cell lines were cultured in RPMI-1640. 293T and 143B cell lines were cultured in DMEM (Life Technologies). DMEM and RPMI-1640 were supplemented with 10% heat-inactivated FBS (Gibco, Life Technologies), 10mM HEPES, 100U/mL penicillin, 100 µg/ml streptomycin and 2 mM L-glutamine (Gibco, Life Technologies).

Primary human T cells were obtained from healthy donor buffy coats using a Pan T cell negative selection kit (Miltenyi Biotec). Donor T cells were then aliquoted and stored in Cryostor (StemCell Technologies) in liquid nitrogen. T cells were cultured in AimV (Gibco, Life Technologies) supplemented with 5% heat-inactivated FBS, 10mM HEPES, 1% glutamax (Gibco, Life Technologies), and 100 u/uL recombinant human IL-2 (Peprotech). Shield-1 and trimethoprim lactate (Sigma Aldrich or Alfa Aesar) were cultured at 1 µM unless otherwise specified.

Lentiviral Production and T Cell Transduction

All DD-CAR lentiviral supernatants were produced via transient transfection of the 293T cell line. Briefly, 293T cells were transfected via Lipofectamine 2000 (Life Technologies) with the plasmids encoding the CARs and plasmids encoding packaging proteins Gag-Pol, REV, and envelope protein VSVG. Supernatants were collected at 24 and 48 hours post-transfection and either immediately frozen or first concentrated via ultracentrifuge spin at 30,000 RPM and then frozen and stored at −80C.

Upon thawing, T cells were activated at a 3:1 bead: cell ratio using anti-$CD3$/anti-CD28-coated magnetic beads (Dynabeads, Thermo Fisher) at a concentration of $1 \times 10^6$ cells/mL. On day 1 post activation, lentivirus was added directly to the T cells. On day 4 post-activation, magnetic beads were removed from culture, and T cells were cultured at $0.5 \times 10^6$ cells/mL every day thereafter. Media supplemented with IL-2 and stabilizing drug was changed every two days. Transduction efficiencies were routinely 70-90% for all CARs.

Flow Cytometry

All samples were analyzed with an LSR Fortessa (BD Bioscience) or a Cytoflex (Beckman Coulter) and data were analyzed using FlowJo. Cells were washed twice with PBS and labelled with stain at $1 \times 10^6$ cells/mL in PBS, followed by two washes with FACS buffer (PBS supplemented with 2% FBS and 0.4% 0.5M EDTA). GD2 CARs were detected with the 14g2a anti-idiotype antibody (clone 1A7). CD19 CARs were detected with the FMC63 anti-idiotype antibody (clone 136.20.1). T cell phenotype was evaluated via: CD4 (OKT4, Biolegend), CD8 (SK1, Biolegend), PD-1 (eBioJ105, eBioscience), TIM-3 (F38-2E2, Biolegend), LAG-3 (3DS223H, eBioscience), CD45RO (UCHL1, eBioscience), CCR7 (150503, BD Biosciences), CD69 (FN50, Biolegend), IL-2 (MQ1-17H12, Biolegend), and IFNγ (4S.B3, Biolegend). For co-culture assays in which cytokine production was assessed, tumor cells and CAR T cells were co-cultured in the presence of 1:1000 monensin (eBioscience) for at least 6 hours. When assessing IL-2 and IFNγ, cells were surface stained, then fixed and permeablized (eBioscience) prior to incubation with intracellular antibodies. All FACS plots displaying CAR T cell phenotype data were pre-gated on CAR+ cells. For mock-transduced T cells, whole T cell populations were used for analysis.

CyTOF

T cells were removed from culture, fixed in 2% PFA for 10 minutes at room temperature, pelleted and frozen at −80C. Upon thawing, each sample was barcoded with a 20-plex Pd harcoding kit (Fluidigm). Cell samples were then pooled and stained for surface marker expression with heavy-metal conjugated antibodies for 30 minutes at room temperature. Cells were then permeablized in methanol and subsequently stained with heavy metal-conjugated anti-human T-bet (4B10, Biolegend) and anti-human Blimp-1 (ROS195G, Biolegend) for 30 minutes at room temperature. Samples were run on a Helios mass cytometer (Fluidigm) and analyses were complete using Cytobank online software.

Incucyte Assay 50,000 NALM6-GL-GD2 tumor cells were co-cultured with T cells at a 1:2 or 1:8 E:T ratio in 200 uL of complete AimV medium without IL-2 supplementation in each well of a 96-well plate. Plates were loaded into the incucyte and 488 nm fluorescent images were acquired every 2 hours for 48-72 hours. GFP+ tumor cells were identified by size and fluorescence intensity masks, and the total integrated GFP intensity of all counted tumor cells was quantified for each individual well. Values were normalized to t=0, and replicate wells were averaged for data display.

For experiments in which HA-GD2.28z.FKBP T cells were expanded in the absence of shield-1, 1 μM shield-1was added to CAR T cells 18-24 hours prior to co-culture with tumor cells.

Cytokine Release Assay 50,000 NALM6-GL-GD2 tumor cells were co-cultured with T cells at a 1:1 E:T ratio in 2004 of complete AimV medium without IL-2 supplementation in each well of a 96-well plate. After 24 hours, supernatants were removed and stored at -20C. IL-2 and IFNγ secretion was assessed via ELISA (Biolegend).

For experiments in which HA-GD2.28z.FKBP T cells were expanded in the absence of shield-1, 1 μM shield-1was added to CAR T cells 18-24 hours prior to co-culture with tumor cells.

Western Blot $2 \times 10^6$ CAR-T cells were removed from culture, pelleted, and resuspended in 100 uL of RIPA lysis buffer (10 mM Tris-Cl pH 8.0, 1 mM EDTA, 1% Triton X-100, 0.1% sodium deoxycholate, 0.1% SDS, 140 mM NaCl) supplemented with phosphatase and protease inhibitors (Thermo Fisher). After incubating for 30 minutes at 4C, supernatants were cleared by centrifugation at 14,000 RPM for 20 minutes at 4C. Protein concentration in the cleared lysates was measured by a colorimetric reaction (BioRad).

15 μg of protein lysate was mixed with 6× loading buffer and loaded onto 10% SDS-PAGE gels assembled into a mini-protean electrophoresis systems (BioRad). Electrophoresis was performed in tris-glycine-SDS buffer (BioRad) at 100V for 20 minutes and later increased to 150V for 50 minutes. Protein transfer into Immobilon-FL PVDF membranes was performed at 100V for 1 hour in tris-glycine buffer 1610771). Primary antibodies targeting CD3-zeta (Cell signaling) and pY142-CD3-zeta (Cell Signaling) were used. The Odyssey (LI-COR) imaging system, LI-COR buffers, and LI-COR secondary antibodies (Goat Anti-Mouse IgG Antibody-800CW-Conjugated and Goat Anti-Rabbit IgG Antibody-680LT-Conjugated) were used for protein detection.

In Vivo Experiments 6-8 week old NSG mice were engrafted with $1 \times 10^6$ NALM6-GL-GD2 via intravenous injection. At day 7 post-engraftment, $1-5 \times 10^6$ GD2.28z.DHFR or HA-GD2.28z.DHFR CAR+ T cells were infused intravenously. NALM6-GL-GD2 tumor burden was evaluated using the Xenogen IVIS Lumina (Caliper Life Sciences). Mice were first injected intraperitoneally with 3 mg D-luciferin (Caliper Life Sciences) and then imaged 4 minutes later with an exposure time of 30 seconds, or, in cases where 30 seconds resulted in signal saturation, "auto" exposure was selected. Luminescence images were analyzed using Living Image software (Caliper Life Sciences).

Mice treated with trimethoprim were injected intraperitoneally at a concentration of 300 mg/kg. Mice treated with vehicle were injected with an equivalent volume of water intraperitoneally.

Blood samples were taken via retro-orbital bleed and briefly stored in EDTA-coated microvettes (Kent Scientific). Spleens were mechanically disaggregated by passage through a 70-μm filter (BD Biosciences). Both blood and spleen were lysed in ACK lysis buffer (Fisher Scientific) for 5 minutes and subsequently stained with surface marker antibodies for FACS analysis.

Construction of CAR Vectors

All CAR sequences were inserted into the pELNS lentiviral backbone under the control of an EF-1 alpha promotor. Destabilization domain sequence insertion downstream of the CD3z domain was accomplished by subcloning a custom gene fragment (IDT Technologies) which included a portion of the CD3z sequence (beginning with the intrinsic BmgBI restriction site) followed by the destabilization domain sequence, a stop codon, and a SalI restriction site. The additional restriction sites not present in either the CD3z or DD sequences was avoided.

Each CAR includes a signal peptide, single chain variable fragment (scFv), extracellular hinge region, transmembrane domain, intracellular co-stimulatory domain, and intracellular CD3-zeta domain.

Results

First, the dose dependent regulation of DD-CAR surface expression was tested for 3 different CARs fused with two different RDDs. CD19.28z, GD2.28z, and a high-affinity GD2.28z (HA-GD2.28z) were each fused to a 12 kDa FK506 binding protein (FKBP) DD or an E. coli-derived dihydrofolate reductase (DHFR) DD. In separate experiments, regulation of a Her2.28z CAR fused to the FKBP DD (FIG. 24) was also tested. The rapalog shield-1 (S1) was used to stabilize FKBP-fused CARs, while the FDA-approved antibiotic trimethoprim (TMP) was used to stabilize DHFR-fused CARs. Stabilizing drug was incubated with DD-CAR T cells for at least 48 hours prior to assessing surface CAR expression via FACS. The data demonstrate precise dose-dependent regulation of surface CAR for all 7 of the CARs tested (See FIGS. 12, 24). The differential $EC_{50}$ values of the DD-CARs (FIG. 22B) demonstrate heterogeneity in the sensitivity of a given DD-CAR protein to the stabilizing drug, regardless of the DD to which the CAR was fused. These studies also demonstrate intrinsic differences in DDs, as each DHFR-fused CAR demonstrated greater sensitivity to stabilizing drug compared to its FKBP-fused counterpart (see FIG. 22). Furthermore, it was observed that not all RDDs confer instability to the CAR protein, even if they do so for other proteins (see FIG. 23). Two previously published iterations of the DHFR DD (see Iwamoto et al., Chemistry & Biology 17, 981-988 (2010)) were tested on the GD2.28z CAR, and one of them allowed for drug-dependent regulation (See FIGS. 12, 22, 23).

Next, the kinetics of the drug-dependent regulation of DD-CARs was tested and characterized. DD-CAR T cells were cultured either in the presence or absence of 1 uM stabilizing drug for at least 48 hours. For DD-CAR T cells cultured in the absence of drug, drug was introduced into the culture and samples removed over the course of 48 hours to assess the increase in CAR surface expression (See FIG. 13, left side of each plot). Conversely, for DD-CAR T cells cultured in the presence of drug, we removed drug from the culture to assess the decrease in CAR surface expression (See FIG. 13, right side of each plot). These studies indicated that DD-CAR surface expression increases gradually over the course of 24 hours subsequent to exposure to drug. However, removal of drug induced a rapid loss of approximately half of the DD-CAR surface expression within the first 2 hours, then a gradual loss of the remaining surface CAR over the next 46 hours. The rapid "off" kinetics of DD-CARs indicated that this method of CAR regulation provides a realistic therapeutic opportunity to mitigate CAR toxicity in a clinical setting.

Figure 14:
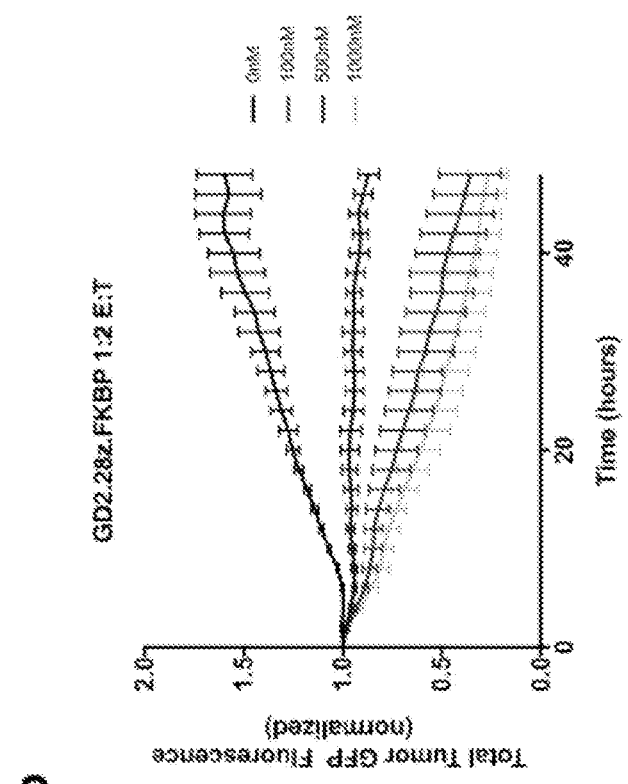
FIG. 14 shows that stabilizing drug regulates RDD-CAR anti-tumor activity. The absence of stabilizing drug results in low CAR surface expression in vitro with accompanying attenuated cytokine secretion in the response to tumor and attenuated cytotoxicity compared to CAR T cells cultured in the presence of stabilizing drug and high CAR surface expression.
Figure 14:
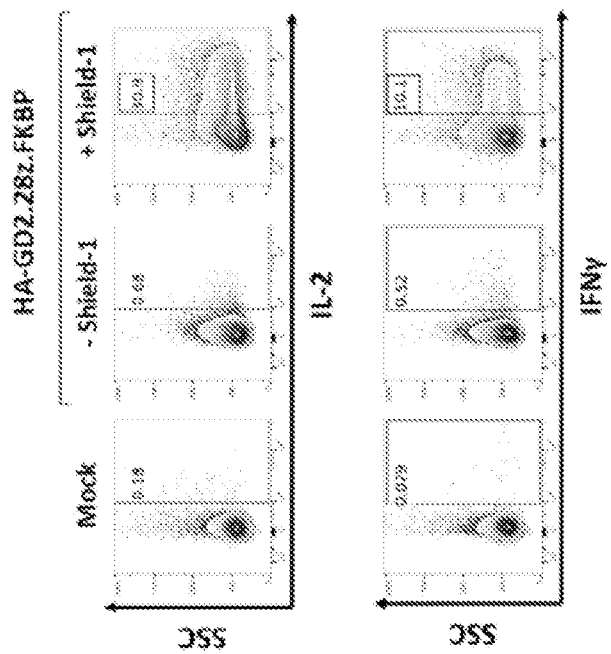

It was next determined whether the differences in DD-CAR surface expression would elicit differential anti-tumor responses. Therefore, it was assessed whether drug-dependent regulation of DD-CAR surface expression would also allow for regulation of T cell activation. Indeed, when DD-CAR T cells were co-cultured with antigen-bearing tumor cells in the absence of drug, negligible levels of cytokine secretion (see FIG. 14A) and cytotoxicity were observed (see FIG. 14B) compared to DD-CAR T cells co-cultured in the presence of stabilizing drug. Experiments were also conducted in an in vivo setting.

Figure 15:
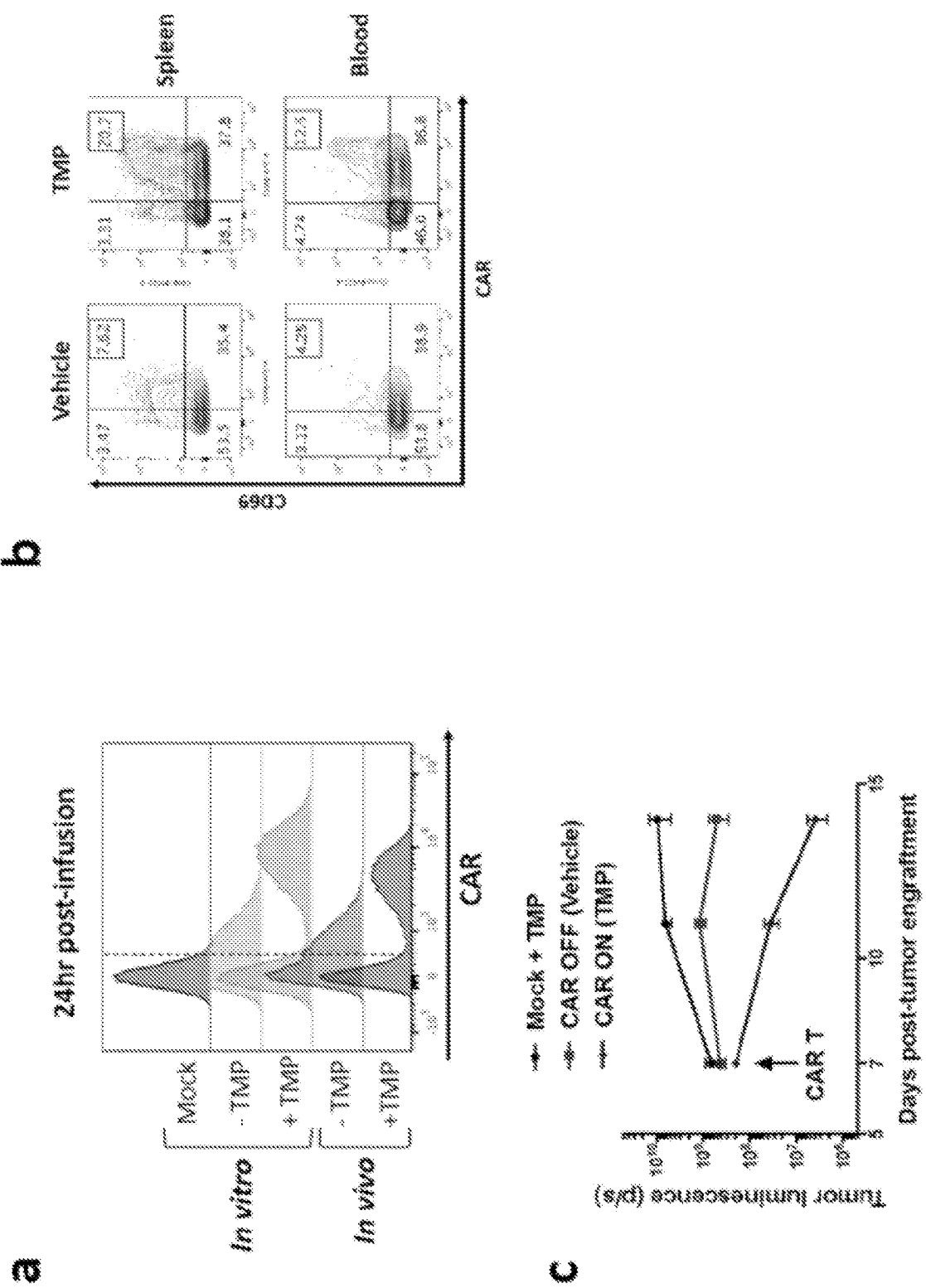
FIG. 15 shows that trimethoprim regulates CAR surface expression and activity of DHFR DD-CARs in vivo.

Mice were engrafted with antigen-bearing tumor and subsequently infused with CAR T cells. Mice were then injected with either stabilizing drug or vehicle control every day thereafter. After only 1 dose of stabilizing drug, drug-dependent upregulation of CAR expression was observed similar to that observed in vitro (See FIG. 15A). Higher levels of CD69 in mice dosed with stabilizing drug were also observed, indicating that the DD-CAR T cells with higher surface expression became more activated in response to tumor. Finally, after 7 days post-CAR infusion, a dramatic reduction in tumor burden was observed in mice receiving stabilizing drug versus those receiving vehicle control. Collectively, these data provide that CAR surface expression is intimately linked to CAR T cell activity, and thus, RDD-CAR T cell activity can be precisely tuned via administration (or lack thereof) of stabilizing drug.

Figure 16:
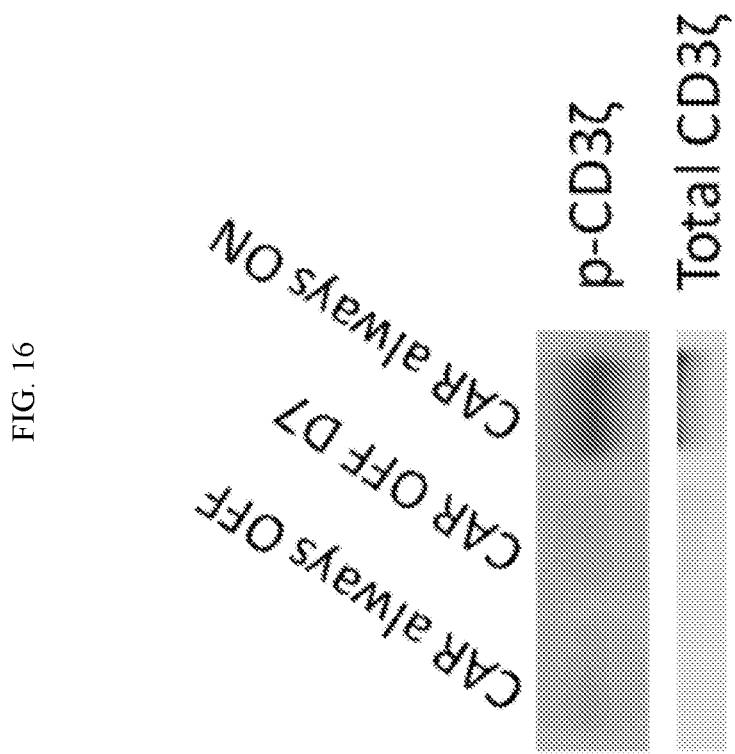
FIG. 16 shows that tonic signaling in HA-GD2.28z is prevented or reversed via a fused RDD. HA-GD2.28z.FKBP CAR tonically signals in the absence of tumor antigen when the CAR is expressed on the T cell surface evidenced by western blotting in which the CAR CD3 zeta domain is phosphorylated at baseline. The tonic signaling leads to T cell exhaustion, which renders these CAR T cells less effective. Tonic signaling is prevented in RDD-CAR T cells by expanding them in the absence of stabilizing drug. When CAR expression was reduced or inhibited and not expressed on the T cell surface (in the absence of shield-1, CAR always OFF), or if the CAR was expressed at one point but then removed from the surface for 72 hours (CAR OFF D7), an attenuation in CD3 zeta phosphorylation was observed.

As described herein, many constitutively expressed CARs exhibit tonic signaling in the absence of antigen, consequently driving them to become exhausted (see Long et al., Nature Medicine 21, 581-590 (2015)). It was determined whether expanding DD-CAR T cells in the absence of stabilizing drug would alleviate this tonic signaling and consequently yield a healthier, more potent CAR T cell infusion product. One readout for tonic signaling is the constitutive phosphorylation of the CAR CD3-zeta domain in the absence of antigen. HA-GD2.28z.FKBP CAR T cells exhibited this phenotype when cultured in the presence of S1 (see FIG. 16, CAR Always ON). However, CD3-zeta phosphorylation was absent in DD-CAR T cells cultured in the absence of S1 (CAR Always OFF), indicating that low CAR surface expression mitigates tonic signaling. This phenotype was also reversible, as indicated by the lack of CD3-zeta phosphorylation in DD-CAR T cells that were initially cultured with S1, but then had drug removed on day 7 of the culture (FIG. 16, CAR OFF D7).

Figure 17:
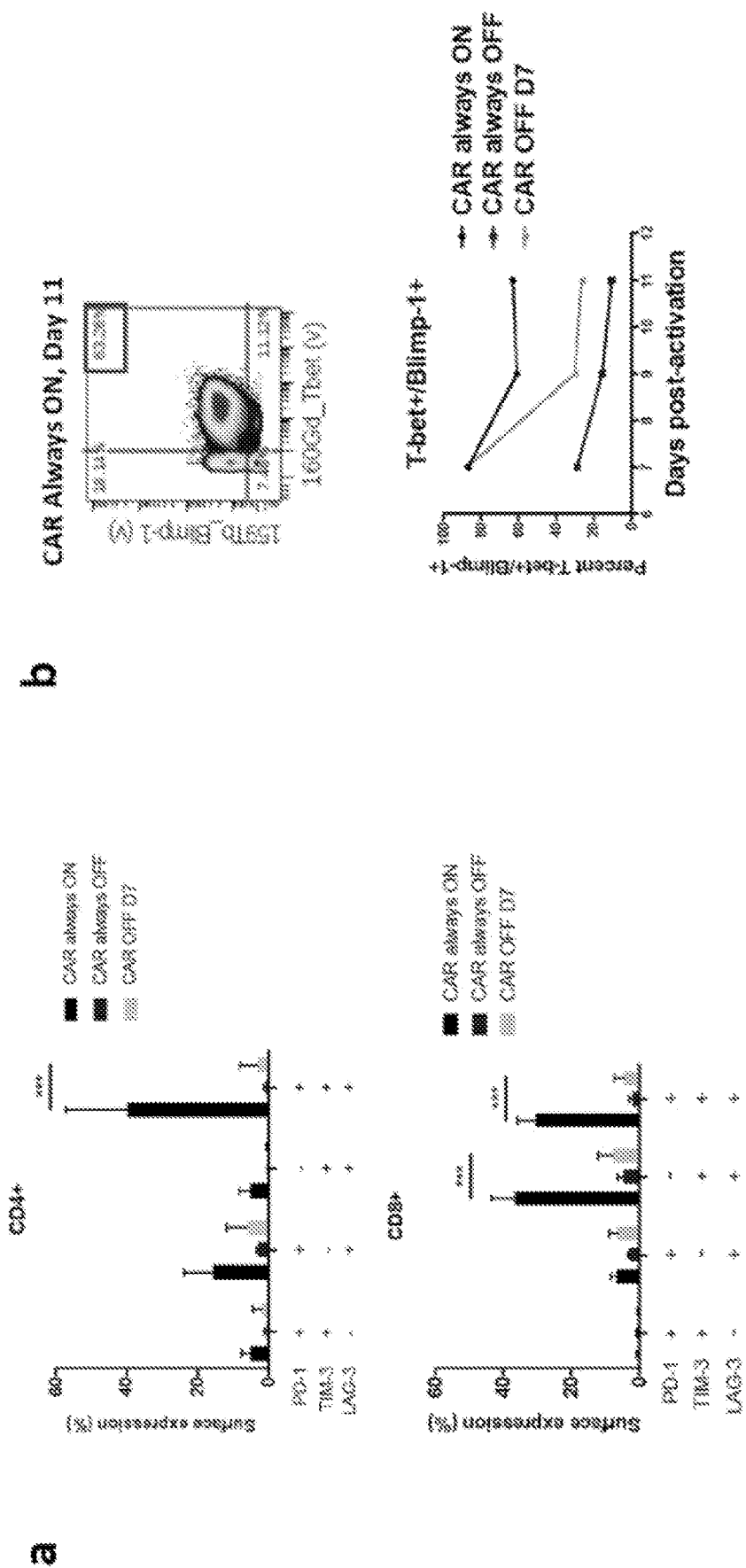
FIG. 17 shows that co-expression of canonical exhaustion markers on HA-GD2.28z.FKBP are rapidly downregulated upon removal of shield-1 from the culture medium and that prevention or reversal of tonic signaling improves the exhaustion phenotype of CAR T cells. The co-expression of PD-1/TIM-3/LAG-3 is correlated with a decrease in effector function. When the CAR is always expressed (cultured with shield-1, "CAR always ON"), these markers are co-expressed in a majority of cells. However, when the CAR is not expressed on the surface (no shield-1, "CAR always OFF"), or cultured in shield-1 for 7 days and then removed, only a fraction of cells that co-express exhaustion markers are observed.
Figure 18:
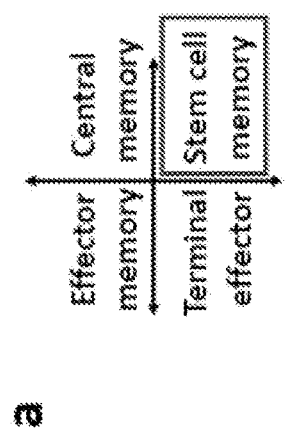
FIG. 18 shows that inhibition or removal of tonic signaling rescues memory phenotype. T cell exhaustion inhibits T cells' ability to form memory. Exhausted (CAR always ON) cells have a high percentage of effector T cells (Teff) and a low percentage of stem cell memory (Tscm). Conversely, non-exhausted cells (CAR always OFF), or those cells in which exhaustion was reversed by removing stabilizing drug from culture (CAR OFF D7 or CAR OFF D10), exhibit an increased stem cell memory compartment.
Figure 18:
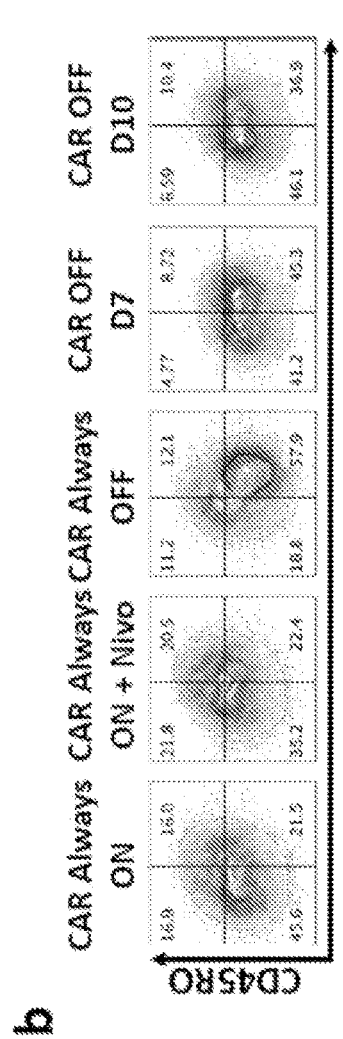
Figure 18:
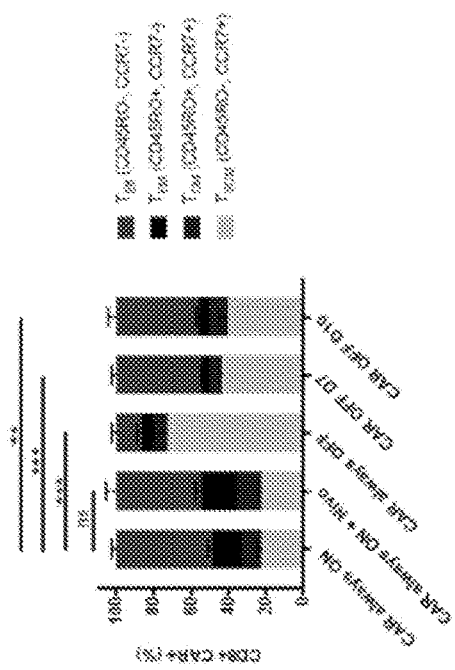

It was next determined whether the prevention or reversal of tonic signaling in HA-GD2.28z.FKBP-expressing CAR T cells altered their exhaustion phenotype. DD-CAR T cells expanded in the presence of drug (CAR Always ON) exhibited co-expression of multiple inhibitory receptors (see FIG. 17A) and transcription factors commonly associated with T cell exhaustion (FIG. 17B). However, DD-CAR T cells expanded in the absence of drug (CAR Always OFF) or those expanded in drug from days 1-7 but not thereafter (CAR OFF D7) exhibited significantly less exhaustion marker co-expression (FIG. 17). Similarly, exhausted DD-CAR T cells expanded in the presence of drug displayed a high frequency of effector T cells and concomitant low frequency of memory cells (FIG. 18), similar to that observed in the literature (see Wherry and Kurachi, Nature Reviews Immunology 15, nri3862 (2015). However, a rescue in DD-CAR T cell memory was observed simply by expanding the cells in the absence of stabilizing drug for at least 4 days, indicating that mitigation of tonic signaling in CAR T cells can simultaneously prevent exhaustion and facilitate memory formation.

Figure 19:
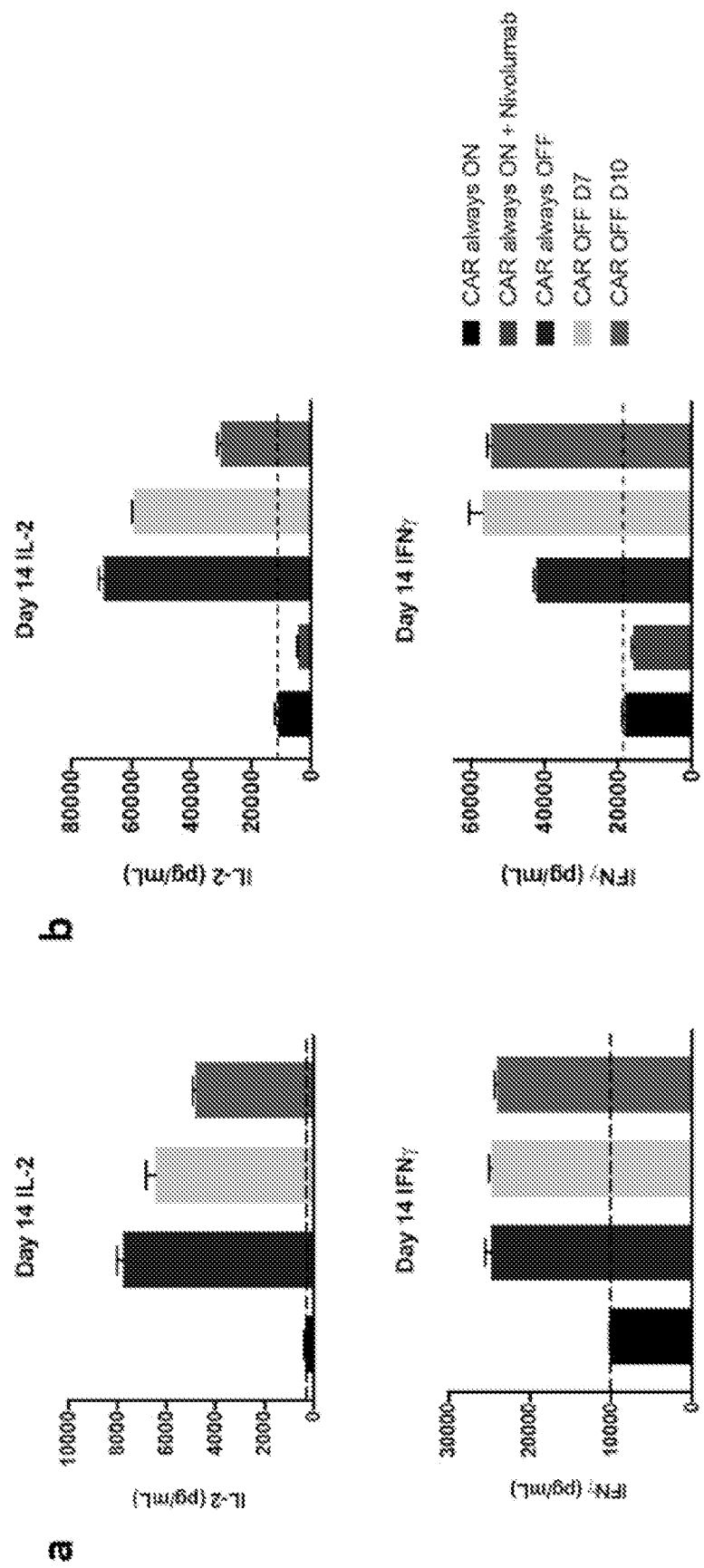
FIG. 19 shows time-dependent regulation of CAR surface expression via a fused FKBP or E. coli-derived DHFR destabilization domain (DD). Exhausted CAR T cells fail to secrete effector cytokines IL-2 and IFNγ in response to tumor. However, CAR T cells in which exhaustion was prevented or reversed exhibit an enhanced capacity to secrete IL-2 and IFNγ.
Figure 20:
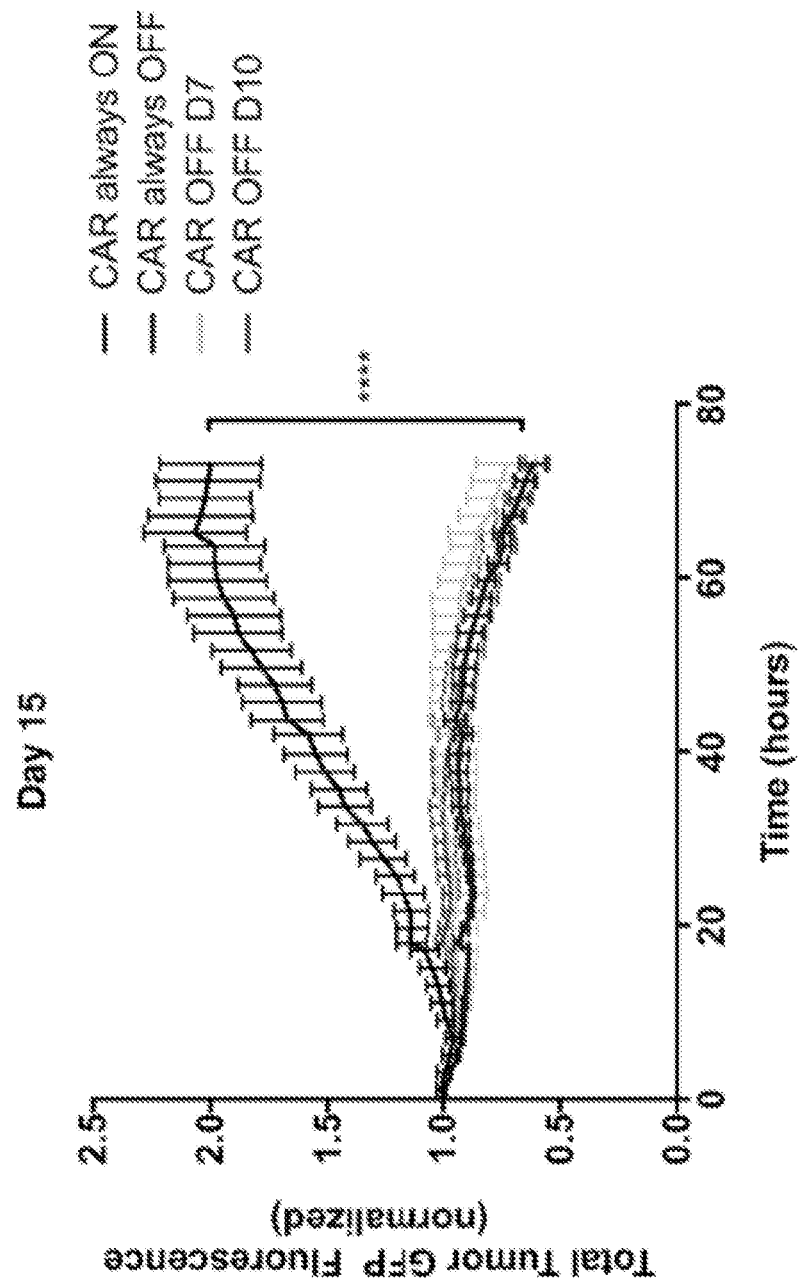
FIG. 20 shows that exhausted CAR T cells have significantly reduced cytotoxicity. However, CAR T cells in which exhaustion was prevented or reversed exhibit enhanced cytotoxicity.

Next, it was determined whether the dramatic phenotypic changes observed when tonic signaling was mitigated may also coincide with an augmentation in T cell function. To test this, DD-CAR T cells were expanded either in the presence (CAR Always ON) or absence (CAR Always OFF) of stabilizing drug. To interrogate the plasticity of exhausted CAR T cells to become reinvigorated, cells were expanded in the presence of drug for either 7 or 10 days, after which drug was removed and T cells were "rested" (CAR OFF D7 and CAR OFF D10, respectively). CAR T cells were then co-cultured with antigen-bearing tumor for 24 hours and cytokine secretion was assessed via ELISA (FIG. 19) or they were co-cultured for 72 hours in an incucyte during which cytotoxicity was assessed (FIG. 20). Importantly, regardless of the conditions in which DD-CAR T cells were cultured, drug was added to each condition 18-24 hours prior to the co-culture assay to ensure normalization of CAR expression during the assay. CAR T cells expanded with drug (CAR Always ON) secreted low levels of IL-2 and IFNy in response to tumor (FIG. 19) and exhibited impaired cytotoxicity (FIG. 20), consistent with the phenotype of exhausted T cells. Conversely, CAR T cells grown in the absence of drug secreted 2-10 fold more cytokine (FIG. 19) and were capable of limiting tumor growth (FIG. 20), indicating that mitigation of tonic signaling profoundly augmented the functional capacity of CAR T cells. Furthermore, CAR T cells that experienced tonic signaling for 7 or 10 days, but were provided 4-7 days of "rest" prior to the co-culture assay, were functionally reinvigorated (FIGS. 19 and 20, CAR OFF D7 and CAR OFF D10). These observations indicated that DD-CAR T cells benefit from periods of "rest", during which DD-CAR expression is low and cells are allowed to quiesce and form memory.

Based on the in vitro functional studies, it was determined whether toggling DD-CAR T cell expression in vivo could provide an opportunity to prolong the CAR T cell anti-tumor response by limiting chronic antigen exposure and mitigating CAR T cell exhaustion. To test this, antigen-bearing tumor cells were engrafted into NSG mice and subsequently infused 2-5E6 HA-GD2.28z.DHFR-expressing T cells. Mice were dosed with TMP everyday thereafter.

Figure 21:
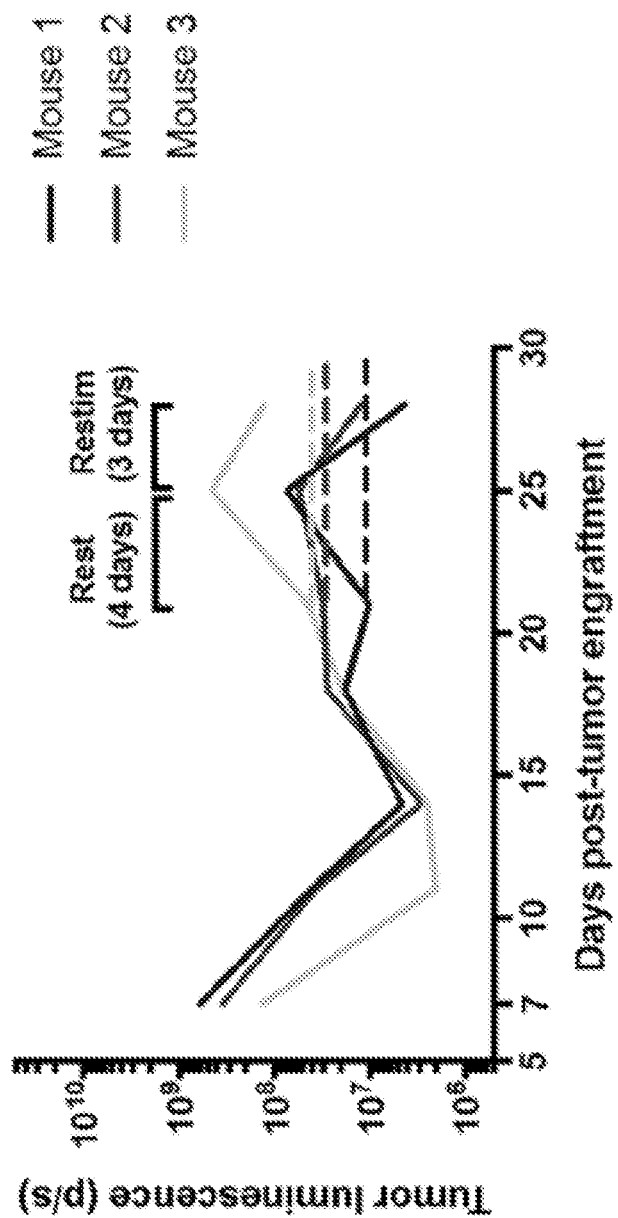
FIG. 21 shows mice that were exposed to iterative dosing with stabilizing drug. Four days of T cell "rest" were provided in which vehicle was injected instead of TMP. TMP injections were then resumed for an additional 3 days. The data show a profound rescue of function where tumor burden was lower after the "rest" period than it was before the "rest" period.
Figure 22:
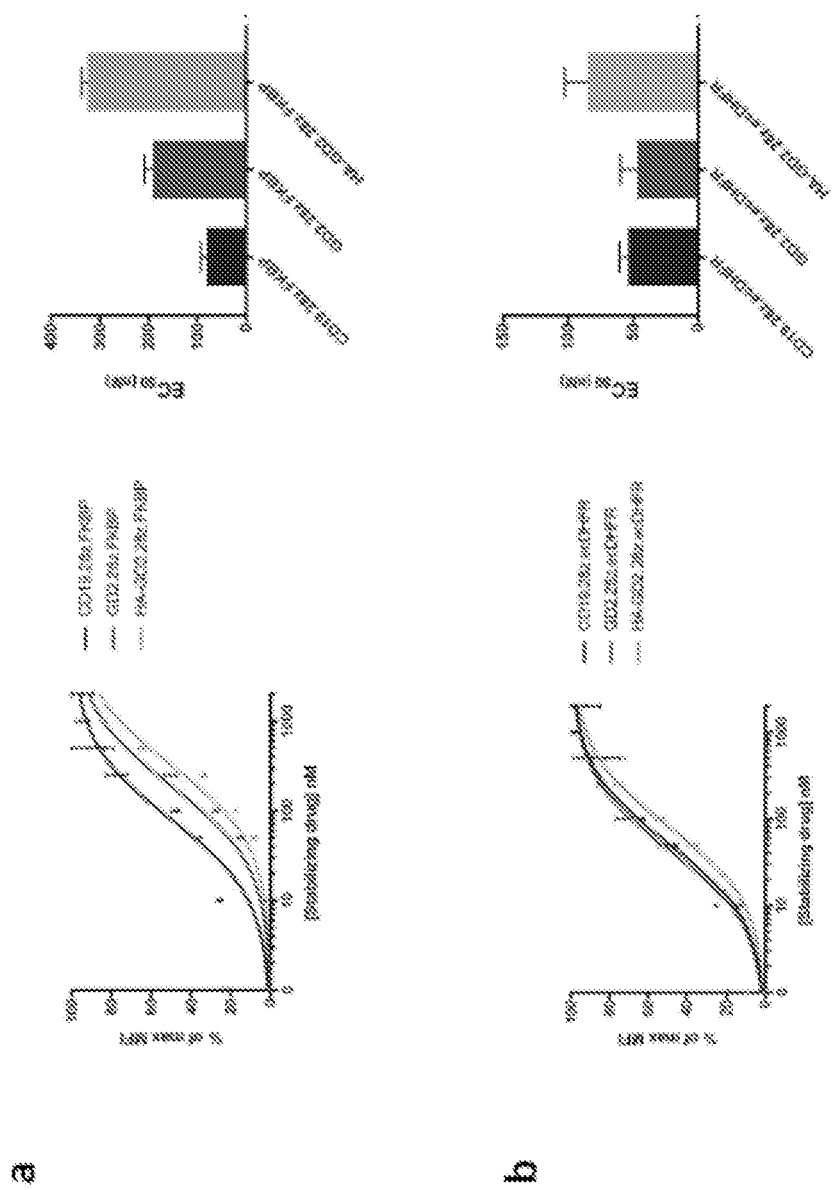
FIG. 22 shows dose response curves and $EC_{50}$ values of various regulatable DD-CARs. CAR Median Fluorescence Intensity (MFI) was calculated by first gating on CAR+ and CAR− cells, then subtracting the MFI of the CAR− population from that of the CAR+ population. Values were normalized to the max CAR MFI in the drug titration study, and a non-linear regression and least squares fit curve was generated. $EC_{50}$ values of each curve are plotted in the bar graphs. For GD2.28z.FKBP, HA-GD2.28z.FKBP, GD2.28z.ecDHFR, n=3 donors. For CD19.28z.FKBP, CD19.28z.ecDHFR, and HA-GD2.28z.ecDHFR, n=2 donors.
Figure 23:
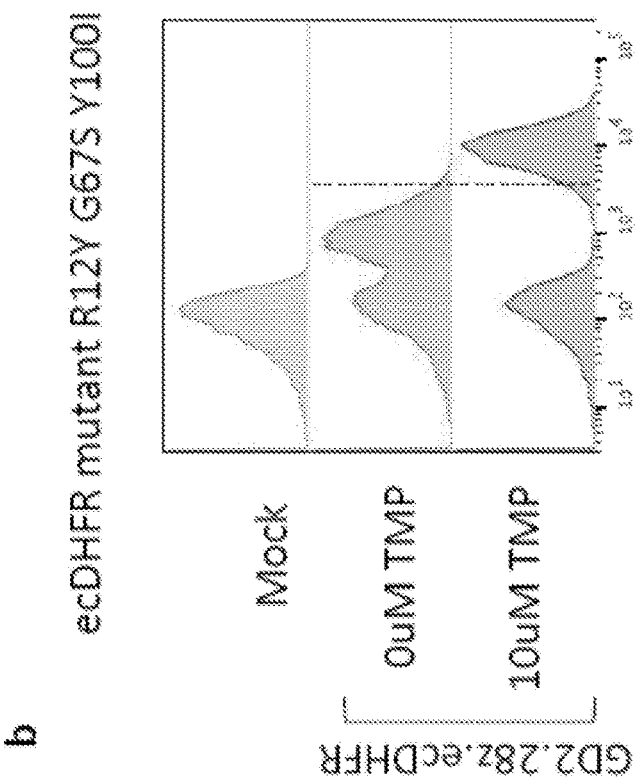
FIG. 23 shows that certain destabilization domains are more optimal for drug-dependent regulation CAR expression. (A) T cells were transduced with lentivirus to express GD2.28z.ecDHFR wherein the ecDHFR domain contained the following mutations: R12H, N18T, V19A, and G67S. T cells were removed from culture and stained with a fluorescent-conjugated anti-idiotype antibody, and CAR surface expression was subsequently assessed via FACS. Slight drug-dependent CAR regulation was observed due to high background expression in the absence of stabilizing drug. (B) T cells were transduced with lentivirus to express GD2.28z.ecDHFR wherein the ecDHFR domain contained the following mutations: R12Y, G67S, Y100I. T cells were again removed from culture, stained with anti-idiotype antibody and CAR expression was assessed via FACS. In this DD-CAR iteration incorporating a different ecDHFR domain, drug-dependent regulation of CAR surface expression was observed. The dotted lines in both subfigures were drawn to highlight the differences in CAR expression level between 0uM TMP and 10 uM TMP.
Figure 23:
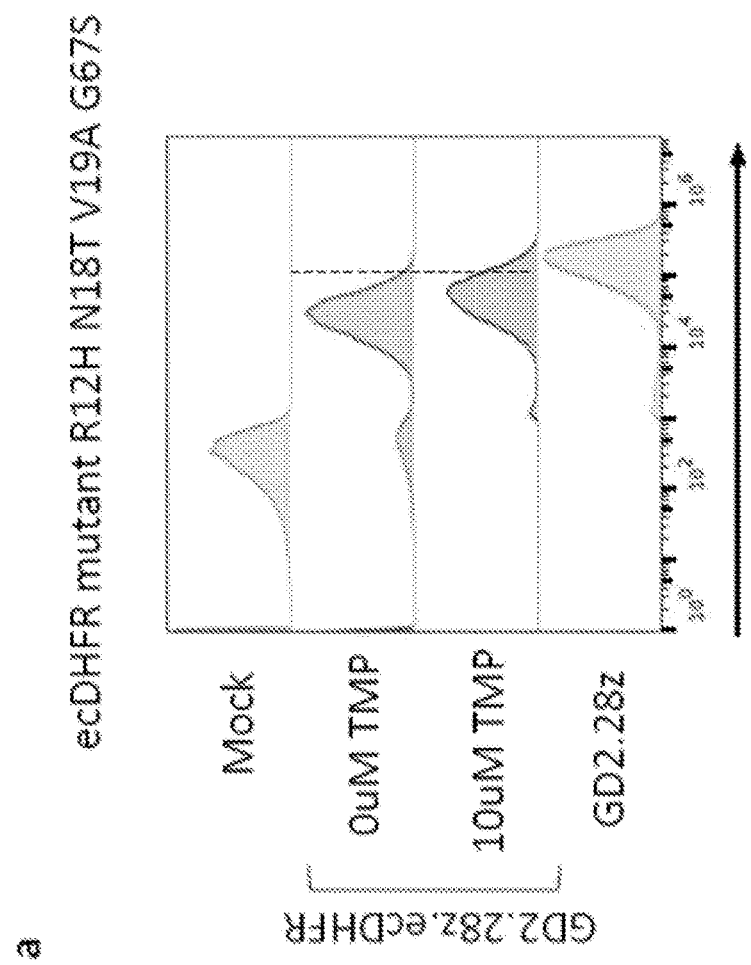
Figure 24:
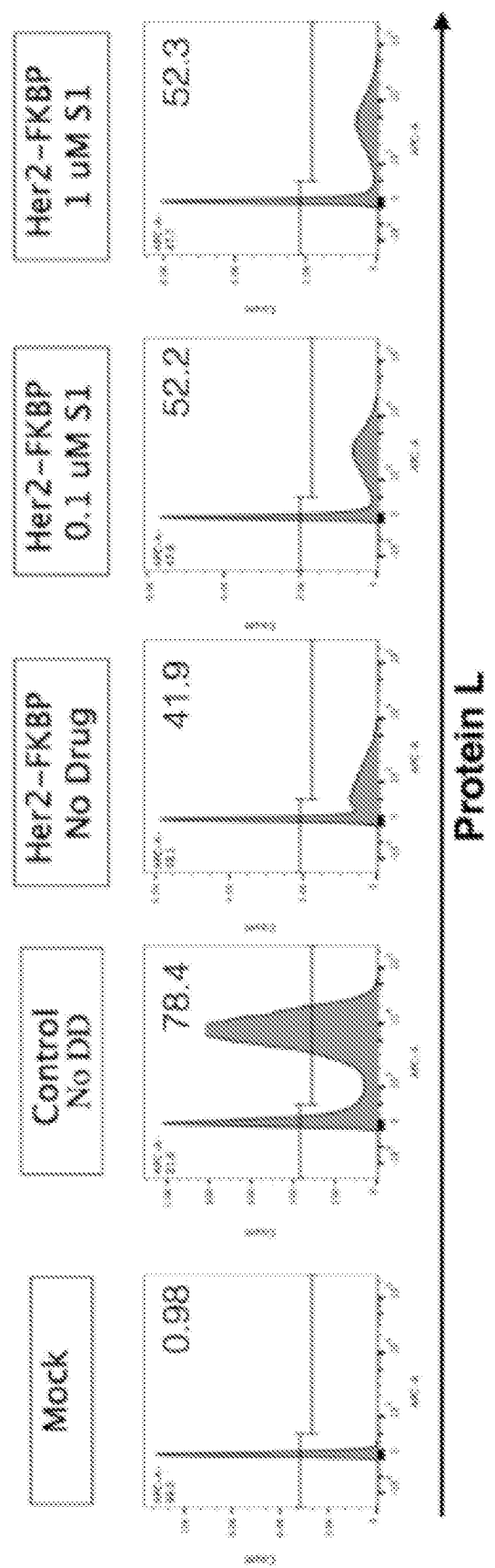
FIG. 24 shows drug-dependent regulation of Her.28z CAR via a fused FKBP DD. The FKBP12 DD domain was fused to the far c-terminus of the Her2.28z CAR. T cells were transduced with lentivirus to express the Her2.28z.FKBP. On day 7 post-activation, CAR T cells were cultured in the presence or absence of shield-1. 24 hours after addition of drug, CAR T cells were stained with protein L and CAR expression was assessed via FACS. Both the percentage of CAR+ cells (quantified in the histograms) as well as CAR MFI are increased upon incubation with either 0.1 uM or 1 uM Shield-1 (S1).

A rapid anti-tumor response was observed upon infusion of the DD-CAR, but eventually the disease relapsed, suggesting that the CAR T cells may have become dysfunctional or exhausted (see FIG. 21). Mice were then dosed with vehicle for 4 days to provide a period during which DD-CAR T cells could recover (see FIG. 21, "rest"). During this time period, tumor burden increased at a more rapid rate compared to the previous period of TMP dosing, indicating that, in fact, the anti-tumor response was being tuned down. Upon reinfusion of TMP for 3 days (FIG. 21, "restim"), a profound reinvigoration of the anti-tumor response was observed in all mice tested (FIG. 21), similar to the observations in vitro (FIGS. 19, 20). Furthermore, 2 out of 3 mice exhibited a lower tumor burden after the reinfusion of TMP than before the period of rest, indicating that the benefits of iterative drug dosing may outweigh the temporary acceleration of tumor growth during vehicle infusion.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A genetically modified T cell comprising an isolated nucleic acid sequence encoding a chimeric antigen receptor (CAR), wherein the CAR comprises:
   a) an extracellular domain comprising an antigen-binding region;
   b) a transmembrane domain;
   c) an intracellular signaling domain; and
   d) a regulatable destabilization domain (RDD), wherein the RDD comprises a dihydrofolate reductase destabilization domain (DHFR DD) or an FK506 binding protein 12 (FKBP) destabilization domain (FKBP DD).

2. The genetically modified T cell of claim 1, characterized by one or more of the following:
   the antigen-binding region is specific for a tumor antigen;
   the antigen-binding region comprises a single chain variable fragment (scFv) domain; and
   the antigen-binding region comprises the amino-acid sequence of SEQ ID NO: 44.

3. The genetically modified T cell of claim 2, wherein the tumor antigen is disialoganglioside GD2.

4. The genetically modified T cell of claim 2, wherein the scFv comprises the variable regions of the heavy ($V_H$) and light chains ($V_L$) of an antibody binding specifically to GD2.

5. The genetically modified T cell of claim 1, wherein the transmembrane domain is a CD28 transmembrane domain.

6. The genetically modified T cell of claim 1, wherein the transmembrane domain comprises the amino acid sequence of SEQ ID NO: 48.

7. The genetically modified T cell of claim 1, wherein the intracellular signaling domain comprises a 4-1BB costimulatory domain.

8. The genetically modified T cell of claim 1, wherein the intracellular signaling domain comprises a CD28 costimulatory domain.

9. The genetically modified T cell of claim 1, wherein the intracellular signaling domain comprises a CD3-zeta signaling domain.

10. The genetically modified T cell of claim 1, wherein the RDD comprises a dihydrofolate reductase destabilization domain (DHFR DD).

11. The genetically modified T cell of claim 10, wherein the DHFR DD is an *Escherichia coli* dihydrofolate reductase destabilization domain (ecDHFR DD).

12. The genetically modified T cell of claim 1, wherein the RDD comprises an FK506 binding protein destabilization domain (FKBP DD).

13. The genetically modified T cell of claim 12, wherein the FKBP DD is a human FKBP DD.

14. The genetically modified T cell of 1, wherein the CAR exhibits antigen-independent tonic signaling.

\* \* \* \* \*

SEQUENCE LISTING

```
<160> NUMBER OF SEQ ID NOS: 136

<210> SEQ ID NO 1
<211> LENGTH: 321
<212> TYPE: DNA
<213> ORGANISM: Artificial Sequence
<220> FEATURE:
<223> OTHER INFORMATION: synthetic

<400> SEQUENCE: 1
atggtgcagg tggaaaccat ctccccagga gacgggcgca ccttccccaa gcgcggccag      60
acctgcgtgg tgcactacac cgggatgctt ggagatggaa agaaagttga ctcctcccgg     120
gacagaaaca agccctttaa gtttatgcta ggcaagcagg aggtgatccg aggctgggaa     180
gaaggggttg cccagatgag tgtgggtcag ggagccaaac tgactatatc tccagattat     240
gcctatggtg ccactgggca cccaggcatc atcccaccac atgccactct cgtcttcgat     300
gtggagcttc tagaactgga a                                              321

<210> SEQ ID NO 2
<211> LENGTH: 107
<212> TYPE: PRT
<213> ORGANISM: Artificial Sequence
<220> FEATURE:
<223> OTHER INFORMATION: synthetic

<400> SEQUENCE: 2

Met Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Gly Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Glu Leu Glu
            100                 105

<210> SEQ ID NO 3
```

<211> LENGTH: 477
<212> TYPE: DNA
<213> ORGANISM: Artificial Sequence
<220> FEATURE:
<223> OTHER INFORMATION: synthetic

<400> SEQUENCE: 3

```
atgatcagtc tgattgcggc gttagcggta gatcacgtta tcggcatgga aaccgtcatg      60
ccgtggaacc tgcctgccga tctcgcctgg tttaaacgca acaccttaaa taaacccgtg     120
attatgggcc gccatacctg gaatcaatc ggtcgtccgt tgccaggacg caaaaatatt      180
atcctcagca gtcaaccgag tacgacgat cgcgtaacgt gggtgaagtc ggtggatgaa      240
gccatcgcgg cgtgtggtga cgtaccagaa atcatggtta ttggcggcgg tcgcgtttat      300
gaacagttct tgccaaaagc gcaaaaactg tatctgacgc atatcgacgc agaagtggaa      360
ggcgacaccc atttcccgga ttacgagccg gatgactggg aatcggtatt cagcgaattc      420
cacgatgctg atgcgcagaa ctctcacagc tattgctttg agattctgga gcggcga        477
```

<210> SEQ ID NO 4
<211> LENGTH: 159
<212> TYPE: PRT
<213> ORGANISM: Artificial Sequence
<220> FEATURE:
<223> OTHER INFORMATION: synthetic

<400> SEQUENCE: 4

```
Met Ile Ser Leu Ile Ala Ala Leu Ala Val Asp His Val Ile Gly Met
1               5                   10                  15

Glu Thr Val Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 5
<211> LENGTH: 477
<212> TYPE: DNA
<213> ORGANISM: Artificial Sequence
<220> FEATURE:
<223> OTHER INFORMATION: synthetic

<400> SEQUENCE: 5

```
atgatcagtc tgattgcggc gttagcggta gattacgtta tcggcatgga aaacgccatg      60
ccgtggaacc tgcctgccga tctcgcctgg tttaaacgca acaccttaaa taaacccgtg     120
attatgggcc gccatacctg gaatcaatc ggtcgtccgt tgccaggacg caaaaatatt      180
```

| | |
|---|---|
| atcctcagca gtcaaccgag tacggacgat cgcgtaacgt gggtgaagtc ggtggatgaa | 240 |
| gccatcgcgg cgtgtggtga cgtaccagaa atcatggtga ttggcggcgg tcgcgttatt | 300 |
| gaacagttct tgccaaaagc gcaaaaactg tatctgacgc atatcgacgc agaagtggaa | 360 |
| ggcgacaccc atttcccgga ttacgagccg gatgactggg aatcggtatt cagcgaattc | 420 |
| cacgatgctg atgcgcagaa ctctcacagc tattgctttg agattctgga gcggcga | 477 |

<210> SEQ ID NO 6
<211> LENGTH: 159
<212> TYPE: PRT
<213> ORGANISM: Artificial Sequence
<220> FEATURE:
<223> OTHER INFORMATION: synthetic

<400> SEQUENCE: 6

Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 7
<211> LENGTH: 1806
<212> TYPE: DNA
<213> ORGANISM: Artificial Sequence
<220> FEATURE:
<223> OTHER INFORMATION: synthetic

<400> SEQUENCE: 7

| | |
|---|---|
| atgctgctgc tcgtgacatc tctgctgctg tgcgagctgc ccacccgc ctttctgctg | 60 |
| atccccgata tcgacatcca gatgacacag actacatcct ccctgtctgc ctctctggga | 120 |
| gacagagtca ccatcagttg cagggcaagt caggacatta gtaaatattt aaattggtat | 180 |
| cagcagaaac cagatggaac tgttaaactc ctgatctacc atacatcaag attacactca | 240 |
| ggagtcccat caaggttcag tggcagtggg tctggaacag attattctct caccattagc | 300 |
| aacctggagc aagaagatat tgccacttac ttttgccaac aggtaatac gcttccgtac | 360 |
| acgttcggag gggggactaa gttggaaata acaggctcca cctctggatc cggcaagccc | 420 |
| ggatctggcg aggatccac caagggcgag gtgaaactgc aggagtcagg acctggcctg | 480 |
| gtggcgccct cacagagcct gtccgtcaca tgtactgtct cagggggtctc attacccgac | 540 |

```
tatggtgtaa gctggattcg ccagcctcca cgaaagggtc tggagtggct gggagtaata    600
tggggtagtg aaaccacata ctataattca gctctcaaat ccagactgac catcatcaag    660
gacaactcca agagccaagt tttcttaaaa atgaacagtc tgcaaactga tgacacagcc    720
atttactact gtgccaaaca ttattactac ggtggtagct atgctatgga ctactggggt    780
caaggaacct cagtcaccgt ctcctcagct agcttcgaaa ttgaagttat gtatcctcct    840
ccttacctag acaatgagaa gagcaatgga accattatcc atgtgaaagg aaacaccttt    900
tgtccaagtc ccctatttcc cggaccttct aagccctttt gggtgctggt ggtggttggg    960
ggagtcctgg cttgctatag cttgctagta acagtggcct ttattatttt ctgggtgagg   1020
agtaagagga gcaggctcct gcacagtgac tacatgaaca tgactccccg ccgccccggg   1080
cccacccgca agcattacca gccctatgcc ccaccacgcg acttcgcagc ctatcgctcc   1140
catatgagag tgaagttcag caggagcgca gacgcccccg cgtacaagca gggccagaac   1200
cagctctata cgagctcaa tctaggacga agagaggagt acgatgtttt ggacaagaga   1260
cgtggccggg accctgagat ggggggaaag ccgagaagga agaaccctca ggaaggcctg   1320
tacaatgaac tgcagaaaga taagatggcg gaggcctaca gtgagattgg gatgaaaggc   1380
gagcgccgga ggggcaaggg gcacgatggc ctttaccagg gtctcagtac agccaccaag   1440
gacacctacg acgcccttca catgcaggcc ctgccccctc gcggagtgca ggtggaaacc   1500
atctccccag agacgggcg caccttcccc aagcgcggcc agacctgcgt ggtgcactac   1560
accgggatgc ttggagatgg aaagaaagtt gactcctccc gggacagaaa caagccctt   1620
aagtttatgc taggcaagca ggaggtgatc cgaggctggg aagaagggt tgcccagatg   1680
agtgtgggtc agggagccaa actgactata tctccagatt atgcctatgg tgccactggg   1740
cacccaggca tcatcccacc acatgccact ctcgtcttcg atgtggagct tctagaactg   1800
gaatga                                                              1806

<210> SEQ ID NO 8
<211> LENGTH: 601
<212> TYPE: PRT
<213> ORGANISM: Artificial Sequence
<220> FEATURE:
<223> OTHER INFORMATION: synthetic

<400> SEQUENCE: 8

Met Leu Leu Leu Val Thr Ser Leu Leu Cys Glu Leu Pro His Pro
1               5                   10                  15

Ala Phe Leu Leu Ile Pro Asp Ile Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Ser Thr Ser Gly Ser Gly Lys Pro Gly Ser Gly Glu
```

```
                130                 135                 140
Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
                180                 185                 190

Gly Leu Glu Trp Leu Gly Val Ile Trp Gly Ser Glu Thr Thr Tyr Tyr
                195                 200                 205

Asn Ser Ala Leu Lys Ser Arg Leu Thr Ile Ile Lys Asp Asn Ser Lys
                210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Ala Ser Phe
                260                 265                 270

Glu Ile Glu Val Met Tyr Pro Pro Pro Tyr Leu Asp Asn Glu Lys Ser
                275                 280                 285

Asn Gly Thr Ile Ile His Val Lys Gly Lys His Leu Cys Pro Ser Pro
                290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
                355                 360                 365

Tyr Ala Pro Pro Arg Asp Phe Ala Ala Tyr Arg Ser His Met Arg Val
                370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg Gly Val
                485                 490                 495

Gln Val Glu Thr Ile Ser Pro Gly Asp Gly Arg Thr Phe Pro Lys Arg
                500                 505                 510

Gly Gln Thr Cys Val Val His Tyr Thr Gly Met Leu Gly Asp Gly Lys
                515                 520                 525

Lys Val Asp Ser Ser Arg Asp Arg Asn Lys Pro Phe Lys Phe Met Leu
                530                 535                 540

Gly Lys Gln Glu Val Ile Arg Gly Trp Glu Glu Gly Val Ala Gln Met
545                 550                 555                 560
```

```
Ser Val Gly Gln Gly Ala Lys Leu Thr Ile Ser Pro Asp Tyr Ala Tyr
            565                 570                 575

Gly Ala Thr Gly His Pro Gly Ile Ile Pro Pro His Ala Thr Leu Val
        580                 585                 590

Phe Asp Val Glu Leu Leu Glu Leu Glu
        595                 600

<210> SEQ ID NO 9
<211> LENGTH: 66
<212> TYPE: DNA
<213> ORGANISM: Artificial Sequence
<220> FEATURE:
<223> OTHER INFORMATION: synthetic

<400> SEQUENCE: 9
atgctgctgc tcgtgacatc tctgctgctg tgcgagctgc cccacccgc ctttctgctg      60 atcccc                                                                66

<210> SEQ ID NO 10
<211> LENGTH: 22
<212> TYPE: PRT
<213> ORGANISM: Artificial Sequence
<220> FEATURE:
<223> OTHER INFORMATION: synthetic

<400> SEQUENCE: 10

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 11
<211> LENGTH: 735
<212> TYPE: DNA
<213> ORGANISM: Artificial Sequence
<220> FEATURE:
<223> OTHER INFORMATION: synthetic

<400> SEQUENCE: 11
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat acactcagg agtcccatca      180 aggttcagtg gcagtgggtc tggaacagat tattctctca ccattagcaa cctggagcaa     240
gaagatattg ccacttactt ttgccaacag gtaatacgc ttccgtacac gttcggaggg      300
gggactaagt tggaaataac aggctccacc tctggatccg gcaagcccgg atctggcgag     360
ggatccacca agggcgaggt gaaactgcag gagtcaggac ctggcctggt ggcgccctca     420
cagagcctgt ccgtcacatg tactgtctca ggggtctcat tacccgacta tggtgtaagc     480
tggattcgcc agcctccacg aaagggtctg gagtggctgg agtaaatatg gggtagtgaa     540
accacatact ataattcagc tctcaaatcc agactgacca tcatcaagga caactccaag     600
agccaagttt tcttaaaaat gaacagtctg caaactgatg acacagccat ttactactgt     660
gccaaacatt attactacgg tggtagctat gctatggact actggggtca aggaacctca     720
gtcaccgtct cctca                                                     735

<210> SEQ ID NO 12
<211> LENGTH: 245
```

```
<212> TYPE: PRT
<213> ORGANISM: Artificial Sequence
<220> FEATURE:
<223> OTHER INFORMATION: synthetic

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 13
<211> LENGTH: 117
<212> TYPE: DNA
<213> ORGANISM: Artificial Sequence
<220> FEATURE:
<223> OTHER INFORMATION: synthetic

<400> SEQUENCE: 13
attgaagtta tgtatcctcc tccttaccta gacaatgaga agagcaatgg aaccattatc    60
catgtgaaag ggaaacacct tgtccaagt cccctatttc ccggaccttc taagccc      117

<210> SEQ ID NO 14
<211> LENGTH: 39
<212> TYPE: PRT
<213> ORGANISM: Artificial Sequence
<220> FEATURE:
<223> OTHER INFORMATION: synthetic

<400> SEQUENCE: 14
```

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 15
<211> LENGTH: 81
<212> TYPE: DNA
<213> ORGANISM: Artificial Sequence
<220> FEATURE:
<223> OTHER INFORMATION: synthetic

<400> SEQUENCE: 15
ttttgggtgc tggtggtggt tgggggagtc ctggcttgct atagcttgct agtaacagtg     60
gcctttatta ttttctgggt g                                               81

<210> SEQ ID NO 16
<211> LENGTH: 27
<212> TYPE: PRT
<213> ORGANISM: Artificial Sequence
<220> FEATURE:
<223> OTHER INFORMATION: synthetic

<400> SEQUENCE: 16

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 17
<211> LENGTH: 123
<212> TYPE: DNA
<213> ORGANISM: Artificial Sequence
<220> FEATURE:
<223> OTHER INFORMATION: synthetic

<400> SEQUENCE: 17
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 18
<211> LENGTH: 41
<212> TYPE: PRT
<213> ORGANISM: Artificial Sequence
<220> FEATURE:
<223> OTHER INFORMATION: synthetic

<400> SEQUENCE: 18

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 19
<211> LENGTH: 336
<212> TYPE: DNA
<213> ORGANISM: Artificial Sequence
```

<220> FEATURE:
<223> OTHER INFORMATION: synthetic

<400> SEQUENCE: 19

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggg aaagccgaga aggaagaacc ctcaggaagg cctgtacaat      180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 20
<211> LENGTH: 112
<212> TYPE: PRT
<213> ORGANISM: Artificial Sequence
<220> FEATURE:
<223> OTHER INFORMATION: synthetic

<400> SEQUENCE: 20

```
Arg Val Lys Phe Ser Arg Ser Ala Asp Ala Pro Ala Tyr Lys Gln Gly
1               5                   10                  15
Gln Asn Gln Leu Tyr Asn Glu Leu Asn Leu Gly Arg Arg Glu Glu Tyr
                20                  25                  30
Asp Val Leu Asp Lys Arg Arg Gly Arg Asp Pro Glu Met Gly Gly Lys
            35                  40                  45
Pro Arg Arg Lys Asn Pro Gln Glu Gly Leu Tyr Asn Glu Leu Gln Lys
        50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

<210> SEQ ID NO 21
<211> LENGTH: 321
<212> TYPE: DNA
<213> ORGANISM: Artificial Sequence
<220> FEATURE:
<223> OTHER INFORMATION: synthetic

<400> SEQUENCE: 21

```
ggagtgcagg tggaaaccat ctccccagga gacgggcgca ccttccccaa gcgcggccag      60
acctgcgtgg tgcactacac cgggatgctt ggagatggaa agaaagttga ctcctcccgg     120
gacagaaaca agccctttaa gtttatgcta ggcaagcagg aggtgatccg aggctgggaa     180
gaaggggttg cccagatgag tgtgggtcag ggagccaaac tgactatatc tccagattat     240
gcctatggtg ccactgggca cccaggcatc atcccaccac atgccactct cgtcttcgat     300
gtggagcttc tagaactgga a                                               321
```

<210> SEQ ID NO 22
<211> LENGTH: 107
<212> TYPE: PRT
<213> ORGANISM: Artificial Sequence
<220> FEATURE:
<223> OTHER INFORMATION: synthetic

<400> SEQUENCE: 22

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Gly Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Glu Leu Glu
            100                 105

<210> SEQ ID NO 23
<211> LENGTH: 1959
<212> TYPE: DNA
<213> ORGANISM: Artificial Sequence
<220> FEATURE:
<223> OTHER INFORMATION: synthetic

<400> SEQUENCE: 23

| | | | | | |
|---|---|---|---|---|---|
| atgctgctgc | tcgtgacatc | tctgctgctg | tgcgagctgc | ccacccccgc | ctttctgctg | 60 |
| atccccgata | tcgacatcca | gatgacacag | actacatcct | ccctgtctgc | ctctctggga | 120 |
| gacagagtca | ccatcagttg | cagggcaagt | caggacatta | gtaaatattt | aaattggtat | 180 |
| cagcagaaac | cagatggaac | tgttaaactc | ctgatctacc | atacatcaag | attacactca | 240 |
| ggagtcccat | caaggttcag | tggcagtggg | tctggaacag | attattctct | caccattagc | 300 |
| aacctggagc | aagaagatat | tgccacttac | ttttgccaac | agggtaatac | gcttccgtac | 360 |
| acgttcggag | gggggactaa | gttggaaata | acaggctcca | cctctggatc | cggcaagccc | 420 |
| ggatctggcg | agggatccac | caagggcgag | gtgaaactgc | aggagtcagg | acctggcctg | 480 |
| gtggcgccct | cacagagcct | gtccgtcaca | tgtactgtct | caggggtctc | attacccgac | 540 |
| tatggtgtaa | gctggattcg | ccagcctcca | cgaaagggtc | tggagtggct | gggagtaata | 600 |
| tggggtagtg | aaaccacata | ctataattca | gctctcaaat | ccagactgac | catcatcaag | 660 |
| gacaactcca | agagccaagt | tttcttaaaa | atgaacagtc | tgcaaactga | tgacacagcc | 720 |
| atttactact | gtgccaaaca | ttattactac | ggtggtagct | atgctatgga | ctactggggt | 780 |
| caaggaacct | cagtcaccgt | ctcctcagct | agcttcgaaa | ttgaagttat | gtatcctcct | 840 |
| ccttacctag | acaatgagaa | gagcaatgga | accattatcc | atgtgaaagg | aaacaccctt | 900 |
| tgtccaagtc | ccctatttcc | cggaccttct | aagccttttt | gggtgctggt | ggtggttggg | 960 |
| ggagtcctgg | cttgctatag | cttgctagta | acagtggcct | ttattatttt | ctgggtgagg | 1020 |
| agtaagagga | gcaggctcct | gcacagtgac | tacatgaaca | tgactccccg | ccgccccggg | 1080 |
| cccacccgca | agcattacca | gccctatgcc | ccaccacgcg | acttcgcagc | ctatcgctcc | 1140 |
| catatgagag | tgaagttcag | caggagcgca | gacgcccccg | cgtacaagca | gggccagaac | 1200 |
| cagctctata | acgagctcaa | tctaggacga | agagaggagt | acgatgtttt | ggacaagaga | 1260 |
| cgtggccggg | accctgagat | ggggggaaag | ccgagaagga | agaaccctca | ggaaggcctg | 1320 |
| tacaatgaac | tgcagaaaga | taagatggcg | gaggcctaca | gtgagattgg | gatgaaaggc | 1380 |
| gagcgccgga | ggggcaaggg | gcacgatggc | ctttaccagg | gtctcagtac | agccaccaag | 1440 |

-continued

```
gacacctacg acgcccttca catgcaggcc ctgcccccte gcatcagtct gattgcggcg    1500
ttagcggtag attacgttat cggcatggaa acgccatgc cgtggaacct gcctgccgat     1560
ctcgcctggt ttaaacgcaa caccttaaat aaacccgtga ttatgggccg ccatacctgg    1620
gaatcaatcg gtcgtccgtt gccaggacgc aaaaatatta tcctcagcag tcaaccgagt    1680
acggacgatc gcgtaacgtg ggtgaagtcg gtggatgaag ccatcgcggc gtgtggtgac    1740
gtaccagaaa tcatggtgat tggcggcggt cgcgttattg aacagttctt gccaaaagcg    1800
caaaaactgt atctgacgca tatcgacgca gaagtggaag cgacaccca tttcccggat     1860 tacgagccgg atgactggga atcggtattc agcgaattcc acgatgctga tgcgcagaac    1920
tctcacagct attgctttga gattctggag cggcgatga                           1959
```

<210> SEQ ID NO 24
<211> LENGTH: 652
<212> TYPE: PRT
<213> ORGANISM: Artificial Sequence
<220> FEATURE:
<223> OTHER INFORMATION: synthetic

<400> SEQUENCE: 24

```
Met Leu Leu Leu Val Thr Ser Leu Leu Cys Glu Leu Pro His Pro
1               5                   10                  15

Ala Phe Leu Leu Ile Pro Asp Ile Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Ser Thr Ser Gly Ser Gly Lys Pro Gly Ser Gly Glu
    130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
        195                 200                 205

Asn Ser Ala Leu Lys Ser Arg Leu Thr Ile Ile Lys Asp Asn Ser Lys
    210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Ala Ser Phe
            260                 265                 270
```

```
Glu Ile Glu Val Met Tyr Pro Pro Tyr Leu Asp Asn Glu Lys Ser
        275                 280                 285

Asn Gly Thr Ile Ile His Val Lys Gly Lys His Leu Cys Pro Ser Pro
290                 295                 300

Leu Phe Pro Gly Pro Ser Lys Pro Phe Trp Val Leu Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser His Met Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg Ile Ser
                485                 490                 495

Leu Ile Ala Ala Leu Ala Val Asp Tyr Val Ile Gly Met Glu Asn Ala
                500                 505                 510

Met Pro Trp Asn Leu Pro Ala Asp Leu Ala Trp Phe Lys Arg Asn Thr
            515                 520                 525

Leu Asn Lys Pro Val Ile Met Gly Arg His Thr Trp Glu Ser Ile Gly
        530                 535                 540

Arg Pro Leu Pro Gly Arg Lys Asn Ile Ile Leu Ser Ser Gln Pro Ser
545                 550                 555                 560

Thr Asp Asp Arg Val Thr Trp Val Lys Ser Val Asp Glu Ala Ile Ala
                565                 570                 575

Ala Cys Gly Asp Val Pro Glu Ile Met Val Ile Gly Gly Gly Arg Val
                580                 585                 590

Ile Glu Gln Phe Leu Pro Lys Ala Gln Lys Leu Tyr Leu Thr His Ile
            595                 600                 605

Asp Ala Glu Val Glu Gly Asp Thr His Phe Pro Asp Tyr Glu Pro Asp
    610                 615                 620

Asp Trp Glu Ser Val Phe Ser Glu Phe His Asp Ala Asp Ala Gln Asn
625                 630                 635                 640

Ser His Ser Tyr Cys Phe Glu Ile Leu Glu Arg Arg
                645                 650

<210> SEQ ID NO 25
<211> LENGTH: 66
<212> TYPE: DNA
<213> ORGANISM: Artificial Sequence
<220> FEATURE:
```

<223> OTHER INFORMATION: synthetic

<400> SEQUENCE: 25

```
atgctgctgc tcgtgacatc tctgctgctg tgcgagctgc cccacccgc ctttctgctg    60
atcccc                                                              66
```

<210> SEQ ID NO 26
<211> LENGTH: 22
<212> TYPE: PRT
<213> ORGANISM: Artificial Sequence
<220> FEATURE:
<223> OTHER INFORMATION: synthetic

<400> SEQUENCE: 26

Met Leu Leu Leu Val Thr Ser Leu Leu Cys Glu Leu Pro His Pro
1               5                   10                  15

Ala Phe Leu Leu Ile Pro
            20

<210> SEQ ID NO 27
<211> LENGTH: 735
<212> TYPE: DNA
<213> ORGANISM: Artificial Sequence
<220> FEATURE:
<223> OTHER INFORMATION: synthetic

<400> SEQUENCE: 27

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat acactcagg agtcccatca    180
aggttcagtg gcagtgggtc tggaacagat tattctctca ccattagcaa cctggagcaa   240
gaagatattg ccacttactt ttgccaacag gtaatacgc ttccgtacac gttcggaggg    300
gggactaagt tggaaataac aggctccacc tctggatccg gcaagcccgg atctggcgag   360
ggatccacca agggcgaggt gaaactgcag gagtcaggac ctggcctggt ggcgccctca   420
cagagcctgt ccgtcacatg tactgtctca ggggtctcat acccgactta ctggtgtaagc   480
tggattcgcc agcctccacg aaagggtctg gagtggctgg agtaatatg gggtagtgaa    540
accacatact ataattcagc tctcaaatcc agactgacca tcatcaagga caactccaag   600
agccaagttt tcttaaaaat gaacagtctg caaactgatg acacagccat ttactactgt   660
gccaaacatt attactacgg tggtagctat gctatggact actggggtca aggaaccctca   720
gtcaccgtct cctca                                                   735
```

<210> SEQ ID NO 28
<211> LENGTH: 245
<212> TYPE: PRT
<213> ORGANISM: Artificial Sequence
<220> FEATURE:
<223> OTHER INFORMATION: synthetic

<400> SEQUENCE: 28

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

```
Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 29
<211> LENGTH: 117
<212> TYPE: DNA
<213> ORGANISM: Artificial Sequence
<220> FEATURE:
<223> OTHER INFORMATION: synthetic

<400> SEQUENCE: 29
attgaagtta tgtatcctcc tccttaccta gacaatgaga agagcaatgg aaccattatc    60
catgtgaaag ggaaacacct ttgtccaagt cccctatttc ccggaccttc taagccc     117

<210> SEQ ID NO 30
<211> LENGTH: 39
<212> TYPE: PRT
<213> ORGANISM: Artificial Sequence
<220> FEATURE:
<223> OTHER INFORMATION: synthetic

<400> SEQUENCE: 30

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
             20                  25                  30

Phe Pro Gly Pro Ser Lys Pro
        35

<210> SEQ ID NO 31
<211> LENGTH: 81
<212> TYPE: DNA
<213> ORGANISM: Artificial Sequence
<220> FEATURE:
<223> OTHER INFORMATION: synthetic
```

<400> SEQUENCE: 31

```
ttttgggtgc tggtggtggt tgggggagtc ctggcttgct atagcttgct agtaacagtg    60
gcctttatta ttttctgggt g                                              81
```

<210> SEQ ID NO 32
<211> LENGTH: 27
<212> TYPE: PRT
<213> ORGANISM: Artificial Sequence
<220> FEATURE:
<223> OTHER INFORMATION: synthetic

<400> SEQUENCE: 32

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 33
<211> LENGTH: 123
<212> TYPE: DNA
<213> ORGANISM: Artificial Sequence
<220> FEATURE:
<223> OTHER INFORMATION: synthetic

<400> SEQUENCE: 33

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                123
```

<210> SEQ ID NO 34
<211> LENGTH: 41
<212> TYPE: PRT
<213> ORGANISM: Artificial Sequence
<220> FEATURE:
<223> OTHER INFORMATION: synthetic

<400> SEQUENCE: 34

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 35
<211> LENGTH: 336
<212> TYPE: DNA
<213> ORGANISM: Artificial Sequence
<220> FEATURE:
<223> OTHER INFORMATION: synthetic

<400> SEQUENCE: 35

```
agagtgaagt tcagcaggag cgcagacgcc cccgcgtaca gcagggcca gaaccagctc     60
tataacgagc tcaatctagg acgaagagag gagtacgatg ttttggacaa gagacgtggc   120
cgggaccctg agatggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                            336
```

<210> SEQ ID NO 36
<211> LENGTH: 112
<212> TYPE: PRT
<213> ORGANISM: Artificial Sequence
<220> FEATURE:
<223> OTHER INFORMATION: synthetic

<400> SEQUENCE: 36

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 37
<211> LENGTH: 474
<212> TYPE: DNA
<213> ORGANISM: Artificial Sequence
<220> FEATURE:
<223> OTHER INFORMATION: synthetic

<400> SEQUENCE: 37

```
atcagtctga ttgcggcgtt agcggtagat tacgttatcg gcatggaaaa cgccatgccg      60
tggaacctgc ctgccgatct cgcctggttt aaacgcaaca ccttaaataa acccgtgatt     120
atgggccgcc atacctggga atcaatcggt cgtccgttgc caggacgcaa aaatattatc     180
ctcagcagtc aaccgagtac ggacgatcgc gtaacgtggg tgaagtcggt ggatgaagcc     240
atcgcggcgt gtggtgacgt accagaaatc atggtgattg gcggcggtcg cgttattgaa     300
cagttcttgc aaaagcgcaaa aaactgtat ctgacgcata tcgacgcaga gtggaaggc      360 gacacccatt tcccggatta cgagccggat gactgggaat cggtattcag cgaattccac     420
gatgctgatg cgcagaactc tcacagctat tgctttgaga ttctggagcg gcga            474
```

<210> SEQ ID NO 38
<211> LENGTH: 158
<212> TYPE: PRT
<213> ORGANISM: Artificial Sequence
<220> FEATURE:
<223> OTHER INFORMATION: synthetic

<400> SEQUENCE: 38

```
Ile Ser Leu Ile Ala Ala Leu Ala Val Asp Tyr Val Ile Gly Met Glu
1               5                   10                  15

Asn Ala Met Pro Trp Asn Leu Pro Ala Asp Leu Ala Trp Phe Lys Arg
            20                  25                  30

Asn Thr Leu Asn Lys Pro Val Ile Met Gly Arg His Thr Trp Glu Ser
        35                  40                  45

Ile Gly Arg Pro Leu Pro Gly Arg Lys Asn Ile Ile Leu Ser Ser Gln
    50                  55                  60
```

```
Pro Ser Thr Asp Asp Arg Val Thr Trp Val Lys Ser Val Asp Glu Ala
 65                  70                  75                  80

Ile Ala Ala Cys Gly Asp Val Pro Glu Ile Met Val Ile Gly Gly Gly
                 85                  90                  95

Arg Val Ile Glu Gln Phe Leu Pro Lys Ala Gln Lys Leu Tyr Leu Thr
            100                 105                 110

His Ile Asp Ala Glu Val Glu Gly Asp Thr His Phe Pro Asp Tyr Glu
        115                 120                 125

Pro Asp Asp Trp Glu Ser Val Phe Ser Glu Phe His Asp Ala Asp Ala
    130                 135                 140

Gln Asn Ser His Ser Tyr Cys Phe Glu Ile Leu Glu Arg Arg
145                 150                 155
```

<210> SEQ ID NO 39
<211> LENGTH: 1791
<212> TYPE: DNA
<213> ORGANISM: Artificial Sequence
<220> FEATURE:
<223> OTHER INFORMATION: synthetic

<400> SEQUENCE: 39

```
atgctgctgc tcgtgacatc tctgctgctg tgcgagctgc cccacccgc ctttctgctg      60 atccccgata tcctgctgac ccagaccct ctgagcctgc ctgtgtctct gggcgatcag     120
gccagcatca gctgcagatc cagccagagc ctggtgcacc ggaacggcaa cacctacctg     180
cactggtatc tgcagaagcc cggccagagc cccaagctgc tgattcacaa ggtgtccaac     240
cggttcagcg gcgtgcccga cagatttctt ggcagcggct ccggcaccga cttcacccctg    300 aagatcagcc gggtggaagc cgaggacctg gcgtgtact tctgcagcca gtccacccac     360
gtgccccccc tgacatttgg cgccggaaca aagctggaac tgaagggcag cacaagcggc     420
agcggcaagc tggatctggc gagggaagc accaagggcg aagtgaagct gcagcagagc     480
ggcccctctc tggtggaacc tggcgcctct gtgatgatct cctgcaaggc cagcggcagc     540
tccttcaccg gctacaacat gaactgggtg cgccagaaca tcggcaagag cctggaatgg     600
atcggcgcca tcgacccta ctacggcgga ccagctaca accagaagtt caagggcaga     660 gccacccctga ccgtggacaa gagcagctcc accgcctaca tgcacctgaa gtccctgacc     720
agcgaggaca gcgccgtgta ctactgcgtg tccggcatgg aatactgggg ccagggcaca     780
agcgtgaccg tgtcctctgc tagcttcgaa attgaagtta tgtatcctcc tccttaccta     840
gacaatgaga gagcaatgg aaccattatc catgtgaaag gaaacacct ttgtccaagt     900 cccctatttc ccggaccttc taagcccttt tgggtgctgg tggtggttgg gggagtcctg     960
gcttgctata gcttgctagt aacagtggcc tttattatt tctgggtgag gagtaagagg    1020
agcaggctcc tgcacagtga ctacatgaac atgactcccc gccgcccgg gcccacccgc    1080 aagcattacc agcccatgc cccaccacgc gacttcgcag cctatcgctc cagagtgaag    1140
ttcagcagga gcgcagacgc ccccgcgtac aagcagggcc agaaccagct ctataacgag    1200
ctcaatctag gacgaagaga ggagtacgat gtttttggaca agagacgtgg ccgggacct    1260 gagatggggg gaaagccgag aaggaagaac cctcaggaag cctgtacaa tgaactgcag    1320 aaagataaga tggcggaggc ctacagtgag attgggatga aggcgagcg ccggaggggc    1380 aaggggcacg atggccttta ccagggtctc agtacagcca ccaaggacac ctacgacgcc    1440
cttcacatgc aggccctgcc cctcgcgga gtgcaggtgg aaaccatctc cccaggagac    1500
```

-continued

```
gggcgcacct tccccaagcg cggccagacc tgcgtggtgc actacaccgg gatgcttgga    1560
gatggaaaga agttgactc ctcccgggac agaaacaagc cctttaagtt tatgctaggc    1620
aagcaggagg tgatccgagg ctgggaagaa ggggttgccc agatgagtgt gggtcaggga    1680
gccaaactga ctatatctcc agattatgcc tatggtgcca ctgggcaccc aggcatcatc    1740
ccaccacatg ccactctcgt cttcgatgtg gagcttctag aactggaatg a             1791
```

<210> SEQ ID NO 40
<211> LENGTH: 596
<212> TYPE: PRT
<213> ORGANISM: Artificial Sequence
<220> FEATURE:
<223> OTHER INFORMATION: synthetic

<400> SEQUENCE: 40

```
Met Leu Leu Leu Val Thr Ser Leu Leu Leu Cys Glu Leu Pro His Pro
1               5                   10                  15

Ala Phe Leu Leu Ile Pro Asp Ile Leu Leu Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Arg Asn Gly Asn Thr Tyr Leu His Trp Tyr Leu
    50                  55                  60

Gln Lys Pro Gly Gln Ser Pro Lys Leu Leu Ile His Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Ser Thr His Val Pro Pro Leu Thr Phe Gly Ala
        115                 120                 125

Gly Thr Lys Leu Glu Leu Lys Gly Ser Thr Ser Gly Ser Gly Lys Pro
    130                 135                 140

Gly Ser Gly Glu Gly Ser Thr Lys Gly Glu Val Lys Leu Gln Gln Ser
145                 150                 155                 160

Gly Pro Ser Leu Val Glu Pro Gly Ala Ser Val Met Ile Ser Cys Lys
                165                 170                 175

Ala Ser Gly Ser Ser Phe Thr Gly Tyr Asn Met Asn Trp Val Arg Gln
            180                 185                 190

Asn Ile Gly Lys Ser Leu Glu Trp Ile Gly Ala Ile Asp Pro Tyr Tyr
        195                 200                 205

Gly Gly Thr Ser Tyr Asn Gln Lys Phe Lys Gly Arg Ala Thr Leu Thr
    210                 215                 220

Val Asp Lys Ser Ser Ser Thr Ala Tyr Met His Leu Lys Ser Leu Thr
225                 230                 235                 240

Ser Glu Asp Ser Ala Val Tyr Tyr Cys Val Ser Gly Met Glu Tyr Trp
                245                 250                 255

Gly Gln Gly Thr Ser Val Thr Val Ser Ser Ala Ser Phe Glu Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320
```

```
Ala Cys Tyr Ser Leu Leu Val Thr Val Ala Phe Ile Ile Phe Trp Val
            325                 330                 335

Arg Ser Lys Arg Ser Arg Leu Leu His Ser Asp Tyr Met Asn Met Thr
        340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Val Gln Val Glu Thr Ile
                485                 490                 495

Ser Pro Gly Asp Gly Arg Thr Phe Pro Lys Arg Gly Gln Thr Cys Val
            500                 505                 510

Val His Tyr Thr Gly Met Leu Gly Asp Gly Lys Lys Val Asp Ser Ser
        515                 520                 525

Arg Asp Arg Asn Lys Pro Phe Lys Phe Met Leu Gly Lys Gln Glu Val
530                 535                 540

Ile Arg Gly Trp Glu Glu Gly Val Ala Gln Met Ser Val Gly Gln Gly
545                 550                 555                 560

Ala Lys Leu Thr Ile Ser Pro Asp Tyr Ala Tyr Gly Ala Thr Gly His
                565                 570                 575

Pro Gly Ile Ile Pro Pro His Ala Thr Leu Val Phe Asp Val Glu Leu
            580                 585                 590

Leu Glu Leu Glu
        595

<210> SEQ ID NO 41
<211> LENGTH: 66
<212> TYPE: DNA
<213> ORGANISM: Artificial Sequence
<220> FEATURE:
<223> OTHER INFORMATION: synthetic

<400> SEQUENCE: 41
atgctgctgc tcgtgacatc tctgctgctg tgcgagctgc cccacccgc ctttctgctg      60 atcccc                                                                66

<210> SEQ ID NO 42
<211> LENGTH: 22
<212> TYPE: PRT
<213> ORGANISM: Artificial Sequence
<220> FEATURE:
<223> OTHER INFORMATION: synthetic

<400> SEQUENCE: 42
```

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 43
<211> LENGTH: 732
<212> TYPE: DNA
<213> ORGANISM: Artificial Sequence
<220> FEATURE:
<223> OTHER INFORMATION: synthetic

<400> SEQUENCE: 43
gatatcctgc tgacccagac ccctctgagc ctgcctgtgt ctctgggcga tcaggccagc      60
atcagctgca gatccagcca gagcctggtg caccggaacg gcaacaccta cctgcactgg    120
tatctgcaga gcccggcca gagccccaag ctgctgattc acaaggtgtc caaccggttc     180
agcggcgtgc ccgacagatt ttctggcagc ggctccggca ccgacttcac cctgaagatc    240
agccgggtgg aagccgagga cctgggcgtg tacttctgca gccagtccac ccacgtgccc    300
cccctgacat tggcgccgg aacaaagctg aactgaagg cagcacaag cggcagcggc      360
aagcctggat ctggcgaggg aagcaccaag ggcgaagtga agctgcagca gagcggcccc    420
tctctggtgg aacctggcgc ctctgtgatg atctcctgca aggccagcgg cagctccttc    480
accggctaca acatgaactg ggtgcgccag aacatcggca gagcctgga atggatcggc    540
gccatcgacc cctactacgg cggcaccagc tacaaccaga gttcaaggg cagagccacc    600
ctgaccgtgg acaagagcag ctccaccgcc tacatgcacc tgaagtccct gaccagcgag    660
gacagcgccg tgtactactg cgtgtccggc atggaatact ggggccaggg cacaagcgtg    720
accgtgtcct ct                                                        732

<210> SEQ ID NO 44
<211> LENGTH: 244
<212> TYPE: PRT
<213> ORGANISM: Artificial Sequence
<220> FEATURE:
<223> OTHER INFORMATION: synthetic

<400> SEQUENCE: 44

Asp Ile Leu Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Ser Thr Ser Gly Ser Gly Lys Pro Gly Ser Gly Glu Gly Ser
        115                 120                 125

Thr Lys Gly Glu Val Lys Leu Gln Gln Ser Gly Pro Ser Leu Val Glu
    130                 135                 140

```
Pro Gly Ala Ser Val Met Ile Ser Cys Lys Ala Ser Gly Ser Ser Phe
145                 150                 155                 160

Thr Gly Tyr Asn Met Asn Trp Val Arg Gln Asn Ile Gly Lys Ser Leu
                165                 170                 175

Glu Trp Ile Gly Ala Ile Asp Pro Tyr Tyr Gly Gly Thr Ser Tyr Asn
            180                 185                 190

Gln Lys Phe Lys Gly Arg Ala Thr Leu Thr Val Asp Lys Ser Ser Ser
        195                 200                 205

Thr Ala Tyr Met His Leu Lys Ser Leu Thr Ser Glu Asp Ser Ala Val
    210                 215                 220

Tyr Tyr Cys Val Ser Gly Met Glu Tyr Trp Gly Gln Gly Thr Ser Val
225                 230                 235                 240

Thr Val Ser Ser
```

<210> SEQ ID NO 45
<211> LENGTH: 117
<212> TYPE: DNA
<213> ORGANISM: Artificial Sequence
<220> FEATURE:
<223> OTHER INFORMATION: synthetic

<400> SEQUENCE: 45
attgaagtta tgtatcctcc tccttaccta gacaatgaga agagcaatgg aaccattatc    60
catgtgaaag ggaaacacct ttgtccaagt cccctatttc ccggaccttc taagccc     117

<210> SEQ ID NO 46
<211> LENGTH: 39
<212> TYPE: PRT
<213> ORGANISM: Artificial Sequence
<220> FEATURE:
<223> OTHER INFORMATION: synthetic

<400> SEQUENCE: 46

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 47
<211> LENGTH: 81
<212> TYPE: DNA
<213> ORGANISM: Artificial Sequence
<220> FEATURE:
<223> OTHER INFORMATION: synthetic

<400> SEQUENCE: 47
ttttgggtgc tggtggtggt tgggggagtc ctggcttgct atagcttgct agtaacagtg    60
gcctttatta ttttctgggt g                                              81

<210> SEQ ID NO 48
<211> LENGTH: 27
<212> TYPE: PRT
<213> ORGANISM: Artificial Sequence
<220> FEATURE:
<223> OTHER INFORMATION: synthetic

<400> SEQUENCE: 48

```
Phe Trp Val Leu Val Val Val Gly Gly Val Leu Ala Cys Tyr Ser Leu
1               5                   10                  15
```

Leu Val Thr Val Ala Phe Ile Ile Phe Trp Val
            20                  25

<210> SEQ ID NO 49
<211> LENGTH: 123
<212> TYPE: DNA
<213> ORGANISM: Artificial Sequence
<220> FEATURE:
<223> OTHER INFORMATION: synthetic

<400> SEQUENCE: 49
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 50
<211> LENGTH: 41
<212> TYPE: PRT
<213> ORGANISM: Artificial Sequence
<220> FEATURE:
<223> OTHER INFORMATION: synthetic

<400> SEQUENCE: 50

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 51
<211> LENGTH: 336
<212> TYPE: DNA
<213> ORGANISM: Artificial Sequence
<220> FEATURE:
<223> OTHER INFORMATION: synthetic

<400> SEQUENCE: 51
agagtgaagt tcagcaggag cgcagacgcc cccgcgtaca gcagggcca gaaccagctc     60 tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc    240
cggaggggca aggggcacga tggcctttac cagggtctca gtacagccac caaggacacc   300
tacgacgccc ttcacatgca ggccctgccc cctcgc                             336

<210> SEQ ID NO 52
<211> LENGTH: 112
<212> TYPE: PRT
<213> ORGANISM: Artificial Sequence
<220> FEATURE:
<223> OTHER INFORMATION: synthetic

<400> SEQUENCE: 52

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 53
<211> LENGTH: 321
<212> TYPE: DNA
<213> ORGANISM: Artificial Sequence
<220> FEATURE:
<223> OTHER INFORMATION: synthetic

<400> SEQUENCE: 53
ggagtgcagg tggaaaccat ctccccagga gacgggcgca ccttccccaa gcgcggccag    60
acctgcgtgg tgcactacac cgggatgctt ggagatggaa agaaagttga ctcctcccgg   120
gacagaaaca gcccctttaa gtttatgcta ggcaagcagg aggtgatccg aggctgggaa   180 gaggggttg cccagatgag tgtgggtcag ggagccaaac tgactatatc tccagattat    240
gcctatggtg ccactgggca cccaggcatc atcccaccac atgccactct cgtcttcgat   300
gtggagcttc tagaactgga a                                             321

<210> SEQ ID NO 54
<211> LENGTH: 107
<212> TYPE: PRT
<213> ORGANISM: Artificial Sequence
<220> FEATURE:
<223> OTHER INFORMATION: synthetic

<400> SEQUENCE: 54

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Gly Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Glu Leu Glu
            100                 105

<210> SEQ ID NO 55
<211> LENGTH: 1944
<212> TYPE: DNA
<213> ORGANISM: Artificial Sequence
<220> FEATURE:
<223> OTHER INFORMATION: synthetic

<400> SEQUENCE: 55
atgctgctgc tcgtgacatc tctgctgctg tgcgagctgc ccacccccgc ctttctgctg    60
atccccgata tcctgctgac ccagacccct ctgagcctgc ctgtgtctct gggcgatcag   120

```
gccagcatca gctgcagatc cagccagagc ctggtgcacc ggaacggcaa caccctacctg      180 cactggtatc tgcagaagcc cggccagagc cccaagctgc tgattcacaa ggtgtccaac      240
cggttcagcg gcgtgcccga cagatttct ggcagcggct ccggcaccga cttcaccctg       300
aagatcagcc gggtggaagc cgaggacctg gcgtgtact tctgcagcca gtccaccca       360 gtgccccccc tgacatttgg cgccggaaca aagctggaac tgaagggcag cacaagcggc      420
agcggcaagc tggatctgg cgagggaagc caagggcg aagtgaagct gcagcagagc         480
ggcccctctc tggtggaacc tggcgcctct gtgatgatct cctgcaaggc agcggcagc      540 tccttcaccg gctacaacat gaactgggtg cgccagaaca tcggcaagag cctggaatgg      600
atcggcgcca tcgacccta ctacggcggc accagctaca accagaagtt caagggcaga      660
gccaccctga ccgtggacaa gagcagctcc accgcctaca tgcacctgaa gtccctgacc      720
agcgaggaca gcgccgtgta ctactgcgtg tccggcatgg aatactgggg ccagggcaca      780
agcgtgaccg tgtcctctgc tagcttcgaa attgaagtta tgtatcctcc tccttaccta      840
gacaatgaga gagcaatgg aaccattatc catgtgaaag ggaaacacct ttgtccaagt      900 cccctattc ccggaccttc taagccctt tgggtgctgg tggtggttgg gggagtcctg        960
gcttgctata gcttgctagt aacagtggcc tttattattt tctgggtgag gagtaagagg     1020
agcaggctcc tgcacagtga ctacatgaac atgactcccc gccgcccgg gcccaccgc       1080 aagcattacc agccctatgc cccaccacgc gacttcgcag cctatcgctc cagagtgaag     1140
ttcagcagga gcgcagacgc cccgcgtac aagcagggcc agaaccagct ctataacgag     1200
ctcaatctag gacgaagaga ggagtacgat gttttggaca agagacgtgg ccgggaccct     1260 gagatgggg gaaagccgag aaggaagaac cctcaggaag gcctgtacaa tgaactgcag     1320
aaagataaga tggcggaggc ctacagtgag attgggatga aggcgagcg ccggagggc      1380 aagggcacg atggcctta ccagggtctc agtacagcca ccaaggacac ctacgacgcc     1440
cttcacatgc aggccctgcc ccctcgcatc agtctgattg cggcgttagc ggtagattac     1500
gttatcggca tggaaaacgc catgccgtgg aacctgcctg ccgatctcgc ctggtttaaa     1560
cgcaacacct aaataaaacc cgtgattatg ggccgccata cctgggaatc aatcggtcgt     1620
ccgttgccag gacgcaaaaa tattatcctc agcagtcaac cgagtacgga cgatcgcgta     1680
acgtgggtga agtcggtgga tgaagccatc gcggcgtgtg tgacgtacc agaaatcatg     1740 gtgattggcg gcggtcgcgt tattgaacag ttcttgccaa agcgcaaaa actgtatctg      1800 acgcatatcg acgcagaagt ggaaggcgac acccatttcc cggattacga gccggatgac     1860
tgggaatcgg tattcagcga attccacgat gctgatgcgc agaactctca cagctattgc     1920
tttgagattc tggagcggcg atga                                              1944
```

<210> SEQ ID NO 56
<211> LENGTH: 647
<212> TYPE: PRT
<213> ORGANISM: Artificial Sequence
<220> FEATURE:
<223> OTHER INFORMATION: synthetic

<400> SEQUENCE: 56

```
Met Leu Leu Leu Val Thr Ser Leu Leu Leu Cys Glu Leu Pro His Pro
 1               5                  10                  15

Ala Phe Leu Leu Ile Pro Asp Ile Leu Leu Thr Gln Thr Pro Leu Ser
            20                  25                  30
```

-continued

```
Leu Pro Val Ser Leu Gly Asp Gln Ala Ser Ile Ser Cys Arg Ser Ser
            35                  40                  45
Gln Ser Leu Val His Arg Asn Gly Asn Thr Tyr Leu His Trp Tyr Leu
 50                  55                  60
Gln Lys Pro Gly Gln Ser Pro Lys Leu Leu Ile His Lys Val Ser Asn
65                  70                  75                  80
Arg Phe Ser Gly Val Pro Asp Arg Phe Ser Gly Ser Gly Ser Gly Thr
                85                  90                  95
Asp Phe Thr Leu Lys Ile Ser Arg Val Glu Ala Glu Asp Leu Gly Val
            100                 105                 110
Tyr Phe Cys Ser Gln Ser Thr His Val Pro Pro Leu Thr Phe Gly Ala
            115                 120                 125
Gly Thr Lys Leu Glu Leu Lys Gly Ser Thr Ser Gly Ser Gly Lys Pro
130                 135                 140
Gly Ser Gly Glu Gly Ser Thr Lys Gly Glu Val Lys Leu Gln Gln Ser
145                 150                 155                 160
Gly Pro Ser Leu Val Glu Pro Gly Ala Ser Val Met Ile Ser Cys Lys
                165                 170                 175
Ala Ser Gly Ser Ser Phe Thr Gly Tyr Asn Met Asn Trp Val Arg Gln
            180                 185                 190
Asn Ile Gly Lys Ser Leu Glu Trp Ile Gly Ala Ile Asp Pro Tyr Tyr
            195                 200                 205
Gly Gly Thr Ser Tyr Asn Gln Lys Phe Lys Gly Arg Ala Thr Leu Thr
            210                 215                 220
Val Asp Lys Ser Ser Ser Thr Ala Tyr Met His Leu Lys Ser Leu Thr
225                 230                 235                 240
Ser Glu Asp Ser Ala Val Tyr Tyr Cys Val Ser Gly Met Glu Tyr Trp
                245                 250                 255
Gly Gln Gly Thr Ser Val Thr Val Ser Ser Ala Ser Phe Glu Ile Glu
            260                 265                 270
Val Met Tyr Pro Pro Pro Tyr Leu Asp Asn Glu Lys Ser Asn Gly Thr
            275                 280                 285
Ile Ile His Val Lys Gly Lys His Leu Cys Pro Ser Pro Leu Phe Pro
290                 295                 300
Gly Pro Ser Lys Pro Phe Trp Val Leu Val Val Val Gly Gly Val Leu
305                 310                 315                 320
Ala Cys Tyr Ser Leu Leu Val Thr Val Ala Phe Ile Ile Phe Trp Val
                325                 330                 335
Arg Ser Lys Arg Ser Arg Leu Leu His Ser Asp Tyr Met Asn Met Thr
            340                 345                 350
Pro Arg Arg Pro Gly Pro Thr Arg Lys His Tyr Gln Pro Tyr Ala Pro
            355                 360                 365
Pro Arg Asp Phe Ala Ala Tyr Arg Ser Arg Val Lys Phe Ser Arg Ser
            370                 375                 380
Ala Asp Ala Pro Ala Tyr Lys Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
            435                 440                 445
Ser Glu Ile Gly Met Lys Gly Glu Arg Arg Arg Gly Lys Gly His Asp
```

Gly Leu Tyr Gln Gly Leu Ser Thr Ala Thr Lys Asp Thr Tyr Asp Ala
465                 470                 475                 480

Leu His Met Gln Ala Leu Pro Pro Arg Ile Ser Leu Ile Ala Ala Leu
            485                 490                 495

Ala Val Asp Tyr Val Ile Gly Met Glu Asn Ala Met Pro Trp Asn Leu
        500                 505                 510

Pro Ala Asp Leu Ala Trp Phe Lys Arg Asn Thr Leu Asn Lys Pro Val
    515                 520                 525

Ile Met Gly Arg His Thr Trp Glu Ser Ile Gly Arg Pro Leu Pro Gly
530                 535                 540

Arg Lys Asn Ile Ile Leu Ser Ser Gln Pro Ser Thr Asp Asp Arg Val
545                 550                 555                 560

Thr Trp Val Lys Ser Val Asp Glu Ala Ile Ala Ala Cys Gly Asp Val
                565                 570                 575

Pro Glu Ile Met Val Ile Gly Gly Gly Arg Val Ile Glu Gln Phe Leu
            580                 585                 590

Pro Lys Ala Gln Lys Leu Tyr Leu Thr His Ile Asp Ala Glu Val Glu
        595                 600                 605

Gly Asp Thr His Phe Pro Asp Tyr Glu Pro Asp Asp Trp Glu Ser Val
    610                 615                 620

Phe Ser Glu Phe His Asp Ala Asp Ala Gln Asn Ser His Ser Tyr Cys
625                 630                 635                 640

Phe Glu Ile Leu Glu Arg Arg
                645

<210> SEQ ID NO 57
<211> LENGTH: 66
<212> TYPE: DNA
<213> ORGANISM: Artificial Sequence
<220> FEATURE:
<223> OTHER INFORMATION: synthetic

<400> SEQUENCE: 57
atgctgctgc tcgtgacatc tctgctgctg tgcgagctgc cccacccgc ctttctgctg     60 atcccc                                                               66

<210> SEQ ID NO 58
<211> LENGTH: 22
<212> TYPE: PRT
<213> ORGANISM: Artificial Sequence
<220> FEATURE:
<223> OTHER INFORMATION: synthetic

<400> SEQUENCE: 58

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 59
<211> LENGTH: 732
<212> TYPE: DNA
<213> ORGANISM: Artificial Sequence
<220> FEATURE:
<223> OTHER INFORMATION: synthetic

<400> SEQUENCE: 59
gatatcctgc tgacccagac ccctctgagc ctgcctgtgt ctctgggcga tcaggccagc     60

```
atcagctgca gatccagcca gagcctggtg caccggaacg gcaacaccta cctgcactgg      120
tatctgcaga agcccggcca gagccccaag ctgctgattc acaaggtgtc caaccggttc      180
agcggcgtgc ccgacagatt ttctggcagc ggctccggca ccgacttcac cctgaagatc      240
agccgggtgg aagccgagga cctgggcgtg tacttctgca gccagtccac ccacgtgccc      300
cccctgacat ttggcgccgg aacaaagctg gaactgaagg cagcacaag cggcagcggc       360 aagcctggat ctggcgaggg aagcaccaag ggcgaagtga agctgcagca gagcggcccc      420
tctctggtgg aacctggcgc ctctgtgatg atctcctgca aggccagcgg cagctccttc      480
accggctaca acatgaactg ggtgcgccag aacatcggca gagcctgga atggatcggc       540 gccatcgacc cctactacgg cggcaccagc tacaaccaga gttcaaggg cagagccacc       600 ctgaccgtgg acaagagcag ctccaccgcc tacatgcacc tgaagtccct gaccagcgag      660
gacagcgccg tgtactactg cgtgtccggc atggaatact ggggccaggg cacaagcgtg      720
accgtgtcct ct                                                         732
```

<210> SEQ ID NO 60
<211> LENGTH: 244
<212> TYPE: PRT
<213> ORGANISM: Artificial Sequence
<220> FEATURE:
<223> OTHER INFORMATION: synthetic

<400> SEQUENCE: 60

```
Asp Ile Leu Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Ser Thr Ser Gly Ser Gly Lys Pro Gly Ser Gly Glu Gly Ser
        115                 120                 125

Thr Lys Gly Glu Val Lys Leu Gln Gln Ser Gly Pro Ser Leu Val Glu
    130                 135                 140

Pro Gly Ala Ser Val Met Ile Ser Cys Lys Ala Ser Gly Ser Ser Phe
145                 150                 155                 160

Thr Gly Tyr Asn Met Asn Trp Val Arg Gln Asn Ile Gly Lys Ser Leu
                165                 170                 175

Glu Trp Ile Gly Ala Ile Asp Pro Tyr Tyr Gly Gly Thr Ser Tyr Asn
            180                 185                 190

Gln Lys Phe Lys Gly Arg Ala Thr Leu Thr Val Asp Lys Ser Ser Ser
        195                 200                 205

Thr Ala Tyr Met His Leu Lys Ser Leu Thr Ser Glu Asp Ser Ala Val
    210                 215                 220

Tyr Tyr Cys Val Ser Gly Met Glu Tyr Trp Gly Gln Gly Thr Ser Val
225                 230                 235                 240
```

Thr Val Ser Ser

<210> SEQ ID NO 61
<211> LENGTH: 117
<212> TYPE: DNA
<213> ORGANISM: Artificial Sequence
<220> FEATURE:
<223> OTHER INFORMATION: synthetic

<400> SEQUENCE: 61
attgaagtta tgtatcctcc tccttaccta gacaatgaga agagcaatgg aaccattatc    60
catgtgaaag ggaaacacct ttgtccaagt cccctatttc ccggaccttc taagccc      117

<210> SEQ ID NO 62
<211> LENGTH: 39
<212> TYPE: PRT
<213> ORGANISM: Artificial Sequence
<220> FEATURE:
<223> OTHER INFORMATION: synthetic

<400> SEQUENCE: 62

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 63
<211> LENGTH: 81
<212> TYPE: DNA
<213> ORGANISM: Artificial Sequence
<220> FEATURE:
<223> OTHER INFORMATION: synthetic

<400> SEQUENCE: 63
ttttgggtgc tggtggtggt tgggggagtc ctggcttgct atagcttgct agtaacagtg    60
gcctttatta ttttctgggt g                                              81

<210> SEQ ID NO 64
<211> LENGTH: 27
<212> TYPE: PRT
<213> ORGANISM: Artificial Sequence
<220> FEATURE:
<223> OTHER INFORMATION: synthetic

<400> SEQUENCE: 64

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 65
<211> LENGTH: 123
<212> TYPE: DNA
<213> ORGANISM: Artificial Sequence
<220> FEATURE:
<223> OTHER INFORMATION: synthetic

<400> SEQUENCE: 65
aggagtaaga ggagcaggct cctgcacagt gactacatga acatgactcc ccgccgcccc    60
gggcccaccc gcaagcatta ccagccctat gccccaccac gcgacttcgc agcctatcgc   120

```
tcc                                                                 123
```

<210> SEQ ID NO 66
<211> LENGTH: 41
<212> TYPE: PRT
<213> ORGANISM: Artificial Sequence
<220> FEATURE:
<223> OTHER INFORMATION: synthetic

<400> SEQUENCE: 66

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 67
<211> LENGTH: 336
<212> TYPE: DNA
<213> ORGANISM: Artificial Sequence
<220> FEATURE:
<223> OTHER INFORMATION: synthetic

<400> SEQUENCE: 67

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc    240 cggagggggca aggggcacga tggcctttac cagggtctca gtacagccac caaggacacc   300
tacgacgccc ttcacatgca ggccctgccc cctcgc                              336
```

<210> SEQ ID NO 68
<211> LENGTH: 112
<212> TYPE: PRT
<213> ORGANISM: Artificial Sequence
<220> FEATURE:
<223> OTHER INFORMATION: synthetic

<400> SEQUENCE: 68

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 69
<211> LENGTH: 474
<212> TYPE: DNA

<213> ORGANISM: Artificial Sequence
<220> FEATURE:
<223> OTHER INFORMATION: synthetic

<400> SEQUENCE: 69

```
atcagtctga ttgcggcgtt agcggtagat tacgttatcg gcatggaaaa cgccatgccg    60
tggaacctgc ctgccgatct cgcctggttt aaacgcaaca ccttaaataa acccgtgatt   120
atgggccgcc atacctggga atcaatcggt cgtccgttgc caggacgcaa aaatattatc   180
ctcagcagtc aaccgagtac ggacgatcgc gtaacgtggg tgaagtcggt ggatgaagcc   240
atcgcggcgt gtggtgacgt accagaaatc atggtgattg cggcggtcg cgttattgaa    300
cagttcttgc caaaagcgca aaaactgtat ctgacgcata tcgacgcaga agtggaaggc   360
gacacccatt tcccggatta cgagccggat gactgggaat cggtattcag cgaattccac   420
gatgctgatg cgcagaactc tcacagctat tgctttgaga ttctggagcg gcga          474
```

<210> SEQ ID NO 70
<211> LENGTH: 158
<212> TYPE: PRT
<213> ORGANISM: Artificial Sequence
<220> FEATURE:
<223> OTHER INFORMATION: synthetic

<400> SEQUENCE: 70

```
Ile Ser Leu Ile Ala Ala Leu Ala Val Asp Tyr Val Ile Gly Met Glu
 1               5                  10                  15

Asn Ala Met Pro Trp Asn Leu Pro Ala Asp Leu Ala Trp Phe Lys Arg
            20                  25                  30

Asn Thr Leu Asn Lys Pro Val Ile Met Gly Arg His Thr Trp Glu Ser
        35                  40                  45

Ile Gly Arg Pro Leu Pro Gly Arg Lys Asn Ile Ile Leu Ser Ser Gln
    50                  55                  60

Pro Ser Thr Asp Asp Arg Val Thr Trp Val Lys Ser Val Asp Glu Ala
65                  70                  75                  80

Ile Ala Ala Cys Gly Asp Val Pro Glu Ile Met Val Ile Gly Gly Gly
                85                  90                  95

Arg Val Ile Glu Gln Phe Leu Pro Lys Ala Gln Lys Leu Tyr Leu Thr
            100                 105                 110

His Ile Asp Ala Glu Val Glu Gly Asp Thr His Phe Pro Asp Tyr Glu
        115                 120                 125

Pro Asp Asp Trp Glu Ser Val Phe Ser Glu Phe His Asp Ala Asp Ala
    130                 135                 140

Gln Asn Ser His Ser Tyr Cys Phe Glu Ile Leu Glu Arg Arg
145                 150                 155
```

<210> SEQ ID NO 71
<211> LENGTH: 1950
<212> TYPE: DNA
<213> ORGANISM: Artificial Sequence
<220> FEATURE:
<223> OTHER INFORMATION: synthetic

<400> SEQUENCE: 71

```
atgctgctgc tcgtgacatc tctgctgctg tgcgagctgc ccacccccgc ctttctgctg    60
atccccgata tcctgctgac ccagacccct ctgagcctgc ctgtgtctct gggcgatcag   120
gccagcatca gctgcagatc cagccagagc ctggtgcacc ggaacggcaa cacctacctg   180
cactggtatc tgcagaagcc cggccagagc cccaagctgc tgattcacaa ggtgtccaac   240
```

```
cggttcagcg gcgtgcccga cagattttct ggcagcggct ccggcaccga cttcaccctg    300
aagatcagcc gggtggaagc cgaggacctg ggcgtgtact tctgcagcca gtccacccac    360 gtgcccccc tgacatttgg cgccggaaca aagctggaac tgaagggcag cacaagcggc     420
agcggcaagc ctggatctgg cgaggaagc accaagggcg aagtgaagct gcagcagagc     480
ggcccctctc tggtggaacc tggcgcctct gtgatgatct cctgcaaggc agcggcagc     540 tccttcaccg gctacaacat gaactgggtg cgccagaaca tcggcaagag cctggaatgg    600
atcggcgcca tcgaccccta ctacggcggc accagctaca accagaagtt caagggcaga    660
gccaccctga ccgtgacaa gagcagctcc accgcctaca tgcacctgaa gtccctgacc     720
agcgaggaca gcgccgtgta ctactgcgtg tccggcatgg aatactgggg ccagggcaca    780
agcgtgaccg tgtcctctgc tagcttcgaa attgaagtta tgtatcctcc tccttaccta    840
gacaatgaga agagcaatgg aaccattatc catgtgaaag ggaaacacct ttgtccaagt    900 cccctattc ccggaccttc taagcccttt gggtgctgg tggtggttgg gggagtcctg      960
gcttgctata gcttgctagt aacagtggcc tttattattt tctgggtgag gagtaagagg    1020
agcaggctcc tgcacagtga ctacatgaac atgactcccc gccgcccgg gcccacccgc     1080 aagcattacc agccctatgc cccaccacgc gacttcgcag cctatcgctc ccatatgaga    1140
gtgaagttca gcaggagcgc agacgccccc gcgtacaagc agggccagaa ccagctctat    1200
aacgagctca atctaggacg aagagaggag tacgatgttt tggacaagag acgtggccgg    1260
gaccctgaga tggggggaaa gccgagaagg aagaaccctc aggaaggcct gtacaatgaa    1320
ctgcagaaag ataagatggc ggaggcctac agtgagattg ggatgaaagg cgagcgccgg    1380 agggcaagg ggcacgatgg cctttaccag ggtctcagta cagccaccaa ggacacctac     1440 gacgccttc acatgcaggc cctgccccct cgcatcagtc tgattgcggc gttagcggta    1500
gattacgtta tcggcatgga aaacgccatg ccgtggaacc tgcctgccga tctcgcctgg    1560
tttaaacgca acaccttaaa taaacccgtg attatgggcc gccatacctg ggaatcaatc    1620
ggtcgtccgt tgccaggacg caaaaatatt atcctcagca gtcaaccgag tacgacgat    1680 cgcgtaacgt gggtgaagtc ggtggatgaa gccatcgcgg cgtgtggtga cgtaccagaa    1740
atcatggtga ttggcggcgg tcgcgttatt gaacagttct tgccaaaagc gcaaaaactg    1800
tatctgacgc atatcgacgc agaagtggaa ggcgacaccc atttcccgga ttacgagccg    1860
gatgactggg aatcggtatt cagcgaattc cacgatgctg atgcgcagaa ctctcacagc    1920
tattgctttg agattctgga gcggcgatga                                      1950
```

<210> SEQ ID NO 72
<211> LENGTH: 649
<212> TYPE: PRT
<213> ORGANISM: Artificial Sequence
<220> FEATURE:
<223> OTHER INFORMATION: synthetic

<400> SEQUENCE: 72

```
Met Leu Leu Leu Val Thr Ser Leu Leu Cys Glu Leu Pro His Pro
1               5                   10                  15

Ala Phe Leu Leu Ile Pro Asp Ile Leu Leu Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Arg Asn Gly Asn Thr Tyr Leu His Trp Tyr Leu
```

-continued

```
            50                  55                  60
Gln Lys Pro Gly Gln Ser Pro Lys Leu Leu Ile His Lys Val Ser Asn
 65                  70                  75                  80

Arg Phe Ser Gly Val Pro Asp Arg Phe Ser Gly Ser Gly Ser Gly Thr
                 85                  90                  95

Asp Phe Thr Leu Lys Ile Ser Arg Val Glu Ala Glu Asp Leu Gly Val
                100                 105                 110

Tyr Phe Cys Ser Gln Ser Thr His Val Pro Pro Leu Thr Phe Gly Ala
                115                 120                 125

Gly Thr Lys Leu Glu Leu Lys Gly Ser Thr Ser Gly Ser Gly Lys Pro
            130                 135                 140

Gly Ser Gly Glu Gly Ser Thr Lys Gly Glu Val Lys Leu Gln Gln Ser
145                 150                 155                 160

Gly Pro Ser Leu Val Glu Pro Gly Ala Ser Val Met Ile Ser Cys Lys
                165                 170                 175

Ala Ser Gly Ser Ser Phe Thr Gly Tyr Asn Met Asn Trp Val Arg Gln
                180                 185                 190

Asn Ile Gly Lys Ser Leu Glu Trp Ile Gly Ala Ile Asp Pro Tyr Tyr
            195                 200                 205

Gly Gly Thr Ser Tyr Asn Gln Lys Phe Lys Gly Arg Ala Thr Leu Thr
            210                 215                 220

Val Asp Lys Ser Ser Ser Thr Ala Tyr Met His Leu Lys Ser Leu Thr
225                 230                 235                 240

Ser Glu Asp Ser Ala Val Tyr Tyr Cys Val Ser Gly Met Glu Tyr Trp
                245                 250                 255

Gly Gln Gly Thr Ser Val Thr Val Ser Ser Ala Ser Phe Glu Ile Glu
                260                 265                 270

Val Met Tyr Pro Pro Pro Tyr Leu Asp Asn Glu Lys Ser Asn Gly Thr
                275                 280                 285

Ile Ile His Val Lys Gly Lys His Leu Cys Pro Ser Pro Leu Phe Pro
            290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
                340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser His Met Arg Val Lys Phe Ser
            370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480
```

```
Asp Ala Leu His Met Gln Ala Leu Pro Pro Arg Ile Ser Leu Ile Ala
                485                 490                 495

Ala Leu Ala Val Asp Tyr Val Ile Gly Met Glu Asn Ala Met Pro Trp
            500                 505                 510

Asn Leu Pro Ala Asp Leu Ala Trp Phe Lys Arg Asn Thr Leu Asn Lys
        515                 520                 525

Pro Val Ile Met Gly Arg His Thr Trp Glu Ser Ile Gly Arg Pro Leu
    530                 535                 540

Pro Gly Arg Lys Asn Ile Ile Leu Ser Ser Gln Pro Ser Thr Asp Asp
545                 550                 555                 560

Arg Val Thr Trp Val Lys Ser Val Asp Glu Ala Ile Ala Ala Cys Gly
                565                 570                 575

Asp Val Pro Glu Ile Met Val Ile Gly Gly Arg Val Ile Glu Gln
            580                 585                 590

Phe Leu Pro Lys Ala Gln Lys Leu Tyr Leu Thr His Ile Asp Ala Glu
        595                 600                 605

Val Glu Gly Asp Thr His Phe Pro Asp Tyr Glu Pro Asp Asp Trp Glu
    610                 615                 620

Ser Val Phe Ser Glu Phe His Asp Ala Asp Ala Gln Asn Ser His Ser
625                 630                 635                 640

Tyr Cys Phe Glu Ile Leu Glu Arg Arg
                645

<210> SEQ ID NO 73
<211> LENGTH: 66
<212> TYPE: DNA
<213> ORGANISM: Artificial Sequence
<220> FEATURE:
<223> OTHER INFORMATION: synthetic

<400> SEQUENCE: 73
atgctgctgc tcgtgacatc tctgctgctg tgcgagctgc cccacccgc ctttctgctg      60 atcccc                                                                66

<210> SEQ ID NO 74
<211> LENGTH: 22
<212> TYPE: PRT
<213> ORGANISM: Artificial Sequence
<220> FEATURE:
<223> OTHER INFORMATION: synthetic

<400> SEQUENCE: 74

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 75
<211> LENGTH: 732
<212> TYPE: DNA
<213> ORGANISM: Artificial Sequence
<220> FEATURE:
<223> OTHER INFORMATION: synthetic

<400> SEQUENCE: 75
gatatcctgc tgacccagac ccctctgagc ctgcctgtgt ctctgggcga tcaggccagc      60
atcagctgca gatccagcca gagcctggtg caccggaacg gcaacaccta cctgcactgg     120
tatctgcaga agcccggcca gagccccaag ctgctgattt acaaggtgtc caaccggttc     180
```

```
agcggcgtgc ccgacagatt ttctggcagc ggctccggca ccgacttcac cctgaagatc      240
agccgggtgg aagccgagga cctgggcgtg tacttctgca gccagtccac ccacgtgccc      300
cccctgacat ttggcgccgg aacaaagctg gaactgaagg gcagcacaag cggcagcggc      360
aagcctggat ctggcgaggg aagcaccaag ggcgaagtga agctgcagca gagcggcccc      420
tctctggtgg aacctggcgc ctctgtgatg atctcctgca aggccagcgg cagctccttc      480
accggctaca acatgaactg ggtgcgccag aacatcggca gagcctggaa atggatcggc      540
gccatcgacc cctactacgg cggcaccagc tacaaccaga gttcaaggg cagagccacc      600 ctgaccgtgg acaagagcag ctccaccgcc tacatgcacc tgaagtccct gaccagcgag      660
gacagcgccg tgtactactg cgtgtccggc atggaatact ggggccaggg cacaagcgtg      720
accgtgtcct ct                                                          732
```

<210> SEQ ID NO 76
<211> LENGTH: 244
<212> TYPE: PRT
<213> ORGANISM: Artificial Sequence
<220> FEATURE:
<223> OTHER INFORMATION: synthetic

<400> SEQUENCE: 76

```
Asp Ile Leu Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Ser Thr Ser Gly Ser Gly Lys Pro Gly Ser Gly Glu Gly Ser
        115                 120                 125

Thr Lys Gly Glu Val Lys Leu Gln Gln Ser Gly Pro Ser Leu Val Glu
    130                 135                 140

Pro Gly Ala Ser Val Met Ile Ser Cys Lys Ala Ser Gly Ser Ser Phe
145                 150                 155                 160

Thr Gly Tyr Asn Met Asn Trp Val Arg Gln Asn Ile Gly Lys Ser Leu
                165                 170                 175

Glu Trp Ile Gly Ala Ile Asp Pro Tyr Tyr Gly Gly Thr Ser Tyr Asn
            180                 185                 190

Gln Lys Phe Lys Gly Arg Ala Thr Leu Thr Val Asp Lys Ser Ser Ser
        195                 200                 205

Thr Ala Tyr Met His Leu Lys Ser Leu Thr Ser Glu Asp Ser Ala Val
    210                 215                 220

Tyr Tyr Cys Val Ser Gly Met Glu Tyr Trp Gly Gln Gly Thr Ser Val
225                 230                 235                 240

Thr Val Ser Ser
```

```
<210> SEQ ID NO 77
<211> LENGTH: 117
<212> TYPE: DNA
<213> ORGANISM: Artificial Sequence
<220> FEATURE:
<223> OTHER INFORMATION: synthetic

<400> SEQUENCE: 77
attgaagtta tgtatcctcc tccttaccta gacaatgaga agagcaatgg aaccattatc    60
catgtgaaag ggaaacacct ttgtccaagt cccctatttc ccggaccttc taagccc     117

<210> SEQ ID NO 78
<211> LENGTH: 39
<212> TYPE: PRT
<213> ORGANISM: Artificial Sequence
<220> FEATURE:
<223> OTHER INFORMATION: synthetic

<400> SEQUENCE: 78

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 79
<211> LENGTH: 81
<212> TYPE: DNA
<213> ORGANISM: Artificial Sequence
<220> FEATURE:
<223> OTHER INFORMATION: synthetic

<400> SEQUENCE: 79
ttttgggtgc tggtggtggt tgggggagtc ctggcttgct atagcttgct agtaacagtg    60
gcctttatta ttttctgggt g                                              81

<210> SEQ ID NO 80
<211> LENGTH: 27
<212> TYPE: PRT
<213> ORGANISM: Artificial Sequence
<220> FEATURE:
<223> OTHER INFORMATION: synthetic

<400> SEQUENCE: 80

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 81
<211> LENGTH: 123
<212> TYPE: DNA
<213> ORGANISM: Artificial Sequence
<220> FEATURE:
<223> OTHER INFORMATION: synthetic

<400> SEQUENCE: 81
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 82
<211> LENGTH: 41
<212> TYPE: PRT
<213> ORGANISM: Artificial Sequence
<220> FEATURE:
<223> OTHER INFORMATION: synthetic

<400> SEQUENCE: 82

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 83
<211> LENGTH: 336
<212> TYPE: DNA
<213> ORGANISM: Artificial Sequence
<220> FEATURE:
<223> OTHER INFORMATION: synthetic

<400> SEQUENCE: 83
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga agataagat ggcggaggcc tacagtgaga ttgggatgaa aggcgagcgc      240
cggaggggca aggggcacga tggcctttac cagggtctca gtacagccac caaggacacc    300
tacgacgccc ttcacatgca ggccctgccc cctcgc                              336

<210> SEQ ID NO 84
<211> LENGTH: 112
<212> TYPE: PRT
<213> ORGANISM: Artificial Sequence
<220> FEATURE:
<223> OTHER INFORMATION: synthetic

<400> SEQUENCE: 84

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 85
<211> LENGTH: 477
<212> TYPE: DNA
<213> ORGANISM: Artificial Sequence
<220> FEATURE:
<223> OTHER INFORMATION: synthetic

<400> SEQUENCE: 85

```
atgatcagtc tgattgcggc gttagcggta gatcacgtta tcggcatgga aaccgtcatg    60
ccgtggaacc tgcctgccga tctcgcctgg tttaaacgca acaccttaaa taaacccgtg   120
attatgggcc gccatacctg ggaatcaatc ggtcgtccgt tgccaggacg caaaaatatt   180
atcctcagca gtcaaccgag tacggacgat cgcgtaacgt gggtgaagtc ggtggatgaa   240
gccatcgcgg cgtgtggtga cgtaccagaa atcatggtta ttggcggcgg tcgcgtttat   300
gaacagttct tgccaaaagc gcaaaaactg tatctgacgc atatcgacgc agaagtggaa   360
ggcgacaccc catttcccgga ttacgagccg gatgactggg aatcggtatt cagcgaattc   420
cacgatgctg atgcgcagaa ctctcacagc tattgctttg agattctgga gcggcga      477
```

<210> SEQ ID NO 86
<211> LENGTH: 158
<212> TYPE: PRT
<213> ORGANISM: Artificial Sequence
<220> FEATURE:
<223> OTHER INFORMATION: synthetic

<400> SEQUENCE: 86

```
Ile Ser Leu Ile Ala Ala Leu Ala Val Asp Tyr Val Ile Gly Met Glu
1               5                   10                  15
Asn Ala Met Pro Trp Asn Leu Pro Ala Asp Leu Ala Trp Phe Lys Arg
            20                  25                  30
Asn Thr Leu Asn Lys Pro Val Ile Met Gly Arg His Thr Trp Glu Ser
        35                  40                  45
Ile Gly Arg Pro Leu Pro Gly Arg Lys Asn Ile Ile Leu Ser Ser Gln
    50                  55                  60
Pro Ser Thr Asp Asp Arg Val Thr Trp Val Lys Ser Val Asp Glu Ala
65                  70                  75                  80
Ile Ala Ala Cys Gly Asp Val Pro Glu Ile Met Val Ile Gly Gly Gly
                85                  90                  95
Arg Val Ile Glu Gln Phe Leu Pro Lys Ala Gln Lys Leu Tyr Leu Thr
            100                 105                 110
His Ile Asp Ala Glu Val Glu Gly Asp Thr His Phe Pro Asp Tyr Glu
        115                 120                 125
Pro Asp Asp Trp Glu Ser Val Phe Ser Glu Phe His Asp Ala Asp Ala
    130                 135                 140
Gln Asn Ser His Ser Tyr Cys Phe Glu Ile Leu Glu Arg Arg
145                 150                 155
```

<210> SEQ ID NO 87
<211> LENGTH: 2538
<212> TYPE: DNA
<213> ORGANISM: Artificial Sequence
<220> FEATURE:
<223> OTHER INFORMATION: synthetic

<400> SEQUENCE: 87

```
atggaattcg gcctgagctg ctgtgtttctg gtggccattc tgaagggcgt gcagtgctcc    60
agagacatcc tgctgacaca gacacctctg agcctgcctg tgtctctggg agatcaggcc   120
agcatcagct gtagaagcag ccagagcctg gtgcacagaa acggcaatac ctacctgcac   180
tggtatctgc agaagcccgg ccagtctcct aagctgctga tccacaaggt gtccaacaga   240
ttcagcggcg tgcccgatag attttctggc tctggcagcg gcaccgactt caccctgaag   300
atctctagag tggaagccga ggacctgggc gtgtacttct gtagccagag cacacatgtg   360
```

```
cctccactga cctttggcgc tggcaccaaa ctggaactta aaggcggcgg aggatctggt    420
ggtggtggat ctggcggagg cggttctgaa gtgaaactgc agcagtctgg cccctctctg    480
gttgaacctg gcgcctctgt gatgatctct tgcaaggcca gcggcagcag cttcaccggc    540
tacaacatga actgggtccg acagaacatc ggcaagagcc tggaatggat cggcgccatc    600
gatccttact acggcggcac cagctacaac cagaagttca agggcagagc cacactgacc    660
gtggacaaga gcagcagcac agcctacatg cacctgaagt ccctgacaag cgaggacagc    720
gccgtgtact actgtgtgtc cggcatgaag tattggggcc agggcacaag cgtgaccgtg    780
tctagcgcta agaccacacc tcctagcgtg tacggcagag tgacagtgtc cagcgccgag    840
cctaagagct gcgacaagac acacacctgt cctccatgtc cagctccaga actgctcggc    900
ggaccctccg ttttcctgtt tccacctaag ccaaaggaca ccctcatgat cagcagaacc    960
cctgaagtga cctgcgtggt ggtcgatgtg tcccacgagg atcccgaagt gaagttcaat   1020
tggtacgtgg acggcgtgga agtgcacaac gccaagacca gcctagaga ggaacagtac   1080
aacagcacct acagagtggt gtccgtgctg accgtgctgc atcaggactg gctgaacggc   1140
aaagagtaca agtgcaaagt ctccaacaag gccctgcctg ctcctatcga aaaaccatc    1200
agcaaggcca agggccagcc aagagaaccc caggtttaca cactgcctcc aagcagggac   1260
gagctgacca agaatcaggt gtccctgacc tgcctggtca agggcttcta cccttccgat   1320
atcgccgtgg aatgggagag caatggccag cctgagaaca actacaagac aaccccctcct 1380
gtgctggaca gcgacggctc attcttcctg tacagcaagc tgacagtgga taagtcccgg   1440
tggcagcagg gcaatgtgtt cagctgttct gtgatgcacg aggccctgca caaccactac   1500
acccagaaaa gcctgtctct gagccccggc aagaaggacc ctaaagctag cttcgaaatt   1560
gaagttatgt atcctcctcc ttacctagac aatgagaaga gcaatggaac cattatccat   1620
gtgaaaggga acacccttg tccaagtccc ctatttcccg accttctaa gccccttttgg    1680
gtgctggtgg tggttggggg agtcctggct tgctatagct tgctagtaac agtggccttt   1740
attattttct gggtgaggag taagaggagc aggctcctgc acagtgacta catgaacatg   1800
actccccgcc gccccgggcc caccccgcaag cattaccagc cctatgccc accacgcgac   1860
ttcgcagcct atcgctccag agtgaagttc agcaggagcg cagacgcccc cgcgtacaag   1920
cagggccaga accagctcta taacgagctc aatctaggac gaagagagga gtacgatgtt   1980
ttggacaaga cgtggccg ggaccctgag atgggggaa agccgagaag gaagaaccct    2040
caggaaggcc tgtacaatga actgcagaaa gataagatgg cggaggccta cagtgagatt   2100
gggatgaaag gcgagcgccg gaggggcaag gggcacgatg gcctttacca gggtctcagt   2160
acagccacca aggacccta cgacgccctt cacatgcagg ccctgccccc tcgcggagtg   2220
caggtggaaa ccatctcccc aggagacggg cgcaccttcc ccaagcgcgg ccagacctgc   2280
gtggtgcact acaccgggat gcttggagat ggaaagaaag ttgactcctc ccgggacaga   2340
aacaagccct ttaagtttat gctaggcaag caggaggtga tccgaggctg ggaagaaggg   2400
gttgcccaga tgagtgtggg tcagggagcc aaactgacta tatctccaga ttatgcctat   2460
ggtgccactg ggcacccagg catcatccca ccacatgcca ctctcgtctt cgatgtggag   2520
cttctagaac tggaatga                                                2538
```

<210> SEQ ID NO 88
<211> LENGTH: 845
<212> TYPE: PRT

<213> ORGANISM: Artificial Sequence
<220> FEATURE:
<223> OTHER INFORMATION: synthetic

<400> SEQUENCE: 88

```
Met Glu Phe Gly Leu Ser Trp Leu Phe Leu Val Ala Ile Leu Lys Gly
1               5                   10                  15

Val Gln Cys Ser Arg Asp Ile Leu Leu Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Arg Asn Gly Asn Thr Tyr Leu His Trp Tyr Leu Gln
    50                  55                  60

Lys Pro Gly Gln Ser Pro Lys Leu Leu Ile His Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Pro Leu Thr Phe Gly Ala Gly
        115                 120                 125

Thr Lys Leu Glu Leu Lys Gly Gly Gly Ser Gly Gly Gly Gly Ser
    130                 135                 140

Gly Gly Gly Gly Ser Glu Val Lys Leu Gln Gln Ser Gly Pro Ser Leu
145                 150                 155                 160

Val Glu Pro Gly Ala Ser Val Met Ile Ser Cys Lys Ala Ser Gly Ser
                165                 170                 175

Ser Phe Thr Gly Tyr Asn Met Asn Trp Val Arg Gln Asn Ile Gly Lys
            180                 185                 190

Ser Leu Glu Trp Ile Gly Ala Ile Asp Pro Tyr Tyr Gly Gly Thr Ser
        195                 200                 205

Tyr Asn Gln Lys Phe Lys Gly Arg Ala Thr Leu Thr Val Asp Lys Ser
    210                 215                 220

Ser Ser Thr Ala Tyr Met His Leu Lys Ser Leu Thr Ser Glu Asp Ser
225                 230                 235                 240

Ala Val Tyr Tyr Cys Val Ser Gly Met Lys Tyr Trp Gly Gln Gly Thr
                245                 250                 255

Ser Val Thr Val Ser Ser Ala Lys Thr Thr Pro Pro Ser Val Tyr Gly
            260                 265                 270

Arg Val Thr Val Ser Ser Ala Glu Pro Lys Ser Cys Asp Lys Thr His
        275                 280                 285

Thr Cys Pro Pro Cys Pro Ala Pro Glu Leu Leu Gly Gly Pro Ser Val
    290                 295                 300

Phe Leu Phe Pro Pro Lys Pro Lys Asp Thr Leu Met Ile Ser Arg Thr
305                 310                 315                 320

Pro Glu Val Thr Cys Val Val Val Asp Val Ser His Glu Asp Pro Glu
                325                 330                 335

Val Lys Phe Asn Trp Tyr Val Asp Gly Val Glu Val His Asn Ala Lys
            340                 345                 350

Thr Lys Pro Arg Glu Glu Gln Tyr Asn Ser Thr Tyr Arg Val Val Ser
        355                 360                 365

Val Leu Thr Val Leu His Gln Asp Trp Leu Asn Gly Lys Glu Tyr Lys
    370                 375                 380

Cys Lys Val Ser Asn Lys Ala Leu Pro Ala Pro Ile Glu Lys Thr Ile
```

-continued

```
            385                 390                 395                 400
        Ser Lys Ala Lys Gly Gln Pro Arg Glu Pro Gln Val Tyr Thr Leu Pro
                        405                 410                 415

Pro Ser Arg Asp Glu Leu Thr Lys Asn Gln Val Ser Leu Thr Cys Leu
                        420                 425                 430

Val Lys Gly Phe Tyr Pro Ser Asp Ile Ala Val Glu Trp Glu Ser Asn
                        435                 440                 445

Gly Gln Pro Glu Asn Asn Tyr Lys Thr Thr Pro Pro Val Leu Asp Ser
        450                 455                 460

Asp Gly Ser Phe Phe Leu Tyr Ser Lys Leu Thr Val Asp Lys Ser Arg
        465                 470                 475                 480

Trp Gln Gln Gly Asn Val Phe Ser Cys Ser Val Met His Glu Ala Leu
                        485                 490                 495

His Asn His Tyr Thr Gln Lys Ser Leu Ser Leu Ser Pro Gly Lys Lys
                        500                 505                 510

Asp Pro Lys Ala Ser Phe Glu Ile Glu Val Met Tyr Pro Pro Pro Tyr
                        515                 520                 525

Leu Asp Asn Glu Lys Ser Asn Gly Thr Ile Ile His Val Lys Gly Lys
        530                 535                 540

His Leu Cys Pro Ser Pro Leu Phe Pro Gly Pro Ser Lys Pro Phe Trp
        545                 550                 555                 560

Val Leu Val Val Val Gly Gly Val Leu Ala Cys Tyr Ser Leu Leu Val
                        565                 570                 575

Thr Val Ala Phe Ile Ile Phe Trp Val Arg Ser Lys Arg Ser Arg Leu
                        580                 585                 590

Leu His Ser Asp Tyr Met Asn Met Thr Pro Arg Arg Pro Gly Pro Thr
                        595                 600                 605

Arg Lys His Tyr Gln Pro Tyr Ala Pro Pro Arg Asp Phe Ala Ala Tyr
                        610                 615                 620

Arg Ser Arg Val Lys Phe Ser Arg Ser Ala Asp Ala Pro Ala Tyr Lys
        625                 630                 635                 640

Gln Gly Gln Asn Gln Leu Tyr Asn Glu Leu Asn Leu Gly Arg Arg Glu
                        645                 650                 655

Glu Tyr Asp Val Leu Asp Lys Arg Arg Gly Arg Asp Pro Glu Met Gly
                        660                 665                 670

Gly Lys Pro Arg Arg Lys Asn Pro Gln Glu Gly Leu Tyr Asn Glu Leu
                        675                 680                 685

Gln Lys Asp Lys Met Ala Glu Ala Tyr Ser Glu Ile Gly Met Lys Gly
                        690                 695                 700

Glu Arg Arg Arg Gly Lys Gly His Asp Gly Leu Tyr Gln Gly Leu Ser
        705                 710                 715                 720

Thr Ala Thr Lys Asp Thr Tyr Asp Ala Leu His Met Gln Ala Leu Pro
                        725                 730                 735

Pro Arg Gly Val Gln Val Glu Thr Ile Ser Pro Gly Asp Gly Arg Thr
                        740                 745                 750

Phe Pro Lys Arg Gly Gln Thr Cys Val Val His Tyr Thr Gly Met Leu
                        755                 760                 765

Gly Asp Gly Lys Lys Val Asp Ser Ser Arg Asp Arg Asn Lys Pro Phe
        770                 775                 780

Lys Phe Met Leu Gly Lys Gln Glu Val Ile Arg Gly Trp Glu Glu Gly
        785                 790                 795                 800

Val Ala Gln Met Ser Val Gly Gln Gly Ala Lys Leu Thr Ile Ser Pro
                        805                 810                 815
```

Asp Tyr Ala Tyr Gly Ala Thr Gly His Pro Gly Ile Ile Pro Pro His
            820                 825                 830

Ala Thr Leu Val Phe Asp Val Glu Leu Leu Glu Leu Glu
        835                 840                 845

<210> SEQ ID NO 89
<211> LENGTH: 63
<212> TYPE: DNA
<213> ORGANISM: Artificial Sequence
<220> FEATURE:
<223> OTHER INFORMATION: synthetic

<400> SEQUENCE: 89
atggaattcg gcctgagctg gctgtttctg gtggccattc tgaagggcgt gcagtgctcc    60
aga                                                                  63

<210> SEQ ID NO 90
<211> LENGTH: 21
<212> TYPE: PRT
<213> ORGANISM: Artificial Sequence
<220> FEATURE:
<223> OTHER INFORMATION: synthetic

<400> SEQUENCE: 90

Met Glu Phe Gly Leu Ser Trp Leu Phe Leu Val Ala Ile Leu Lys Gly
1               5                   10                  15

Val Gln Cys Ser Arg
            20

<210> SEQ ID NO 91
<211> LENGTH: 1482
<212> TYPE: DNA
<213> ORGANISM: Artificial Sequence
<220> FEATURE:
<223> OTHER INFORMATION: synthetic

<400> SEQUENCE: 91
gacatcctgc tgacacagac acctctgagc ctgcctgtgt ctctgggaga tcaggccagc    60
atcagctgta aagcagcca gagcctggtg cacagaaacg gcaataccta cctgcactgg   120
tatctgcaga agcccggcca gtctcctaag ctgctgatcc acaaggtgtc caacagattc   180
agcggcgtgc ccgatagatt ttctggctct ggcagcggca ccgacttcac cctgaagatc   240
tctagagtgg aagccgagga cctgggcgtg tacttctgta gccagagcac acatgtgcct   300
ccactgacct ttggcgctgg caccaaactg gaacttaaag gcggcggagg atctggtggt   360
ggtggatctg gcggaggcgg ttctgaagtg aaactgcagc agtctggccc ctctctggtt   420
gaacctggcg cctctgtgat gatctcttgc aaggccagcg gcagcagctt caccggctac   480
aacatgaact gggtccgaca gaacatcggc aagagcctgg aatggatcgg cgccatcgat   540
ccttactacg gcggcaccag ctacaaccag aagttcaagg gcagagccac actgaccgtg   600
gacaagagca gcagcacagc ctacatgcac ctgaagtccc tgacaagcga ggacagcgcc   660
gtgtactact gtgtgtccgg catgaagtat tgggggccagg gcacaagcgt gaccgtgtct   720
agcgctaaga ccacacctcc tagcgtgtac ggcagagtga cagtgtccag cgccgagcct   780
aagagctgcg acaagacaca cacctgtcct ccatgtccag ctccagaact gctcggcgga   840 cccctccgttt tcctgtttcc acctaagcca aaggacaccc tcatgatcag cagaccccct   900
gaagtgacct gcgtggtggt cgatgtgtcc cacgaggatc ccgaagtgaa gttcaattgg   960

```
tacgtggacg gcgtggaagt gcacaacgcc aagaccaagc ctagagagga acagtacaac    1020
agcacctaca gagtggtgtc cgtgctgacc gtgctgcatc aggactggct gaacggcaaa    1080
gagtacaagt gcaaagtctc caacaaggcc ctgcctgctc ctatcgagaa aaccatcagc    1140
aaggccaagg gccagccaag agaacccag gtttacacac tgcctccaag cagggacgag     1200
ctgaccaaga atcaggtgtc cctgacctgc ctggtcaagg gcttctaccc ttccgatatc    1260
gccgtggaat gggagagcaa tggccagcct gagaacaact acaagacaac ccctcctgtg    1320
ctggacagcg acggctcatt cttcctgtac agcaagctga cagtggataa gtcccggtgg    1380
cagcagggca atgtgttcag ctgttctgtg atgcacgagg ccctgcacaa ccactacacc    1440
cagaaaagcc tgtctctgag ccccggcaag aaggacccta aa                       1482
```

<210> SEQ ID NO 92
<211> LENGTH: 494
<212> TYPE: PRT
<213> ORGANISM: Artificial Sequence
<220> FEATURE:
<223> OTHER INFORMATION: synthetic

<400> SEQUENCE: 92

```
Asp Ile Leu Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Gly Gly Gly Ser Gly Gly Gly Ser Gly Gly Gly Ser
        115                 120                 125

Glu Val Lys Leu Gln Gln Ser Gly Pro Ser Leu Val Glu Pro Gly Ala
    130                 135                 140

Ser Val Met Ile Ser Cys Lys Ala Ser Gly Ser Ser Phe Thr Gly Tyr
145                 150                 155                 160

Asn Met Asn Trp Val Arg Gln Asn Ile Gly Lys Ser Leu Glu Trp Ile
                165                 170                 175

Gly Ala Ile Asp Pro Tyr Tyr Gly Gly Thr Ser Tyr Asn Gln Lys Phe
            180                 185                 190

Lys Gly Arg Ala Thr Leu Thr Val Asp Lys Ser Ser Ser Thr Ala Tyr
        195                 200                 205

Met His Leu Lys Ser Leu Thr Ser Glu Asp Ser Ala Val Tyr Tyr Cys
    210                 215                 220

Val Ser Gly Met Lys Tyr Trp Gly Gln Gly Thr Ser Val Thr Val Ser
225                 230                 235                 240

Ser Ala Lys Thr Thr Pro Pro Ser Val Tyr Gly Arg Val Thr Val Ser
                245                 250                 255

Ser Ala Glu Pro Lys Ser Cys Asp Lys Thr His Thr Cys Pro Pro Cys
            260                 265                 270
```

-continued

```
Pro Ala Pro Glu Leu Leu Gly Gly Pro Ser Val Phe Leu Phe Pro Pro
            275                 280                 285

Lys Pro Lys Asp Thr Leu Met Ile Ser Arg Thr Pro Glu Val Thr Cys
        290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Lys Asp Pro Lys
                485                 490

<210> SEQ ID NO 93
<211> LENGTH: 117
<212> TYPE: DNA
<213> ORGANISM: Artificial Sequence
<220> FEATURE:
<223> OTHER INFORMATION: synthetic

<400> SEQUENCE: 93
attgaagtta tgtatcctcc tccttaccta gacaatgaga agagcaatgg aaccattatc    60
catgtgaaag ggaaacacct ttgtccaagt cccctatttc ccggaccttc taagccc     117

<210> SEQ ID NO 94
<211> LENGTH: 39
<212> TYPE: PRT
<213> ORGANISM: Artificial Sequence
<220> FEATURE:
<223> OTHER INFORMATION: synthetic

<400> SEQUENCE: 94

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 95
<211> LENGTH: 81
<212> TYPE: DNA
```

```
<213> ORGANISM: Artificial Sequence
<220> FEATURE:
<223> OTHER INFORMATION: synthetic

<400> SEQUENCE: 95
ttttgggtgc tggtggtggt tgggggagtc ctggcttgct atagcttgct agtaacagtg    60
gcctttatta ttttctgggt g                                              81

<210> SEQ ID NO 96
<211> LENGTH: 27
<212> TYPE: PRT
<213> ORGANISM: Artificial Sequence
<220> FEATURE:
<223> OTHER INFORMATION: synthetic

<400> SEQUENCE: 96

Phe Trp Val Leu Val Val Val Gly Gly Val Leu Ala Cys Tyr Ser Leu
1               5                  10                  15

Leu Val Thr Val Ala Phe Ile Ile Phe Trp Val
            20                  25

<210> SEQ ID NO 97
<211> LENGTH: 123
<212> TYPE: DNA
<213> ORGANISM: Artificial Sequence
<220> FEATURE:
<223> OTHER INFORMATION: synthetic

<400> SEQUENCE: 97
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 98
<211> LENGTH: 41
<212> TYPE: PRT
<213> ORGANISM: Artificial Sequence
<220> FEATURE:
<223> OTHER INFORMATION: synthetic

<400> SEQUENCE: 98

Arg Ser Lys Arg Ser Arg Leu Leu His Ser Asp Tyr Met Asn Met Thr
1               5                  10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 99
<211> LENGTH: 336
<212> TYPE: DNA
<213> ORGANISM: Artificial Sequence
<220> FEATURE:
<223> OTHER INFORMATION: synthetic

<400> SEQUENCE: 99
agagtgaagt tcagcaggag cgcagacgcc cccgcgtaca gcagggccga gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
```

```
cggaggggca agggcacga tggcctttac cagggtctca gtacagccac caaggacacc      300
tacgacgccc ttcacatgca ggccctgccc cctcgc                              336
```

<210> SEQ ID NO 100
<211> LENGTH: 112
<212> TYPE: PRT
<213> ORGANISM: Artificial Sequence
<220> FEATURE:
<223> OTHER INFORMATION: synthetic

<400> SEQUENCE: 100

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 101
<211> LENGTH: 321
<212> TYPE: DNA
<213> ORGANISM: Artificial Sequence
<220> FEATURE:
<223> OTHER INFORMATION: synthetic

<400> SEQUENCE: 101

```
ggagtgcagg tggaaaccat ctccccagga gacgggcgca ccttccccaa gcgcggccag      60
acctgcgtgg tgcactacac cgggatgctt ggagatggaa agaaagttga ctcctcccgg     120
gacagaaaca agccctttaa gtttatgcta ggcaagcagg aggtgatccg aggctgggaa     180 gaagggttg cccagatgag tgtgggtcag ggagccaaac tgactatatc tccagattat     240
gcctatggtg ccactgggca cccaggcatc atcccaccac atgccactct cgtcttcgat     300
gtggagcttc tagaactgga a                                              321
```

<210> SEQ ID NO 102
<211> LENGTH: 107
<212> TYPE: PRT
<213> ORGANISM: Artificial Sequence
<220> FEATURE:
<223> OTHER INFORMATION: synthetic

<400> SEQUENCE: 102

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Gly Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60
```

```
Gln Met Ser Val Gly Gln Gly Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Glu Leu Glu
            100                 105

<210> SEQ ID NO 103
<211> LENGTH: 2691
<212> TYPE: DNA
<213> ORGANISM: Artificial Sequence
<220> FEATURE:
<223> OTHER INFORMATION: synthetic

<400> SEQUENCE: 103
```

| | | | | | |
|---|---|---|---|---|---|
| atggaattcg | gcctgagctg | gctgtttctg | gtggccattc | tgaagggcgt | gcagtgctcc | 60 |
| agagacatcc | tgctgacaca | gacacctctg | agcctgcctg | tgtctctggg | agatcaggcc | 120 |
| agcatcagct | gtagaagcag | ccagagcctg | gtgcacagaa | acggcaatac | ctacctgcac | 180 |
| tggtatctgc | agaagcccgg | ccagtctcct | aagctgctga | tccacaaggt | gtccaacaga | 240 |
| ttcagcggcg | tgcccgatag | attttctggc | tctggcagcg | gcaccgactt | caccctgaag | 300 |
| atctctagag | tggaagccga | ggacctgggc | gtgtacttct | gtagccagag | cacacatgtg | 360 |
| cctccactga | cctttggcgc | tggcaccaaa | ctgaactta | aggcggcgg | aggatctggt | 420 |
| ggtggtggat | ctggcggagg | cggttctgaa | gtgaaactgc | agcagtctgg | ccctctctg | 480 |
| gttgaacctg | gcgcctctgt | gatgatctct | tgcaaggcca | gcggcagcag | cttcaccggc | 540 |
| tacaacatga | actgggtccg | acagaacatc | ggcaagagcc | tggaatggat | cggcgccatc | 600 |
| gatccttact | acggcggcac | cagctacaac | cagaagttca | agggcagagc | cacactgacc | 660 |
| gtggacaaga | gcagcagcac | agcctacatg | cacctgaagt | ccctgacaag | cgaggacagc | 720 |
| gccgtgtact | actgtgtgtc | cggcatgaag | tattgggggcc | agggcacaag | cgtgaccgtg | 780 |
| tctagcgcta | agaccacacc | tcctagcgtg | tacggcagag | tgacagtgtc | cagcgccgag | 840 |
| cctaagagct | cgacaagac | acacacctgt | cctccatgtc | cagctccaga | actgctcggc | 900 |
| ggaccctccg | tttcctgtt | tccacctaag | ccaaaggaca | ccctcatgat | cagcagaacc | 960 |
| cctgaagtga | cctgcgtggt | ggtcgatgtg | tcccacgagg | atcccgaagt | gaagttcaat | 1020 |
| tggtacgtgg | acggcgtgga | agtgcacaac | gccaagacca | agcctagaga | ggaacagtac | 1080 |
| aacagcacct | acagagtggt | gtccgtgctg | accgtgctgc | atcaggactg | gctgaacggc | 1140 |
| aaagagtaca | agtgcaaagt | ctccaacaag | gccctgcctg | ctcctatcga | aaaaccatc | 1200 |
| agcaaggcca | agggccagcc | aagagaaccc | caggtttaca | cactgcctcc | aagcagggac | 1260 |
| gagctgacca | agaatcaggt | gtccctgacc | tgcctggtca | agggcttcta | cccttccgat | 1320 |
| atcgccgtgg | aatgggagag | caatggccag | cctgagaaca | actacaagac | aaccctcct | 1380 |
| gtgctggaca | gcgacggctc | attcttcctg | tacagcaagc | tgacagtgga | taagtcccgg | 1440 |
| tggcagcagg | gcaatgtgtt | cagctgttct | gtgatgcacg | aggccctgca | caaccactac | 1500 |
| acccagaaaa | gcctgtctct | gagccccggc | aagaaggacc | ctaaagctag | cttcgaaatt | 1560 |
| gaagttatgt | atcctcctcc | ttacctagac | aatgagaaga | gcaatggaac | cattatccat | 1620 |
| gtgaaaggga | aacacctttg | tccaagtccc | ctatttcccg | accttctaa | gcccttttgg | 1680 |
| gtgctggtgg | tggttggggg | agtcctggct | tgctatagct | tgctagtaac | agtggccttt | 1740 |
| attattttct | gggtgaggag | taagaggagc | aggctcctgc | acagtgacta | catgaacatg | 1800 |

```
actcccccgcc gccccgggcc cacccgcaag cattaccagc cctatgcccc accacgcgac    1860
ttcgcagcct atcgctccag agtgaagttc agcaggagcg cagacgcccc cgcgtacaag    1920
cagggccaga accagctcta taacgagctc aatctaggac gaagagagga gtacgatgtt    1980
ttggacaaga gacgtggccg ggaccctgag atggggggaa agccgagaag gaagaaccct    2040
caggaaggcc tgtacaatga actgcagaaa gataagatgg cggaggccta cagtgagatt    2100
gggatgaaag gcgagcgccg gaggggcaag gggcacgatg gcctttacca gggtctcagt    2160
acagccacca aggacaccta cgacgccctt cacatgcagg ccctgccccc tcgcatcagt    2220
ctgattgcgg cgttagcggt agattacgtt atcggcatgg aaaacgccat gccgtggaac    2280
ctgcctgccg atctcgcctg gtttaaacgc aacaccttaa ataaacccgt gattatgggc    2340
cgccatacct gggaatcaat cggtcgtccg ttgccaggac gcaaaaatat tatcctcagc    2400
agtcaaccga gtacggacga tcgcgtaacg tgggtgaagt cggtggatga agccatcgcg    2460
gcgtgtggtg acgtaccaga aatcatggtg attggcggcg gtcgcgttat tgaacagttc    2520
ttgccaaaag cgcaaaaact gtatctgacg catatcgacg cagaagtgga aggcgacacc    2580
catttcccgg attacgagcc ggatgactgg gaatcggtat tcagcgaatt ccacgatgct    2640
gatgcgcaga actctcacag ctattgcttt gagattctgg agcggcgatg a           2691
```

<210> SEQ ID NO 104
<211> LENGTH: 896
<212> TYPE: PRT
<213> ORGANISM: Artificial Sequence
<220> FEATURE:
<223> OTHER INFORMATION: synthetic

<400> SEQUENCE: 104

```
Met Glu Phe Gly Leu Ser Trp Leu Phe Leu Val Ala Ile Leu Lys Gly
1               5                   10                  15

Val Gln Cys Ser Arg Asp Ile Leu Leu Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Arg Asn Gly Asn Thr Tyr Leu His Trp Tyr Leu Gln
    50                  55                  60

Lys Pro Gly Gln Ser Pro Lys Leu Leu Ile His Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Pro Leu Thr Phe Gly Ala Gly
        115                 120                 125

Thr Lys Leu Glu Leu Lys Gly Gly Gly Ser Gly Gly Gly Ser
    130                 135                 140

Gly Gly Gly Gly Ser Glu Val Lys Leu Gln Gln Ser Gly Pro Ser Leu
145                 150                 155                 160

Val Glu Pro Gly Ala Ser Val Met Ile Ser Cys Lys Ala Ser Gly Ser
                165                 170                 175

Ser Phe Thr Gly Tyr Asn Met Asn Trp Val Arg Gln Asn Ile Gly Lys
            180                 185                 190

Ser Leu Glu Trp Ile Gly Ala Ile Asp Pro Tyr Tyr Gly Gly Thr Ser
        195                 200                 205
```

```
Tyr Asn Gln Lys Phe Lys Gly Arg Ala Thr Leu Thr Val Asp Lys Ser
    210                 215                 220

Ser Ser Thr Ala Tyr Met His Leu Lys Ser Leu Thr Ser Glu Asp Ser
225                 230                 235                 240

Ala Val Tyr Tyr Cys Val Ser Gly Met Lys Tyr Trp Gly Gln Gly Thr
                245                 250                 255

Ser Val Thr Val Ser Ser Ala Lys Thr Thr Pro Pro Ser Val Tyr Gly
            260                 265                 270

Arg Val Thr Val Ser Ser Ala Glu Pro Lys Ser Cys Asp Lys Thr His
            275                 280                 285

Thr Cys Pro Pro Cys Pro Ala Pro Glu Leu Leu Gly Gly Pro Ser Val
290                 295                 300

Phe Leu Phe Pro Pro Lys Pro Lys Asp Thr Leu Met Ile Ser Arg Thr
305                 310                 315                 320

Pro Glu Val Thr Cys Val Val Asp Val Ser His Glu Asp Pro Glu
                325                 330                 335

Val Lys Phe Asn Trp Tyr Val Asp Gly Val Glu Val His Asn Ala Lys
                340                 345                 350

Thr Lys Pro Arg Glu Glu Gln Tyr Asn Ser Thr Tyr Arg Val Val Ser
            355                 360                 365

Val Leu Thr Val Leu His Gln Asp Trp Leu Asn Gly Lys Glu Tyr Lys
    370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys Lys
            500                 505                 510

Asp Pro Lys Ala Ser Phe Glu Ile Glu Val Met Tyr Pro Pro Pro Tyr
        515                 520                 525

Leu Asp Asn Glu Lys Ser Asn Gly Thr Ile Ile His Val Lys Gly Lys
    530                 535                 540

His Leu Cys Pro Ser Pro Leu Phe Pro Gly Pro Ser Lys Pro Phe Trp
545                 550                 555                 560

Val Leu Val Val Val Gly Gly Val Leu Ala Cys Tyr Ser Leu Leu Val
                565                 570                 575

Thr Val Ala Phe Ile Ile Phe Trp Val Arg Ser Lys Arg Ser Arg Leu
            580                 585                 590

Leu His Ser Asp Tyr Met Asn Met Thr Pro Arg Arg Pro Gly Pro Thr
        595                 600                 605

Arg Lys His Tyr Gln Pro Tyr Ala Pro Pro Arg Asp Phe Ala Ala Tyr
    610                 615                 620

Arg Ser Arg Val Lys Phe Ser Arg Ser Ala Asp Ala Pro Ala Tyr Lys
```

```
                625                 630                 635                 640
    Gln Gly Gln Asn Gln Leu Tyr Asn Glu Leu Asn Leu Gly Arg Arg Glu
                    645                 650                 655

Glu Tyr Asp Val Leu Asp Lys Arg Arg Gly Arg Asp Pro Glu Met Gly
                    660                 665                 670

Gly Lys Pro Arg Arg Lys Asn Pro Gln Glu Gly Leu Tyr Asn Glu Leu
                    675                 680                 685

Gln Lys Asp Lys Met Ala Glu Ala Tyr Ser Glu Ile Gly Met Lys Gly
                    690                 695                 700

Glu Arg Arg Arg Gly Lys Gly His Asp Gly Leu Tyr Gln Gly Leu Ser
    705                 710                 715                 720

Thr Ala Thr Lys Asp Thr Tyr Asp Ala Leu His Met Gln Ala Leu Pro
                    725                 730                 735

Pro Arg Ile Ser Leu Ile Ala Ala Leu Ala Val Asp Tyr Val Ile Gly
                    740                 745                 750

Met Glu Asn Ala Met Pro Trp Asn Leu Pro Ala Asp Leu Ala Trp Phe
                    755                 760                 765

Lys Arg Asn Thr Leu Asn Lys Pro Val Ile Met Gly Arg His Thr Trp
                    770                 775                 780

Glu Ser Ile Gly Arg Pro Leu Pro Gly Arg Lys Asn Ile Ile Leu Ser
    785                 790                 795                 800

Ser Gln Pro Ser Thr Asp Asp Arg Val Thr Trp Val Lys Ser Val Asp
                    805                 810                 815

Glu Ala Ile Ala Ala Cys Gly Asp Val Pro Glu Ile Met Val Ile Gly
                    820                 825                 830

Gly Gly Arg Val Ile Glu Gln Phe Leu Pro Lys Ala Gln Lys Leu Tyr
                    835                 840                 845

Leu Thr His Ile Asp Ala Glu Val Glu Gly Asp Thr His Phe Pro Asp
                    850                 855                 860

Tyr Glu Pro Asp Asp Trp Glu Ser Val Phe Ser Glu Phe His Asp Ala
    865                 870                 875                 880

Asp Ala Gln Asn Ser His Ser Tyr Cys Phe Glu Ile Leu Glu Arg Arg
                    885                 890                 895

<210> SEQ ID NO 105
<211> LENGTH: 63
<212> TYPE: DNA
<213> ORGANISM: Artificial Sequence
<220> FEATURE:
<223> OTHER INFORMATION: synthetic

<400> SEQUENCE: 105
atggaattcg gcctgagctg gctgtttctg gtggccattc tgaagggcgt gcagtgctcc      60
aga                                                                   63

<210> SEQ ID NO 106
<211> LENGTH: 21
<212> TYPE: PRT
<213> ORGANISM: Artificial Sequence
<220> FEATURE:
<223> OTHER INFORMATION: synthetic

<400> SEQUENCE: 106

Met Glu Phe Gly Leu Ser Trp Leu Phe Leu Val Ala Ile Leu Lys Gly
1               5                   10                  15

Val Gln Cys Ser Arg
            20
```

<210> SEQ ID NO 107
<211> LENGTH: 1482
<212> TYPE: DNA
<213> ORGANISM: Artificial Sequence
<220> FEATURE:
<223> OTHER INFORMATION: synthetic

<400> SEQUENCE: 107

```
gacatcctgc tgacacagac acctctgagc ctgcctgtgt ctctgggaga tcaggccagc      60
atcagctgta gaagcagcca gagcctggtg cacagaaacg gcaataccta cctgcactgg     120
tatctgcaga gcccggcca gtctcctaag ctgctgatcc acaaggtgtc caacagattc     180
agcggcgtgc ccgatagatt ttctggctct ggcagcggca ccgacttcac cctgaagatc     240
tctagagtgg aagccgagga cctgggcgtg tacttctgta gccagagcac acatgtgcct     300
ccactgacct ttggcgctgg caccaaactg gaacttaaag gcggcggagg atctggtggt     360
ggtggatctg gcggaggcgg ttctgaagtg aaactgcagc agtctggccc ctctctggtt     420
gaacctggcg cctctgtgat gatctcttgc aaggccagcg gcagcagctt caccggctac     480
aacatgaact gggtccgaca gaacatcggc aagagcctgg aatggatcgg cgccatcgat     540
ccttactacg gcggcaccag ctacaaccag aagttcaagg gcagagccac actgaccgtg     600
gacaagagca gcagcacagc ctacatgcac ctgaagtccc tgacaagcga ggacagcgcc     660
gtgtactact gtgtgtccgg catgaagtat tggggccagg gcacaagcgt gaccgtgtct     720
agcgctaaga ccacacctcc tagcgtgtac ggcagagtga cagtgtccag cgccgagcct     780
aagagctgcg acaagacaca cacctgtcct ccatgtccag ctccagaact gctcggcgga     840
ccctccgttt tcctgttttcc acctaagcca aggacacccc tcatgatcag cagaaccccct     900
gaagtgacct gcgtggtggt cgatgtgtcc cacgaggatc ccgaagtgaa gttcaattgg     960
tacgtggacg gcgtggaagt gcacaacgcc aagaccaagc ctagagagga cagtacaac    1020
agcacctaca gagtggtgtc cgtgctgacc gtgctgcatc aggactggct gaacggcaaa    1080
gagtacaagt gcaaagtctc caacaaggcc ctgcctgctc ctatcgagaa aaccatcagc    1140
aaggccaagg gccagccaag agaaccccag gttttacacac tgcctccaag cagggacgag    1200
ctgaccaaga atcaggtgtc cctgacctgc ctggtcaagg gcttctaccc ttccgatatc    1260
gccgtggaat gggagagcaa tggccagcct gagaacaact acaagacaac ccctcctgtg    1320
ctggacagcg acggctcatt cttcctgtac agcaagctga cagtggataa gtcccggtgg    1380
cagcagggca atgtgttcag ctgttctgtg atgcacgagg ccctgcacaa ccactacacc    1440
cagaaaagcc tgtctctgag ccccggcaag aaggacccta aa                     1482
```

<210> SEQ ID NO 108
<211> LENGTH: 494
<212> TYPE: PRT
<213> ORGANISM: Artificial Sequence
<220> FEATURE:
<223> OTHER INFORMATION: synthetic

<400> SEQUENCE: 108

```
Asp Ile Leu Leu Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45
```

-continued

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Glu Val Lys Leu Gln Gln Ser Gly Pro Ser Leu Val Glu Pro Gly Ala
    130                 135                 140

Ser Val Met Ile Ser Cys Lys Ala Ser Gly Ser Ser Phe Thr Gly Tyr
145                 150                 155                 160

Asn Met Asn Trp Val Arg Gln Asn Ile Gly Lys Ser Leu Glu Trp Ile
                165                 170                 175

Gly Ala Ile Asp Pro Tyr Tyr Gly Gly Thr Ser Tyr Asn Gln Lys Phe
            180                 185                 190

Lys Gly Arg Ala Thr Leu Thr Val Asp Lys Ser Ser Thr Ala Tyr
    195                 200                 205

Met His Leu Lys Ser Leu Thr Ser Glu Asp Ser Ala Val Tyr Tyr Cys
    210                 215                 220

Val Ser Gly Met Lys Tyr Trp Gly Gln Gly Thr Ser Val Thr Val Ser
225                 230                 235                 240

Ser Ala Lys Thr Thr Pro Pro Ser Val Tyr Gly Arg Val Thr Val Ser
                245                 250                 255

Ser Ala Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
    275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
    355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Lys Asp Pro Lys
                485                 490

<210> SEQ ID NO 109
<211> LENGTH: 117
<212> TYPE: DNA
<213> ORGANISM: Artificial Sequence
<220> FEATURE:
<223> OTHER INFORMATION: synthetic

<400> SEQUENCE: 109
attgaagtta tgtatcctcc tccttaccta gacaatgaga agagcaatgg aaccattatc      60
catgtgaaag ggaaacacct ttgtccaagt cccctatttc ccggaccttc taagccc       117

<210> SEQ ID NO 110
<211> LENGTH: 39
<212> TYPE: PRT
<213> ORGANISM: Artificial Sequence
<220> FEATURE:
<223> OTHER INFORMATION: synthetic

<400> SEQUENCE: 110

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 111
<211> LENGTH: 81
<212> TYPE: DNA
<213> ORGANISM: Artificial Sequence
<220> FEATURE:
<223> OTHER INFORMATION: synthetic

<400> SEQUENCE: 111
ttttgggtgc tggtggtggt tgggggagtc ctggcttgct atagcttgct agtaacagtg      60
gcctttatta ttttctgggt g                                               81

<210> SEQ ID NO 112
<211> LENGTH: 27
<212> TYPE: PRT
<213> ORGANISM: Artificial Sequence
<220> FEATURE:
<223> OTHER INFORMATION: synthetic

<400> SEQUENCE: 112

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 113
<211> LENGTH: 123
<212> TYPE: DNA
<213> ORGANISM: Artificial Sequence
<220> FEATURE:
<223> OTHER INFORMATION: synthetic

<400> SEQUENCE: 113

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 114
<211> LENGTH: 41
<212> TYPE: PRT
<213> ORGANISM: Artificial Sequence
<220> FEATURE:
<223> OTHER INFORMATION: synthetic

<400> SEQUENCE: 114

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 115
<211> LENGTH: 336
<212> TYPE: DNA
<213> ORGANISM: Artificial Sequence
<220> FEATURE:
<223> OTHER INFORMATION: synthetic

<400> SEQUENCE: 115

```
agagtgaagt tcagcaggag cgcagacgcc cccgcgtaca agcagggcca gaaccagctc    60
tataacgagc tcaatctagg acgaagagag gagtacgatg tttttggacaa gagacgtggc   120 cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 116
<211> LENGTH: 112
<212> TYPE: PRT
<213> ORGANISM: Artificial Sequence
<220> FEATURE:
<223> OTHER INFORMATION: synthetic

<400> SEQUENCE: 116

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 117
<211> LENGTH: 474
<212> TYPE: DNA
<213> ORGANISM: Artificial Sequence
<220> FEATURE:
<223> OTHER INFORMATION: synthetic

<400> SEQUENCE: 117

```
atcagtctga ttgcggcgtt agcggtagat tacgttatcg gcatggaaaa cgccatgccg        60
tggaacctgc ctgccgatct cgcctggttt aaacgcaaca ccttaaataa acccgtgatt       120
atgggccgcc ataccgggga atcaatcggt cgtccgttgc caggacgcaa aaatattatc       180
ctcagcagtc aaccgagtac ggacgatcgc gtaacgtggg tgaagtcggt ggatgaagcc       240
atcgcggcgt gtggtgacgt accagaaatc atggtgattg cggcggtcg cgttattgaa        300
cagttcttgc caaaagcgca aaaactgtat ctgacgcata tcgacgcaga gtggaaggc        360
gacacccatt tcccggatta cgagccggat gactgggaat cggtattcag cgaattccac       420
gatgctgatg cgcagaactc tcacagctat tgctttgaga ttctggagcg gcga             474
```

<210> SEQ ID NO 118
<211> LENGTH: 158
<212> TYPE: PRT
<213> ORGANISM: Artificial Sequence
<220> FEATURE:
<223> OTHER INFORMATION: synthetic

<400> SEQUENCE: 118

```
Ile Ser Leu Ile Ala Ala Leu Ala Val Asp Tyr Val Ile Gly Met Glu
1               5                   10                  15

Asn Ala Met Pro Trp Asn Leu Pro Ala Asp Leu Ala Trp Phe Lys Arg
            20                  25                  30

Asn Thr Leu Asn Lys Pro Val Ile Met Gly Arg His Thr Trp Glu Ser
        35                  40                  45

Ile Gly Arg Pro Leu Pro Gly Arg Lys Asn Ile Ile Leu Ser Ser Gln
    50                  55                  60

Pro Ser Thr Asp Asp Arg Val Thr Trp Val Lys Ser Val Asp Glu Ala
65                  70                  75                  80

Ile Ala Ala Cys Gly Asp Val Pro Glu Ile Met Val Ile Gly Gly Gly
                85                  90                  95

Arg Val Ile Glu Gln Phe Leu Pro Lys Ala Gln Lys Leu Tyr Leu Thr
            100                 105                 110

His Ile Asp Ala Glu Val Glu Gly Asp Thr His Phe Pro Asp Tyr Glu
        115                 120                 125

Pro Asp Asp Trp Glu Ser Val Phe Ser Glu Phe His Asp Ala Asp Ala
    130                 135                 140

Gln Asn Ser His Ser Tyr Cys Phe Glu Ile Leu Glu Arg Arg
145                 150                 155
```

<210> SEQ ID NO 119
<211> LENGTH: 1818
<212> TYPE: DNA
<213> ORGANISM: Artificial Sequence
<220> FEATURE:
<223> OTHER INFORMATION: synthetic

<400> SEQUENCE: 119

```
atgctgctgc tcgtgacatc tctgctgctg tgcgagctgc ccacccccgc ctttctgctg        60
atccccgata tccagatgac ccagtccccg agctccctgt ccgcctctgt gggcgatagg       120
```

```
gtcaccatca cctgccgtgc cagtcaggat gtgaatactg ctgtagcctg gtatcaacag    180
aaaccaggaa aagctccgaa actactgatt tactcggcat ccttcctttta ttctggagtc    240 ccttctcgct tctctggatc tagatctggg acggatttca ctctgaccat cagcagtctg    300
cagccggaag acttcgcaac ttattactgt cagcaacatt atactactcc tcccacgttc    360 ggacaggta ccaaggtgga gatcaaaggg tctacatctg gatctgggaa gccgggttct    420 ggtgaggtt ctggtgaggt tcagctggtg gagtctggcg gtggcctggt gcagccaggg    480
ggctcactcc gtttgtcctg tgcagcttct ggcttcaaca ttaaagacac ctatatacac    540
tgggtgcgtc aggcccccggg taagggcctg aatgggttg caaggattta tcctacgaat    600
ggttatacta gatatgccga tagcgtcaag ggccgtttca ctataagcgc agacacatcc    660
aaaaacacag cctacctgca gatgaacagc ctgcgtgctg aggacactgc cgtctattat    720
tgttctagat ggggaggga cggcttctat gctatggacg tgggggtca aggaaccctg    780 gtcaccgtct cctcggctag cgaacaaaaa ctcatctcag aagaggatct gttcgaaatt    840
gaagttatgt atcctcctcc ttacctagac aatgagaaga gcaatggaac cattatccat    900
gtgaaaggga aacacctttg tccaagtccc ctatttcccg gaccttctaa gcccttttgg    960
gtgctggtgg tggttggggg agtcctggct tgctatagct tgctagtaac agtggccttt    1020
attattttct gggtgaggag taagaggagc aggctcctgc acagtgacta catgaacatg    1080
actccccgcc gccccgggcc cacccgcaag cattaccagc cctatgcccc accacgcgac    1140
ttcgcagcct atcgctccag agtgaagttc agcaggagcg cagacgcccc cgcgtacaag    1200
cagggccaga accagctcta taacgagctc aatctaggac gaagagagga gtacgatgtt    1260
ttggacaaga cgtggccg ggaccctgag atgggggaa agccgagaag gaagaaccct    1320
caggaaggcc tgtacaatga actgcagaaa gataagatgg cggaggccta cagtgagatt    1380
gggatgaaag gcgagcgccg gaggggcaag gggcacgatg gcctttacca gggtctcagt    1440
acagccacca aggacaccta cgacgccctt cacatgcagg ccctgccccc tcgcggagtg    1500
caggtggaaa ccatctcccc aggagacggg cgcaccttcc ccaagcgcgg ccagacctgc    1560
gtggtgcact acaccgggat gcttggagat ggaaagaaag ttgactcctc ccgggacaga    1620
aacaagccct ttaagtttat gctaggcaag caggaggtga tccgaggctg ggaagaaggg    1680
gttgcccaga tgagtgtggg tcagggagcc aaactgacta tatctccaga ttatgcctat    1740
ggtgccactg gcacccagg catcatccca ccacatgcca ctctcgtctt cgatgtggag    1800
cttctagaac tggaatga                                                  1818
```

<210> SEQ ID NO 120
<211> LENGTH: 605
<212> TYPE: PRT
<213> ORGANISM: Artificial Sequence
<220> FEATURE:
<223> OTHER INFORMATION: synthetic

<400> SEQUENCE: 120

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60
```

```
Ala Pro Lys Leu Leu Ile Tyr Ser Ala Ser Phe Leu Tyr Ser Gly Val
 65                  70                  75                  80

Pro Ser Arg Phe Ser Gly Ser Arg Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Ser Gly Lys Pro Gly Ser Gly Glu Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Thr Tyr Ile His Trp Val Arg Gln Ala Pro Gly Lys Gly Leu Glu Trp
            180                 185                 190

Val Ala Arg Ile Tyr Pro Thr Asn Gly Tyr Thr Arg Tyr Ala Asp Ser
        195                 200                 205

Val Lys Gly Arg Phe Thr Ile Ser Ala Asp Thr Ser Lys Asn Thr Ala
210                 215                 220

Tyr Leu Gln Met Asn Ser Leu Arg Ala Glu Asp Thr Ala Val Tyr Tyr
225                 230                 235                 240

Cys Ser Arg Trp Gly Gly Asp Gly Phe Tyr Ala Met Asp Val Trp Gly
                245                 250                 255

Gln Gly Thr Leu Val Thr Val Ser Ala Ser Glu Gln Lys Leu Ile
            260                 265                 270

Ser Glu Glu Asp Leu Phe Glu Ile Glu Val Met Tyr Pro Pro Pro Tyr
        275                 280                 285

Leu Asp Asn Glu Lys Ser Asn Gly Thr Ile Ile His Val Lys Gly Lys
290                 295                 300

His Leu Cys Pro Ser Pro Leu Phe Pro Gly Pro Ser Lys Pro Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Ser Lys Arg Ser Arg Leu
            340                 345                 350

Leu His Ser Asp Tyr Met Asn Met Thr Pro Arg Arg Pro Gly Pro Thr
        355                 360                 365

Arg Lys His Tyr Gln Pro Tyr Ala Pro Pro Arg Asp Phe Ala Ala Tyr
370                 375                 380

Arg Ser Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
450                 455                 460

Glu Arg Arg Arg Gly Lys Gly His Asp Gly Leu Tyr Gln Gly Leu Ser
465                 470                 475                 480
```

```
Thr Ala Thr Lys Asp Thr Tyr Asp Ala Leu His Met Gln Ala Leu Pro
                485                 490                 495

Pro Arg Gly Val Gln Val Glu Thr Ile Ser Pro Gly Asp Gly Arg Thr
            500                 505                 510

Phe Pro Lys Arg Gly Gln Thr Cys Val Val His Tyr Thr Gly Met Leu
        515                 520                 525

Gly Asp Gly Lys Lys Val Asp Ser Ser Arg Asp Arg Asn Lys Pro Phe
    530                 535                 540

Lys Phe Met Leu Gly Lys Gln Glu Val Ile Arg Gly Trp Glu Glu Gly
545                 550                 555                 560

Val Ala Gln Met Ser Val Gly Gln Gly Ala Lys Leu Thr Ile Ser Pro
                565                 570                 575

Asp Tyr Ala Tyr Gly Ala Thr Gly His Pro Gly Ile Ile Pro Pro His
            580                 585                 590

Ala Thr Leu Val Phe Asp Val Glu Leu Leu Glu Leu Glu
        595                 600                 605

<210> SEQ ID NO 121
<211> LENGTH: 66
<212> TYPE: DNA
<213> ORGANISM: Artificial Sequence
<220> FEATURE:
<223> OTHER INFORMATION: synthetic

<400> SEQUENCE: 121
atgctgctgc tcgtgacatc tctgctgctg tgcgagctgc cccaccccgc ctttctgctg      60
atcccc                                                                 66

<210> SEQ ID NO 122
<211> LENGTH: 22
<212> TYPE: PRT
<213> ORGANISM: Artificial Sequence
<220> FEATURE:
<223> OTHER INFORMATION: synthetic

<400> SEQUENCE: 122

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 123
<211> LENGTH: 729
<212> TYPE: DNA
<213> ORGANISM: Artificial Sequence
<220> FEATURE:
<223> OTHER INFORMATION: synthetic

<400> SEQUENCE: 123
cagatgaccc agtccccgag ctccctgtcc gcctctgtgg gcgatagggt caccatcacc      60
tgccgtgcca gtcaggatgt gaatactgct gtagcctggt atcaacagaa accaggaaaa     120
gctccgaaac tactgattta ctcggcatcc ttcctttatt ctggagtccc ttctcgcttc     180
tctggatcta gatctgggac ggatttcact ctgaccatca gcagtctgca gccggaagac     240
ttcgcaactt attactgtca gcaacattat actactcctc ccacgttcgg acagggtacc     300
aaggtggaga tcaaagggtc tacatctgga tctgggaagc cgggttctgg tgagggttct     360
ggtgaggttc agctggtgga gtctggcggt ggcctggtgc agccaggggg ctcactccgt     420
ttgtcctgtg cagcttctgg cttcaacatt aaagacacct atatacactg ggtgcgtcag     480
```

```
gccccgggta agggcctgga atgggttgca aggatttatc ctacgaatgg ttatactaga      540
tatgccgata gcgtcaaggg ccgtttcact ataagcgcag acacatccaa aaacacagcc      600
tacctgcaga tgaacagcct gcgtgctgag gacactgccg tctattattg ttctagatgg      660
ggaggggacg gcttctatgc tatggacgtg tggggtcaag aaccctggt caccgtctcc       720 tcggctagc                                                              729
```

```
<210> SEQ ID NO 124
<211> LENGTH: 243
<212> TYPE: PRT
<213> ORGANISM: Artificial Sequence
<220> FEATURE:
<223> OTHER INFORMATION: synthetic

<400> SEQUENCE: 124
```

Gln Met Thr Gln Ser Pro Ser Ser Leu Ser Ala Ser Val Gly Asp Arg
1               5                   10                  15

Val Thr Ile Thr Cys Arg Ala Ser Gln Asp Val Asn Thr Ala Val Ala
            20                  25                  30

Trp Tyr Gln Gln Lys Pro Gly Lys Ala Pro Lys Leu Leu Ile Tyr Ser
        35                  40                  45

Ala Ser Phe Leu Tyr Ser Gly Val Pro Ser Arg Phe Ser Gly Ser Arg
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln His Tyr Thr Thr Pro Pro Thr Phe
                85                  90                  95

Gly Gln Gly Thr Lys Val Glu Ile Lys Gly Ser Thr Ser Gly Ser Gly
            100                 105                 110

Lys Pro Gly Ser Gly Glu Gly Ser Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Asn Ile Lys Asp Thr Tyr Ile His Trp Val Arg Gln
145                 150                 155                 160

Ala Pro Gly Lys Gly Leu Glu Trp Val Ala Arg Ile Tyr Pro Thr Asn
                165                 170                 175

Gly Tyr Thr Arg Tyr Ala Asp Ser Val Lys Gly Arg Phe Thr Ile Ser
            180                 185                 190

Ala Asp Thr Ser Lys Asn Thr Ala Tyr Leu Gln Met Asn Ser Leu Arg
        195                 200                 205

Ala Glu Asp Thr Ala Val Tyr Tyr Cys Ser Arg Trp Gly Gly Asp Gly
    210                 215                 220

Phe Tyr Ala Met Asp Val Trp Gly Gln Gly Thr Leu Val Thr Val Ser
225                 230                 235                 240

Ser Ala Ser

```
<210> SEQ ID NO 125
<211> LENGTH: 30
<212> TYPE: DNA
<213> ORGANISM: Artificial Sequence
<220> FEATURE:
<223> OTHER INFORMATION: synthetic

<400> SEQUENCE: 125
gaacaaaaac tcatctcaga agaggatctg                                        30
```

<210> SEQ ID NO 126
<211> LENGTH: 10
<212> TYPE: PRT
<213> ORGANISM: Artificial Sequence
<220> FEATURE:
<223> OTHER INFORMATION: synthetic

<400> SEQUENCE: 126

Glu Gln Lys Leu Ile Ser Glu Glu Asp Leu
1               5                   10

<210> SEQ ID NO 127
<211> LENGTH: 117
<212> TYPE: DNA
<213> ORGANISM: Artificial Sequence
<220> FEATURE:
<223> OTHER INFORMATION: synthetic

<400> SEQUENCE: 127
attgaagtta tgtatcctcc tccttaccta gacaatgaga agagcaatgg aaccattatc      60
catgtgaaag ggaaacacct tgtccaagt cccctatttc ccggaccttc taagccc        117

<210> SEQ ID NO 128
<211> LENGTH: 39
<212> TYPE: PRT
<213> ORGANISM: Artificial Sequence
<220> FEATURE:
<223> OTHER INFORMATION: synthetic

<400> SEQUENCE: 128

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 129
<211> LENGTH: 81
<212> TYPE: DNA
<213> ORGANISM: Artificial Sequence
<220> FEATURE:
<223> OTHER INFORMATION: synthetic

<400> SEQUENCE: 129
ttttgggtgc tggtggtggt tgggggagtc ctggcttgct atagcttgct agtaacagtg      60
gcctttatta ttttctgggt g                                                81

<210> SEQ ID NO 130
<211> LENGTH: 27
<212> TYPE: PRT
<213> ORGANISM: Artificial Sequence
<220> FEATURE:
<223> OTHER INFORMATION: synthetic

<400> SEQUENCE: 130

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 131

-continued

<211> LENGTH: 123
<212> TYPE: DNA
<213> ORGANISM: Artificial Sequence
<220> FEATURE:
<223> OTHER INFORMATION: synthetic

<400> SEQUENCE: 131

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 132
<211> LENGTH: 41
<212> TYPE: PRT
<213> ORGANISM: Artificial Sequence
<220> FEATURE:
<223> OTHER INFORMATION: synthetic

<400> SEQUENCE: 132

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 133
<211> LENGTH: 336
<212> TYPE: DNA
<213> ORGANISM: Artificial Sequence
<220> FEATURE:
<223> OTHER INFORMATION: synthetic

<400> SEQUENCE: 133

```
agagtgaagt tcagcaggag cgcagacgcc cccgcgtaca gcagggcca gaaccagctc     60
tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga aagataagat ggcggaggcc tacagtgaga ttgggatgaa aggcgagcgc   240
cggagggggca agggcacga tggcctttac cagggtctca gtacagccac caaggacacc   300
tacgacgccc ttcacatgca ggccctgccc cctcgc                             336
```

<210> SEQ ID NO 134
<211> LENGTH: 112
<212> TYPE: PRT
<213> ORGANISM: Artificial Sequence
<220> FEATURE:
<223> OTHER INFORMATION: synthetic

<400> SEQUENCE: 134

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 135
<211> LENGTH: 321
<212> TYPE: DNA
<213> ORGANISM: Artificial Sequence
<220> FEATURE:
<223> OTHER INFORMATION: synthetic

<400> SEQUENCE: 135
ggagtgcagg tggaaaccat ctccccagga gacgggcgca ccttccccaa gcgcggccag    60
acctgcgtgg tgcactacac cgggatgctt ggagatggaa agaaagttga ctcctcccgg   120
gacagaaaca agccctttaa gtttatgcta ggcaagcagg aggtgatccg aggctgggaa   180
gaaggggttg cccagatgag tgtgggtcag ggagccaaac tgactatatc tccagattat   240
gcctatggtg ccactgggca cccaggcatc atcccaccac atgccactct cgtcttcgat   300
gtggagcttc tagaactgga a                                             321

<210> SEQ ID NO 136
<211> LENGTH: 107
<212> TYPE: PRT
<213> ORGANISM: Artificial Sequence
<220> FEATURE:
<223> OTHER INFORMATION: synthetic

<400> SEQUENCE: 136

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Gly Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Glu Leu Glu
            100                 105
```